United States Patent
Luo et al.

(10) Patent No.: US 11,905,276 B2
(45) Date of Patent: Feb. 20, 2024

(54) BICYCLIC COMPOUND THAT ACTS AS CRBN PROTEIN REGULATOR

(71) Applicant: MEDSHINE DISCOVERY INC., Jiangsu (CN)

(72) Inventors: Yunfu Luo, Shanghai (CN); Maoyi Lei, Shanghai (CN); Yu Xu, Shanghai (CN); Junmiao Li, Shanghai (CN); Guoli Zhang, Shanghai (CN); Jinghong Dong, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 50 days.

(21) Appl. No.: 17/642,064

(22) PCT Filed: Sep. 14, 2020

(86) PCT No.: PCT/CN2020/115126
§ 371 (c)(1),
(2) Date: Mar. 10, 2022

(87) PCT Pub. No.: WO2021/047674
PCT Pub. Date: Mar. 18, 2021

(65) Prior Publication Data
US 2023/0348441 A1  Nov. 2, 2023

(30) Foreign Application Priority Data

Sep. 12, 2019 (CN) .......................... 201910865754.6
Sep. 12, 2019 (CN) .......................... 201910866549.1
Sep. 12, 2019 (CN) .......................... 201910867013.1

(51) Int. Cl.
| C07D 405/04 | (2006.01) |
| C07D 405/14 | (2006.01) |
| C07D 491/107 | (2006.01) |
| C07D 409/04 | (2006.01) |
| C07D 491/048 | (2006.01) |
| C07D 487/08 | (2006.01) |
| C07D 487/04 | (2006.01) |
| C07D 495/04 | (2006.01) |
| C07D 498/04 | (2006.01) |
| C07D 413/04 | (2006.01) |

(52) U.S. Cl.
CPC ......... *C07D 405/04* (2013.01); *C07D 405/14* (2013.01); *C07D 409/04* (2013.01); *C07D 413/04* (2013.01); *C07D 487/04* (2013.01); *C07D 487/08* (2013.01); *C07D 491/048* (2013.01); *C07D 491/107* (2013.01); *C07D 495/04* (2013.01); *C07D 498/04* (2013.01)

(58) Field of Classification Search
CPC ................................................... C07D 405/04
USPC .......................................................... 544/130
See application file for complete search history.

(56) References Cited

FOREIGN PATENT DOCUMENTS

| WO | 2010056344 A1 | 5/2010 | |
| WO | 2014039960 A1 | 3/2014 | |
| WO | 2017152076 A1 | 9/2017 | |
| WO | WO-2020048547 A1 * | 3/2020 | ......... A61K 31/4525 |

OTHER PUBLICATIONS

International Search Report (English and Chinese) and Written Opinion of the ISA (English and Chinese) issued in PCT/CN2020/115126, dated Dec. 11, 2020; ISA/CN.
Aug. 23, 2022 Japanese Office Action issued in Japanese Patent Application No. 2022-516456.

* cited by examiner

*Primary Examiner* — Kahsay Habte
(74) *Attorney, Agent, or Firm* — Harness, Dickey & Pierce, P.L.C.

(57) ABSTRACT

A compound represented by formula (III) or a pharmaceutically acceptable salt thereof, and disclosed is an application thereof in the preparation of a medication for treating diseases related to a CRBN receptor.

(III)

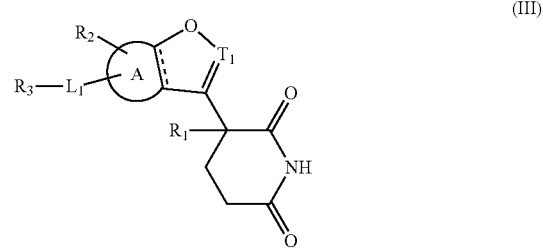

11 Claims, 1 Drawing Sheet

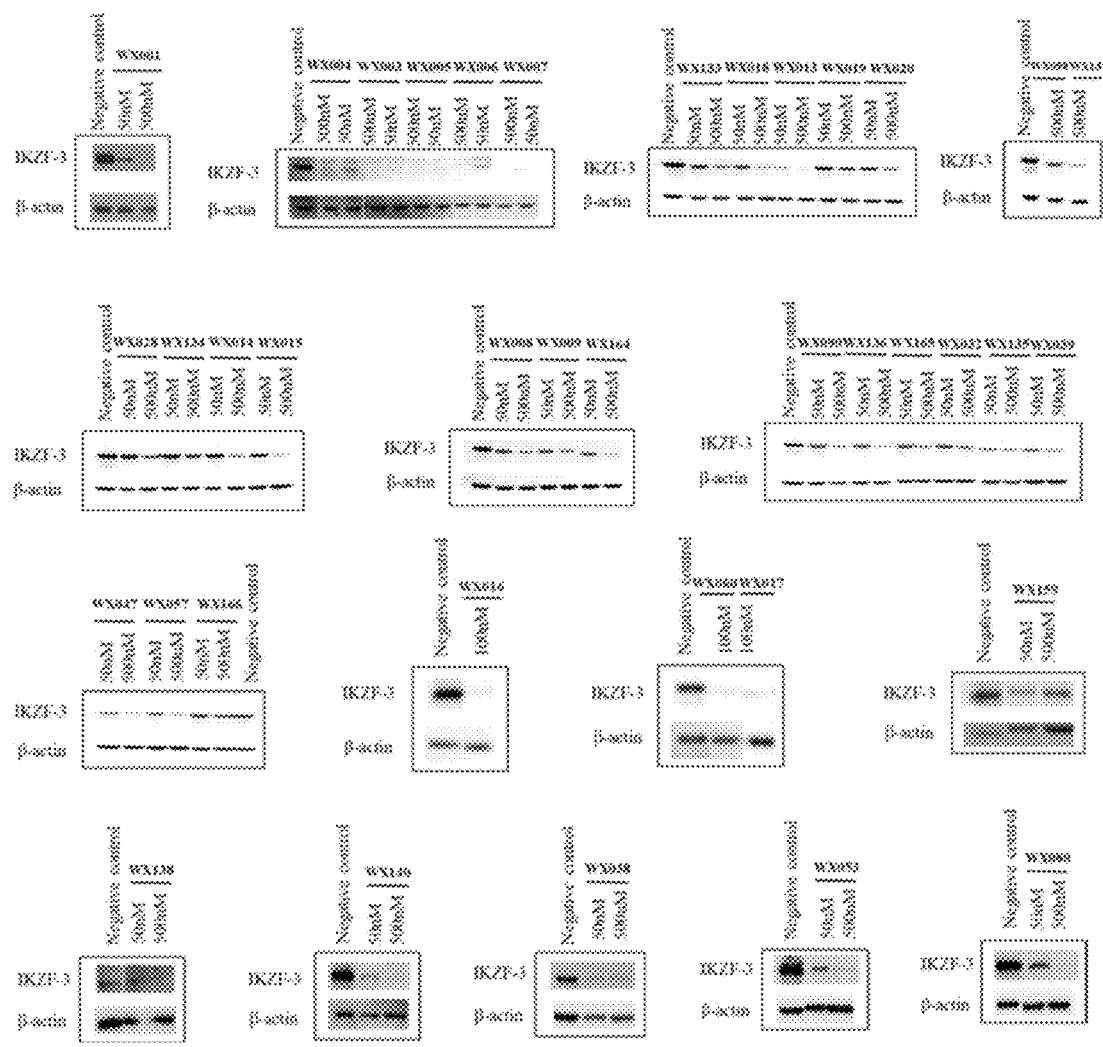

BICYCLIC COMPOUND THAT ACTS AS CRBN PROTEIN REGULATOR

CROSS-REFERENCE TO RELATED APPLICATIONS

This application is a U.S. National Phase Application under 35 U.S.C. 371 of International Application No. PCT/CN2020/115126, filed on Sep. 14, 2020, which claims the benefit of Chinese Patent Application No. 201910866549.1, filed on Sep. 12, 2019, and Chinese Patent Application No. 201910867013.1, filed on Sep. 12, 2019, and Chinese Patent Application No. 201910865754.6, filed on Sep. 12, 2019. The entire disclosures of the above applications are incorporated herein by reference.

TECHNICAL FIELD

The present disclosure relates to a compound represented by formula (III) or a pharmaceutically acceptable salt thereof, and relates to a use thereof in the manufacture of a medicament for treating diseases related to a CRBN receptor.

BACKGROUND

Thalidomide, with the trade name of neurosedyn, was first synthesized by Grunenthal Company of Germany. From the second half of the 1950s to the early 1960s, it was sold in more than 40 countries as a sedative, and it was also widely used as an antiemetic for pregnant women, resulting in the tragedy of tens of thousands of babies with seal limb deformities (morphological disorders) and withdrawing from the market.

Since the "Thalidomide" event, the teratogenic mechanism of thalidomide has aroused great interest of researchers. It has been confirmed that the protein Cereblon (CRBN) was the target protein of thalidomide teratogenesis. Thalidomide combines with CRBN, DNA damage binding protein DDB1 (Damaged DNA Binding Protein 1), CUL4A (Cullin-4a) and Cullins 1 regulator (ROC1) to form E3 ubiquitin ligase complex, which ubiquitinates a variety of substrate proteins and forms ubiquitination chains, so that substrate proteins can be recognized and hydrolyzed by proteasome. Domide drugs are called Immunomodulatory Drugs (IMiDs), which activate the ubiquitination of transcription factors IKZF1 and IKZF3 resulting from E3 ubiquitin ligase complex formed with CRBN, and then the above ubiquitinated transcription factors IKZF1 and IKZF3 are recognized and degraded by proteasome, thus producing toxic effects on Multiple Myeloma. The deletion of these two transcription factors would stop the growth of myeloma. At present, domide drugs such as lenalidomide and pomadomide are the first-line drugs for treating multiple myeloma.

CRBN is a protein of 442 amino acids conserved from plants to humans, which is located on the short arm of p26.3 of human chromosome 3 with a molecular weight of 51 kDa. In humans, the CRBN gene has been identified as a candidate gene for autosomal recessive nonsyndromic mental retardation (ARNSMR). CRBN is widely expressed in testis, spleen, prostate, liver, pancreas, placenta, kidney, lung, skeletal muscle, ovary, small intestine, peripheral blood leukocytes, colon, brain and retina, while the expression in brain tissue (including retina) and testis is significantly higher than other tissues.

As an important target of anti-tumor and immunomodulator drugs, CRBN has been proved to have definite curative effect on various hematological malignant tumors such as multiple myeloma and chronic lymphocytic leukemia, skin diseases such as leprosy erythema nodosum, and autoimmune diseases such as systemic lupus erythematosus. Domide drugs have many side effects, especially peripheral neuropathy. At present, there is an urgent need to develop CRBN modulators with no teratogenicity, less peripheral neuropathy, stronger immunomodulation and higher antitumor activity, so as to improve the clinical treatment effect, reduce clinical side effects and benefit patients for long-term use.

CONTENT OF THE PRESENT INVENTION

The present disclosure provides a compound represented by formula (III) or a pharmaceutically acceptable salt thereof,

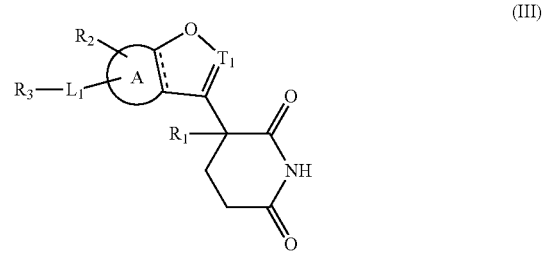

(III)

wherein,

⫽ is selected from a single bond and a double bond;
$T_1$ is selected from $C(R_4)$ and N;
ring A is selected from phenyl, pyridyl and thienyl;
$R_1$ is selected from H, F, Cl, Br and I;
$R_2$ is selected from H, F, Cl, Br, I, OH, $NH_2$ and $OCH_3$;
$L_1$ is selected from a bond, —$(CR_5)_n$—, —$O(CR_5)_n$—, —$S(CR_5)_n$—, —$NH(CR_5)_n$—, #—NHCO—, —$CONHCH_2$—, —$SOCH_2$—, —$SO_2CH_2$—, —$NHSO_2$—, —CH=CH—, —N=C(Ph)-, —O-cyclobutyl-, —O-cyclopentyl-, —CO-piperazinyl-, and —$SO_2$-piperazinyl-;
$R_3$ is selected from H, F, Cl, Br, I, OH, $NH_2$, CN, COOH, NHCOOH, $COOC_{1-4}$ alkyl, $C_{1-3}$ alkyl, $C_{1-3}$ alkoxy, $C_{2-3}$ alkenyl, phenyl, pyridyl, tetrahydropyranyl,

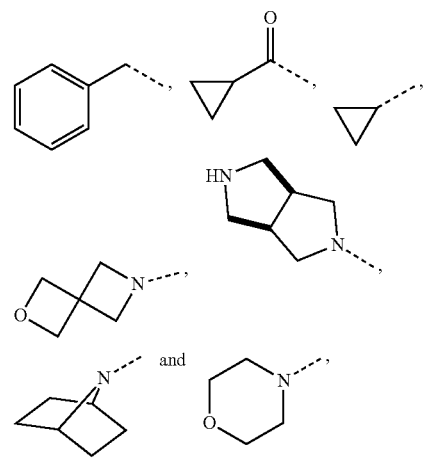

and the COOH, NHCOOH, COOC$_{1-4}$ alkyl, C$_{1-3}$ alkyl, C$_{1-3}$ alkoxy, C$_{2-3}$ alkenyl, phenyl, pyridyl, tetrahydropyranyl,

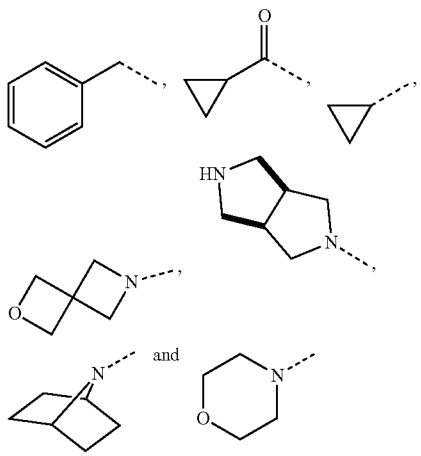

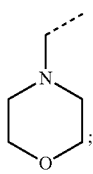

are optionally substituted by 1, 2, or 3 R$_a$;

R$_4$ is selected from H, F, Cl, Br, I and CH$_3$;

R$_5$ is selected from H, F, Cl, Br and I;

R$_a$ is selected from H, F, Cl, Br, I, OH, NRR', CN, C$_{1-4}$ alkyl, C$_{1-3}$ alkoxy, COOCH$_3$, CONH$_2$ and

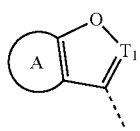

R and R' are each independently selected from H and CH$_3$;

n is selected from 1, 2, 3;

a site with "#" is the site connected with R$_3$ group.

In some embodiments of the present disclosure, the structural unit

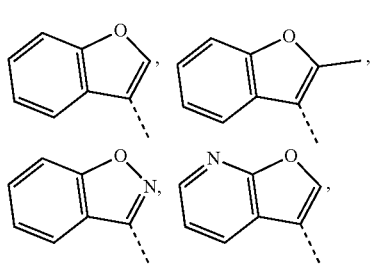

is selected from

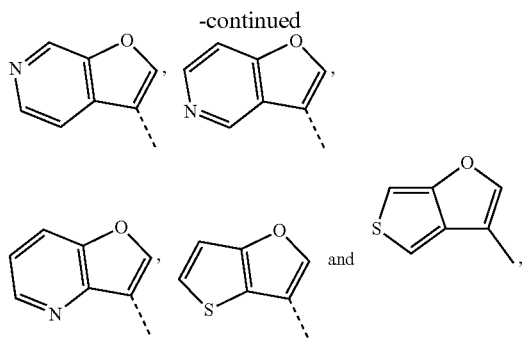

and other variables are defined herein.

In some embodiments of the present disclosure, the L$_1$ is selected from a bond, —CH$_2$—, —OCH$_2$—, —OCH$_2$CH$_2$—, —OCH$_2$CH$_2$CH$_2$—, —OCF$_2$—, —SCH$_2$—, —NHCH$_2$—, #—NHCO—, —CON(CH$_3$)—, —CONHCH$_2$—, —SOCH$_2$—, —SO$_2$CH$_2$—, —NHSO$_2$—, —CH=CH—, —N=C(Ph)-,

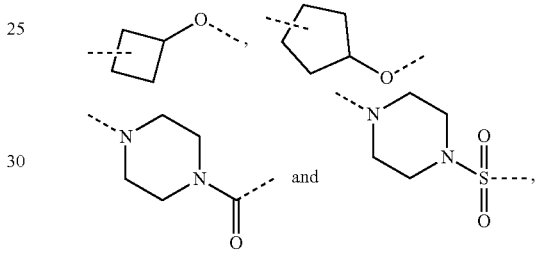

and other variables are defined herein.

In some embodiments of the present disclosure, the R$_a$ is selected from H, F, Cl, Br, I, OH, NH$_2$, N(CH$_3$)$_2$, CN, CH$_3$, CH$_2$CH$_3$, C(CH$_3$)$_3$, OCH$_3$, COOCH$_3$, CONH$_2$ and

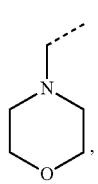

and other variables are defined herein.

In some embodiments of the present disclosure, the R$_3$ is selected from H, F, Cl, Br, I, OH, NH$_2$, CN, CH$_3$, CH$_2$CH$_3$, CH$_2$CH$_2$CH$_3$, OCH$_3$, COOCH$_2$CH$_3$, COOH, NHCOOH, CH=CH$_2$,

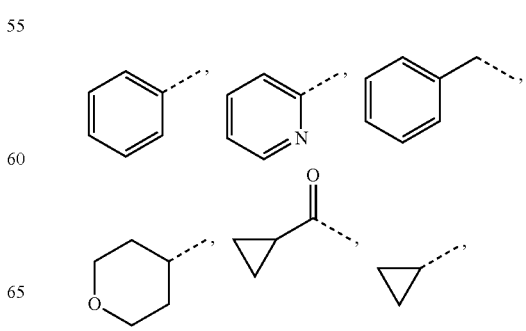

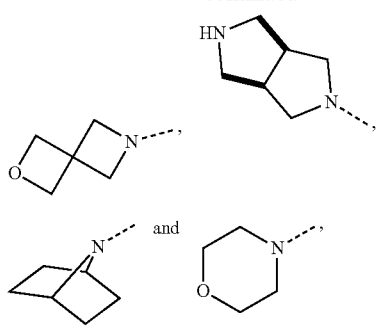
and the CH₃, CH₂CH₃, CH₂CH₂CH₃, OCH₃, COOCH₂CH₃, COOH, NHCOOH, CH=CH₂,
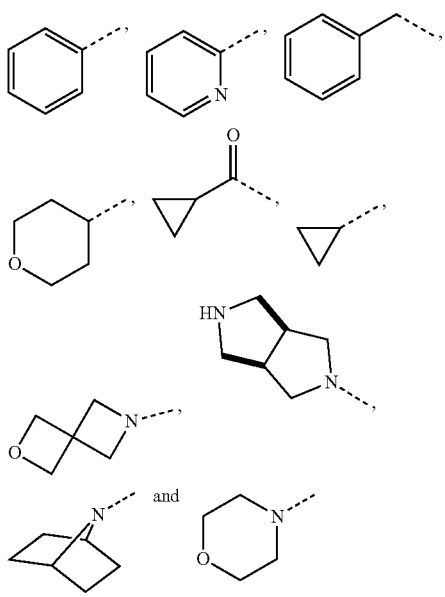
are optionally substituted by 1, 2, or 3 $R_a$, and other variables are defined herein.
In some embodiments of the present disclosure, the $R_3$ is selected from H, F, Cl, Br, I, OH, NH₂, CN, CH₃, CH₂CH₃, CH₂CH₂CH₃, OCH₃, CHF₂, CF₃, CH₂NH₂, CH₂CH₂F, COOCH₂CH₃, COOH, CH=CH₂,
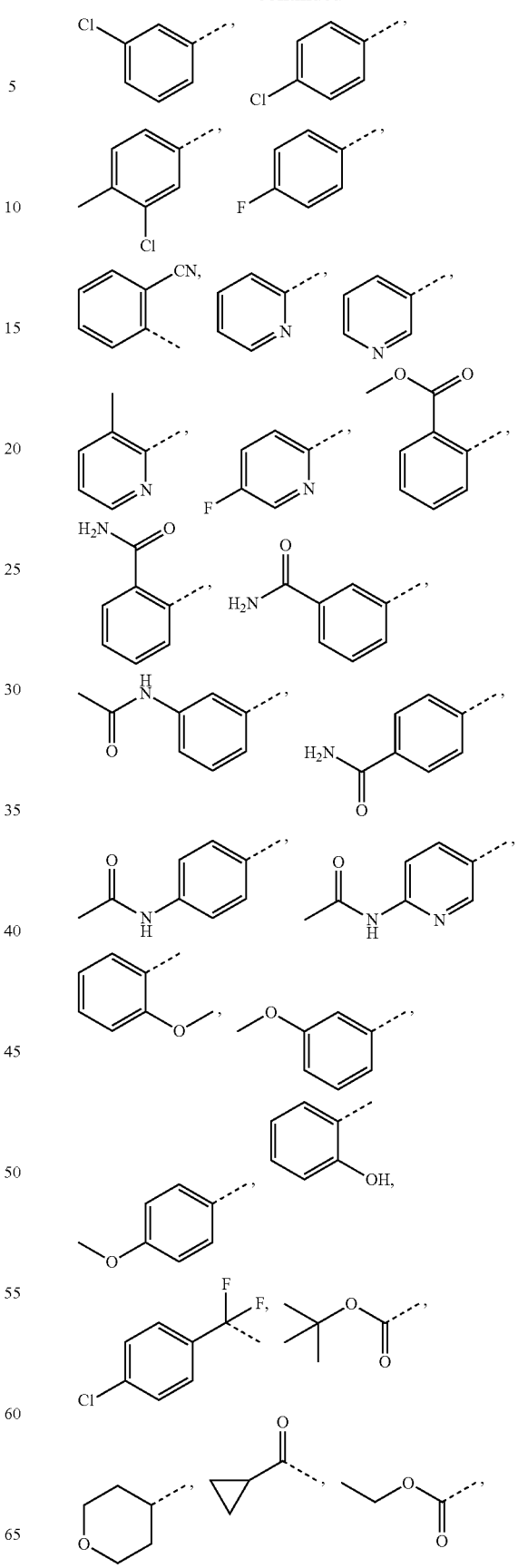

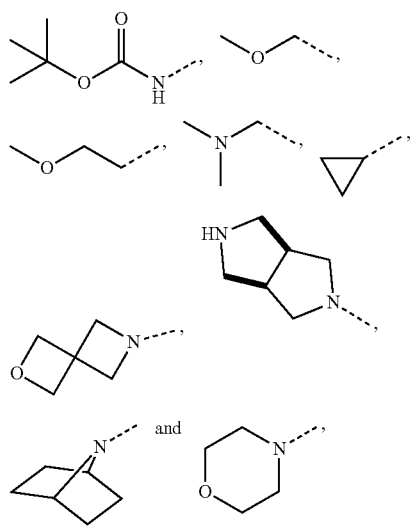
and other variables are defined herein.
In some embodiments of the present disclosure, the structural unit -L$_1$-R$_3$ is selected from H, F, Cl, Br, I, OH, NH$_2$, CN, CH$_3$, OCH$_3$,
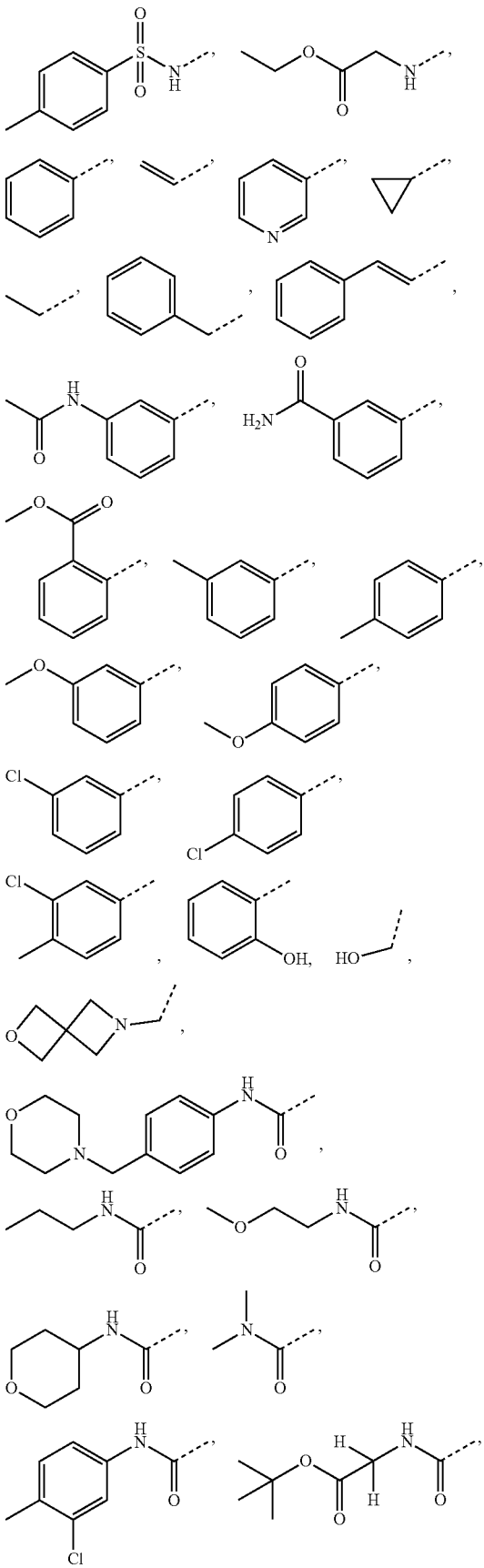

-continued
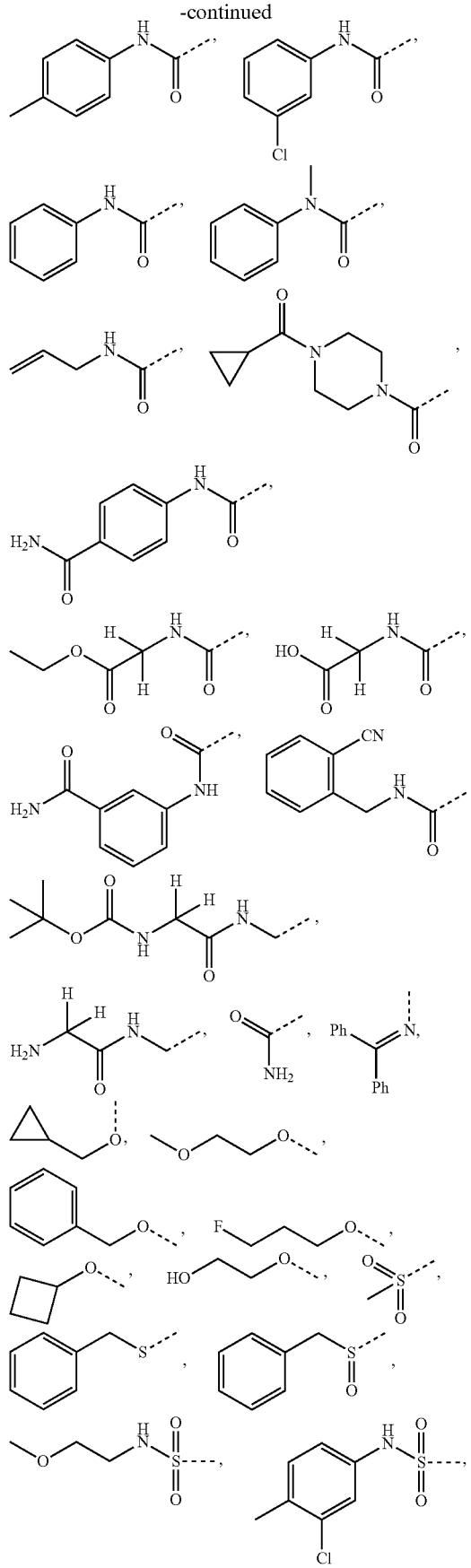
-continued
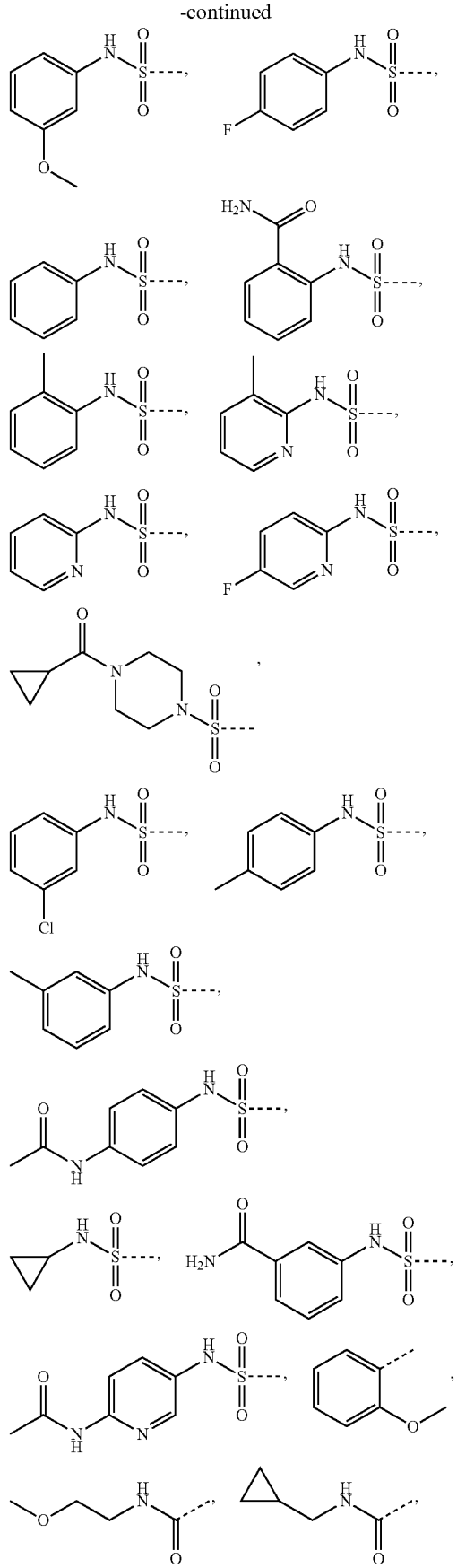

-continued

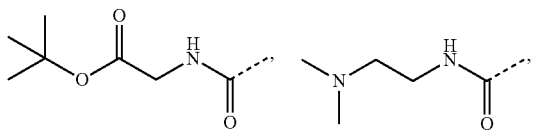

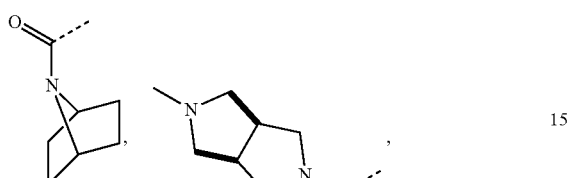

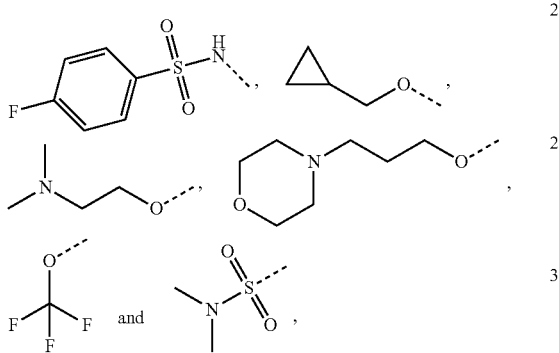

and other variables are defined herein.

In some embodiments of the present disclosure, the compound or the pharmaceutically acceptable salt thereof is selected from, (III-1)

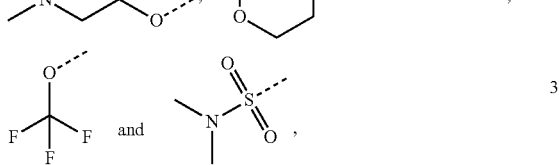

(III-2)

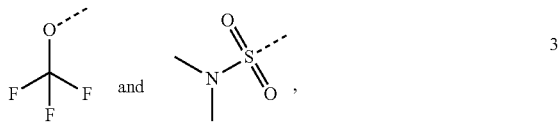

wherein,
$T_1$, $R_1$, $R_2$, $R_3$ and $L_1$ are defined herein.

In some embodiments of the present disclosure, the compound or the pharmaceutically acceptable salt thereof is selected from, (III-1-1)

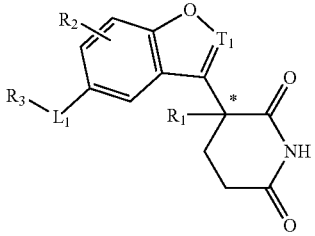

(III-1-2)

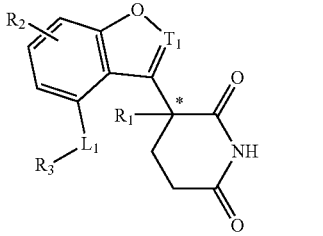

wherein,
the carbon atom with "*" is a chiral carbon atom, which exists in a (R) or (S) single enantiomer form or an enantiomer-rich form;
$T_1$, $R_1$, $R_2$, $R_3$ and $L_1$ are defined herein.

There are also some embodiments of the present disclosure that are formed by any combination of the above variables.

The present disclosure also provides the following compounds, or pharmaceutically acceptable salts thereof,

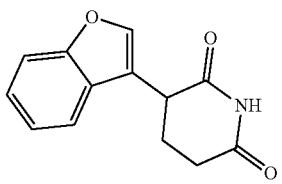

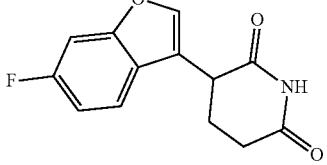

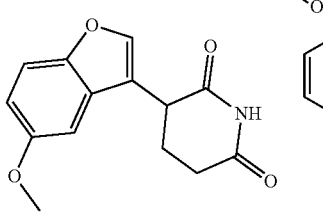

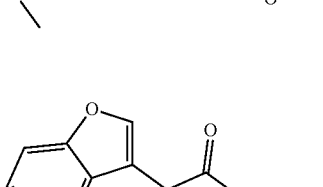

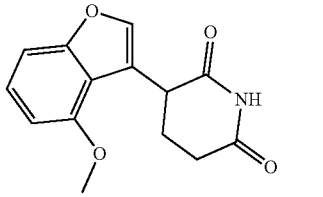

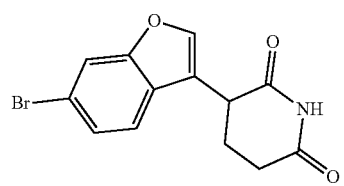
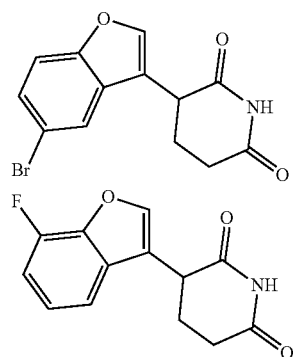
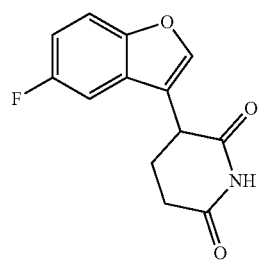
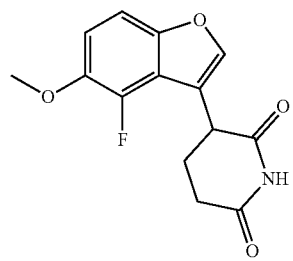
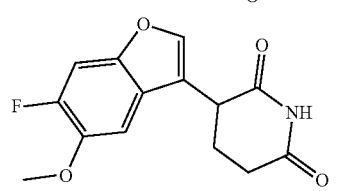
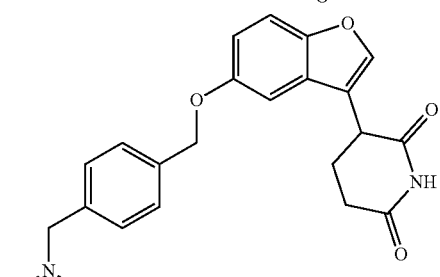
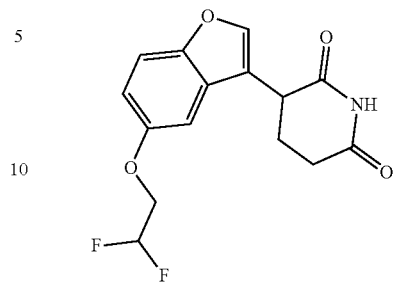
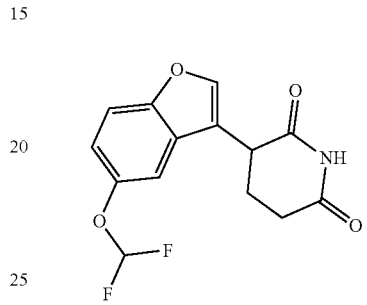
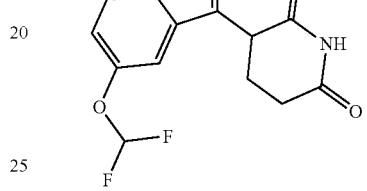
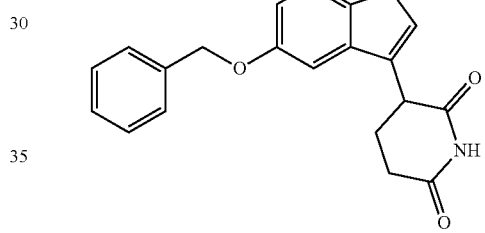
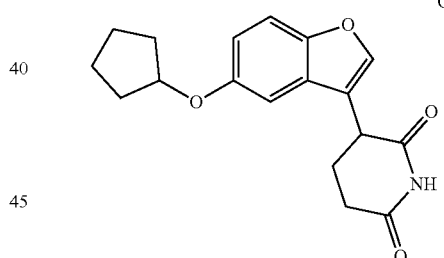
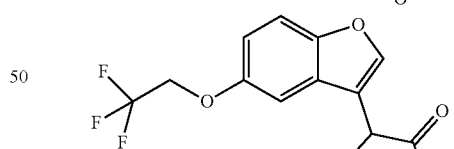
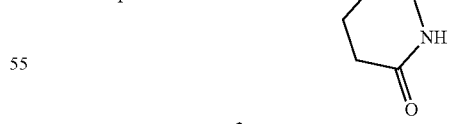
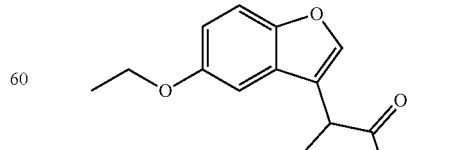

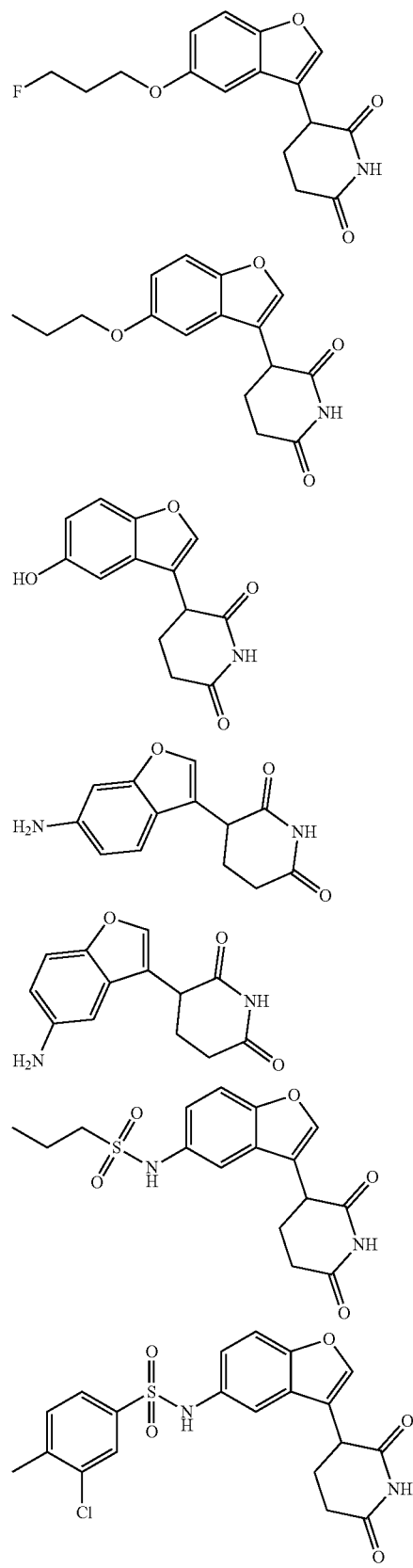
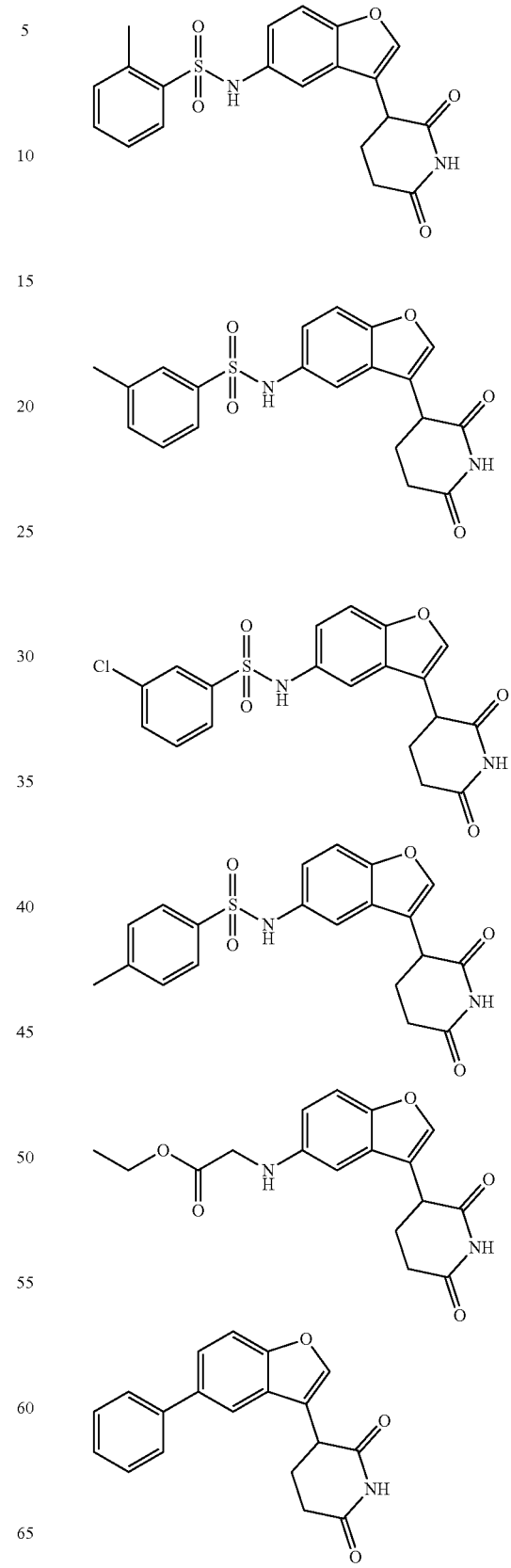

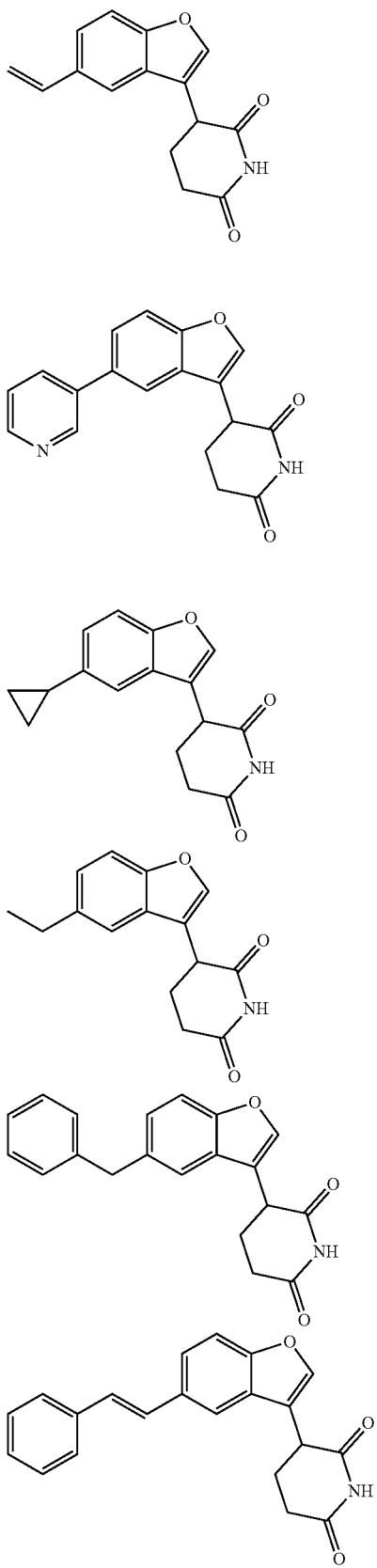
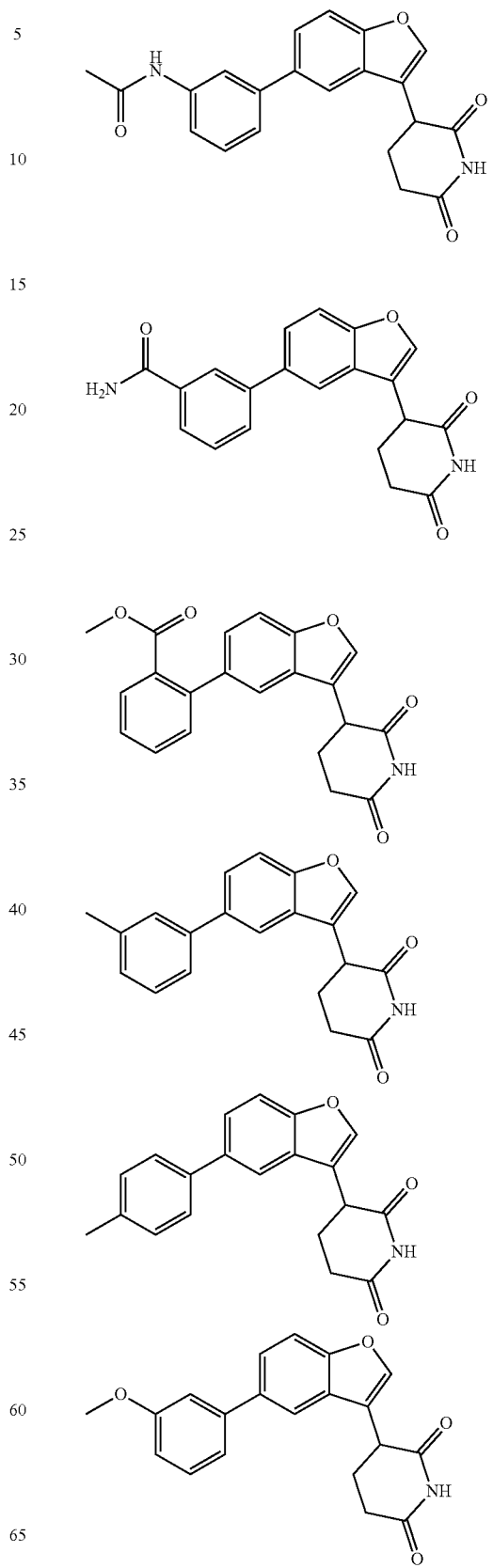

-continued
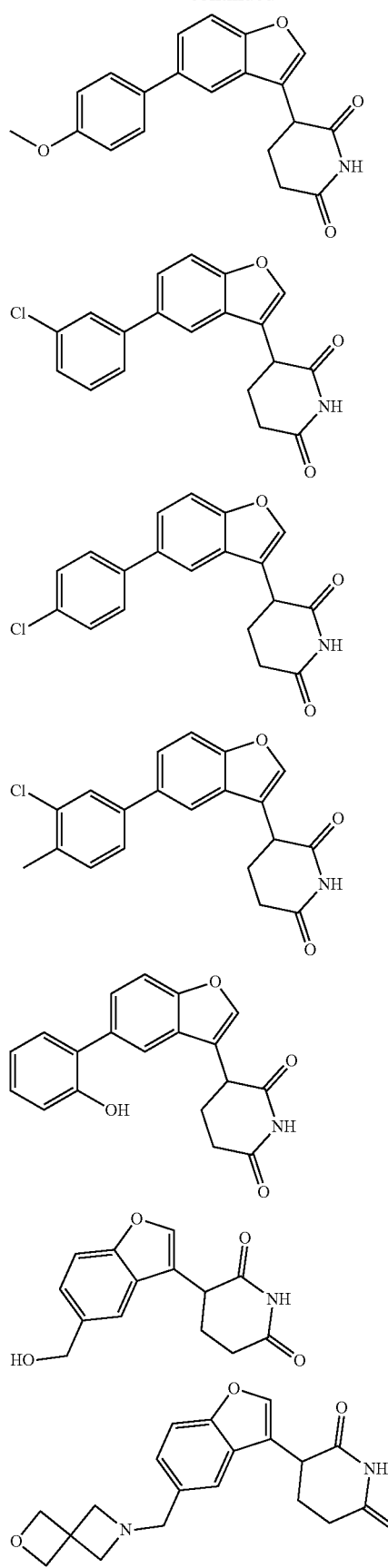
-continued
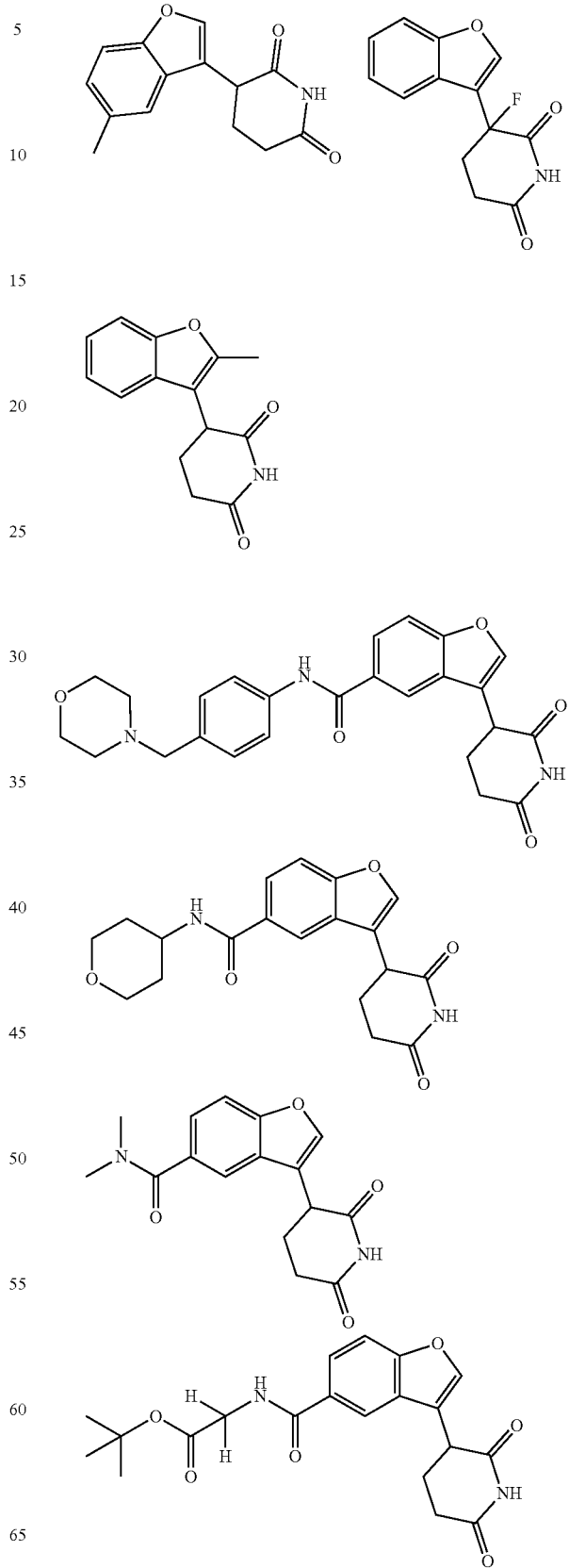

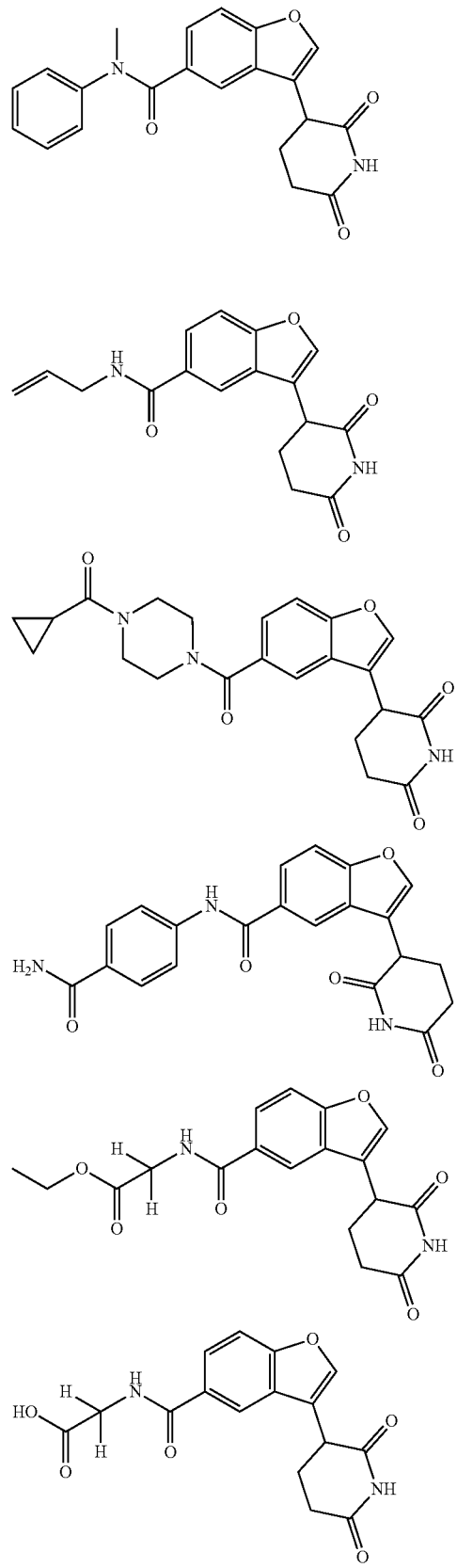
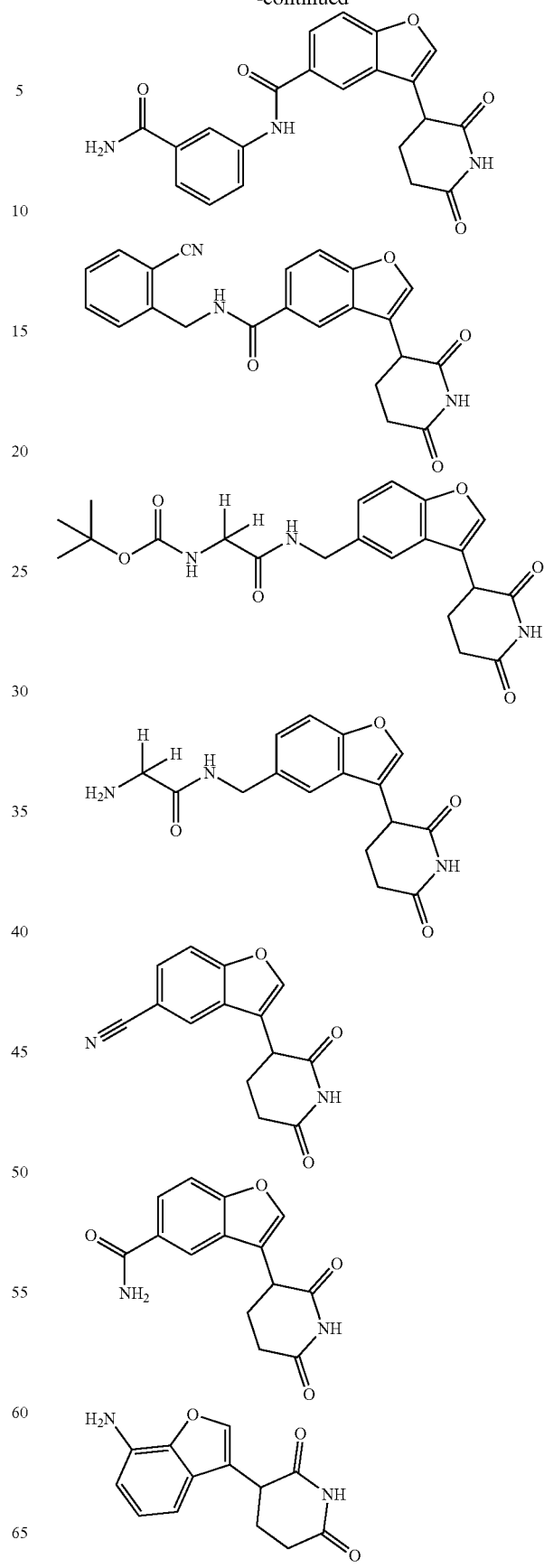

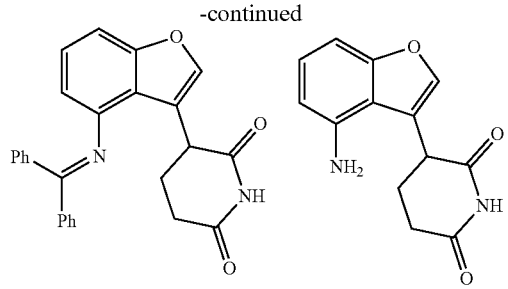
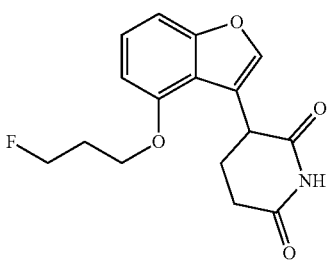
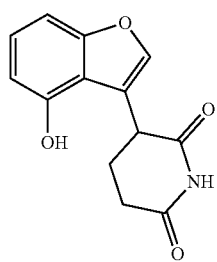
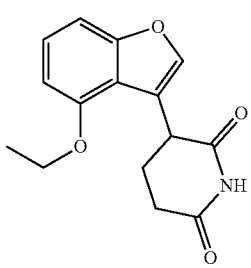
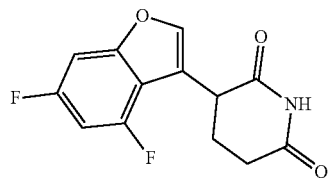
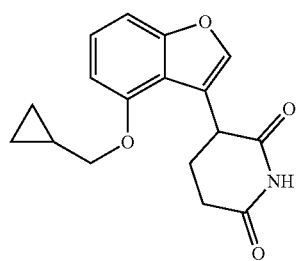
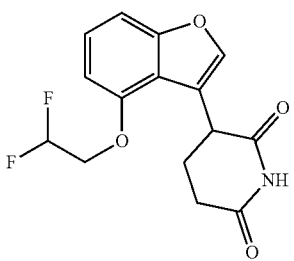
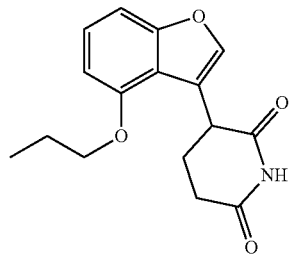
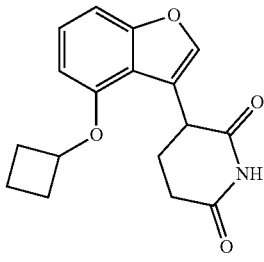
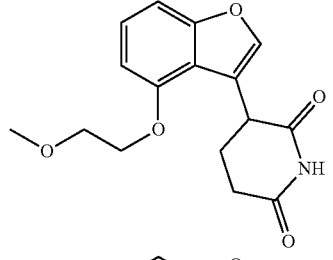
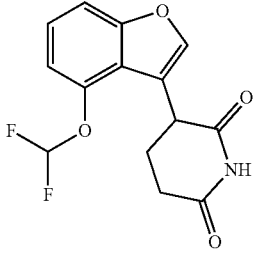
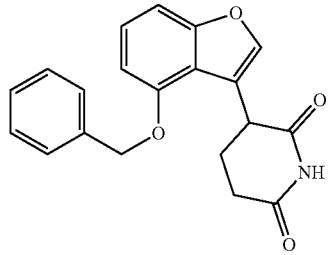
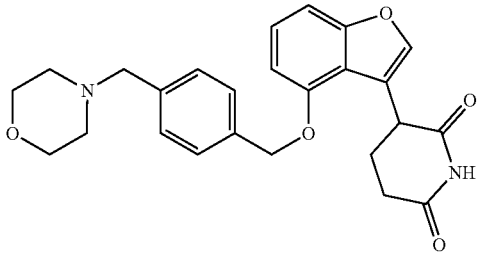

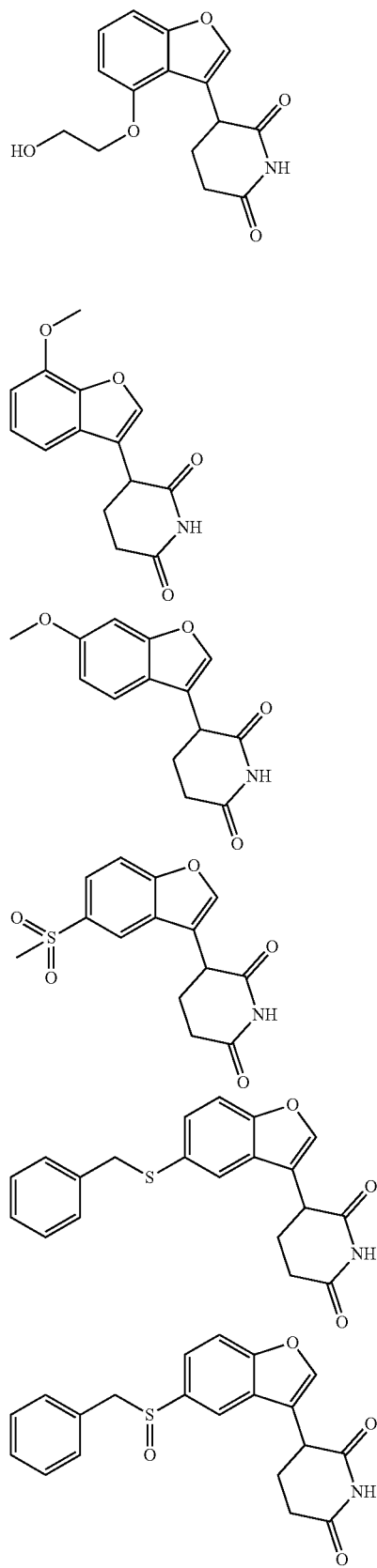
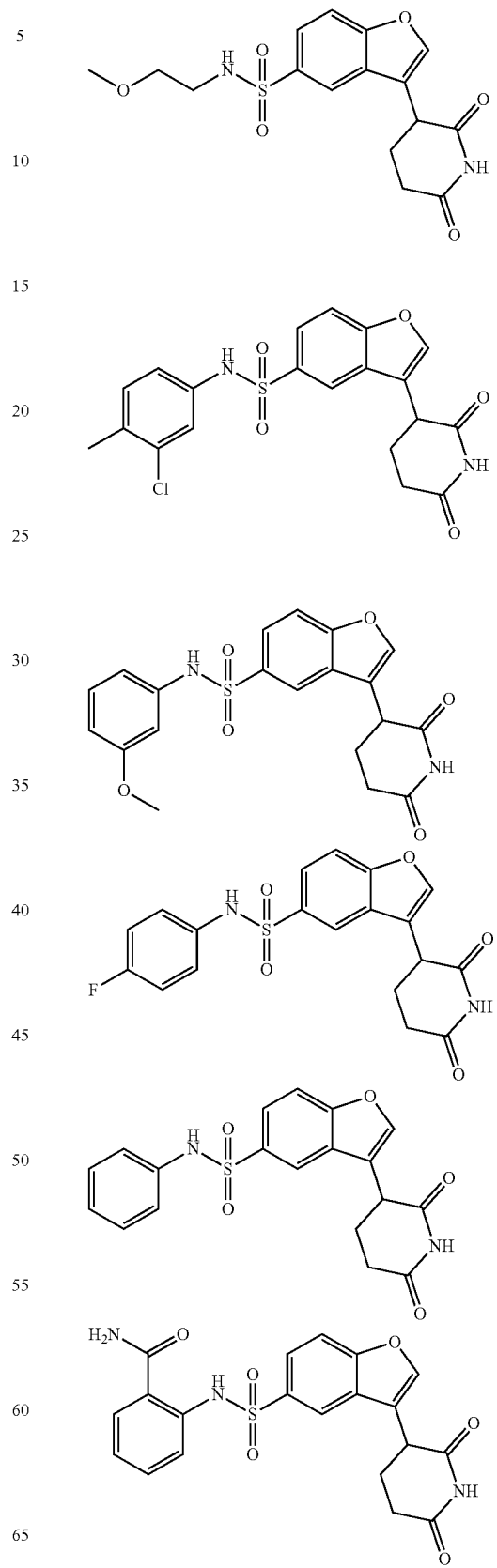

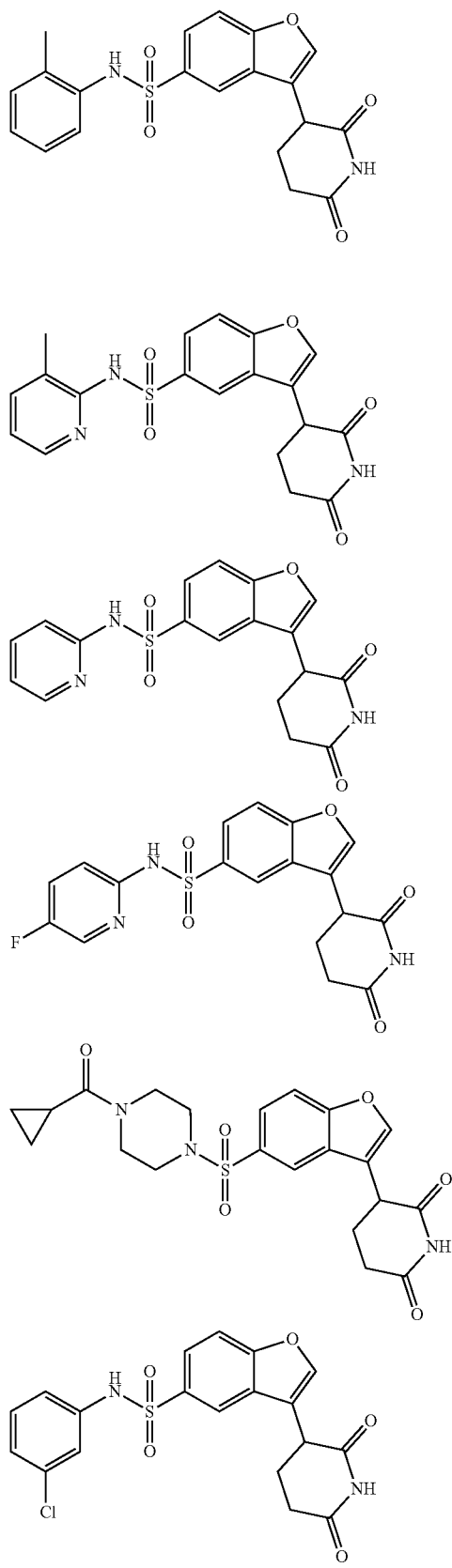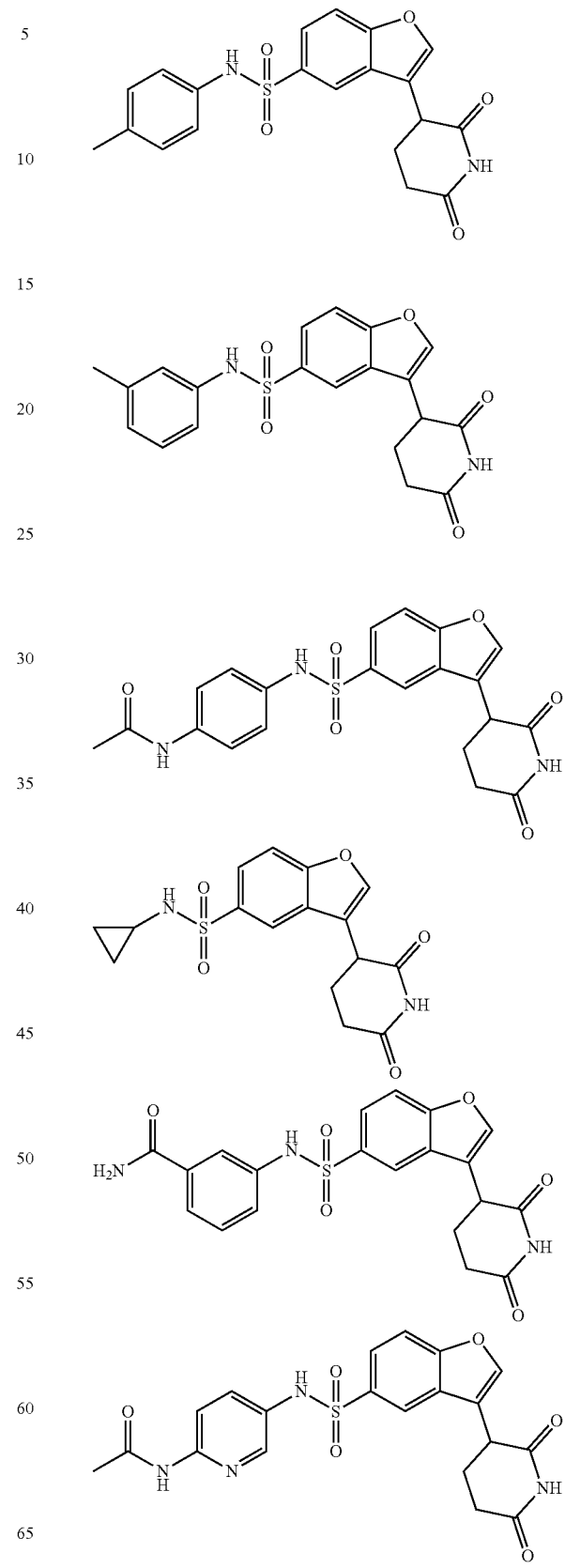

29
-continued
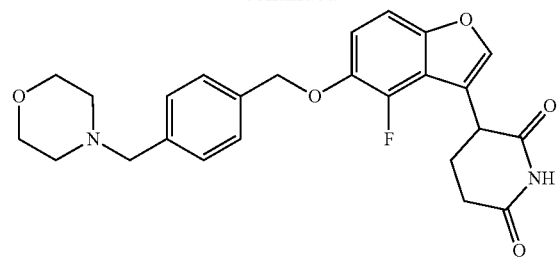
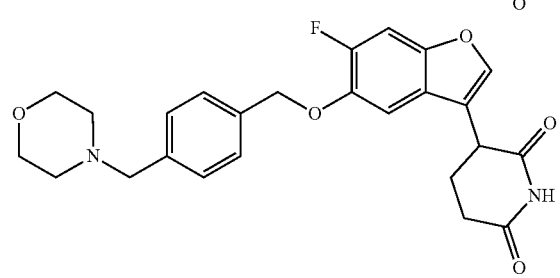
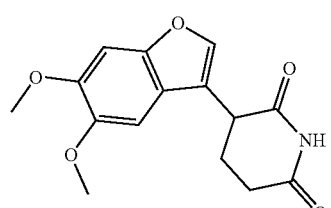
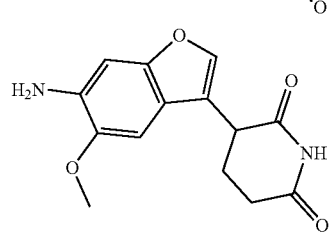
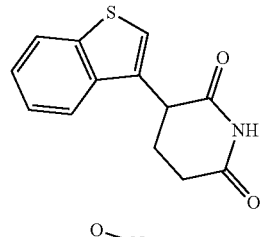
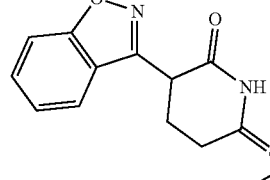
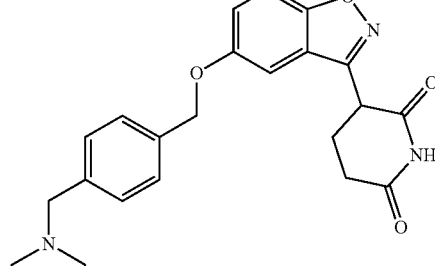
30
-continued
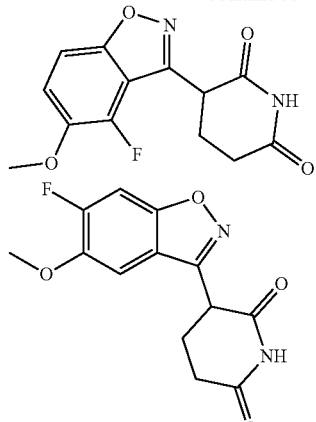
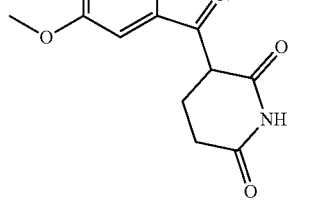
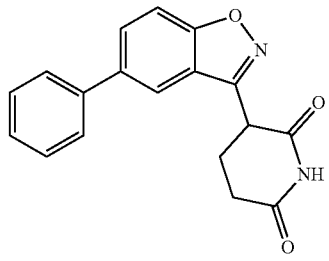
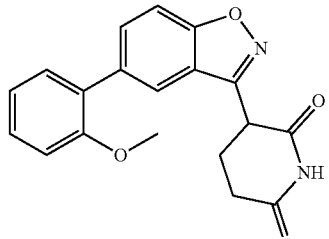
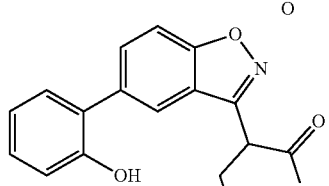
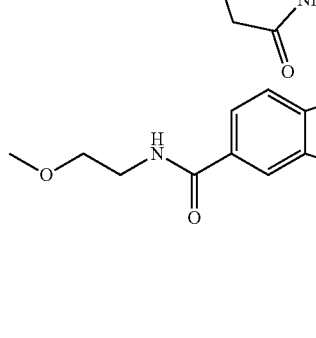

31
-continued
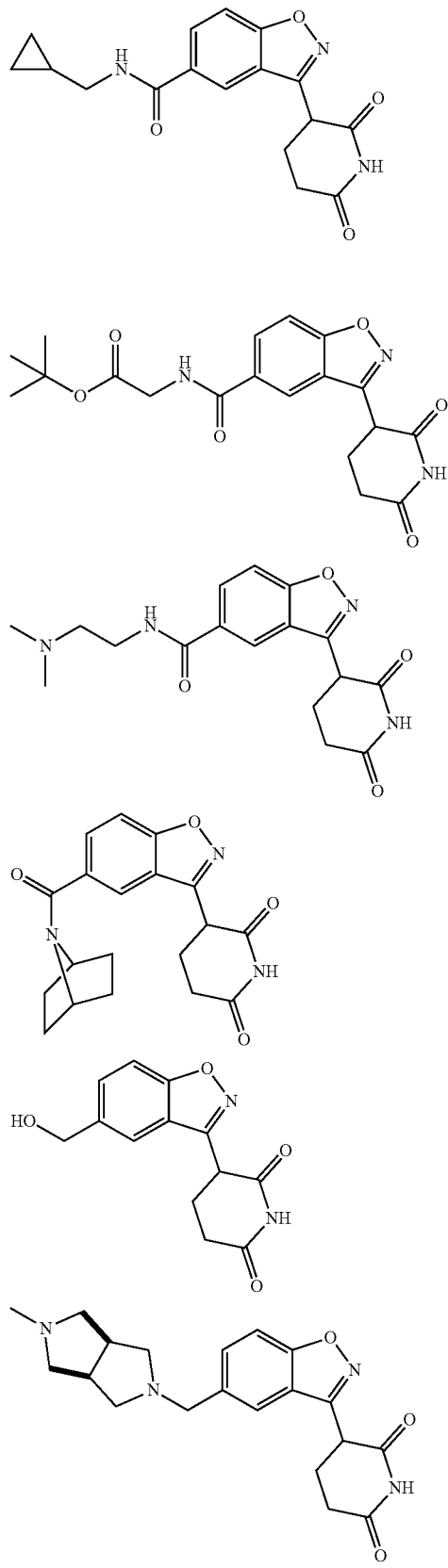
32
-continued
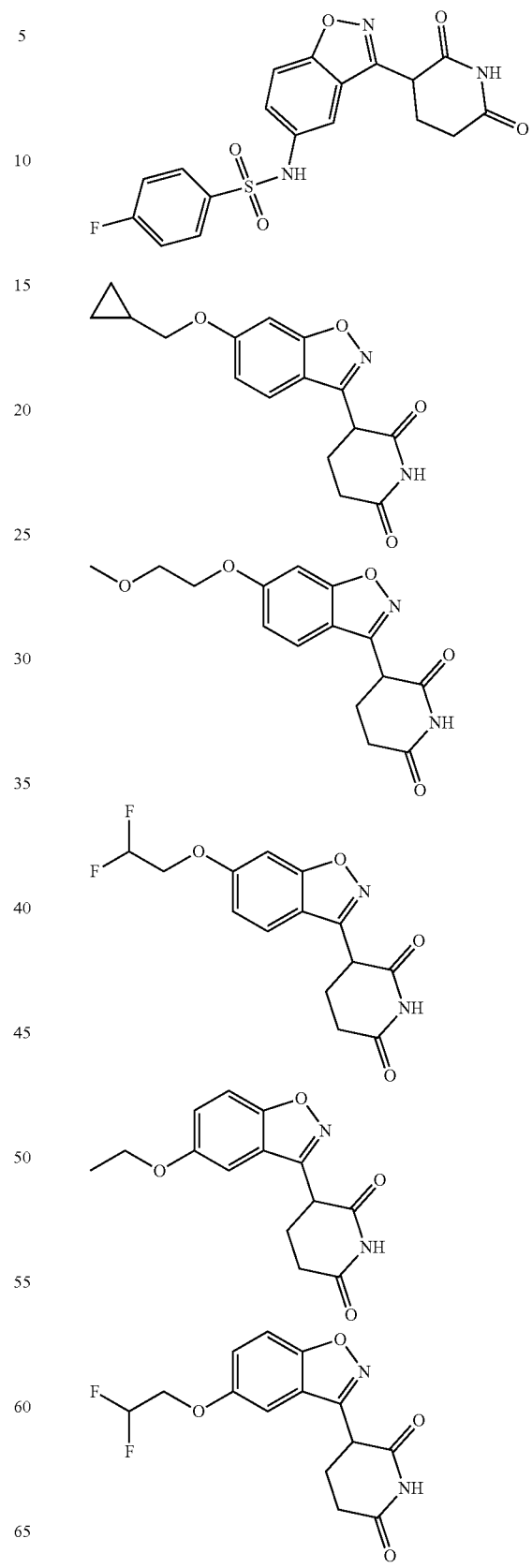

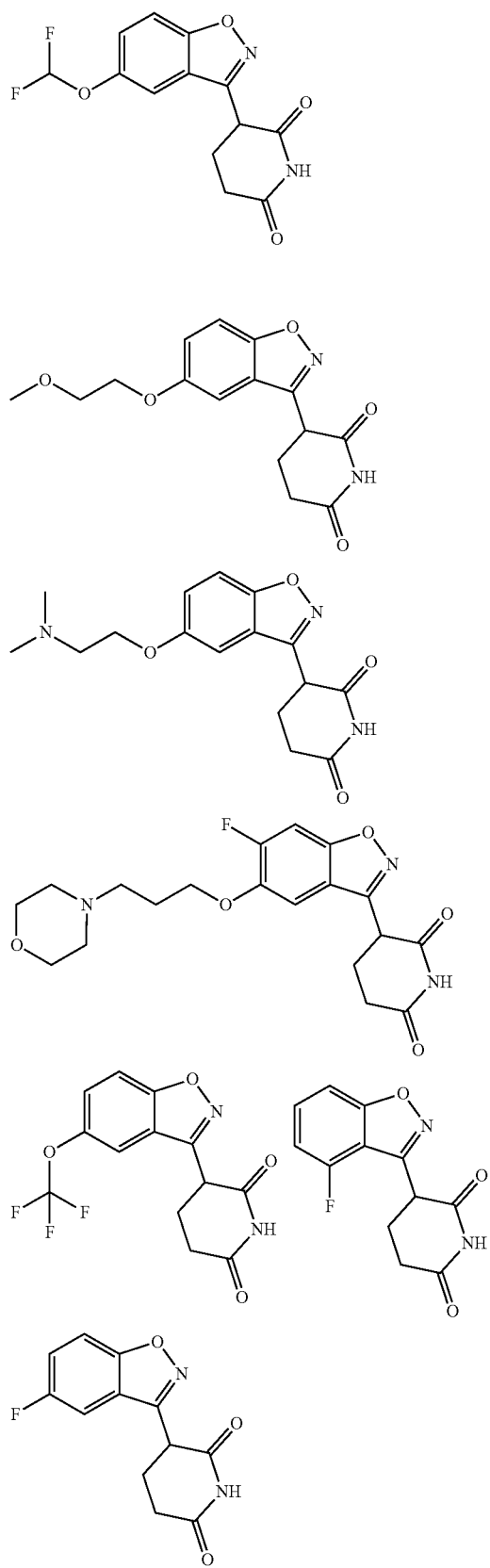
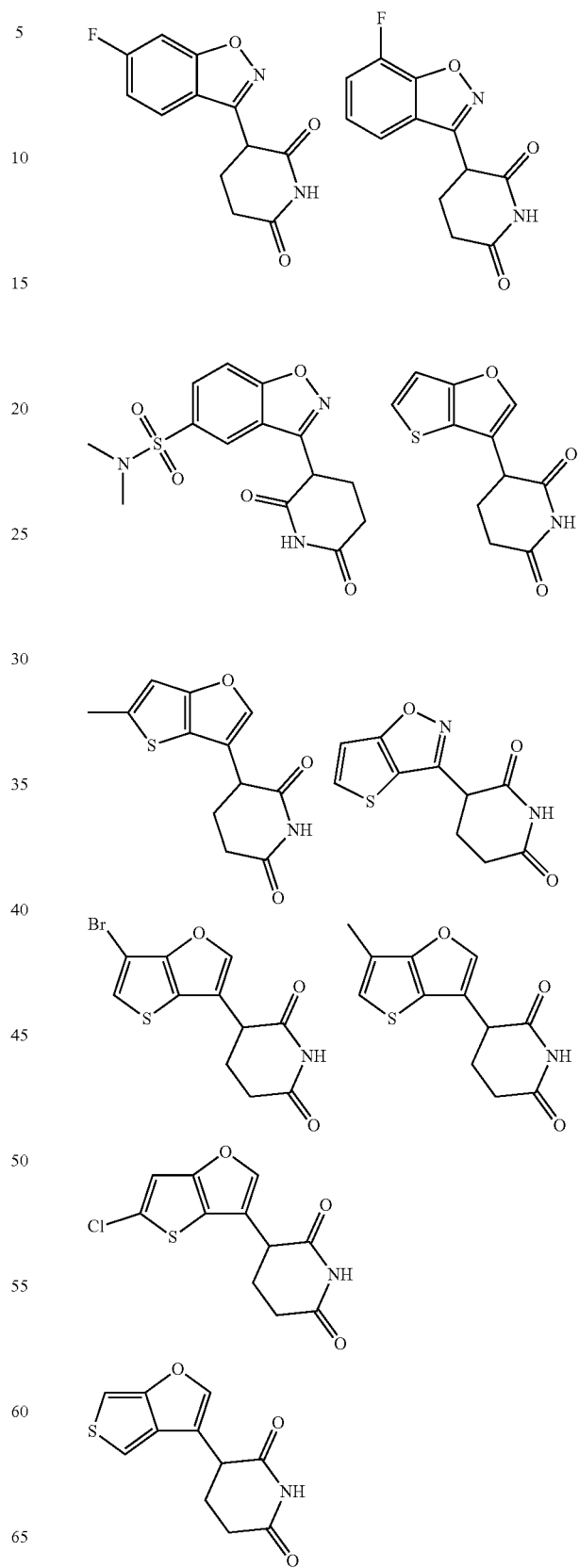

In some embodiments of the present disclosure, the compound or the pharmaceutically acceptable salt thereof is selected from,

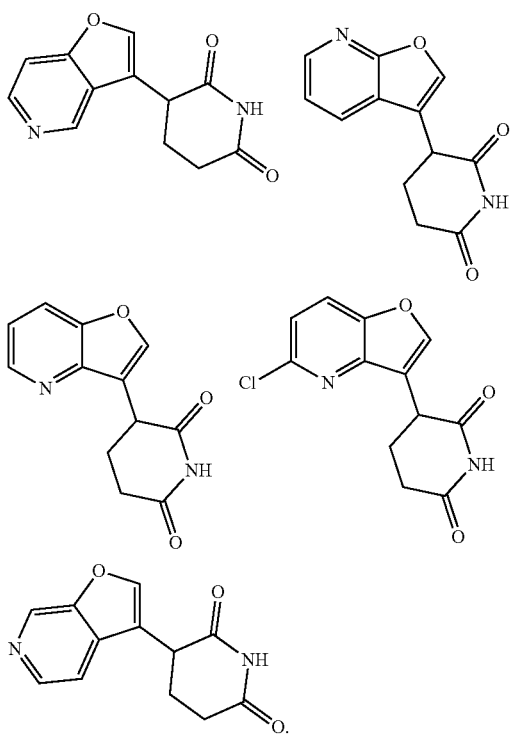

The present disclosure also provides a use of the compound or the pharmaceutically acceptable salt thereof in the manufacture of a medicament for treating diseases related to a CRBN receptor.

Technical Effects

The compound of the present disclosure exhibits a significant down-regulation effect on IKZF3 protein level in multiple myeloma cells MM.1S; the compound of the present disclosure exhibits a significant tumor shrinking effect on the in vivo pharmacodynamic model of human myeloma NCI-H929.

Definition and description

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(+)" refers to dextrorotation, "(−)" refers to levorotation, and or "(±)" refers to racemic.

Unless otherwise specified, the absolute configuration of a stereogenic center is represented by a wedged solid bond (( ◆ )) and a wedged dashed bond (( ◆ )), and the relative configuration of a stereogenic center is represented by a straight solid bond (( ◆ )) and a straight dashed bond (( ◆ )), a wave line (( ◆ )) is used to represent a wedged solid bond (( ◆ )) or a wedged dashed bond (( ◆ )), or the wave line (( ◆ )) is used to represent a straight solid bond (( ◆ )) or a straight dashed bond (( ◆ )).

Unless otherwise specified, the terms "enriched in one isomer", "enriched in isomers", "enriched in one enantiomer" or "enriched in enantiomers" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine). The compound of the present disclosure may contain an unnatural proportion of atomic isotope at one or more than one atom(s) that constitute the compound. For example, the compound can be radiolabeled with a radioactive isotope, such as tritium ($^{3}H$), iodine-125 ($^{125}I$) or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

The term "substituted" means one or more than one hydrogen atom(s) on a specific atom is substituted with the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When the number of a substituent is 0, it means that the substituent does not exist, for example, -A-(R)$_0$ means that the structure is actually A.

When a substituent is vacant, it means that the substituent does not exist, for example, when X is vacant in A-X, the structure of A-X is actually A.

When one of the variables is selected from a single bond, it means that the two groups linked by the single bond are connected directly. For example, when L in A-L-Z represents a single bond, the structure of A-L-Z is actually A-Z.

When the bonds of a substituent can be cross-bonded to more than two atoms in a ring, the substituent can be bonded to any atom in the ring, for example, the structural unit

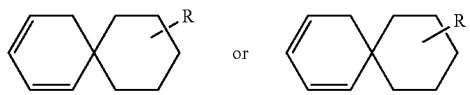

substituent R representing it can be substituted at any position on cyclohexyl or cyclohexadiene. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

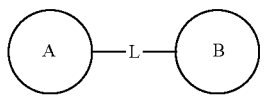

is -M-W—, then -M-W— can link ring A and ring B to form

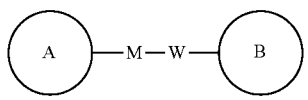

in the direction same as left-to-right reading order, and form

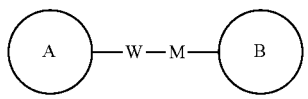

in the direction contrary to left-to-right reading order. A combination of the linking groups, substituents and/or variables thereof is allowed only when such combination can result in a stable compound.

Unless otherwise specified, when a group has one or more linkable sites, any one or more sites of the group can be linked to other groups through chemical bonds. When the linking site of the chemical bond is not positioned, and there is H atom at the linkable site, then the number of H atom at the site will decrease correspondingly with the number of chemical bond linking thereto so as to meet the corresponding valence. The chemical bond between the site and other groups can be represented by a straight solid bond (╱), a straight dashed bond (╱) or a wavy line () For example, the straight solid bond in —OCH$_3$ means that it is linked to other groups through the oxygen atom in the group; the straight dashed bonds in

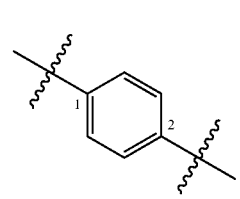 [SMILES: *c1ccc(*)cc1]

means that it is linked to other groups through the two ends of nitrogen atom in the group; the wave lines in

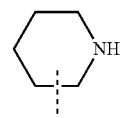

means that the phenyl group is linked to other groups through carbon atoms at position 1 and position 2;

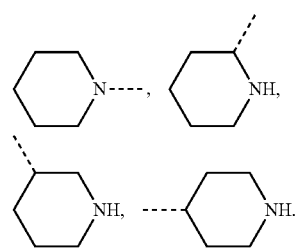

means that it can be linked to other groups through any linkable sites on the piperidinyl by one chemical bond, including at least four types of linkage, including Even though the H atom is drawn on the —N—,

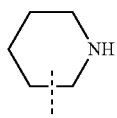

still includes the linkage of

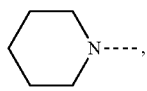

merely when one chemical bond was connected, the H of this site will be reduced by one to the corresponding monovalent piperidinyl.

Unless otherwise specified, the number of atoms in a ring is generally defined as the number of ring members, e.g., "5-7 membered ring" refers to a "ring" of 5-7 atoms arranged around it.

Unless otherwise specified, the term "$C_{1-4}$ alkyl" refers to a linear or branched saturated hydrocarbon group containing 1 to 4 carbon atoms. The $C_{1-4}$ alkyl includes $C_{1-2}$, $C_{1-3}$ and $C_{2-3}$ alkyl groups and the like. It can be monovalent (such as methyl), divalent (such as methylene) or multivalent (such as methine). Examples of $C_{1-4}$ alkyl include but are not limited to methyl (Me), ethyl (Et), propyl (including n-propyl and isopropyl), butyl (including n-butyl, isobutyl, s-butyl, and t-butyl), etc.

Unless otherwise specified, the term "$C_{1-3}$ alkyl" refers to a linear or branched saturated hydrocarbon group containing 1 to 3 carbon atoms. The $C_{1-3}$ alkyl group includes $C_{1-2}$ and $C_{2-3}$ alkyl groups and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl), etc.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy, etc. Examples of $C_{1-3}$ alkoxy include, but are not limited to, methoxy, ethoxy, propoxy (including n-propoxy and isopropoxy), etc.

Unless otherwise specified, "$C_{2-3}$ alkenyl" refers to a linear or branched hydrocarbon group containing 2 to 3 carbon atoms containing at least one carbon-carbon double bond, which can be located anywhere in the group. The $C_{2-3}$ alkenyl includes $C_3$, and $C_2$ alkenyl groups. It can be monovalent, divalent or multivalent. Examples of $C_{2-3}$ alkenyl include, but are not limited to, vinyl, propenyl, etc.

Unless otherwise specified, "$C_{2-3}$ alkynyl" refers to a linear or branched hydrocarbon group containing 2 to 3 carbon atoms containing at least one carbon-carbon triple bond, which can be located anywhere in the group. It can be monovalent, bivalent or multivalent. The $C_{2-3}$ alkynyl includes $C_3$, and $C_2$ alkynyl, etc. Examples of $C_{2-3}$ alkynyl include, but are not limited to, ethynyl, propynyl, etc.

Unless otherwise specified, $C_{n-n+m}$ or $C_{n-Cn+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc.; similarly, n membered to n+m membered means that the number of atoms on the ring is from n to n+m, for example, 3-12 membered ring includes 3 membered ring, 4 membered ring, membered ring, 6 membered ring, 7 membered ring, 8 membered ring, 9 membered ring, 10 membered ring, 11 membered ring, and 12 membered ring, and any range from n to n+m is also included, for example, 3-12 membered ring includes 3-6 membered ring, 3-9 membered ring, 5-6 membered ring, 5-7 membered ring, 6-7 membered ring, 6-8 membered ring, and 6-10 membered ring, etc.

Unless otherwise specified, when double bond structure, such as carbon-carbon double bond, carbon-nitrogen double bond, and nitrogen-nitrogen double bond, exists in the compound, and each of the atoms on the double bond is connected to two different substituents (including the condition where a double bond contains a nitrogen atom, the lone pair of electrons attached on the nitrogen atom is regarded as a substituent connected).

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The structure of the compounds of the present disclosure can be confirmed by conventional methods known to those skilled in the art, and if the disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: φ/ω scan, and after collecting the relevant data, the crystal structure can be further analyzed by direct method (Shelxs97).

The solvent used in the present disclosure is commercially available.

The compounds of the present disclosure are named according to the conventional naming principles in the art or by ChemDraw® software, and the commercially available compounds use the supplier catalog names.

BRIEF DESCRIPTION OF THE DRAWINGS

FIG. 1 shows the changes of the intracellular IKZF3 protein level detected by WB after treating the multiple myeloma cells MM.'S with the compounds of the present disclosure at the concentrations of 100 nM, 500 nM and 50 nM. Wherein, negative control represents negative control.

DETAILED DESCRIPTION OF THE PREFERRED EMBODIMENT

The present disclosure is described in detail by the embodiments below, but it does not mean that there are any adverse restrictions on the present disclosure. The present disclosure has been described in detail herein, wherein specific embodiments thereof are also disclosed, and it will be apparent to those skilled in the art that various variations and improvements can be made to specific embodiments of the present disclosure without departing from the spirit and scope of the present disclosure.

Reference Embodiment 1: Fragment BB-1

Synthetic Route:

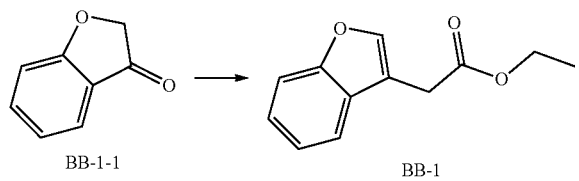

Compound BB-1-1 (4.26 g, 31.73 mmol) was added to toluene (50 mL) at room temperature, then ethyl(triphenylphosphine)acetic acid (13.26 g, 38.08 mmol) was added, and the reaction mixture was heated to 130° C. and reacted with stirring for 40 hours under the protection of nitrogen. After the reaction was completed, the mixture was cooled to room temperature, concentrated under reduced pressure to remove the solvent, and the obtained residue was separated by column chromatography (eluent: petroleum ether/ethyl acetate=80/1-40/1, v/v) to obtain target compound BB-1. MS-ESI m/z: 205.0 [M+H]$^+$. $^1$H NMR (400 MHz, CDCl$_3$) δ: 755 (s, 1H), 7.49 (d, J=8.0 Hz, 1H), 7.40 (d, J=8.0 Hz, 1H), 7.22 (td, J=1.2, 7.3 Hz, 1H), 7.17 (td, J=1.2, 7.6 Hz, 1H), 4.11 (q, J=7.2 Hz, 2H), 3.61 (s, 2H), 1.19 (t, J=7.2 Hz, 3H).

Reference Embodiment 2: Fragment BB-2

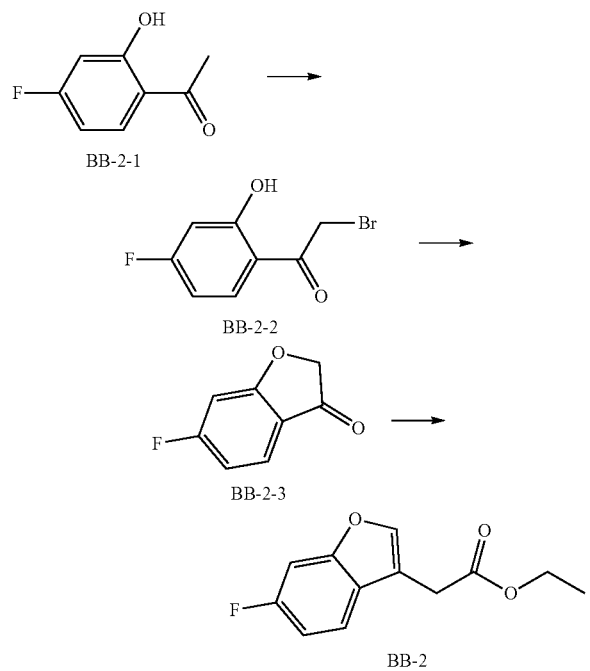

Step 1: Synthesis of Compound BB-2-2

Compound BB-2-1 (10 g, 64.88 mmol) was added to ethyl acetate (200 mL) at room temperature, then copper bromide (17.39 g, 77.85 mmol) was added, and the reaction mixture was heated to 80° C. and reacted with stirring for 12 hours under the protection of nitrogen. After the reaction was completed, the mixture was cooled to room temperature, filtered, and the filter cake was washed with ethyl acetate (150 mL), and the organic phases were combined to obtain an ethyl acetate solution of compound BB-2-2 (350 mL, crude product).

Step 2: Synthesis of Compound BB-2-3

Triethylamine (13.09 g, 129.32 mmol, 18.00 mL) was added to the ethyl acetate (315 mL) solution of compound BB-2-2 (57.93 mmol, crude product) at room temperature, and the reaction mixture was reacted with stirring at room temperature for 12 hours. After the reaction was completed, the mixture was filtered, and the organic phase was washed saturated sodium sulfite solution (50 mL×3), dried with anhydrous sodium sulfate, filtered, and the filtrate was concentrated under reduced pressure to remove the solvent, and the obtained residue was separated by column chromatography (eluent: petroleum ether/ethyl acetate=100/0-19/1, v/v) to obtain compound BB-2-3. $^1$H NMR (400 MHz, CDCl$_3$) δ: 7.68 (dd, J=5.7, 9.0 Hz, 1H), 6.86-6.78 (m, 2H), 4.68 (s, 2H).

Step 3: Synthesis of Compound BB-2

Compound BB-2-3 (2.7 g, 17.75 mmol) was added to toluene (150 mL) at room temperature, then ethyl(triphenylphosphoranylidene)acetate (9.27 g, 26.62 mmol) was added, and the reaction mixture was stirred at 130° C. for 36 hours under the protection of nitrogen. After the reaction was completed, the mixture was cooled to room temperature, concentrated under reduced pressure to remove the solvent. The obtained residue was added with methyl tert-butyl ether (100 mL) to slurry at room temperature, and the mixture was filtered, and the filtrate was concentrated under reduced pressure to remove the solvent, and the obtained residue was separated by column chromatography (eluent: petroleum ether/ethyl acetate=100/0-19/1, v/v) to obtain target compound BB-2. $^1$H NMR (400 MHz, CDCl$_3$) δ: 7.63 (s, 1H), 7.50 (dd, J=5.4, 8.7 Hz, 1H), 7.20 (dd, J=2.2, 9.0 Hz, 1H), 7.08-7.00 (m, 1H), 4.20 (q, J=7.1 Hz, 2H), 3.68 (d, J=1.0 Hz, 2H), 1.28 (t, J=7.1 Hz, 3H).

Reference Embodiment 3: Fragment BB-3

Synthetic Route:

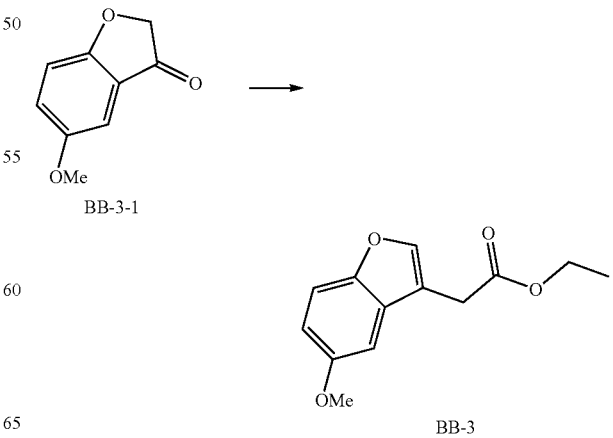

Compound BB-3-1 (5 g, 30.46 mmol) was added to toluene (250 mL) at room temperature, then ethyl(triphenylphosphoranylidene)acetate (15.92 g, 45.69 mmol) was added, and the reaction mixture was heated to 130° C. and reacted with stirring for 48 hours. After the reaction was completed, the mixture was cooled to room temperature, concentrated under reduced pressure to remove the solvent. The obtained residue was added with methyl tert-butyl ether (100 mL) to slurry at room temperature, filtered, and the filtrate was concentrated under reduced pressure to remove the solvent, and the obtained residue was separated by column chromatography (eluent: petroleum ether/ethyl acetate=100/0-19/1, v/v) to obtain target compound BB-3. $^1$H NMR (400 MHz, CDCl$_3$) δ: 7.61 (s, 1H), 7.37 (d, J=8.9 Hz, 1H), 7.02 (d, J=2.6 Hz, 1H), 6.92 (dd, J=2.5, 8.9 Hz, 1H), 4.20 (q, J=7.1 Hz, 2H), 3.86 (s, 3H), 3.67 (s, 2H), 1.29 (t, J=7.2 Hz, 3H).

Reference Embodiment 4: Fragment BB-4

Synthetic Route:

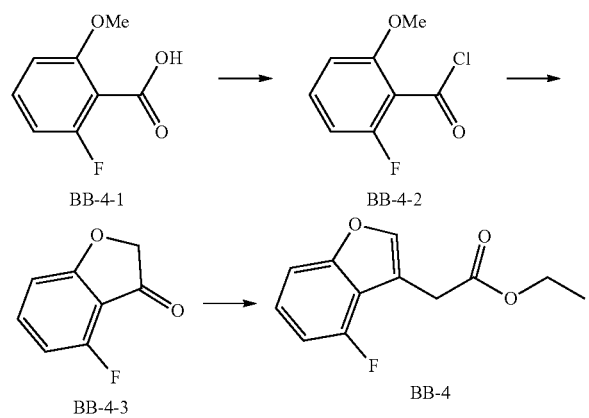

Step 1: Synthesis of Compound BB-4-2

Compound BB-4-1 (3 g, 17.63 mmol) was added to dichloromethane (30 mL) at room temperature, and then the reaction mixture was cooled to 0° C. N,N-dimethylformamide (5.70 mg, 77.98 μmol, 6.00 μL) and oxalyl chloride (6.71 g, 52.90 mmol, 4.63 mL) were added, and the reaction mixture was raised to 25° C. and reacted with stirring for 1 hour under the protection of nitrogen. After the reaction was completed, the solvent was removed by nitrogen flow, and a crude product of compound BB-4-2 was obtained, which can be directly used in the next step.

Step 2: Synthesis of Compound BB-4-3

At room temperature, the crude product of compound BB-4-2 (17.63 mmol, crude product) from the previous step was dissolved in tetrahydrofuran (30 mL), then the reaction mixture was cooled to 0° C., and trimethylsilyldiazomethane (35.26 mmol, 22.04 mL, 2M) was added. The reaction mixture was reacted with stirring at room temperature for 12 hours under the protection of nitrogen. After the reaction was completed, the mixture was cooled to 0° C., quenched by adding glacial acetic acid (6 mL), then water (100 mL) was added, and the mixture was extracted with ethyl acetate (60 mL×3). The organic phases were combined, washed with saturated brine (50 mL×2), dried with anhydrous sodium sulfate, filtered, and the filtrate was concentrated under reduced pressure to remove the solvent, and the obtained residue was separated by column chromatography (eluent: petroleum ether/ethyl acetate=50/1-20/1, v/v), to obtain compound BB-4-3. MS-ESI m/z: 153.0 [M+H]$^+$. $^1$H NMR (400 MHz, CDCl$_3$) δ: 7.58 (td, J=5.6, 8.4 Hz, 1H), 6.93 (d, J=8.8 Hz, 1H), 6.72 (t, J=8.4 Hz, 1H), 4.66 (s, 2H).

Step 3: Synthesis of Compound BB-4

Compound BB-4-3 (1.85 g, 12.16 mmol) was added to toluene (30 mL) at room temperature, then ethyl(triphenylphosphoranylidene)acetate (5.08 g, 14.59 mmol) was added, and the reaction mixture was heated to 130° C. and reacted with stirring for 48 hours. After the reaction was completed, the mixture was cooled to room temperature, concentrated under reduced pressure to remove the solvent, and the obtained residue was separated by column chromatography (eluent: petroleum ether/ethyl acetate=50/1-30/1, v/v), to obtain target compound BB-4. MS-ESI m/z: 223.0 [M+H]$^+$. $^1$H NMR (400 MHz, CDCl$_3$) δ: 7.45 (s, 1H), 7.13 (d, J=8.0 Hz, 1H), 7.08 (td, J=5.6, 8.0 Hz, 1H), 6.76 (t, J=9.2 Hz, 1H), 4.08 (q, J=7.2 Hz, 2H), 3.68 (s, 2H), 1.15 (t, J=7.0 Hz, 3H).

Reference Embodiment 5 and Reference Embodiment 5': Fragment BB-5 and Fragment BB-5'

Synthetic Route:

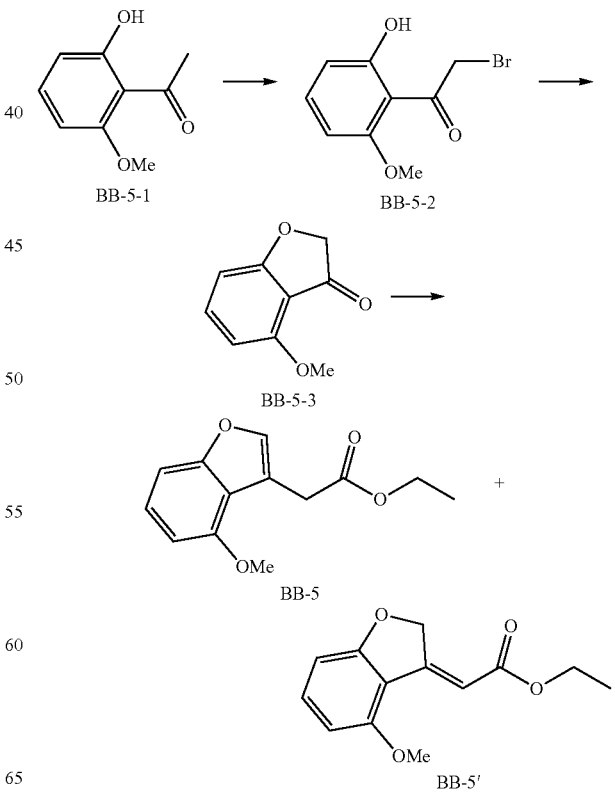

Step 1: Synthesis of Compound BB-5-2

Compound BB-5-1 (3.8 g, 22.87 mmol) was added to ethyl acetate (100 mL) at room temperature, then copper bromide (7.66 g, 34.30 mmol, 1.61 mL) was added, and the reaction mixture was heated to 80° C. and reacted with stirring for hours under the protection of nitrogen. After the reaction was completed, the mixture was cooled to room temperature and filtered to remove insoluble solids. The filtrate was washed with water (50 mL×3) and saturated brine (50 mL), dried with anhydrous sodium sulfate, filtered, and the filtrate was concentrated under reduced pressure to remove the solvent, and the obtained residue was separated by column chromatography (eluent: petroleum ether/ethyl acetate=10/1, v/v), to obtain compound BB-5-2. MS-ESI m/z: 244.8 [M+H]$^+$, 246.8 [M+H+2]$^+$.

Step 2: Synthesis of Compound BB-5-3

Compound BB-5-2 (2.6 g, 10.61 mmol) was added to ethyl acetate (20 mL) at room temperature, then triethylamine (3.22 g, 31.83 mmol, 4.43 mL) was added, and the reaction mixture was reacted with stirring at room temperature for 5 hours under the protection of nitrogen. After the reaction was completed, the solvent was removed under reduced pressure, and the obtained residue was added with water (50 mL), and extracted with ethyl acetate (50 mL×3). The organic phases were combined, washed with saturated brine (50 mL), dried with anhydrous sodium sulfate, filtered, and the filtrate was concentrated under reduced pressure to remove the solvent, and the obtained residue was separated by column chromatography (eluent: petroleum ether/ethyl acetate=1/1, v/v), to obtain compound BB-5-3. $^1$H NMR (400 MHz, CDCl$_3$) δ: 7.53 (t, J=8.2 Hz, 1H), 6.69 (d, J=8.4 Hz, 1H), 6.48 (d, J=8.0 Hz, 1H), 4.61 (s, 2H), 3.97 (s, 3H).

Step 3: Synthesis of a Mixture of BB-5 and BB-5'

Compound BB-5-3 (900 mg, 5.48 mmol) was added to toluene (30 mL) at room temperature, then ethyl(triphenylphosphoranylidene)acetate (2.29 g, 6.58 mmol) was added, and the reaction mixture was heated to 130° C. and reacted with stirring for 20 hours under the protection of nitrogen. After the reaction was completed, the mixture was cooled to room temperature, then the solvent was removed under reduced pressure, and water (30 mL) was added to the residue, and the mixture was extracted with ethyl acetate (30 mL×3). The organic phases were combined, washed with saturated brine (30 mL), dried with anhydrous sodium sulfate, filtered, and the filtrate was concentrated under reduced pressure to remove the solvent, and the obtained residue was separated by column chromatography (eluent: petroleum ether/ethyl acetate=10/1, v/v), to obtain a mixture of compound BB-5 and BB-5' (BB-5/BB-5'=1/5), which was directly used in the next reaction.

Reference Embodiment 6: Fragment BB-6

Synthetic Route:

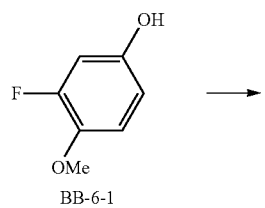

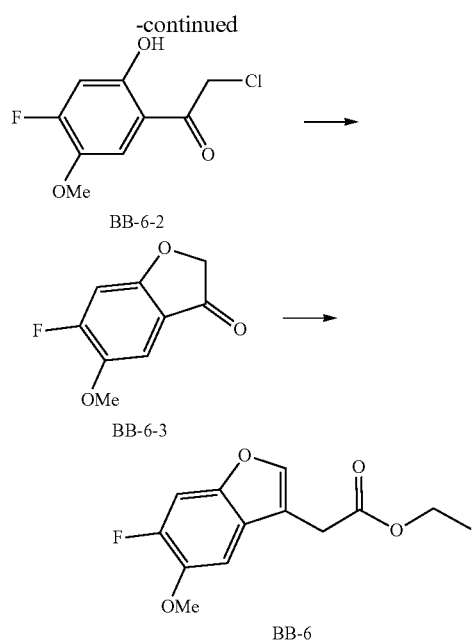

Step 1: Synthesis of Compound BB-6-2

A dichloromethane (10 mL) solution of compound BB-6-1 (2 g, 14.07 mmol) was slowly added dropwise to a dichloromethane solution of boron trichloride (1 M, 16.89 mL) at 0° C. (dropwise time was about 15 minutes), then chloroacetonitrile (1.27 g, 16.89 mmol, 1.07 mL) was slowly added dropwise, and finally aluminum chloride (1876.36 mg, 14.08 mmol) was added in two batches, and the reaction mixture was reacted with stirring at room temperature for 5 hours. After the reaction was completed, water (20 mL) and dichloromethane (20 mL) were added to dilute, and the phases were separated, then the organic phases were collected, and the aqueous phase was extracted with dichloromethane (10 mL×2). The organic phases were combined, dried with anhydrous sodium sulfate, filtered to obtain a dichloromethane (60 mL) solution of compound BB-6-2, which was directly used in the next reactio.

Step 2: Synthesis of Compound BB-6-3

Triethylamine (2.78 g, 27.44 mmol, 3.82 mL) was added to a dichloromethane (60 mL) solution of compound BB-6-2 (14.07 mmol, crude product) at room temperature, and the reaction mixture was stirred at room temperature for 4 hours. After the reaction was completed, the mixture was diluted with water (20 mL), and the phases were separated, then the organic phases were collected, then the aqueous phase was extracted with dichloromethane (20 mL×2); the organic phases were combined, dried with anhydrous sodium sulfate, filtered, and the filtrate was concentrated under reduced pressure to remove the solvent, and the obtained residue was separated by column chromatography (eluent: petroleum ether/ethyl acetate=100/0-4/1, v/v), to obtain compound BB-6-3. $^1$H NMR (400 MHz, CDCl$_3$) δ: 7.17 (d, J=8.4 Hz, 1H), 6.90 (d, J=10.4 Hz, 1H), 4.65 (s, 2H), 3.89 (s, 3H).

Step 3: Synthesis of Compound BB-6

Compound BB-6-3 (900.00 mg, 4.94 mmol) was added to toluene (15 mL) at room temperature, then ethyl(triphenylphosphoranylidene)acetate (2.58 g, 7.41 mmol) was added, and the reaction mixture was heated to 130° C. and reacted with stirring for 40 hours. After the reaction was completed, the solvent was concentrated under reduced pressure. The obtained residue was added with methyl tert-butyl ether (10 mL), filtered, and the filtrate was concentrated under reduced pressure to remove the solvent, and the obtained residue was separated by column chromatography (eluent: petroleum ether/ethyl acetate=100/0-4/1, v/v) to obtain target compound BB-6. $^1$H NMR (400 MHz, CDCl$_3$) δ: 7.59 (s, 1H), 7.24 (d, J=10.8 Hz, 1H), 7.08 (d, J=8.0 Hz, 1H), 4.19 (q, J=7.2 Hz, 2H), 3.93 (s, 3H), 3.66 (s, 2H), 1.27 (t, J=7.2 Hz, 3H).

Reference Embodiment 7: Fragment BB-7

Synthetic Route:

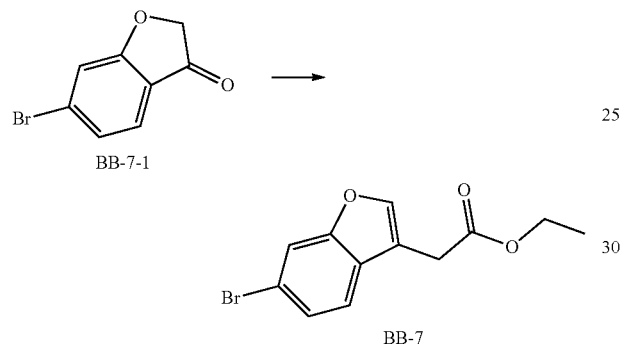

Compound BB-7-1 (2 g, 9.39 mmol) was added to toluene (50 mL) at room temperature, then ethyl(triphenylphosphoranylidene)acetate (3.92 g, 11.27 mmol) was added, and the reaction mixture was heated to 130° C. and reacted with stirring for 48 hours under the protection of nitrogen. After the reaction was completed, the mixture was cooled to room temperature, concentrated under reduced pressure to remove the solvent, and the obtained residue was separated by column chromatography (eluent: petroleum ether/ethyl acetate=20/1-10/1, v/v) to obtain target compound BB-7. MS-ESI m/z: 282.9 [M+H]$^+$, 284.9 [M+H+2]$^+$. $^1$H NMR (400 MHz, CDCl$_3$) δ: 7.58 (d, J=1.6 Hz, 1H), 7.53 (s, 1H), 7.36 (d, J=8.4 Hz, 1H), 7.30 (d, J=8.4 Hz, 1H), 4.12 (q, J=7.2 Hz, 2H), 3.60 (s, 2H), 1.20 (t, J=7.2 Hz, 3H).

Reference Embodiment 8: Fragment BB-8

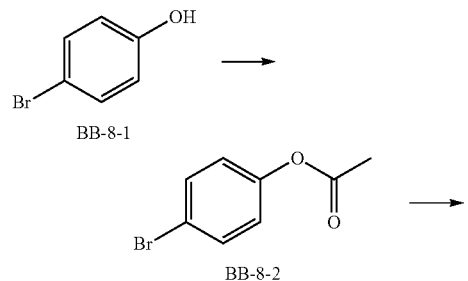

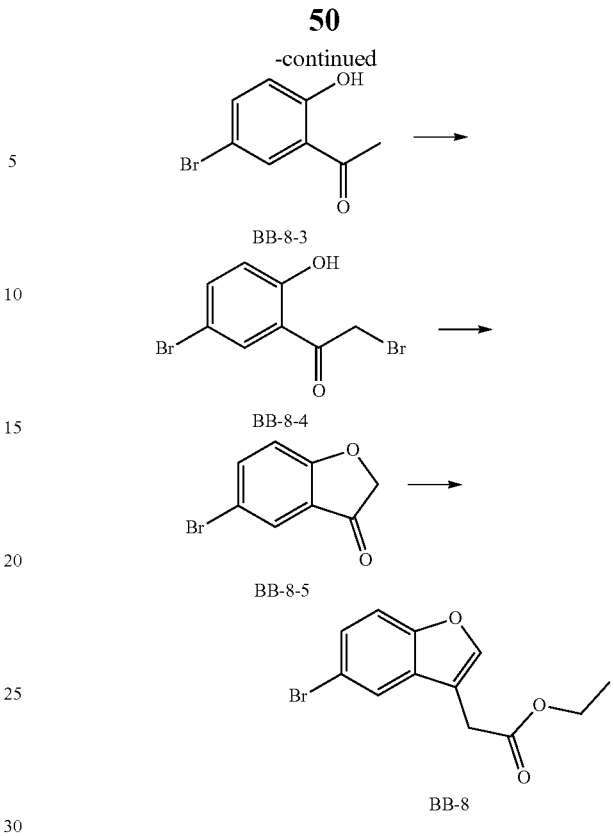

Step 1: Synthesis of Compound BB-8-2

Compound BB-8-1 (10.00 g, 57.80 mmol) and triethylamine (8.77 g, 86.70 mmol, 12.07 mL) were added to dichloromethane (80.00 mL) at 0° C., then acetyl chloride (5.44 g, 69.36 mmol, 4.95 mL) was added, and the reaction mixture was raised to room temperature and reacted with stirring for 2 hours under the protection of nitrogen. After the reaction was completed, the mixture was washed with water (100 mL×3), dried with anhydrous sodium sulfate, filtered, and the filtrate was concentrated under reduced pressure to remove the solvent, and the obtained residue was separated by column chromatography (eluent: petroleum ether/ethyl acetate=1/0-10/1, v/v) to obtain compound BB-8-2. $^1$H NMR (400 MHz, CDCl$_3$) δ: 7.52-7.47 (m, 2H), 7.01-6.97 (m, 2H), 2.30 (s, 3H).

Step 2: Synthesis of Compound BB-8-3

Compound BB-8-2 (10.00 g, 46.50 mmol) was added to trifluoromethanesulfonic acid (34.89 g, 232.51 mmol, 20.53 mL) at 0° C., and the reaction mixture was heated to 60° C. and reacted with stirring for 1.5 hours under the protection of nitrogen. After the reaction was completed, the mixture was cooled to room temperature, and water (100 mL) was added. The reaction mixture was adjusted to pH=8 to 9 with saturated sodium bicarbonate solution and extracted with dichloromethane (100 mL×3). The organic phases were combined, washed with water (200 mL×2), dried with anhydrous sodium sulfate, filtered, and the filtrate was concentrated under reduced pressure to remove the solvent, and the obtained residue was separated by column chromatography (eluent: petroleum ether/ethyl acetate=1/0-10/1, v/v) to obtain compound BB-8-3. $^1$H NMR (400 MHz, CDCl$_3$) δ: 12.17 (s, 1H), 7.84 (d, J=2.4 Hz, 1H), 7.55 (dd, J=2.2, 9.0 Hz, 1H), 6.90 (d, J=8.8 Hz, 1H), 2.63 (s, 3H).

Step 3: Synthesis of Compound BB-8-4

Compound BB-8-3 (5.90 g, 27.44 mmol) was added to chloroform (30 mL) and ethyl acetate (30 mL) at room temperature, then copper bromide (12.26 g, 54.87 mmol, 2.57 mL) was added, and the reaction mixture was heated to 100° C. and reacted with stirring for 20 hours under the protection of nitrogen. After the reaction was completed, the mixture was cooled to room temperature, filtered, and the filtrate was concentrated under reduced pressure to remove the solvent; and the obtained residue was added with water (50 mL), and extracted with dichloromethane (50 mL×3). The organic phases were combined, washed with saturated brine (100 mL×2), dried with anhydrous sodium sulfate and filtered. A dichloromethane solution (150 mL) of target compound BB-8-4 was obtained, which was directly used in the next reaction.

Step 4: Synthesis of Compound BB-8-5

The crude product of compound BB-8-4 (27.44 mmol) from the previous step was added to dichloromethane (150.00 mL) at room temperature, then triethylamine (11.11 g, 109.76 mmol, 15.28 mL) was added, and the reaction mixture was reacted with stirring at room temperature for 0.5 hours under the protection of nitrogen. After the reaction was completed, water (100 mL) was added, and the phases were separated, and the aqueous phase was extracted with dichloromethane (100 mL×3). The organic phases were combined, washed with saturated brine (200 mL×2), dried with anhydrous sodium sulfate, filtered, and the filtrate was concentrated under reduced pressure to remove the solvent, and the obtained residue was separated by column chromatography (eluent: petroleum ether/ethyl acetate=1/0-10/1, v/v) to obtain compound BB-8-5. $^1$H NMR (400 MHz, CDCl$_3$) δ: 7.80 (d, J=2.4 Hz, 1H), 7.69 (dd, J=2.4, 8.8 Hz, 1H), 7.07 (d, J=8.8 Hz, 1H), 4.67 (s, 2H).

Step 5: Synthesis of Compound BB-8

Compound BB-8-5 (3.00 g, 14.08 mmol) was added to toluene (20.00 mL) at room temperature, then ethyl(triphenylphosphoranylidene)acetate (5.89 g, 16.90 mmol) was added, and the reaction mixture was heated to 130° C. and reacted with stirring for 44 hours under the protection of nitrogen. After the reaction was completed, the mixture was cooled to room temperature, and water (50 mL) was added, and the mixture was extracted with dichloromethane (50 mL×3). The organic phases were combined, washed with saturated brine (80 mL×2), dried with anhydrous sodium sulfate, filtered, and the filtrate was concentrated under reduced pressure to remove the solvent, and the obtained residue was separated by column chromatography (eluent: petroleum ether/ethyl acetate=1/0-10/1, v/v) to obtain target compound BB-8. $^1$H NMR (400 MHz, CDCl$_3$) δ: 7.72 (d, J=2.0 Hz, 1H), 7.64 (s, 1H), 7.43-7.39 (m, 1H), 7.37-7.34 (m, 1H), 4.21 (q, J=7.0 Hz, 2H), 3.66 (s, 2H), 1.29 (t, J=7.2 Hz, 3H).

Reference Embodiment 9: Fragment BB-9

Synthetic Route:

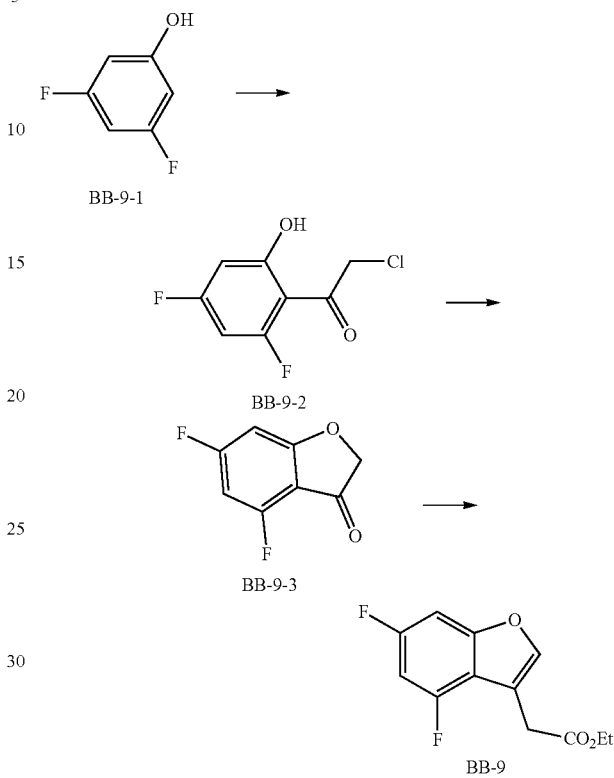

Step 1: Synthesis of Compound BB-9-2

A dichloromethane (10 mL) solution of compound BB-9-1 (2 g, 14.07 mmol) was slowly added dropwise to a dichloromethane solution of boron trichloride (1 M, 9.22 mL) at 0° C. (dropwise time was about 15 minutes), then chloroacetonitrile (696.40 mg, 9.22 mmol) was slowly added dropwise, and finally aluminum chloride (512.49 mg, 3.84 mmol) was added in two batches, and the reaction mixture was reacted with stirring at room temperature for 12 hours, and was then heated to 80° C. and reacted with stirring at 80° C. for 3 hours. After the reaction was completed, the reaction mixture was poured into ice water (30 mL), and extracted with dichloromethane (50 mL×2). The organic phases were combined, dried with anhydrous sodium sulfate, filtered to obtain a dichloromethane (about 100 mL) solution of compound BB-9-2. The reaction solution was directly used in the next reaction.

Step 2: Synthesis of Compound BB-9-3

Triethylamine (2.91 g, 28.74 mmol, 4 mL) was added to the dichloromethane solution of compound BB-9-2 (14.07 mmol, 100 mL) at room temperature, and the reaction mixture was reacted with stirring at room temperature for 1 hour. After the reaction was completed, water (10 mL) was added to dilute, and the phases were separated, then the organic phases were collected, and the aqueous phase was extracted with dichloromethane (10 mL×2). The organic phases were combined, dried with anhydrous sodium sulfate, filtered, and the filtrate was concentrated under reduced pressure to remove the solvent, and the obtained residue was separated by column chromatography (eluent: petroleum ether/ethyl acetate=100/0-9/1, v/v), to obtain compound BB-9-3. $^1$H NMR (400 MHz, CDCl$_3$) δ: 6.69-6.63 (m, 1H), 6.54-6.47 (m, 1H), 4.70 (s, 2H).

Step 3: Synthesis of Compound BB-9

Compound BB-9-3 (200 mg, 1.18 mmol) was dissolved in toluene (10 mL) at room temperature under the protection of nitrogen, then ethyl(triphenylphosphoranylidene)acetate (614.37 mg, 1.76 mmol) was added, and the reaction mixture was heated to 130° C. and reacted with stirring at 130° C. for 48 hours. After the reaction was completed, the mixture was cooled to room temperature, and concentrated under reduced pressure to remove the solvent. The obtained residue was added with methyl tert-butyl ether (10 mL), filtered, and the filtrate was concentrated under reduced pressure to remove the solvent, and the obtained residue was separated by column chromatography (eluent: petroleum ether/ethyl acetate=100/0-9/1, v/v) to obtain target compound BB-9. $^1$H NMR (400 MHz, CDCl$_3$) δ: 7.58 (s, 1H), 7.06-7.00 (m, 1H), 6.74 (dt, J=2.1, 9.9 Hz, 1H), 4.22 (q, J=7.2 Hz, 2H), 3.79 (d, J=1.0 Hz, 2H), 1.29 (t, J=7.0 Hz, 3H).

Reference Embodiment 10: Fragment BB-10

Synthetic Route:

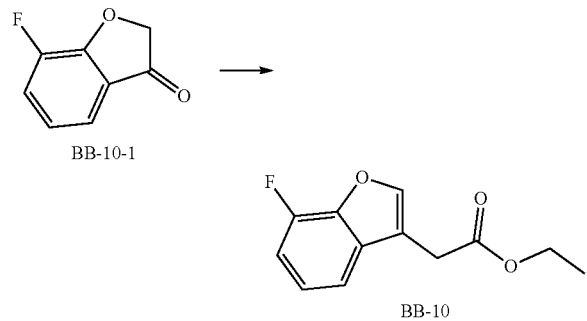

Step 1: Synthesis of Compound BB-10

Compound BB-10-1 (1 g, 6.57 mmol) was added to toluene (20 mL) at room temperature, then ethoxyformylmethylene triphenylphosphine (2.29 g, 6.57 mmol) was added, and the reaction mixture was heated to 130° C. and reacted with stirring at 130° C. for 48 hours. After the reaction was completed, the reaction mixture was directly concentrated under reduced pressure to remove the solvent, and the obtained residue was diluted with water (50 mL), and extracted with ethyl acetate (50 mL×3). The organic phases were combined, washed with saturated brine (50 mL), dried with anhydrous sodium sulfate, filtered, and the filtrate was concentrated under reduced pressure to remove the solvent. The obtained residue was separated by column chromatography (eluent: petroleum ether/ethyl acetate=10/1, v/v), to obtain compound BB-10. MS-ESI m/z: 222.9 [M+H]$^+$.

Reference Embodiment 11: Fragment BB-11

Synthetic Route:

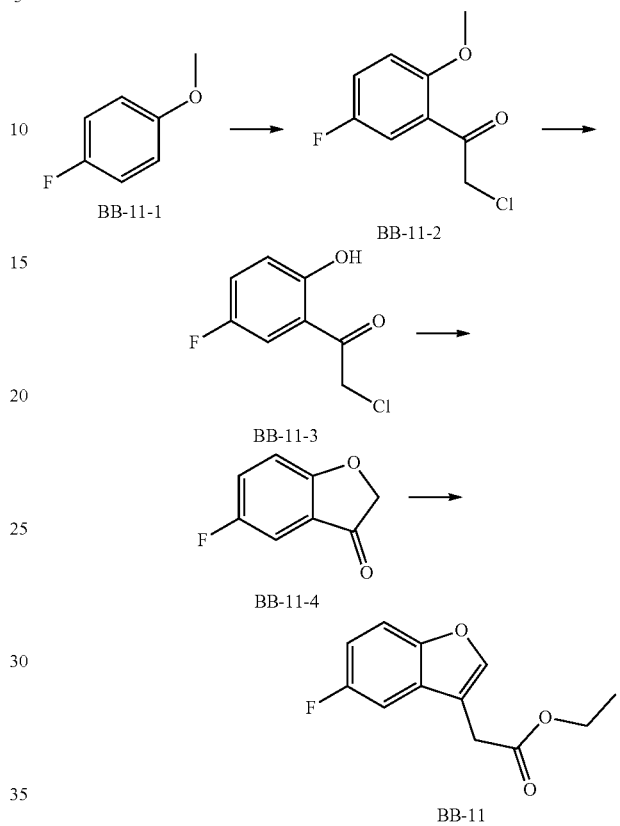

Step 1: Synthesis of Compound BB-11-2

Compound BB-11-1 (4 g, 31.71 mmol, 3.57 mL) was dissolved in dichloromethane (50 mL) under the protection of nitrogen at 0° C., and chloroacetyl chloride (3.94 g, 34.89 mmol, 2.77 mL) was added, then the reaction mixture was stirred at 0° C. for 1 hour, and aluminum chloride (4.65 g, 34.89 mmol) was added, and the reaction mixture was reacted with stirring at room temperature for 39 hours. After the reaction was completed, the reaction mixture was poured into ice water (100 mL), and extracted with dichloromethane (80 mL×3). The organic phases were combined, washed with saturated brine (80 mL×2), dried with anhydrous sodium sulfate, filtered, and the filtrate was concentrated under reduced pressure to remove the solvent. The obtained residue was separated by column chromatography (eluent: petroleum ether/ethyl acetate=100/1-50/1, v/v), to obtain compound BB-11-2. MS-ESI m/z: 202.9 [M+H]$^+$. $^1$H NMR (400 MHz, CDCl$_3$) δ: 7.51 (dd, J=3.4, 8.6 Hz, 1H), 7.20-7.13 (m, 1H), 6.89 (dd, J=4.0, 9.2 Hz, 1H), 4.70 (s, 2H), 3.87 (s, 3H).

Step 2: Synthesis of Compound BB-11-3

Compound BB-11-2 (1.3 g, 6.42 mmol) was dissolved in dichloromethane (20 mL) under the protection of nitrogen at 0° C., and aluminum chloride (1.71 g, 12.83 mmol) was added, then the reaction mixture was reacted with stirring at room temperature for 12 hours. After the reaction was completed, the reaction system was poured into ice water (60 mL), and extracted with dichloromethane (40 mL×3). The organic phases were combined, washed with saturated brine (30 mL×2), dried with anhydrous sodium sulfate, filtered, and the filtrate was concentrated under reduced pressure to remove the solvent. The obtained residue was separated by column chromatography (eluent: petroleum ether/ethyl acetate=100/1-40/1, v/v), to obtain compound BB-11-3. MS-ESI m/z: 349.1 [M+H]$^+$. $^1$H NMR (400 MHz, CDCl$_3$) δ: 11.35 (s, 1H), 7.30 (dd, J=2.8, 8.4 Hz, 1H), 7.25-7.18 (m, 1H), 6.94 (dd, J=4.6, 9.4 Hz, 1H).

Step 3: Synthesis of Compound BB-11-4

Compound BB-11-3 (1.13 g, 5.99 mmol) was dissolved in methanol (20 mL) under the protection of nitrogen at room temperature, and sodium acetate (983.10 mg, 11.98 mmol) was added, then the reaction mixture was heated to 70° C. and reacted with stirring for 2 hours. After the reaction was completed, the mixture was cooled to room temperature, and the reaction system was added with water (50 mL), and extracted with ethyl acetate (30 mL×3). The organic phases were combined, washed with saturated brine (30 mL×2), dried with anhydrous sodium sulfate, filtered, and the filtrate was concentrated under reduced pressure to remove the solvent. The obtained residue was separated by column chromatography (eluent: petroleum ether/ethyl acetate=100/1-30/1, v/v), to obtain compound BB-11-4. MS-ESI m/z: 152.9 [M+H]$^+$. $^1$H NMR (400 MHz, CDCl$_3$) δ: 7.32-7.22 (m, 2H), 7.04 (dd, J=3.4, 9.0 Hz, 1H), 4.61 (s, 2H).

Step 4: Synthesis of Compound BB-11

Compound BB-11-4 (0.9 g, 5.04 mmol, purity:85.12%) was dissolved in toluene (30 mL) at room temperature, then ethoxyformylmethylene triphenylphosphine (2.11 g, 6.04 mmol) was added, and the reaction mixture was heated to 130° C. and reacted with stirring at 130° C. for 48 hours. After the reaction was completed, the mixture was directly concentrated under reduced pressure to remove the solvent, and the obtained residue was separated by column chromatography (eluent: petroleum ether/ethyl acetate=50/1-30/1, v/v) to obtain compound BB-11. MS-ESI m/z: 241.1 [M+H]$^+$. $^1$H NMR (400 MHz, CDCl$_3$) δ: 7.59 (s, 1H), 7.32 (dd, J=4.0, 9.2 Hz, 1H), 7.21-7.12 (m, 1H), 6.95 (td, J=2.4, 9.0 Hz, 1H), 4.13 (q, J=7.6 Hz, 2H), 3.58 (d, J=0.8 Hz, 2H), 1.21 (t, J=7.2 Hz, 3H).

Reference Embodiment 12: Fragment BB-12

Synthetic Route:

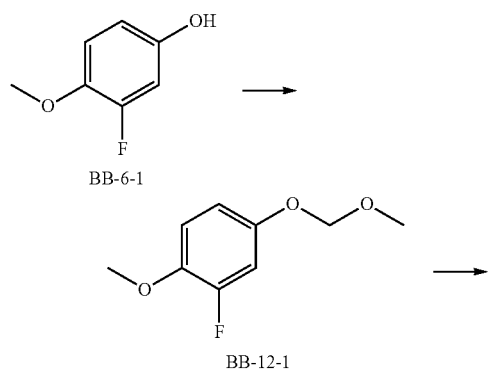

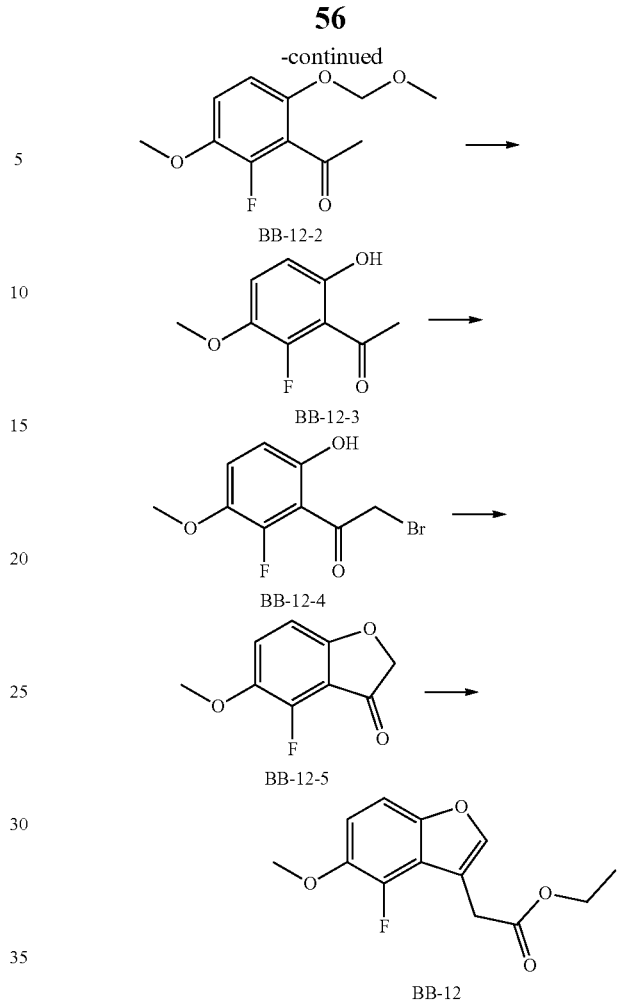

Step 1: Synthesis of Compound BB-12-1

Compound BB-6-1 (20 g, 140.72 mmol) was dissolved in dichloromethane (200 mL) under the protection of nitrogen at room temperature, then diisopropylethylamine (63.65 g, 492.52 mmol, 85.79 mL) was added. The mixture was cooled to 0° C., and chloromethyl methyl ether (21.53 g, 267.37 mmol, 20.31 mL) was added, then the reaction mixture was naturally reacted with stirring for 3 hours at room temperature. After the reaction was completed, water (50 mL) was added to dilute the reaction solution, and the phases were separated, then the organic phases were collected, and the aqueous phase was extracted with dichloromethane (30 mL×2). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-4/1, v/v), to obtain compound BB-12-1. $^1$H NMR (400 MHz, CDCl$_3$) δ: 6.94-6.82 (m, 2H), 6.80-6.65 (m, 1H), 5.11 (s, 2H), 3.86 (s, 3H), 3.48 (s, 3H).

Step 2: Synthesis of Compound BB-12-2

Compound BB-12-1 (10 g, 53.71 mmol) was dissolved in tetrahydrofuran (100 mL) under the protection of nitrogen at room temperature, then the mixture was cooled to −60° C., and n-butyl lithium (2.5 M, 21.48 mL) was added, then the mixture was stirred for 30 minutes, and N-methoxy-N-methylacetamide (6.65 g, 64.45 mmol, 6.85 mL) was added dropwise; the reaction mixture was naturally raised to room temperature and reacted with stirring for 12 hours. After the reaction was completed, the reaction system was added with water (50 mL) and ethyl acetate (50 mL), and the aqueous phase was extracted with ethyl acetate (50 mL×2). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-9/1, v/v), to obtain compound BB-12-2. ¹H NMR (400 MHz, CDCl₃) δ: 6.97-6.84 (m, 2H), 5.12 (s, 2H), 3.86 (s, 3H), 3.47 (s, 3H), 2.56 (d, J=1.1 Hz, 3H).

Step 3: Synthesis of Compound BB-12-3

Compound BB-12-2 (1.4 g, 6.13 mmol) was added to hydrochloric acid/ethyl acetate (4 M, 30 mL) at room temperature, and the reaction mixture was reacted with stirring at room temperature for 12 hours. After the reaction was completed, the reaction system was added with water (20 mL), and the phases were separated, then the organic phases were collected, and the aqueous phase was extracted with ethyl acetate (20 mL×2). The organic phases were combined, dried with anhydrous sodium sulfate, filtered, and the filtrate was concentrated under reduced pressure to remove the solvent to obtain compound BB-12-3. ¹H NMR (400 MHz, CDCl₃) δ: 12.07 (s, 1H), 7.19 (t, J=9.3 Hz, 1H), 6.73 (dd, J=1.9, 9.2 Hz, 1H), 3.87 (s, 3H), 2.72 (d, J=7.5 Hz, 3H).

Step 4: Synthesis of Compound BB-12-4

Compound BB-12-3 (1.1 g, 5.97 mmol) was dissolved in ethyl acetate (20 mL) under the protection of nitrogen at room temperature, then copper bromide (1.60 g, 7.17 mmol) was added, and the reaction mixture was heated to 80° C. and reacted with stirring for 3 hours; the generation of a white solid and the change of reaction solution from yellow to green were observed. After the reaction was completed, the mixture was directly filtered, and the filter cake was washed with ethyl acetate (10 mL), and the filtrate was collected to obtain an ethyl acetate (30 mL) solution of compound BB-12-4.

Step 5: Synthesis of Compound BB-12-5

Triethylamine (1.45 g, 14.37 mmol, 2 mL) was added to the ethyl acetate (30 mL) solution of compound BB-12-4 (1.57 g, 5.97 mmol) at room temperature, and the reaction mixture was reacted with stirring at room temperature for 2 hours. After the reaction was completed, the reaction system was added with water (10 mL), and the phases were separated, then the organic phases were collected, and the aqueous phase was extracted with ethyl acetate (10 mL×2). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-9/1, v/v), to obtain compound BB-12-5. ¹H NMR (400 MHz, CDCl₃) δ: 7.32 (t, J=8.6 Hz, 1H), 6.85 (dd, J=1.2, 8.9 Hz, 1H), 4.64 (s, 2H), 3.90 (s, 3H).

Step 6: Synthesis of Compound BB-12

Compound BB-12-5 (100 mg, 549.00 mmol) was dissolved in toluene (5 mL) at room temperature under the protection of nitrogen, then ethyl(triphenylphosphoranylidene)acetate (286.89 mg, 823.51 mmol) was added, and the reaction mixture was heated to 130° C. and reacted with stirring for 38 hours. After the reaction was completed, the reaction solution was concentrated directly under reduced pressure to remove the solvent. The obtained residue was slurried at room temperature with 5 mL of methyl tert-butyl ether, and the mixture was filtered, then the filtrate was collected and concentrated under reduced pressure to remove the solvent. The obtained residue was separated by column chromatography (eluent: petroleum ether/ethyl acetate=1/0-9/1, v/v), to obtain compound BB-12. ¹H NMR (400 MHz, CDCl₃) δ: 7.55 (s, 1H), 7.18 (dd, J=1.1, 8.8 Hz, 1H), 6.99 (t, J=8.5 Hz, 1H), 4.22 (q, J=7.1 Hz, 2H), 3.93 (s, 3H), 3.81 (d, J=0.9 Hz, 2H), 1.29 (t, J=7.2 Hz, 3H).

Embodiment 1: WX001

Synthetic Route:

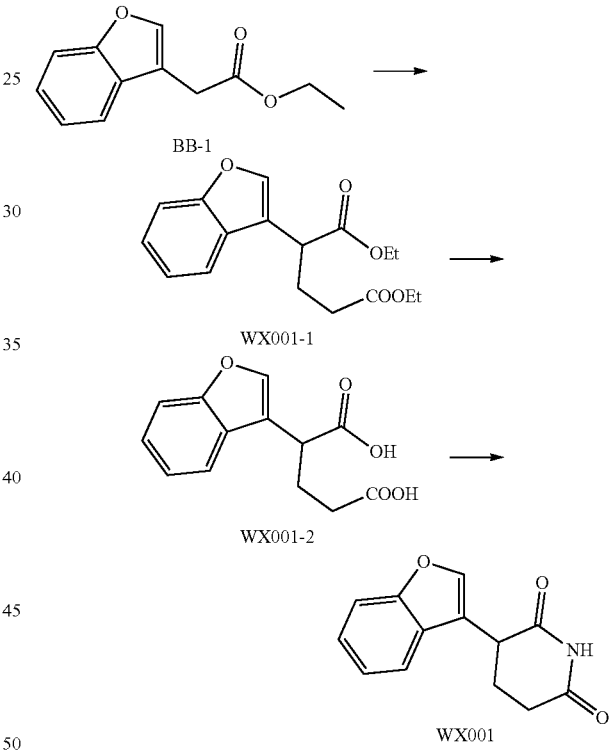

Step 1: Synthesis of Compound WX001-1

Compound BB-1 (2 g, 9.79 mmol) was added to N,N-dimethylformamide (5 mL) and tert-butanol (20 mL) under the protection of nitrogen at room temperature, and the mixture was cooled to 0° C., and sodium hydride (274.21 mg, 6.86 mmol, purity: 60%) was added and the mixture was stirred for 30 minutes; finally ethyl acrylate (1.08 g, 10.77 mmol, 1.17 mL) was added, and the reaction mixture was naturally raised to 8° C. and continued to react with stirring for 2.5 hours. After the reaction was completed, saturated ammonium chloride solution (30 mL) and ethyl acetate (30 mL) were added to dilute, and the phases were separated, then the organic phases were collected, dried with anhydrous sodium sulfate, filtered, and the filtrate was concentrated under reduced pressure to remove the solvent, and the obtained residue was separated by column chromatography (eluent: petroleum ether/ethyl acetate=100/0-50/1, v/v), to obtain compound WX001-1. ¹H NMR (400 MHz, CDCl₃) δ: 7.66 (d, J=7.7 Hz, 1H), 7.59 (s, 1H), 7.48 (d, J=7.9 Hz, 1H), 7.33-7.28 (m, 1H), 7.26-7.22 (m, 1H), 4.23-4.07 (m, 4H), 3.87 (t, J=7.4 Hz, 1H), 2.45-2.26 (m, 4H), 1.23 (dt, J=3.0, 7.1 Hz, 6H).

Step 2: Synthesis of Compound WX001-2

Compound WX001-1 (0.5 g, 1.64 mmol) was added to tetrahydrofuran (8 mL), water (2 mL) and methanol (1 mL) at room temperature, then lithium hydroxide (236.07 mg, 9.86 mmol) was added, the reaction mixture was heated to 35° C. and reacted with stirring for 5 hours. After the reaction was completed, the pH was adjusted to 4 to 5 with 1 M dilute hydrochloric acid, and the mixture was diluted with ethyl acetate (15 mL), and the phases were separated, then the organic phases were collected, and the aqueous phase was extracted with ethyl acetate (10 mL). The organic phases were combined, dried with anhydrous sodium sulfate, filtered, and the filtrate was concentrated under reduced pressure to remove the solvent to obtain compound WX001-2. ¹H NMR (400 MHz, CDCl₃) δ: 7.69 (s, 1H), 7.63 (d, J=7.5 Hz, 1H), 7.49 (d, J=7.9 Hz, 1H), 7.35-7.26 (m, 2H), 3.98-3.92 (m, 1H), 2.63-2.46 (m, 3H), 2.38-2.27 (m, 1H).

Step 3: Synthesis of Compound WX001

Compound WX001-2 (200 mg, 805.70 μmol) was dissolved in N,N-dimethylformamide (5 mL) at room temperature, then 2,2,2-trifluoroacetamide (91.08 mg, 805.70 μmol), 1-hydroxybenzotriazole (424.58 mg, 3.14 mmol), 1-(3-dimethylaminopropyl)-3-ethylcarbodiimide hydrochloride (586.92 mg, 3.06 mmol) and triethylamine (448.41 mg, 4.43 mmol, 616.79 μL) were added, and the reaction mixture was heated to 30° C. and reacted with stirring for 17 hours under the protection of nitrogen. After the reaction was completed, the filtrate was diluted with water (20 mL) and ethyl acetate (20 mL), and the phases were separated, then the organic phases were collected, and the aqueous phase was extracted with dichloromethane (10 mL×2); the organic phases were combined, dried with anhydrous sodium sulfate, filtered, and the filtrate was concentrated under reduced pressure to remove the solvent, and the obtained residue was separated by column chromatography (eluent: petroleum ether/ethyl acetate=20/1-2/1, v/v), and the obtained compound was slurried with methanol (3 mL) at room temperature to obtain target compound WX001. MS-ESI m/z: 230.1 [M+H]⁺. ¹H NMR (400 MHz, DMSO-d₆) δ: 10.92 (s, 1H), 7.91 (s, 1H), 7.63-7.54 (m, 2H), 7.37-7.29 (m, 1H), 7.29-7.20 (m, 1H), 4.15 (dd, J=4.8, 12.1 Hz, 1H), 2.82-2.66 (m, 1H), 2.63-2.54 (m, 1H), 2.50-2.30 (m, 1H), 2.17-2.08 (m, 1H).

Embodiment 2 and Embodiment 3: WX002 and WX003

Synthetic Route:

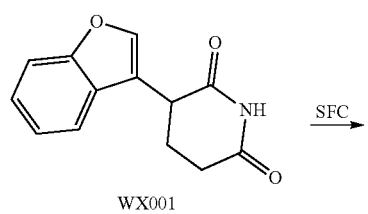

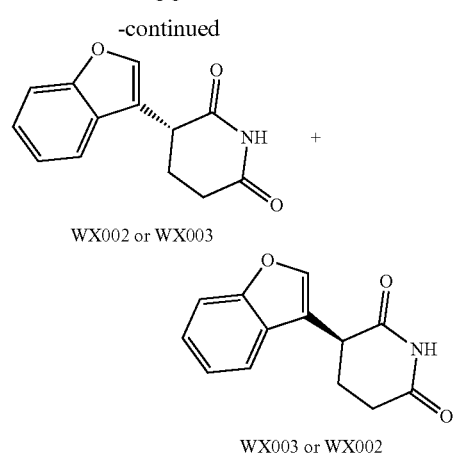

Compound WX001 (200.00 mg, 872.49 μmol) was separated by supercritical fluid chromatography (separation conditions, chromatographic column: Chiralpak AY-H 250*30 mm, 5 μm; mobile phase: A: carbon dioxide; B: methanol, 40%; column temperature: 40° C.; wavelength: 220 nm), the sample with a retention time of 3.708 min was collected to obtain WX002 (ee %: 99.70%) and the sample with a retention time of 4.476 min was collected to obtain WX003 (ee %: 99.65%).

Embodiment 4: WX004

Synthetic Route:

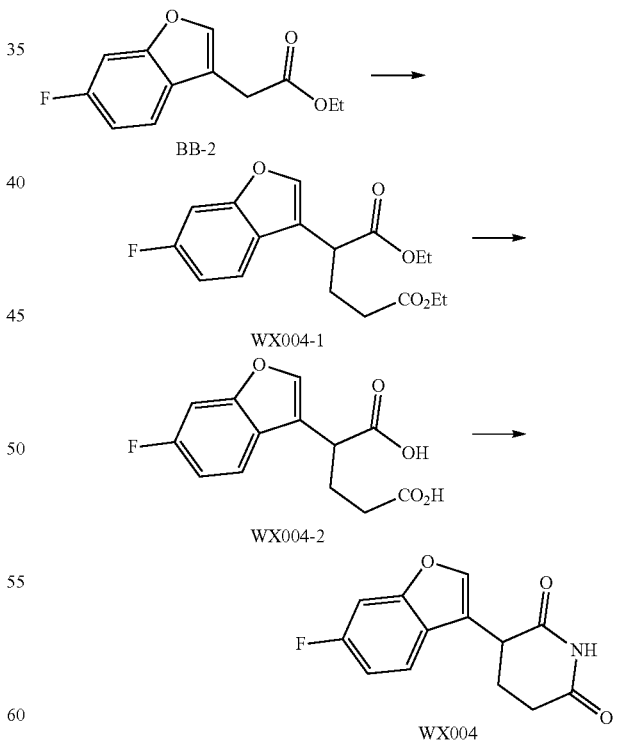

Step 1: Synthesis of Compound WX004-1

Compound BB-2 (1.5 g, 6.75 mmol) was added to N,N-dimethylformamide (15 mL) at room temperature, then ethyl acrylate (675.81 mg, 6.75 mmol, 733.78 μL) was added, and the reaction mixture was cooled to 0° C. under the protection of nitrogen, then potassium tert-butoxide (75.75 mg, 675.03 μmol) was added, and the reaction mixture was raised to room temperature and reacted with stirring for 2 hours. After the reaction was completed, water (50 mL) and ethyl acetate (60 mL) were added to dilute, and the phases were separated, then the organic phases were collected, and the aqueous phase was extracted with ethyl acetate (50 mL). The organic phases were combined, washed with semi-saturated brine (50 mL×2), dried with anhydrous sodium sulfate, filtered, and the filtrate was concentrated under reduced pressure to remove the solvent, and the obtained residue was separated by column chromatography (eluent: petroleum ether/ethyl acetate=100/0-19/1, v/v), to obtain compound WX004-1. $^1$H NMR (400 MHz, CDCl$_3$) δ: 7.65-7.55 (m, 2H), 7.19 (dd, J=2.3, 8.9 Hz, 1H), 7.02 (dt, J=2.3, 9.0 Hz, 1H), 4.24-4.06 (m, 4H), 3.88-3.80 (m, 1H), 2.46-2.19 (m, 4H), 1.24 (dt, J=4.2, 7.1 Hz, 6H).

Step 2: Synthesis of Compound WX004-2

Compound WX004-1 (1.3 g, 4.03 mmol) was added to tetrahydrofuran (16 mL), water (4 mL) and methanol (2 mL) at room temperature, then lithium hydroxide (579.57 mg, 24.20 mmol) was added, and the reaction mixture was stirred at room temperature for 12 hours. After the reaction was completed, the pH was adjusted to 3 to 4 with 2 M dilute hydrochloric acid, and the mixture was extracted with ethyl acetate (20 mL×3), then the organic phases were combined, dried with anhydrous sodium sulfate, filtered, and the filtrate was concentrated under reduced pressure to remove the solvent to obtain compound WX004-2. $^1$H NMR (400 MHz, CDCl$_3$) δ: 7.66 (s, 1H), 7.56 (dd, J=5.4, 8.7 Hz, 1H), 7.21 (dd, J=2.2, 8.8 Hz, 1H), 7.03 (dt, J=2.3, 9.0 Hz, 1H), 3.96-3.86 (m, 1H), 2.61-2.41 (m, 3H), 2.35-2.18 (m, 1H).

Step 3: Synthesis of Compound WX004

Compound WX004-2 (1.0 g, 3.76 mmol) was added to N,N-dimethylformamide (15 mL) at room temperature, then 2,2,2-trifluoroacetamide (424.60 mg, 3.76 mmol), 1-hydroxybenzotriazole (1.98 g, 14.65 mmol), 1-(3-dimethylaminopropyl)-3-ethylcarbodiimide hydrochloride (2.74 g, 14.27 mmol) and triethylamine (2.09 g, 20.66 mmol, 2.88 mL) were added, and the reaction mixture was heated to 40° C. and reacted with stirring for 3 hours under the protection of nitrogen. After the reaction was completed, the mixture was diluted with water (20 mL) and ethyl acetate (20 mL), and the phases were separated, then the organic phases were collected, and the aqueous phase was extracted with ethyl acetate (10 mL×2); the organic phases were combined, dried with anhydrous sodium sulfate, filtered, and the filtrate was concentrated under reduced pressure to remove the solvent, and the obtained residue was separated by column chromatography (eluent: petroleum ether/ethyl acetate=100/0-1/1, v/v), then the obtained compound was slurried with methanol (3 mL) at room temperature to obtain target compound WX004. MS-ESI m/z: 248.0 [M+H]$^+$. $^1$H NMR (400 MHz, DMSO_d$_6$) δ: 10.89 (s, 1H), 7.93 (s, 1H), 7.61 (dd, J=5.5, 8.6 Hz, 1H), 7.53 (dd, J=2.2, 9.5 Hz, 1H), 7.14 (t, J=5.4 Hz, 1H), 4.14 (dd, J=4.8, 12.4 Hz, 1H), 2.81-2.69 (m, 1H), 2.62-2.49 (m, 1H), 2.35-2.25 (m, 1H), 2.17-2.06 (m, 1H).

Embodiment 5: WX005

Synthetic Route:

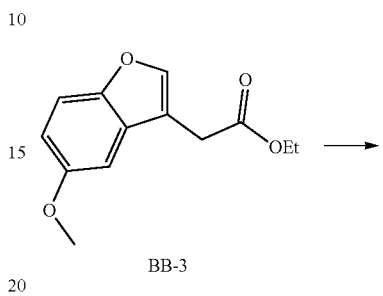

BB-3

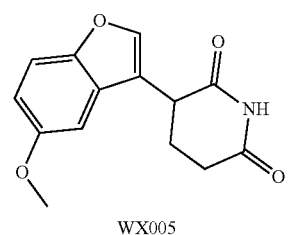

WX005

Compound BB-3 (1.0 g, 4.27 mmol) was added to N,N-dimethylformamide (15 mL) at room temperature, and the reaction mixture was cooled to 0° C., then potassium tert-butoxide (479.02 mg, 4.27 mmol) and acrylamide (303.43 mg, 4.27 mmol) were added, and the reaction mixture was raised to room temperature and reacted with stirring for 2 hours under the protection of nitrogen. After the reaction was completed, water (15 mL) and ethyl acetate (30 mL) were added to dilute, and the phases were separated, then the organic phases were collected, and the aqueous phase was extracted with ethyl acetate (20 mL×2). The organic phases were combined, washed with semi-saturated brine (20 mL×3), dried with anhydrous sodium sulfate, filtered, and the filtrate was concentrated under reduced pressure to remove the solvent, and the obtained residue was separated by column chromatography (eluent: petroleum ether/ethyl acetate=100/0-1/1, v/v), and the obtained compound was slurried with methanol (2 mL) at room temperature to obtain target compound WX005. MS-ESI m/z: 260.0 [M+H]$^+$. $^1$H NMR (400 MHz, DMSO_d$_6$) δ: 10.88 (s, 1H), 7.84 (s, 1H), 7.46 (d, J=9.0 Hz, 1H), 7.10 (d, J=2.5 Hz, 1H), 6.90 (dd, J=2.5, 8.9 Hz, 1H), 4.11 (dd, J=4.9, 11.9 Hz, 1H), 3.77 (s, 3H), 2.81-2.66 (m, 1H), 2.57 (td, J=4.0, 17.3 Hz, 1H), 2.34 (dq, J=4.5, 12.4 Hz, 1H), 2.16-2.05 (m, 1H).

Referring to the synthesis method in Embodiment 5 (i.e., BB-3 of Embodiment 5 was replaced by Fragment 1 in operation), each embodiment in Table 1 is synthesized, and the LCMS and HNMR data are shown in Table 2.

TABLE 1
| Embodiments | Fragment 1 | Fragment 2 | Structure | Compound |
|---|---|---|---|---|
| 6 | 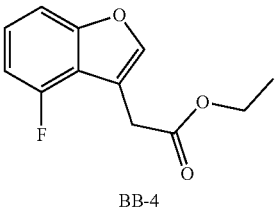 [SMILES: CCOC(=O)Cc1coc2cccc(F)c12 ; "BB-4"]<br>BB-4 | 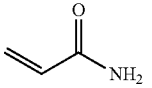 | 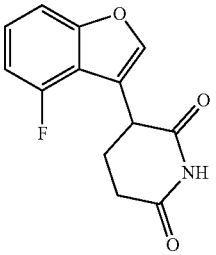 [SMILES: O=C1CCC(c2coc3cccc(F)c23)C(=O)N1] | WX006 |
| 7 | 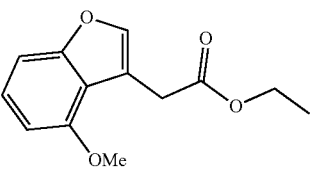<br>BB-5<br>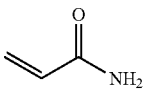<br>BB-5'<br>BB-5/BB-5' = 1/5 | 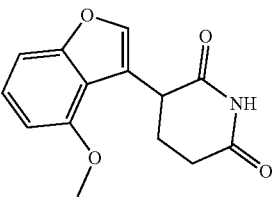 [SMILES: COc1cccc2occ(C3CCC(=O)NC3=O)c12] | 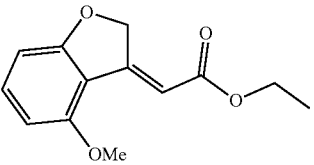 | WX007 |
| 8 | 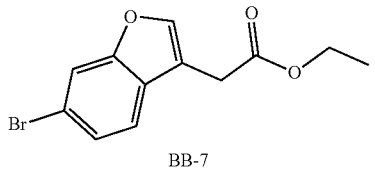<br>BB-7 | 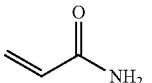 | 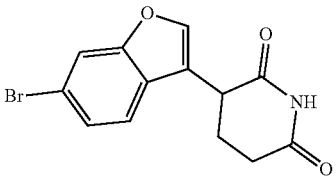 [SMILES: O=C1CCC(c2coc3cc(Br)ccc23)C(=O)N1] | WX008 |
| 9 | 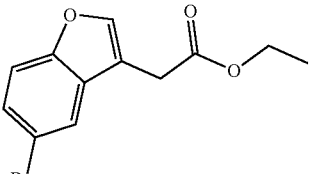<br>BB-8 | 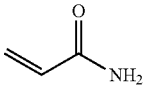 | 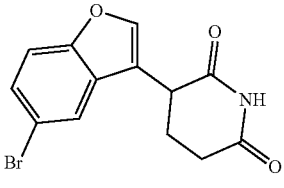 [SMILES: O=C1CCC(c2coc3ccc(Br)cc23)C(=O)N1] | WX009 |
| 10 | 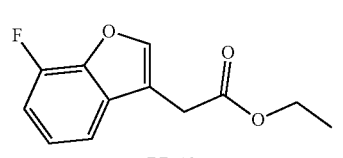<br>BB-10 | 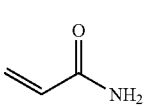 | 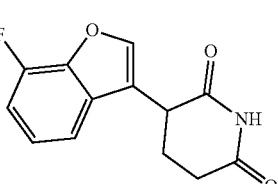 | WX010 |
| 11 | 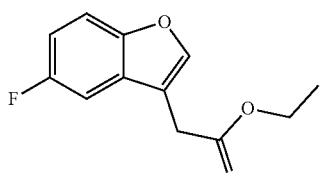<br>BB-11 | 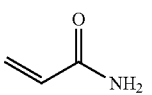 | 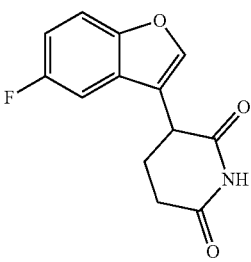 | WX011 |

TABLE 1-continued

| Embodiments | Fragment 1 | Fragment 2 | Structure | Compound |
|---|---|---|---|---|
| 12 | 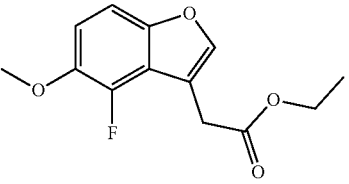<br>BB-12 | 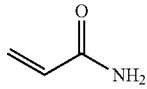 | 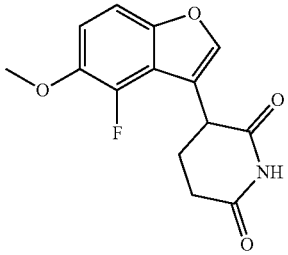 [SMILES: COc1ccc2occ(C3CCC(=O)NC3=O)c2c1F] | WX012 |

TABLE 2

| Embodiments | Compound | HNMR | LCMS |
|---|---|---|---|
| 6 | WX006 | $^1$H NMR (400 MHZ, DMSO_$d_6$) δ: 10.93 (s, 1H), 7.96 (s, 1H), 7.47 (d, J = 8.4 Hz, 1H), 7.34 (td, J = 5.2, 8.4 Hz, 1H), 7.06 (dd, J = 8.0, 10.4 Hz, 1H), 4.16 (dd, J = 5.4, 12.6 Hz, 1H), 2.86-2.72 (m, 1H), 2.63-2.55 (m, 1H), 2.28-2.15 (m, 1H), 2.14-2.04 (m, 1H). | MS-ESI m/z: 248.0 [M + H]$^+$. |
| 7 | WX007 | $^1$H NMR (400 MHZ, DMSO_$d_6$) δ: 10.82 (s, 1H), 7.79 (s, 1H), 7.30-7.21 (m, 1H), 7.19-7.13 (m, 1H), 6.77 (d, J = 7.8 Hz, 1H), 4.05 (dd, J = 5.0, 12.2 Hz, 1H), 3.79 (s, 3H), 2.84-2.63 (m, 1H), 2.58-2.53 (m, 1H), 2.35-2.20 (m, 1H), 2.04-1.92 (m, 1H). | MS-ESI m/z: 260.0 [M + H]$^+$. |
| 8 | WX008 | $^1$H NMR (400 MHZ, DMSO_$d_6$) δ: 10.92 (s, 1H), 7.95 (s, 1H), 7.90 (d, J = 1.6 Hz, 1H), 7.58 (d, J = 8.4 Hz, 1H), 7.43 (dd, J = 1.4, 8.2 Hz, 1H), 4.16 (dd, J = 4.8, 12.4 Hz, 1H), 2.81-2.67 (m, 1H), 2.63-2.54 (m, 1H), 2.32 (qd, J = 4.6, 12.8 Hz, 1H), 2.17-2.06 (m, 1H). | MS-ESI m/z: 308.0 [M + H]$^+$. 310.0 [M + H + 2]$^+$. |
| 9 | WX009 | $^1$H NMR (400 MHZ, DMSO_$d_6$) δ: 10.89 (s, 1H), 7.97 (s, 1H), 7.85 (d, J = 1.6 Hz, 1H), 7.57 (d, J = 8.8 Hz, 1H), 7.46 (dd, J = 1.6, 8.8 Hz, 1H), 4.15 (dd, J = 4.8, 12.4 Hz, 1H), 2.78-2.66 (m, 1H), 2.59 (m, 1H), 2.42-2.30 (m,1H), 2.13-2.04 (m, 1H). | MS-ESI m/z: 307.9 [M + H]$^+$. 309.9 [M + H + 2]$^+$. |
| 10 | WX010 | $^1$H NMR (400 MHZ, DMSO_$d_6$) δ: 10.93 (s, 1H), 8.02 (s, 1H), 7.49-7.36 (m, 1H), 7.27-7.15 (m, 2H), 4.19 (dd, J = 4.8, 12.3 Hz, 1H), 2.84-2.70 (m, 1H), 2.70-2.58 (m, 1H), 2.37-2.31 (m, 1H), 2.18-2.02 (m, 1H). | MS-ESI m/z: 248.0 [M + H]$^+$. |
| 11 | WX011 | $^1$H NMR (400 MHZ, DMSO_$d_6$) δ: 10.96 (s, 1H), 8.04 (s, 1H), 7.67 (dd, J = 4.2, 9.0 Hz, 1H), 7.50 (dd, J = 2.8, 9.0 Hz, 1H), 7.22 (td, J = 2.4, 9.2 Hz, 1H), 4.19 (dd, J = 5.0, 12.2 Hz, 1H), 2.85-2.73 (m, 1H), 2.69-2.60 (m, 1H), 2.48-2.34 (m, 1H), 2.21-2.11 (m, 1H). | MS-ESI m/z: 248.0 [M + H]$^+$. |
| 12 | WX012 | $^1$H NMR (400 MHZ, DMSO_$d_6$) δ: 10.91 (s, 1H), 7.90 (s, 1H), 7.38 (d, J = 8.8 Hz, 1H), 7.20 (t, J = 8.7 Hz, 1H), 4.13 (dd, J = 5.0, 12.5 Hz, 1H), 3.85 (s, 3H), 2.85-2.72 (m, 1H), 2.58 (br d, J = 17.1 Hz, 1H), 2.26-2.12 (m, 1H), 2.11-2.03 (m, 1H). | MS-ESI m/z: 278.0 [M + H]$^+$. |

Embodiment 13: WX013

Synthetic Route:

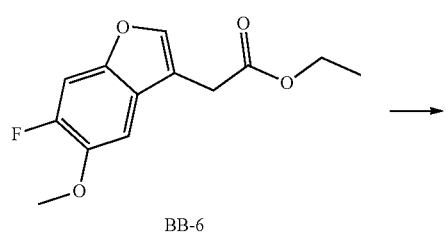

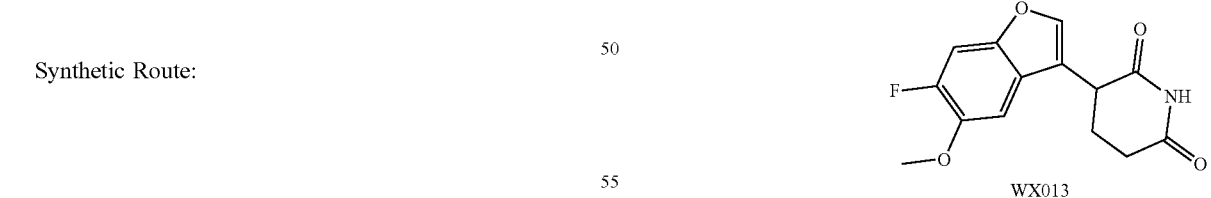

Compound BB-6 (200 mg, 792.90 μmol) was added to tetrahydrofuran (5 mL) at room temperature, then potassium tert-butoxide (88.97 mg, 792.90 μmol) and acrylamide (56.36 mg, 792.90 μmol) were added, and the reaction mixture was stirred at room temperature for 2 hours. After the reaction was completed, water (5 mL) and ethyl acetate (10 mL) were added to the reaction system to dilute, and the phases were separated, then the organic phases were collected, and the aqueous phase was extracted with ethyl acetate (10 mL×2). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-1/1, v/v), and the obtained crude product was slurried with 2 mL of methanol at room temperature to obtain target compound WX013. MS-ESI m/z: 278.0 [M+H]$^+$. $^1$H NMR (400 MHz, DMSO-$d_6$) δ: 10.89 (s, 1H), 7.87 (s, 1H), 7.59 (d, J=10.8 Hz, 1H), 7.32 (d, J=8.4 Hz, 1H), 4.13 (dd, J=4.8, 12.0 Hz, 1H), 3.85 (s, 3H), 2.79-2.65 (m, 1H), 2.63-2.54 (m, 1H), 2.40-2.32 (m, 1H), 2.14-2.05 (m, 1H).

Embodiment 14 and Embodiment 15: WX014 and WX015

Synthetic Route:

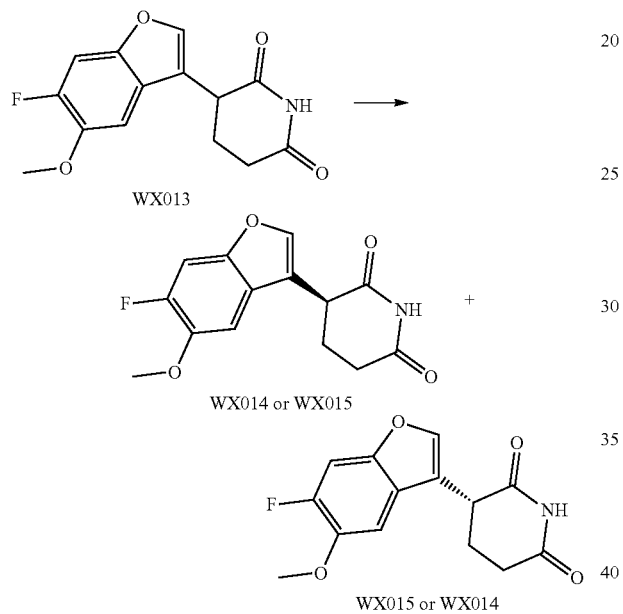

Compound WX013 (0.95 g, 3.43 mmol) was separated by supercritical fluid chromatography (separation conditions, chromatographic column: DAICEL CHIRALCEL OJ-H (250 mm*30 mm, 5 μm), mobile phase: A: carbon dioxide; B: methanol, 40%; column temperature: 40° C.; wavelength: 220 nm), the sample with a retention time of 3.298 min was collected to obtain WX014 (ee %: 99.58%) and the sample with a retention time of 3.519 min was collected to obtain WX015 (ee %: 98.62%).

Embodiment 16 and Embodiment 17: WX016 and WX017

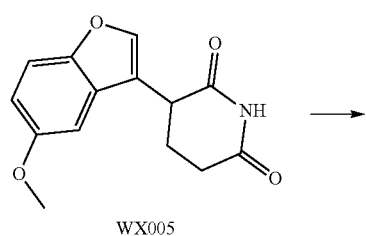

WX005

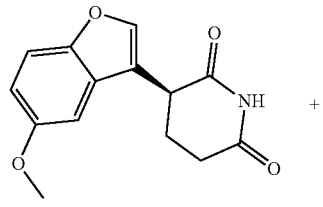

WX016 or WX017

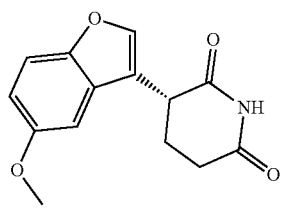

WX017 or WX016

Compound WX005 (0.200 g, 771.44 μmol) was separated by supercritical fluid chromatography (separation conditions, chromatographic column: Chiralcel OD-3 150 mm*4.6 mm I.D., 5 μm; mobile phase: A: carbon dioxide; B: ethanol, 40%; column temperature: 40° C.; wavelength: 220 nm), and the sample with a retention time of 5.135 min was collected, and then separated by preparative HPLC (mobile phase: acetonitrile/water; acidic system: 0.05% HCl) to obtain WX016 (ee %: 96.98%) with retention time of 5.151 min; the sample with a retention time of 5.695 min was collected and separated by preparative HPLC (mobile phase: acetonitrile/water; acidic system: 0.05% HCl) to obtain WX017 (ee %: 97.22%) with retention time of 5.762 min.

Embodiment 18: WX018

Synthetic Route:

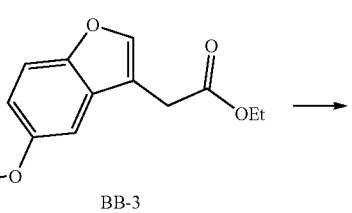

BB-3

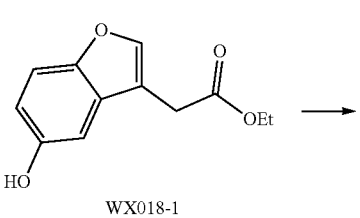

WX018-1

-continued

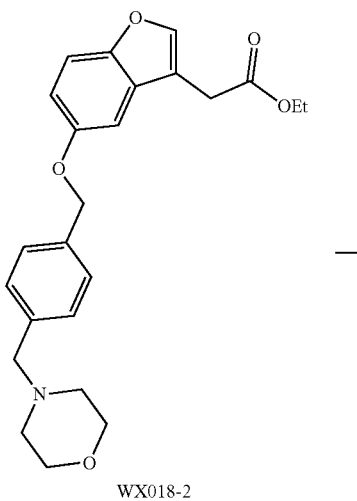

WX018-2

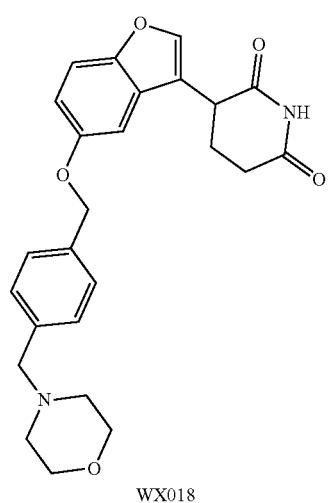

WX018

Step 1: Synthesis of Compound WX018-1

A dichloromethane (80 mL) solution of compound BB-3 (4.00 g, 17.08 mmol) was added a dichloromethane (20 mL) solution of boron tribromide (25.67 g, 102.46 mmol, 9.87 mL) under the protection of nitrogen at −78° C., and the reaction mixture was raised to room temperature and reacted with stirring for 3 hours. After the reaction was completed, water (100 mL) was added to quench, and extracted with dichloromethane (100 mL×3). The organic phases were combined, washed with saturated brine (80 mL×2), dried with anhydrous sodium sulfate, filtered, and the filtrate was concentrated under reduced pressure to remove the solvent, and the obtained residue was separated by column chromatography (eluent: petroleum ether/ethyl acetate=10/1-4/1, v/v) to obtain compound WX018-1. MS-ESI m/z: 221.0 [M+H]$^+$. $^1$H NMR (400 MHz, CDCl$_3$) δ: 7.59 (s, 1H), 7.32 (d, J=8.8 Hz, 1H), 6.98 (d, J=2.8 Hz, 1H), 6.82 (dd, J=2.4, 8.8 Hz, 1H), 4.20 (q, J=7.2 Hz, 2H), 3.64 (s, 2H), 1.27 (t, J=3.6 Hz, 3H).

Step 2: Synthesis of Compound WX018-2

Compound WX018-1 (0.2 g, 908.18 μmol), [4-(morpholinomethyl)phenyl]methanol (376.47 mg, 1.82 mmol) and triphenylphosphine (524.05 mg, 2.00 mmol) were sequentially added to a tetrahydrofuran (20 mL) solution of diethyl azodicarboxylate (347.97 mg, 2.00 mmol, 363.23 μL) at 70° C. under the protection of nitrogen, and the reaction mixture was reacted with stirring at 70° C. for 2 hours. After the reaction was completed, the mixture was cooled to room temperature, diluted with water (100 mL), and extracted with dichloromethane (50 mL×3). The organic phases were combined, washed with water (50 mL×3), dried with anhydrous sodium sulfate, filtered, and the filtrate was concentrated under reduced pressure to remove the solvent, and the obtained residue was separated by column chromatography (eluent: petroleum ether/ethyl acetate=10/1— 3/1, v/v) to obtain compound WX018-2. MS-ESI m/z: 410.2 [M+H]$^+$. $^1$H NMR (400 MHz, CDCl$_3$) δ: 7.53 (s, 1H), 7.35 (d, J=8.0 Hz, 2H), 7.32-7.25 (m, 3H), 7.04 (d, J=2.4 Hz, 1H), 6.91 (dd, J=2.4, 8.8 Hz, 1H), 5.01 (s, 2H), 4.11 (q, J=7.2 Hz, 2H), 3.64 (t, J=4.6 Hz, 4H), 3.58 (s, 2H), 3.44 (s, 2H), 2.39 (s, 4H), 1.20 (t, J=7.2 Hz, 3H).

Step 3: Synthesis of Compound WX018

Compound WX018-2 (0.22 g, 537.27 μmol) was dissolved in N,N-dimethylformamide (5 mL) at 0° C., then potassium tert-butoxide (60.29 mg, 537.27 μmol) was added, and the reaction mixture was reacted with stirring at 0° C. for 1 hour, then acrylamide (38.19 mg, 537.27 mmol) was added, and the reaction mixture was raised to room temperature and reacted with stirring for 2 hours. After the reaction was completed, water (50 mL) was added to dilute, and the mixture was extracted with ethyl acetate (30 mL×3). The organic phases were combined, washed with saturated brine (30 mL×2), dried with anhydrous sodium sulfate, filtered, and the filtrate was concentrated under reduced pressure to remove the solvent, and the obtained residue was separated by preparative HPLC (eluent: acetonitrile/water; acidic system: 0.05% HCl) to obtain target compound WX018. MS-ESI m/z: 435.0[M+H]$^+$. $^1$H NMR (400 MHz, DMSO_d$_6$) δ: 10.89 (s, 1H), 7.85 (s, 1H), 7.48 (d, J=8.8 Hz, 1H), 7.43 (d, J=8.0 Hz, 2H), 7.33 (d, J=8.0 Hz, 2H), 7.22 (d, J=2.4 Hz, 1H), 6.98 (dd, J=2.4, 8.8 Hz, 1H), 5.08 (s, 2H), 4.11 (dd, J=4.8, 12.0 Hz, 1H), 3.59-3.55 (m, 4H), 3.46 (s, 2H), 2.80-2.65 (m, 1H), 2.61-2.56 (m, 1H), 2.37-2.32 (m, 4H), 2.16-2.02 (m, 2H).

Referring to the synthesis method in Embodiment 18, each embodiment in Table 3 is synthesized, and the LCMS and HNMR data are shown in Table 4.

TABLE 3

| Embodiments | Fragment 1 | Fragment 2 | Structure | Compound |
|---|---|---|---|---|
| 19 | WX018-1 | | 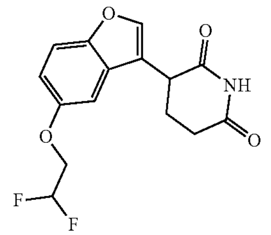 [SMILES: O=C1CCC(c2coc3ccc(OCC(F)F)cc23)C(=O)N1] | WX019 |
| 20 | WX018-1 | | 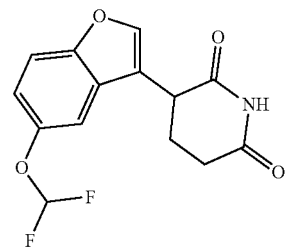 [SMILES: O=C1CCC(c2coc3ccc(OC(F)F)cc23)C(=O)N1] | WX020 |

TABLE 4

| Embodiments | Compound | HNMR | LCMS |
|---|---|---|---|
| 19 | WX019 | $^1$H NMR (400 MHZ, DMSO_d6) δ: 10.89 (s, 1H), 7.88 (s, 1H), 7.51 (d, J = 8.8 Hz, 1H), 7.23 (d, J = 2.4 Hz, 1H), 6.99 (dd, J = 2.4, 8.8 Hz, 1H), 6.58-6.19 (m, 1H), 4.40-4.23 (m, 2H), 4.11 (dd, J = 4.8, 12.0 Hz, 1H), 2.79-2.67 (m, 1H), 2.62-2.56 (m, 1H), 2.43-2.32 (m, 1H), 2.14-2.03 (m, 1H). | MS-ESI m/z: 310.0 [M + H]$^+$. |
| 20 | WX020 | $^1$H NMR (400 MHZ, DMSO_d$_6$) δ: 10.92 (s, 1H), 7.99 (s, 1H), 7.64 (d, J = 8.8 Hz, 1H), 7.45 (d, J = 2.0 Hz, 1H), 7.38-6.95 (m, 2H), 4.16 (dd, J = 4.6, 12.2 Hz, 1H), 2.81-2.67 (m, 1H), 2.63-2.55 (m, 1H), 2.36 (qd, J = 4.6, 12.2 Hz, 1H), 2.16-2.04 (m, 1H). | MS-ESI m/z: 296.0 [M + H]$^+$. |

Embodiment 21: WX021

Synthetic Route:

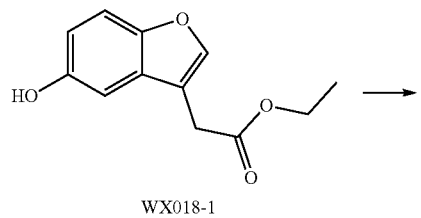

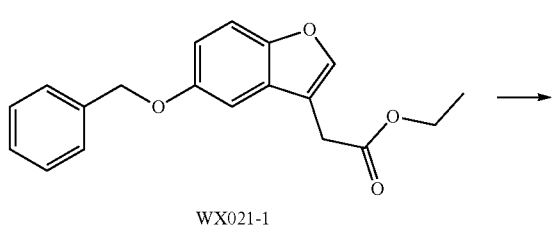

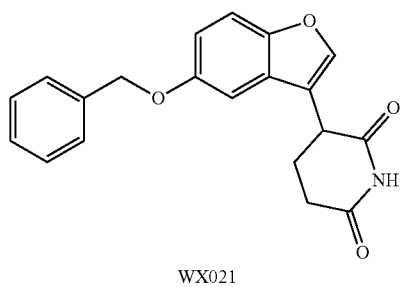

Step 1: Synthesis of Compound WX021-1

Compound WX018-1 (0.2 g, 908.18 μmol) was dissolved in N,N-dimethylformamide (5 mL) under the protection of nitrogen at room temperature, then potassium carbonate (376.55 mg, 2.72 mmol) was added. After the reaction mixture was reacted with stirring at room temperature for 1 hour, benzyl bromide (232.99 mg, 1.36 mmol, 161.80 μL) was added, and the reaction mixture was continued to react with stirring at room temperature for 10 hours. After the reaction was completed, the obtained residue was added with water (50 mL), and extracted with ethyl acetate (30 mL×3). The organic phases were combined, washed with saturated brine (30 mL×2), dried with anhydrous sodium sulfate, filtered, and the filtrate was concentrated under reduced pressure to remove the solvent, and the obtained residue was separated by column chromatography (eluent: petroleum ether/ethyl acetate=50/1-10/1 v/v) to obtain compound WX021-1. MS-ESI m/z: 311.0 [M+H]$^+$. $^1$H NMR (400 MHz, CDCl$_3$) δ: 7.53 (s, 1H), 7.39 (d, J=7.2 Hz, 2H), 7.35-7.23 (m, 4H), 7.03 (d, J=2.4 Hz, 1H), 6.91 (dd, J=2.6, 9.0 Hz, 1H), 5.03 (s, 2H), 4.10 (q, J=6.8 Hz, 2H), 3.58 (s, 2H), 1.19 (t, J=7.2 Hz, 3H).

Step 2: Synthesis of Compound WX021

Compound WX021-1 (0.1 g, 322.22 μmol) was dissolved in N,N-dimethylformamide (5 mL) at 0° C., then potassium tert-butoxide (36.16 mg, 322.22 μmol) was added, and the reaction mixture was stirred at 0° C. for 1 hour. Then, acrylamide (22.90 mg, 322.22 μmol) was added to the above reaction solution, and the reaction mixture was raised to room temperature and continued to react with stirring for 2 hours. After the reaction was completed, water (50 mL) was added to dilute, and the mixture was extracted with ethyl acetate (30 mL×3). The organic phases were combined, washed with saturated brine (30 mL×2), dried with anhydrous sodium sulfate, filtered, and the filtrate was concentrated under reduced pressure to remove the solvent, and the obtained residue was separated by preparative HPLC (mobile phase: acetonitrile/water; acidic system: 0.05% HCl) to obtain target compound WX021. MS-ESI m/z: 336.0 [M+H]$^+$. $^1$H NMR (400 MHz, DMSO_d$_6$) δ: 10.89 (s, 1H), 7.86 (s, 1H), 7.48 (d, J=8.4 Hz, 3H), 7.40 (t, J=7.4 Hz, 2H), 7.37-7.30 (m, 1H), 7.23 (d, J=2.0 Hz, 1H), 6.99 (dd, J=2.2, 9.0 Hz, 1H), 5.15-5.05 (m, 2H), 4.11 (dd, J=4.8, 12.0 Hz, 1H), 2.83-2.67 (m, 1H), 2.61-2.57 (m, 1H), 2.41-2.28 (m, 1H), 2.17-2.02 (m, 1H).

Referring to the synthesis method in Embodiment 21, each embodiment in Table 5 is synthesized, and the LCMS and HNMR data are shown in Table 6.

TABLE 5

| Embodiments | Fragment 1 | Fragment 2 | Structure | Compound |
|---|---|---|---|---|
| 22 | WX018-1 | cyclopentyl-Br | 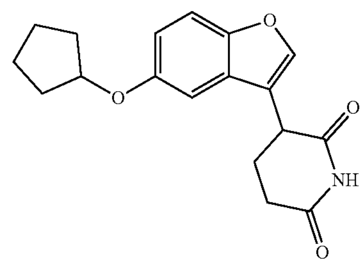 [SMILES: O=C1CCC(c2coc3ccc(OC4CCCC4)cc23)C(=O)N1] | WX022 |
| 23 | WX018-1 | triflate ester | 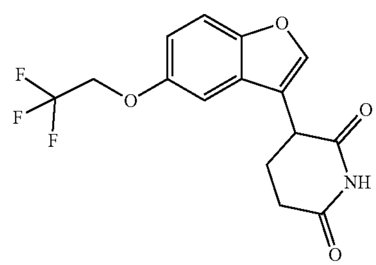 [SMILES: O=C1CCC(c2coc3ccc(OCC(F)(F)F)cc23)C(=O)N1] | WX023 |
| 24 | WX018-1 | ethyl iodide | 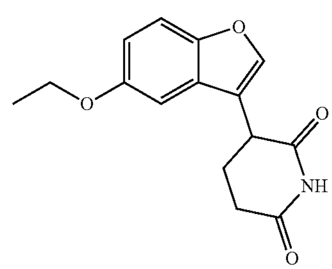 [SMILES: CCOc1ccc2occ(C3CCC(=O)NC3=O)c2c1] | WX024 |
| 25 | WX018-1 | 1-fluoro-3-iodopropane | 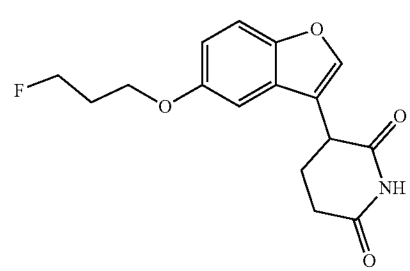 [SMILES: O=C1CCC(c2coc3ccc(OCCCF)cc23)C(=O)N1] | WX025 |

TABLE 5-continued

| Embodiments | Fragment 1 | Fragment 2 | Structure | Compound |
|---|---|---|---|---|
| 26 | 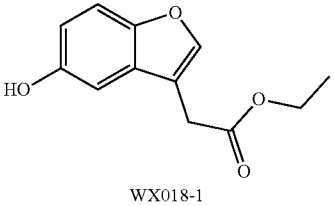 WX018-1 |  | 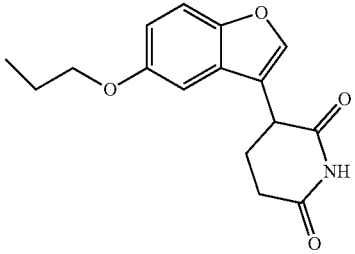 [SMILES: CCCOc1ccc2occ(C3CCC(=O)NC3=O)c2c1] | WX026 |

TABLE 6

| Embodiments | Compound | HNMR | LCMS |
|---|---|---|---|
| 22 | WX022 | $^1$H NMR (400 MHZ, DMSO_$d_6$) δ: 10.88 (s, 1H), 7.83 (s, 1H), 7.44 (d, J = 8.8 Hz, 1H), 7.06 (d, J = 2.4 Hz, 1H), 6.87 (dd, J = 2.6, 9.0 Hz, 1H), 4.82 (t, J = 5.8 Hz, 1H), 4.11 (dd, J = 4.8, 7.6 Hz, 1H), 2.78-2.67 (m, 1H), 2.63-2.55 (m, 1H), 2.38-2.28 (m, 1H), 2.14-2.07 (m, 1H), 1.96-1.84 (m, 2H), 1.78-1.67 (m, 4H), 1.63-1.51 (m, 2H). | MS-ESI m/z: 314.0 [M + H]$^+$. |
| 23 | WX023 | $^1$H NMR (400 MHZ, DMSO_$d_6$) δ: 10.90 (s, 1H), 7.90 (s, 1H), 7.53 (d, J = 8.8 Hz, 1H), 7.29 (d, J = 1.6 Hz, 1H), 7.03 (dd, J = 2.0, 9.2 Hz, 1H), 4.86-4.67 (m, 2H), 4.10 (dd, J = 14.6, 12.2 Hz, 1H), 2.81-2.67 (m, 1H), 2.64-2.55 (m, 1H), 2.45-2.38 (m, 1H), 2.17-2.00 (m, 1H). | MS-ESI m/z: 328.0 [M + H]$^+$. |
| 24 | WX024 | $^1$H NMR (400 MHZ, CDCl$_3$) δ: 7.94 (s, 1H), 7.47 (s, 1H), 7.32 (d, J = 9.6 Hz, 1H), 6.89-6.82 (m, 2H), 3.99 (q, J = 7.0 Hz, 2H), 3.90 (t, J = 7.4 Hz, 1H), 2.78-2.58 (m, 2H), 2.36-2.24 (m, 2H), 1.36 (t, J = 7.0 Hz, 3H). | MS-ESI m/z: 274.1 [M + H]$^+$. |
| 25 | WX025 | $^1$H NMR (400 MHZ, DMSO_$d_6$) δ: 10.88 (s, 1H), 7.85 (s, 1H), 7.47 (d, J = 8.8 Hz, 1H), 7.14 (d, J = 2.8 Hz, 1H), 6.93 (dd, J = 2.6, 9.0 Hz, 1H), 4.69 (t, J = 6.0 Hz, 1H), 4.58 (t, J = 6.0 Hz, 1H), 4.18-4.04 (m, 3H), 2.79-2.65(m, 1H), 2.62-2.55 (m, 1H), 2.39-2.32 (m, 1H), 2.19-2.06 (m, 3H). | MS-ESI m/z: 306.0 [M + H]$^+$. |
| 26 | WX026 | $^1$H NMR (400 MHZ, DMSO_$d_6$) δ: 10.88 (s, 1H), 7.84 (s, 1H), 7.46 (d, J = 8.8 Hz, 1H), 7.09 (d, J = 2.4Hz, 1H), 6.90 (dd, J = 2.6, 9.0 Hz, 1H), 4.11 (dd, J = 4.8, 12.0 Hz, 1H), 4.01-3.88 (m, 2H), 2.78-2.67 (m, 1H), 2.64-2.55 (m, 1H), 2.40-2.29 (m, 1H), 2.18-2.05 (m, 1H), 1.82-1.68 (m, 2H), 1.00 (t, J = 7.4 Hz, 3H). | MS-ESI m/z: 288.0 [M + H]$^+$. |

Embodiment 27: WX027

Synthetic Route:

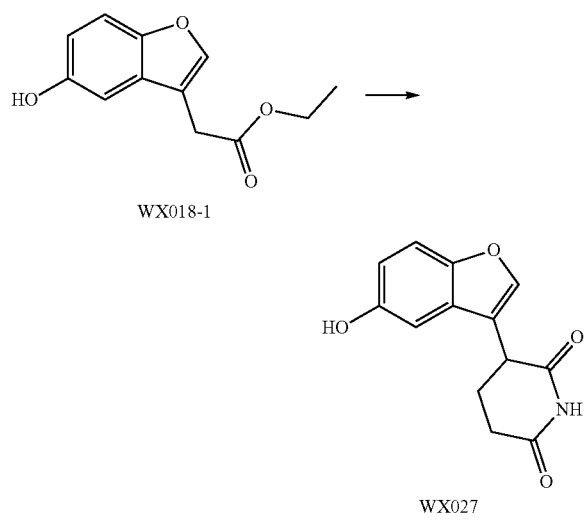

Compound WX018-1 (0.1 g, 454.09 μmol) was dissolved in N,N-dimethylformamide (5 mL) under the protection of nitrogen at 0° C., and potassium tert-butoxide (50.95 mg, 454.09 μmol) was added, then the reaction mixture was reacted with stirring at 0° C. for 1 hour. Then, acrylamide (32.28 mg, 454.09 μmol) was added to the above reaction solution, and the reaction mixture was raised to room temperature and the reaction was continued to react with stirring for 2 hours. After the reaction was completed, water (50 mL) was added to dilute, and the mixture was extracted with ethyl acetate (30 mL×3). The organic phases were combined, washed with saturated brine (30 mL×2), dried with anhydrous sodium sulfate, filtered, and the filtrate was concentrated under reduced pressure to remove the solvent, and the obtained residue was separated by preparative HPLC (mobile phase: acetonitrile/water; acidic system: 0.05% HCl) to obtain target compound WX027. MS-ESI m/z: 246.0 [M+H]$^+$. $^1$H NMR (400 MHz, DMSO_$d_6$) δ: 10.90 (s, 1H), 9.17 (s, 1H), 7.79 (s, 1H), 7.35 (d, J=8.8 Hz, 1H), 6.84 (d, J=2.4 Hz, 1H), 6.75 (dd, J=2.4, 8.8 Hz, 1H), 4.06 (dd, J=5.0, 11.8 Hz, 1H), 2.79-2.69 (m, 1H), 2.62-2.56 (m, 1H), 2.36-2.21 (m, 1H), 2.16-2.03 (m, 1H).

Embodiment 28: WX028

Synthetic Route:

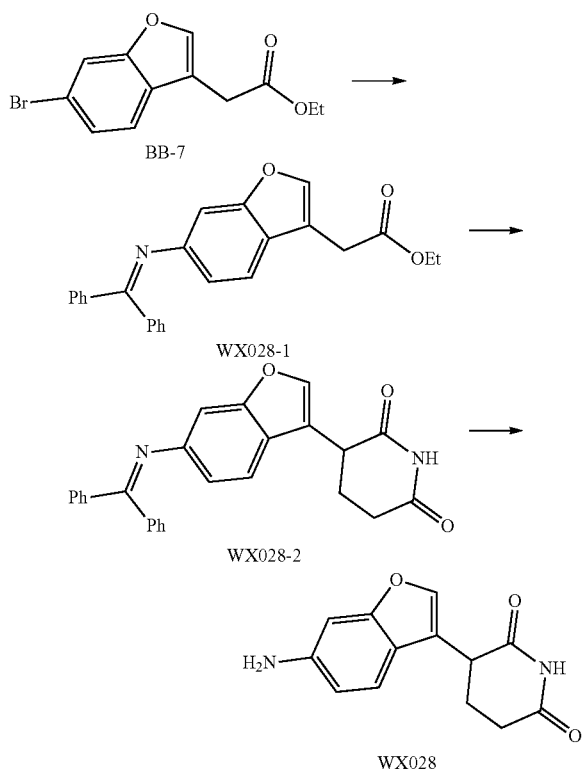

Step 1: Synthesis of Compound WX028-1

Compound BB-7 (0.7 g, 2.47 mmol) and benzophenone imine (492.90 mg, 2.72 mmol) were added to dioxane (5 mL) at room temperature, then tris(dibenzylideneacetone)dipalladium (113.20 mg, 123.62 μmol), 4,5-bis(diphenylphosphino)-9,9-dimethylxanthene (143.06 mg, 247.25 μmol) and cesium carbonate (2.42 g, 7.42 mmol) were sequentially added, and the reaction mixture was heated to 80° C. and reacted with stirring for 3 hours. After the reaction was completed, the mixture was cooled to room temperature, diluted with water (50 mL), and extracted with dichloromethane (30 mL×3). The organic phases were combined, washed with saturated brine (30 mL×2), dried with anhydrous sodium sulfate, filtered, and the filtrate was concentrated under reduced pressure to remove the solvent, and the obtained residue was separated by column chromatography (eluent: petroleum ether/ethyl acetate=1/0-10/1, v/v) to obtain compound WX028-1. MS-ESI m/z: 384.1 [M+H]$^+$. $^1$H NMR (400 MHz, CDCl$_3$) δ: 7.68 (d, J=7.2 Hz, 2H), 7.44-7.37 (m, 2H), 7.37-7.31 (m, 2H), 7.23 (d, J=8.0 Hz, 1H), 7.19-7.12 (m, 3H), 7.09-7.04 (m, 2H), 6.77 (d, J=1.6 Hz, 1H), 6.61 (dd, J=1.8, 8.2 Hz, 1H), 4.09 (q, J=7.0 Hz, 2H), 3.54 (s, 2H), 1.17 (t, J=7.2 Hz, 3H).

Step 2: Synthesis of Compound WX028-2

Compound WX028-1 (475 mg, 607.63 μmol, purity: 49.05%) was added to N,N-dimethylformamide (5 mL) at then potassium tert-butoxide (68.18 mg, 607.63 μmol) was added, and the reaction mixture was reacted with stirring at ° C. for 1 hour, then acrylamide (43.19 mg, 607.63 μmol) was added to the above reaction solution, and the reaction mixture was raised to room temperature and continued to react with stirring for 2 hours. After the reaction was completed, water (50 mL) was added to dilute, and the mixture was extracted with ethyl acetate (30 mL×3). The organic phases were combined, washed with saturated brine (30 mL×2), dried with anhydrous sodium sulfate, filtered, and the filtrate was concentrated under reduced pressure to remove the solvent, and the obtained residue was separated by column chromatography (eluent: petroleum ether/ethyl acetate=5/1— 1/5, v/v) to obtain compound WX028-2. MS-ESI m/z: 409.1 [M+H]$^+$. $^1$H NMR (400 MHz, DMSO_d$_6$) δ: 10.86 (s, 1H), 7.74 (s, 1H), 7.69-7.64 (m, 2H), 7.58-7.52 (m, 1H), 7.51-7.45 (m, 2H), 7.38-7.29 (m, 4H), 7.20 (dd, J=1.8, 7.4 Hz, 2H), 6.88 (d, J=1.6 Hz, 1H), 6.66 (dd, J=1.6, 8.4 Hz, 1H), 4.04 (dd, J=4.8, 12.0 Hz, 1H), 2.72-2.64 (m, 1H), 2.61-2.54 (m, 1H), 2.36-2.20 (m, 1H), 2.13-2.03 (m, 1H).

Step 3: Synthesis of Compound WX028

Compound WX028-2 (248 mg, 457.08 μmol, purity: 75.28%) was added to hydrochloric acid/ethyl acetate (4 M, 5 mL) at room temperature, and the reaction mixture was reacted with stirring at room temperature for 3 hours. After the reaction was completed, the solvent was removed under reduced pressure, and the obtained residue was separated by preparative HPLC (mobile phase: acetonitrile/water; acidic system: 0.05% HCl) to obtain target compound WX028. MS-ESI m/z: 245.0 [M+H]$^+$. $^1$H NMR (400 MHz, DMSO_d$_6$) δ: 10.93 (s, 1H), 10.14 (s, 2H), 7.99 (s, 1H), 7.67 (d, J=8.4 Hz, 1H), 7.58 (d, J=1.2 Hz, 1H), 7.22 (dd, J=1.6, 8.4 Hz, 1H), 4.17 (dd, J=5.0, 12.2 Hz, 1H), 2.82-2.66 (m, 1H), 2.64-2.53 (m, 1H), 2.41-2.27 (m, 1H), 2.19-2.04 (m, 1H).

Embodiment 31: WX031

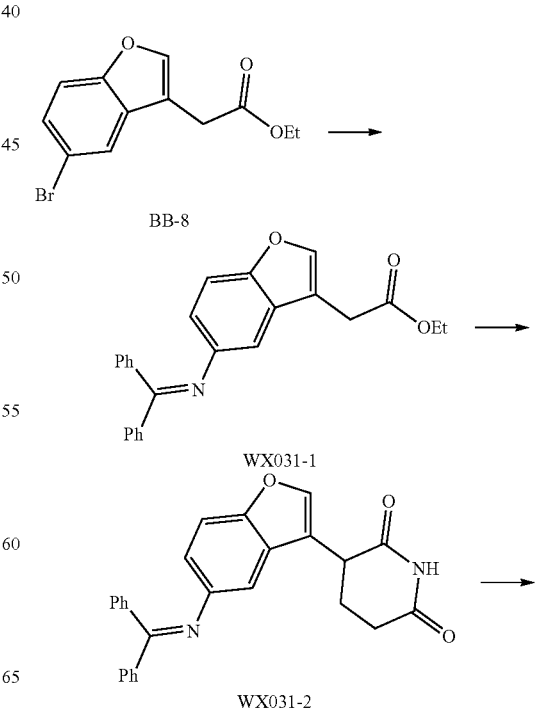

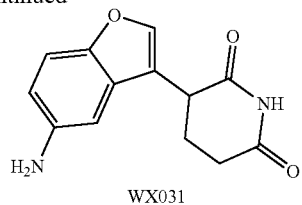

Step 1: Synthesis of Compound WX031-1

Compound BB-8 (500 mg, 1.77 mmol), benzophenone imine (352.07 mg, 1.94 mmol, 325.99 μL) were dissolved in dioxane (5 mL) at room temperature under the protection of nitrogen, and then tris(dibenzylideneacetone)dipalladium (80.86 mg, 88.30 μmol), 4,5-bis(diphenylphosphino)-9,9-dimethylxanthene (102.19 mg, 176.61 μmol) and cesium carbonate (1.73 g, 5.30 mmol) were sequentially added, and the reaction mixture was heated to 80° C. and reacted with stirring for 3 hours. After the reaction was completed, the mixture was cooled to room temperature, diluted with water (50 mL), and extracted with ethyl acetate (30 mL×3). The organic phases were combined, washed with saturated brine (30 mL×2), dried with anhydrous sodium sulfate, filtered, and the filtrate was concentrated under reduced pressure to remove the solvent, and the obtained residue was separated by preparative chromatographic plate (eluent: petroleum ether/ethyl acetate=5/1, v/v) to obtain compound WX031-1. MS-ESI m/z: 383.9 [M+H]$^+$. $^1$H NMR (400 MHz, CDCl$_3$) δ: 7.79-7.71 (m, 2H), 7.56 (s, 1H), 7.51-7.46 (m, 1H), 7.42 (t, J=7.4 Hz, 2H), 7.27-7.19 (m, 4H), 7.16-7.10 (m, 2H), 6.94 (d, J=2.0 Hz, 1H), 6.66 (dd, J=2.0, 8.4 Hz, 1H), 4.15 (q, J=6.8 Hz, 2H), 3.56 (s, 2H), 1.27 (t, J=7.4 Hz, 3H).

Step 2: Synthesis of Compound WX031-2

Compound WX031-1 (350 mg, 304.78 μmol, purity: 33.39%) was added to N,N-dimethylformamide (5 mL) at 0° C., then potassium tert-butoxide (34.20 mg, 304.78 μmol) was added, and the reaction mixture was reacted with stirring at ° C. for 1 hour, then acrylamide (21.66 mg, 304.78 μmol) was added to the above reaction solution, and the reaction mixture was raised to room temperature and continued to react with stirring for 2 hours. After the reaction was completed, the mixture was diluted with water (50 mL), and extracted with ethyl acetate (30 mL×3). The organic phases were combined, washed with saturated brine (30 mL×2), dried with anhydrous sodium sulfate, filtered, and the filtrate was concentrated under reduced pressure to remove the solvent, and the obtained residue was separated by column chromatography (eluent: petroleum ether/ethyl acetate=5/1-1/3, v/v) to obtain compound WX031-2. $^1$H NMR (400 MHz, CDCl$_3$) δ: 7.93 (s, 1H), 7.81-7.75 (m, 2H), 7.53-7.48 (m, 2H), 7.47-7.41 (m, 2H), 7.33-7.29 (m, 2H), 7.28-7.25 (m, 1H), 7.17-7.11 (m, 2H), 6.83 (dd, J=2.0, 8.8 Hz, 1H), 6.78 (d, J=2.0 Hz, 1H), 3.87 (dd, J=5.2, 7.2 Hz, 1H), 2.70-2.57 (m, 2H), 2.23-2.15 (m, 1H), 2.14-2.07 (m, 1H).

Step 3: Synthesis of Compound WX031

Compound WX031-2 (124 mg, 303.59 μmol) was added to hydrochloric acid/ethyl acetate (4 M, 10 mL) at room temperature, and the reaction mixture was reacted with stirring at room temperature for 3 hours. After the reaction was completed, the solvent was removed under reduced pressure, and the obtained residue was separated by preparative HPLC (mobile phase: acetonitrile/water; acidic system: 0.05% HCl), to obtain target compound WX031. MS-ESI m/z: 245.0 [M+H]$^+$. $^1$H NMR (400 MHz, DMSO_d$_6$) δ: 10.97 (s, 1H), 10.34 (s, 2H), 8.05 (s, 1H), 7.72 (d, J=8.8 Hz, 1H), 7.58 (d, J=2.0 Hz, 1H), 7.35 (dd, J=2.2, 8.6 Hz, 1H), 4.20 (dd, J=5.0, 12.2 Hz, 1H), 2.85-2.73 (m, 1H), 2.69-2.57 (m, 1H), 2.36-2.24 (m, 1H), 2.20-2.10 (m, 1H).

Embodiment 32: WX032

Synthetic Route:

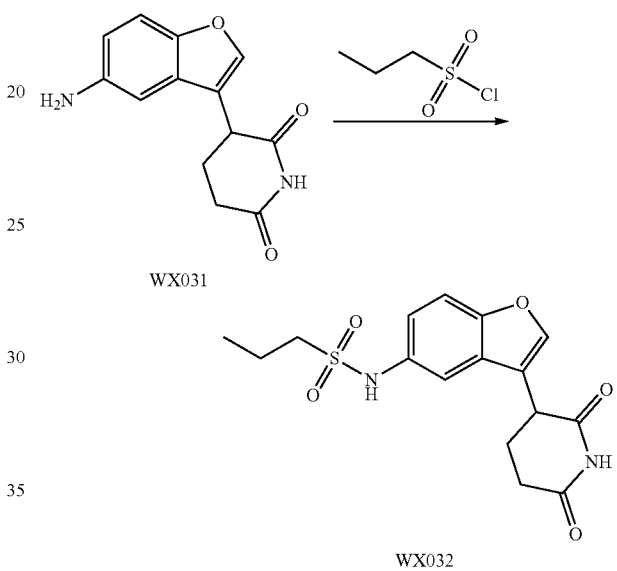

Compound WX031 (200 mg, 818.85 μmol) was dissolved in N,N-dimethylformamide (1 mL) and tetrahydrofuran (3 mL) at room temperature, then triethylamine (165.72 mg, 1.64 mmol, 227.95 μL) and propanesulfonyl chloride (116.77 mg, 818.85 μmol) were sequentially added, and the reaction mixture was reacted with stirring at room temperature for 2 hours. After the reaction was completed, water (10 mL) and ethyl acetate (10 mL) were added, and the phases were separated, then the organic phases were collected, and the aqueous phase was extracted with ethyl acetate (10 mL×2). The organic phases were combined, dried with anhydrous sodium sulfate, filtered, and the filtrate was concentrated under reduced pressure to remove the solvent, and the obtained residue was separated by column chromatography (eluent: petroleum ether/ethyl acetate=100/0-7/3, v/v), and then separated by preparative HPLC (mobile phase: acetonitrile/water; acidic system: 0.05% HCl) to obtain target compound WX032. MS-ESI m/z: 351.0 [M+H]$^+$. $^1$H NMR (400 MHz, DMSO_d$_6$) δ: 10.91 (s, 1H), 9.62 (s, 1H), 7.91 (s, 1H), 7.54 (d, J=8.8 Hz, 1H), 7.40 (d, J=2.0 Hz, 1H), 7.18 (dd, J=2.2, 8.6 Hz, 1H), 4.13 (dd, J=5.2, 12.0 Hz, 1H), 3.02-2.92 (m, 2H), 2.83-2.71 (m, 1H), 2.69-2.55 (m, 1H), 2.35-2.08 (m, 2H), 1.75-1.61 (m, 2H), 0.92 (t, J=7.6 Hz, 3H).

Referring to the synthesis method in Embodiment 32, each embodiment in Table 7 is synthesized, and the LCMS and HNMR data are shown in Table 8.

TABLE 7

| Embodiments | Fragment 1 | Fragment 2 | Structure | Compound |
|---|---|---|---|---|
| 33 | | | 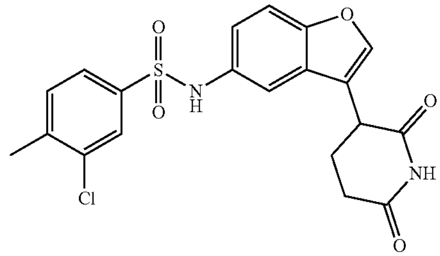 [SMILES: Cc1ccc(S(=O)(=O)Nc2ccc3occ(C4CCC(=O)NC4=O)c3c2)cc1Cl] | WX033 |
| 34 | | | 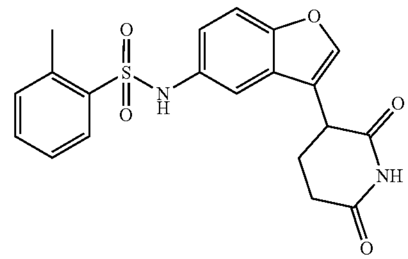 [SMILES: Cc1ccccc1S(=O)(=O)Nc1ccc2occ(C3CCC(=O)NC3=O)c2c1] | WX034 |
| 35 | | | 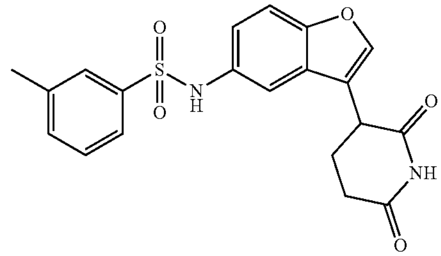 [SMILES: Cc1cccc(S(=O)(=O)Nc2ccc3occ(C4CCC(=O)NC4=O)c3c2)c1] | WX035 |
| 36 | | | 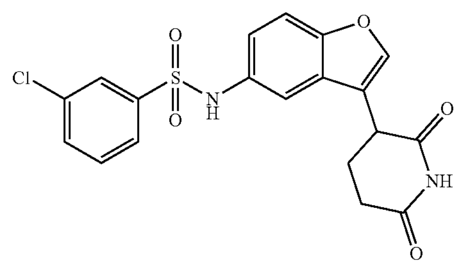 [SMILES: O=C1CCC(c2coc3ccc(NS(=O)(=O)c4cccc(Cl)c4)cc23)C(=O)N1] | WX036 |
| 37 | | | 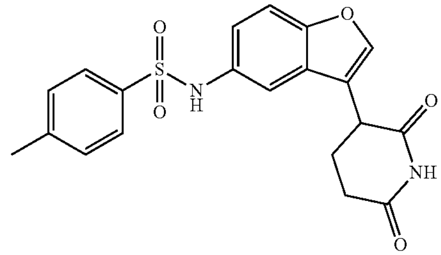 [SMILES: Cc1ccc(S(=O)(=O)Nc2ccc3occ(C4CCC(=O)NC4=O)c3c2)cc1] | WX037 |

TABLE 8

| Embodiments | Compound | HNMR | LCMS |
|---|---|---|---|
| 33 | WX033 | $^1$H NMR (400 MHZ, DMSO_d$_6$) δ: 10.94 (s, 1H), 10.17 (s, 1H), 7.89 (s, 1H), 7.70 (d, J = 1.6 Hz, 1H), 7.56-7.44 (m, 3H), 7.26 (d, J = 2.0 Hz, 1H), 6.97 (dd, J = 2.0, 8.8 Hz, 1H), 4.10 (dd, J = 5.4, 11.4 Hz, 1H), 2.83-2.71 (m, 1H), 2.62-2.55 (m, 1H), 2.35 (s, 3H), 2.21-2.04 (m, 2H). | MS-ESI m/z: 450.2 [M + H$_2$O]$^+$. |

TABLE 8-continued

| Embodiments | Compound | HNMR | LCMS |
|---|---|---|---|
| 34 | WX034 | $^1$H NMR (400 MHZ, MeOD_$d_4$) δ: 7.84 (d, J = 8.0 Hz, 1H), 7.68 (s, 1H), 7.46-7.40 (m, 1H), 7.35-7.29 (m, 2H), 7.25 (t, J = 7.8 Hz, 1H), 7.13 (d, J = 2.0 Hz, 1H), 6.99 (dd, J = 2.4, 8.8 Hz, 1H), 4.02 (t, J = 8.4 Hz, 1H), 2.82-2.64 (m, 2H), 2.61 (s, 3H), 2.18-2.10 (m, 2H). | MS-ESI m/z: 416.1 [M + $H_2O$]$^+$. |
| 35 | WX035 | $^1$H NMR (400 MHZ, MeOD_$d_4$) δ: 7.70 (s, 1H), 7.53 (s, 1H), 7.48 (d, J = 7.6 Hz, 1H), 7.39-7.29 (m, 3H), 7.20 (d, J = 2.0 Hz, 1H), 6.99 (dd, J = 2.0, 8.8 Hz, 1H), 4.08-4.01 (m, 1H), 2.84-2.64 (m, 2H), 2.33 (s, 3H), 2.24-2.15 (m, 2H). | MS-ESI m/z: 416.1 [M + $H_2O$]$^+$. |
| 36 | WX036 | $^1$H NMR (400 MHZ, DMSO_$d_6$) δ: 10.92 (s, 1H), 10.21 (s, 1H), 7.88 (s, 1H), 7.73-7.68 (m, 2H), 7.60 (d, J = 1.6 Hz, 1H), 7.56-7.54 (m, 1H), 7.47-7.45 (m, 1H), 7.25 (s, 1H), 6.98-6.94 (m, 1H), 4.09 (dd, J = 5.2, 11.6 Hz, 1H), 2.80-2.55 (m, 2H), 2.11-2.05 (m, 2H). | MS-ESI m/z: 436.1 [M + $H_2O$]$^+$, 438.1 [M + $H_2O$ + 2]$^+$. |
| 37 | WX037 | $^1$H NMR (400 MHZ, DMSO_$d_6$) δ: 10.94 (s, 1H), 10.05 (s, 1H), 7.87 (s, 1H), 7.60 (d, J = 8.4 Hz, 2H), 7.43 (d, J = 8.8 Hz, 1H), 7.26-6.96 (m, 3H), 6.97 (d, J = 8.8 Hz, 1H), 4.08 (dd, J = 5.6, 11.2 Hz, 1H), 2.77-2.60 (m, 2H), 2.32 (s, 3H), 2.11-2.08 (m, 2H). | MS-ESI m/z: 416.1 [M + $H_2O$]$^+$. |

Embodiment 38: WX038

Synthetic Route:

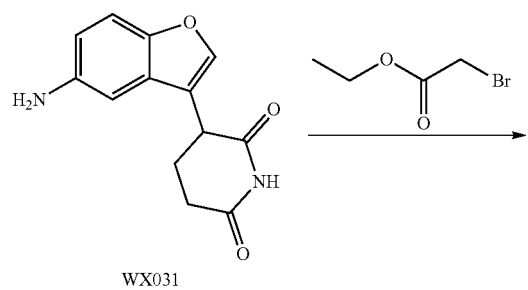

WX031

WX038

Compound WX031 (201.00 mg, 716.05 μmol, hydrochloride) and ethyl 2-bromoacetate (119.58 mg, 716.05 μmol, 79.19 μL) were dissolved in acetonitrile (5 mL) under the protection of nitrogen at room temperature, then N,N-diisopropylethylamine (185.08 mg, 1.43 mmol, 249.44 μL) was added, and the reaction mixture was heated to 60° C. and reacted with stirring for 14 hours. After the reaction was completed, the mixture was cooled to room temperature, and water (30 mL) was added, and the mixture was extracted with ethyl acetate (30 mL×3). The organic phases were combined, washed with saturated brine (50 mL×2), dried with anhydrous sodium sulfate, filtered, and the filtrate was concentrated under reduced pressure to remove the solvent, and the obtained residue was separated by silica gel plate (eluent: petroleum ether/ethyl acetate=1/1, v/v) to obtain target compound WX038. MS-ESI m/z: 331.0 [M+H]$^+$. $^1$H NMR (400 MHz, DMSO_$d_6$) δ: 10.89 (s, 1H), 7.78 (s, 1H), 7.38 (d, J=8.8 Hz, 1H), 6.82 (s, 2H), 4.16-4.11 (m, 2H), 4.07-4.01 (m, 1H), 4.00 (s, 2H), 2.80-2.65 (m, 1H), 2.58-2.54 (m, 1H), 2.35-2.24 (m, 1H), 2.14-2.04 (m, 1H), 1.19 (t, J=6.8 Hz, 3H).

Embodiment 39: WX039

Synthetic Route:

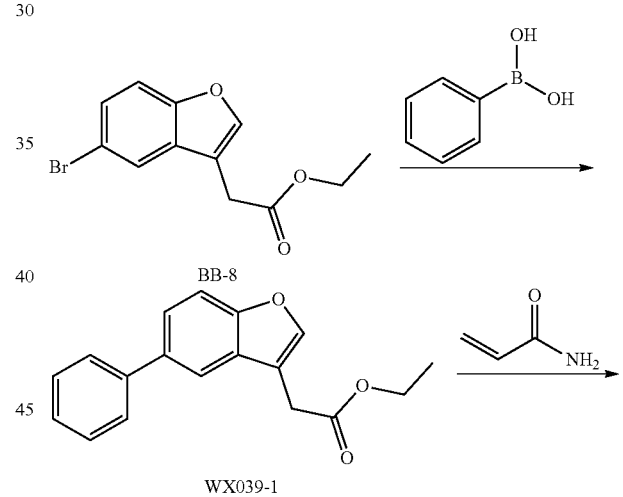

BB-8

WX039-1

WX039

Step 1: Synthesis of Compound WX039-1

Compound BB-8 (250.00 mg, 883.03 μmol) was dissolved in a mixed solution of dioxane (4.00 mL) and water (1.00 mL) under the protection of nitrogen at room temperature. Phenylboronic acid (107.67 mg, 883.03 μmol), potassium carbonate (244.09 mg, 1.77 mmol) and 1,1'-bis(diphenylphosphino)ferrocene-palladium(II) dichloride dichloromethane complex (72.11 mg, 88.30 μmol) were sequentially added. The reaction mixture was heated to 80° C. and reacted with stirring for 17 hours at 80° C. After the reaction was completed, the mixture was cooled to room temperature, and the solvent was removed under reduced pressure. The obtained residue was diluted with water (30 mL), and extracted with ethyl acetate (30 mL×3). The organic phases were combined, washed with water (50 mL×2), dried with anhydrous sodium sulfate, filtered, and the filtrate was concentrated under reduced pressure to remove the solvent, and the obtained residue was separated by preparative chromatographic plate (eluent: petroleum ether/ethyl acetate=5/1, v/v) to obtain compound WX039-1. MS-ESI m/z: 280.9 [M+H]$^+$.

Step 2: Synthesis of Compound WX039

Compound WX039-1 (181.00 mg, 558.79 mmol, purity: 86.54%) was dissolved in N,N-dimethylformamide (3 mL), then potassium tert-butoxide (62.70 mg, 558.79 μmol) was added, and the reaction mixture was stirred at 0° C. for 1 hour, then acrylamide (39.72 mg, 558.79 μmol) was added, and the reaction mixture was raised to room temperature and continued to react with stirring for 2 hours. After the reaction was completed, water (30 mL) was added to dilute, and the mixture was extracted with ethyl acetate (30 mL×3). The organic phases were combined, washed with saturated brine (50 mL×2), dried with anhydrous sodium sulfate, filtered, and the filtrate was concentrated under reduced pressure to remove the solvent, and the obtained residue was separated by preparative HPLC (mobile phase: acetonitrile/water; acidic system: 0.05% HCl) and then separated by preparative chromatographic plate (eluent: petroleum ether/ethyl acetate=2/1, v/v) to obtain target compound WX039. MS-ESI m/z: 306.1 [M+H]$^+$. $^1$H NMR (400 MHz, DMSO_$d_6$) δ: 10.89 (s, 1H), 7.94 (s, 1H), 7.86 (d, J=1.6 Hz, 1H), 7.71-7.63 (m, 3H), 7.62-7.58 (m, 1H), 7.47 (t, J=7.6 Hz, 2H), 7.39-7.33 (m, 1H), 4.21 (dd, J=4.8, 12.0 Hz, 1H), 2.80-2.66 (m, 1H), 2.64-2.55 (m, 1H), 2.46-2.39 (m, 1H), 2.18-2.10 (m, 1H).

Referring to the synthesis method in embodiment 39, each embodiment in Table 9 is synthesized, and LCMS and HNMR data are shown in Table 10.

TABLE 9

| Embodiments | Fragment 1 | Fragment 2 | Structure | Compound |
|---|---|---|---|---|
| 41 | BB-8 | | 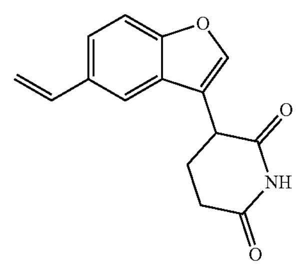 [SMILES: C=Cc1ccc2occ(C3CCC(=O)NC3=O)c2c1] | WX041 |
| 42 | BB-8 | | 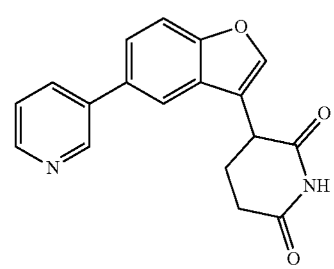 [SMILES: O=C1CCC(c2coc3ccc(-c4cccnc4)cc23)C(=O)N1] | WX042 |
| 43 | BB-8 | | 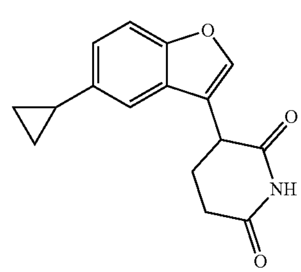 [SMILES: O=C1CCC(c2coc3ccc(C4CC4)cc23)C(=O)N1] | WX043 |

TABLE 9-continued
| Embodiments | Fragment 1 | Fragment 2 | Structure | Compound |
|---|---|---|---|---|
| 44 | 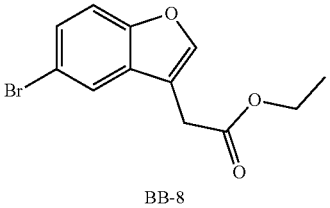 BB-8 | 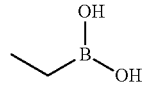 | 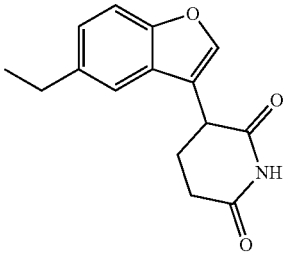 [SMILES: CCc1ccc2occ(C3CCC(=O)NC3=O)c2c1] | WX044 |
| 45 | 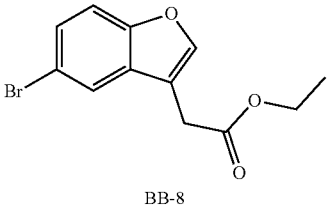 BB-8 | 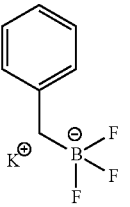 [SMILES: F[B-](F)(F)Cc1ccccc1 ; [K+]] | 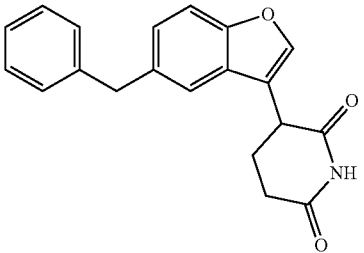 [SMILES: O=C1CCC(c2coc3ccc(Cc4ccccc4)cc23)C(=O)N1] | WX045 |
| 46 |  BB-8 | 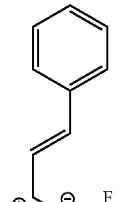 | 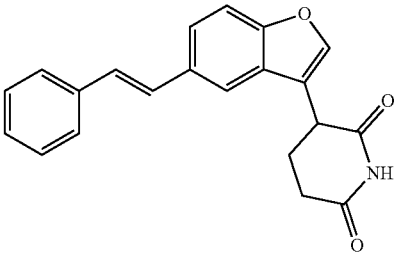 [SMILES: O=C1CCC(c2coc3ccc(/C=C/c4ccccc4)cc23)C(=O)N1] | WX046 |
| 47 | 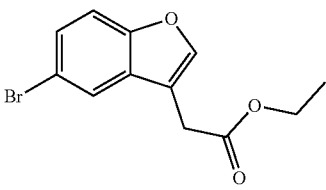 [SMILES: CCOC(=O)Cc1coc2ccc(Br)cc12] BB-8 | 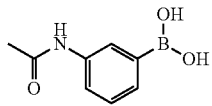 | 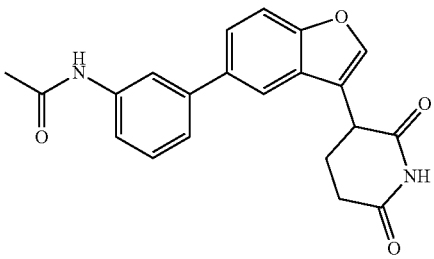 [SMILES: CC(=O)Nc1cccc(-c2ccc3occ(C4CCC(=O)NC4=O)c3c2)c1] | WX047 |
| 48 | 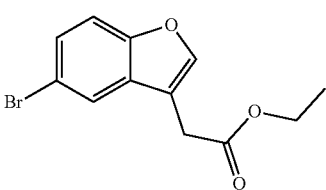 [SMILES: CCOC(=O)Cc1coc2ccc(Br)cc12] BB-8 | 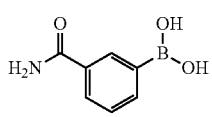 | 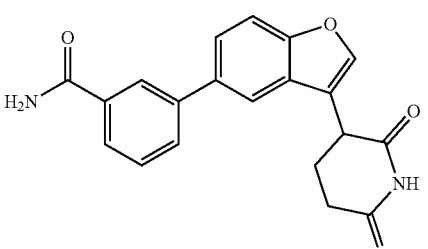 | WX048 |

TABLE 9-continued
| Embodiments | Fragment 1 | Fragment 2 | Structure | Compound |
|---|---|---|---|---|
| 49 | 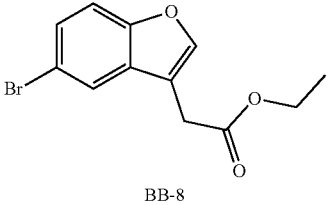<br>BB-8 | 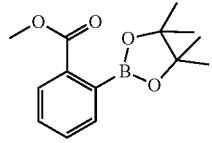 | 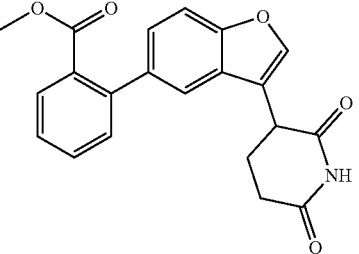 [SMILES: COC(=O)c1ccccc1-c1ccc2occ(C3CCC(=O)NC3=O)c2c1] | WX049 |
| 50 | <br>BB-8 | 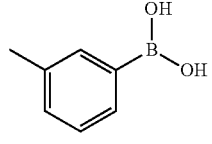 | 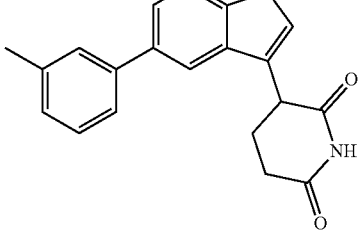 | WX050 |
| 51 | <br>BB-8 | 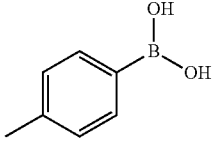 | 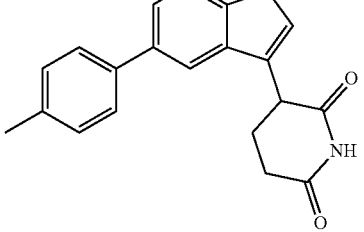 | WX051 |
| 52 | <br>BB-8 | 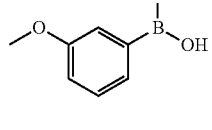 | 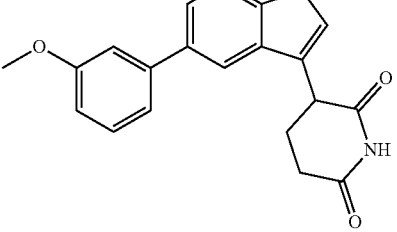 | WX052 |
| 53 | 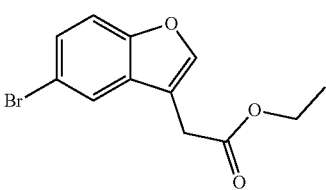 [SMILES: CCOC(=O)Cc1coc2ccc(Br)cc12]<br>BB-8 | 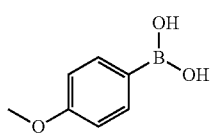 | 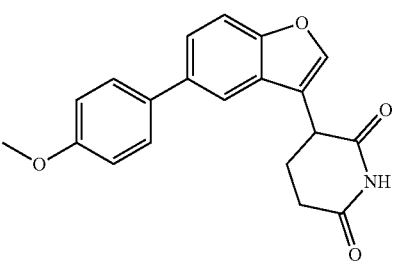 [SMILES: COc1ccc(-c2ccc3occ(C4CCC(=O)NC4=O)c3c2)cc1] | WX053 |

TABLE 9-continued

| Embodiments | Fragment 1 | Fragment 2 | Structure | Compound |
|---|---|---|---|---|
| 54 | BB-8 | | 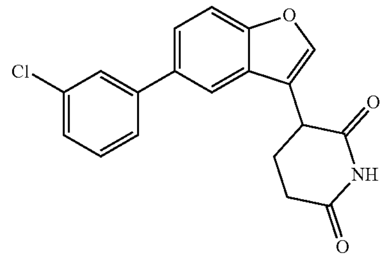 [SMILES: O=C1CCC(c2coc3ccc(-c4cccc(Cl)c4)cc23)C(=O)N1] | WX054 |
| 55 | BB-8 | | 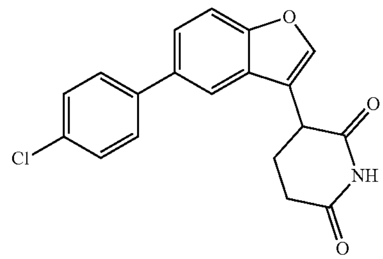 [SMILES: O=C1CCC(c2coc3ccc(-c4ccc(Cl)cc4)cc23)C(=O)N1] | WX055 |
| 56 | BB-8 | | 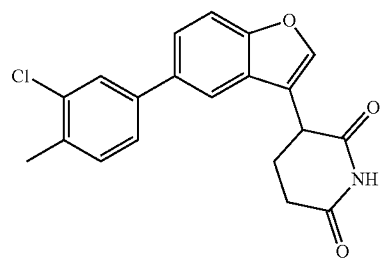 [SMILES: Cc1ccc(-c2ccc3occ(C4CCC(=O)NC4=O)c3c2)cc1Cl] | WX056 |

TABLE 10

| Embodiments | Compound | HNMR | LCMS |
|---|---|---|---|
| 41 | WX041 | $^1$H NMR (400 MHZ, DMSO_$d_6$) δ: 10.91 (s, 1H), 7.90 (s, 1H), 7.67 (s, 1H), 7.59-7.51 (m, 1H), 7.50-7.44 (m, 1H), 6.82 (dd, J = 11.2, 17.6 Hz, 1H), 5.81 (d, J = 18.0 Hz, 1H), 5.22 (d, J = 11.2 Hz, 1H), 4.15 (dd, J = 4.8, 12.0 Hz, 1H), 2.83-2.68 (m, 1H), 2.64-2.54 (m, 1H), 2.44-2.31 (m, 1H), 2.17-2.05 (m, 1H). | MS-ESI m/z: 256.0 [M + H]$^+$. |
| 42 | WX042 | $^1$H NMR (400 MHZ, DMSO_$d_6$) δ: 10.92 (s, 1H), 9.16 (s, 1H), 8.78 (s, 1H), 8.63 (d, J = 8.0 Hz, 1H), 8.13-8.07 (m, 1H), 8.04-7.99 (m, 1H), 7.96-7.89 (m, 1H), 7.77 (s, 2H), 4.21 (dd, J = 4.2, 12.2 Hz, 1H), 2.81-2.72 (m, 1H), 2.67-2.60 (m, 1H), 2.45-2.30 (m, 1H), 2.19-2.09 (m, 1H). | MS-ESI m/z: 307.0 [M + H]$^+$. |
| 43 | WX043 | $^1$H NMR (400 MHZ, DMSO_$d_6$) δ: 10.88 (s, 1H), 7.83 (s, 1H), 7.43 (d, J = 8.4 Hz, 1H), 7.29 (d, J = 1.6 Hz, 1H), 7.02 (dd, J = 1.6, 8.4 Hz, 1H), 4.11 (dd, J = 5.2, 12.0 Hz, 1H), 2.78-2.66 (m, 1H), 2.61-2.54 (m, 1H), 2.39-2.27 (m, 1H), 2.13-2.05 (m, 1H), 2.04-1.96 (m, 1H), 0.96-0.91 (m, 2H), 0.68-0.64 (m, 2H). | MS-ESI m/z: 270.1 [M + H]$^+$. |
| 44 | WX044 | $^1$H NMR (400 MHZ, DMSO_$d_6$) δ: 10.89 (s, 1H), 7.85 (s, 1H), 7.46 (d, J = 8.4 Hz, 1H), 7.40 (s, 1H), 7.16 (dd, J = 1.2, 8.4 Hz, 1H), 4.11 (dd, J = 4.8, 12.0 Hz, 1H), 2.79-2.70 (m, 1H), 2.70-2.64 (m, 2H), 2.61-2.53 (m, 1H), 2.39-2.28 (m, 1H), 2.14-2.06 (m, 1H), 1.21 (t, J = 7.6 Hz, 3H). | MS-ESI m/z: 258.0 [M + H]$^+$. |
| 45 | WX045 | $^1$H NMR (400 MHZ, DMSO_$d_6$) δ: 10.88 (s, 1H), 7.86 (s, 1H), 7.51 (d, J = 1.2 Hz, 1H), 7.47 (d, J = 8.4 Hz, 1H), 7.29-7.22 (m, 4H), 7.19-7.13 (m, 2H), 4.11 (dd, J = 4.8, 12.0 Hz, 1H), 4.01 (s, 2H), 2.79-2.69 (m, 1H), 2.61-2.54 (m, 1H), 2.39-2.30 (m, 1H), 2.13-2.06 (m, 1H). | MS-ESI m/z: 337.1 [M + H$_2$O]$^+$. |
| 46 | WX046 | $^1$H NMR (400 MHZ, DMSO_$d_6$) δ: 10.93 (s, 1H), 7.91 (s, 1H), 7.82 (s, 1H), 7.63-7.58 (m, 4H), 7.41-7.34 (m, 3H), 7.29-7.21 (m, 2H), 4.17 (dd, J = 4.8, 12.0 Hz, 1H), 2.82-2.72 (m, 1H), 2.69-2.61 (m, 1H), 2.44-2.31 (m, 1H), 2.18-2.10 (m, 1H). | MS-ESI m/z: 354.1 [M + Na]$^+$. |

TABLE 10-continued

| Embodiments | Compound | HNMR | LCMS |
|---|---|---|---|
| 47 | WX047 | $^1$H NMR (400 MHZ, DMSO_$d_6$) δ: 10.91 (s, 1H), 10.05 (s, 1H), 7.96 (s, 1H), 7.84 (s, 1H), 7.80 (d, J = 1.6 Hz, 1H), 7.67 (d, J = 8.4 Hz, 1H), 7.61 (d, J = 8.0 Hz, 1H), 7.53 (dd, J = 1.8, 8.2 Hz, 1H), 7.38 (t, J = 7.8 Hz, 1H), 7.33 (d, J = 7.6 Hz, 1H), 4.22 (dd, J = 4.8, 12.0 Hz, 1H), 2.83-2.70 (m, 1H), 2.68-2.57 (m, 1H), 2.46-2.32 (m, 1H), 2.20-2.10 (m, 1H), 2.07 (s, 3H). | MS-ESI m/z: 363.1 [M + H]$^+$. |
| 48 | WX048 | $^1$H NMR (400 MHZ, DMSO_$d_6$) δ: 10.93 (s, 1H), 8.15 (s, 1H), 8.11 (s, 1H), 7.96 (s, 1H), 7.93 (s, 1H), 7.82-7.88 (m, 2H), 7.65-7.73 (m, 2H), 7.55 (t, J = 7.7 Hz, 1H), 7.45 (s, 1H), 4.24 (dd, J = 4.8, 12.0 Hz, 1H), 2.76-2.73 (m, 1H), 2.63-2.58 (m, 1H), 2.46-2.43 (m, 1H), 2.18-2.16 (m, 1H). | MS-ESI m/z: 349.0 [M + H]$^+$. |
| 49 | WX049 | $^1$H NMR (400 MHZ, DMSO_$d_6$) δ: 10.88 (s, 1H), 7.95 (s, 1H), 7.72 (d, J = 7.6 Hz, 1H), 7.64-7.57 (m, 2H), 7.51-7.43 (m, 3H), 7.22 (dd, J = 1.8, 8.6 Hz, 1H), 4.16 (dd, J = 4.8, 12.0 Hz, 1H), 3.57 (s, 3H), 2.80-2.68 (m, 1H), 2.67-2.54 (m, 1H), 2.36-2.28 (m, 1H), 2.15-2.07 (m, 1H). | MS-ESI m/z: 386.1 [M + Na]$^+$. |
| 50 | WX050 | $^1$H NMR (400 MHZ, DMSO_$d_6$) δ: 10.90 (s, 1H), 7.94 (s, 1H), 7.84 (d, J = 1.6 Hz, 1H), 7.67-7.63 (m, 1H), 7.61-7.56 (m, 1H), 7.51-7.44 (m, 2H), 7.36 (t, J = 7.6 Hz, 1H), 7.18 (d, J = 7.6 Hz, 1H), 4.23 (dd, J = 4.8, 12.0 Hz, 1H), 2.82-2.72 (m, 1H), 2.70-2.61 (m, 1H), 2.40 (s, 3H), 2.36-2.30 (m, 1H), 2.20-2.11 (m, 1H). | MS-ESI m/z: 320.1 [M + H]$^+$. |
| 51 | WX051 | $^1$H NMR (400 MHZ, MeOD_$d_4$) δ: 7.75 (s, 2H), 7.57-7.47 (m, 4H), 7.25 (d, J = 8.0 Hz, 2H), 4.19 (dd, J = 5.2, 11.2 Hz, 1H), 2.87-2.68 (m, 2H), 2.49-2.39 (m, 1H), 2.37 (s, 3H), 2.36-2.29 (m, 1H). | MS-ESI m/z: 337.1 [M + 18]$^+$. |
| 52 | WX052 | $^1$H NMR (400 MHZ, DMSO_$d_6$) δ: 10.92 (s, 1H), 7.94 (s, 1H), 7.85 (d, J = 1.2 Hz, 1H), 7.68-7.55 (m, 2H), 7.38 (t, J = 7.8 Hz, 1H), 7.24 (d, J = 8.0 Hz, 1H), 7.20 (t, J = 2.0 Hz, 1H), 6.94 (dd, J = 2.4, 8.2 Hz, 1H), 4.21 (dd, J = 4.4, 12.0 Hz, 1H), 3.83 (s, 3H), 2.82-2.69 (m, 1H), 2.68-2.53 (m, 1H), 2.45-2.30 (m, 1H), 2.18-2.10 (m, 1H). | MS-ESI m/z: 353.1 [M + H$_2$O]$^+$. |
| 53 | WX053 | $^1$H NMR (399 MHZ, MeOD_$d_4$) δ: 7.73(s, 1H), 7.71 (t, J = 1.6 Hz, 1H), 7.56 (d, J = 2.0 Hz, 1H), 7.54 (d, J = 2.0 Hz, 1H), 7.52 (d, J = 1.6 Hz, 2H), 7.00 (d, J = 2.4 Hz, 1H), 6.98 (d, J = 2.0 Hz, 1H), 4.19 (dd, J = 4.8, 11.2 Hz, 1H), 3.83 (s, 3H), 2.87-2.69 (m, 2H), 2.50-2.37 (m, 1H), 2.36-2.27 (m, 1H). | MS-ESI m/z: 353.1 [M + H$_2$O]$^+$. |
| 54 | WX054 | $^1$H NMR (400 MHZ, DMSO_$d_6$) δ: 10.91 (s, 1H), 7.96 (s, 1H), 7.93 (s, 1H), 7.74 (t, J = 2.0 Hz, 1H), 7.69-7.60 (m, 3H), 7.50 (t, J = 8.0 Hz, 1H), 7.44-7.39 (m, 1H), 4.22 (dd, J = 4.8, 12.4 Hz, 1H), 2.83-2.70 (m, 1H), 2.69-2.57 (m, 1H), 2.46-2.37 (m, 1H), 2.21-2.02 (m, 1H). | MS-ESI m/z: 340.1 [M + H]$^+$. |
| 55 | WX055 | $^1$H NMR (399 MHz, MeOD_$d_4$) δ: 7.78 (t, J = 1.4 Hz, 1H), 7.77 (s, 1H), 7.65-7.60 (m, 2H), 7.56 (d, J = 1.2 Hz, 2H), 7.45-7.41 (m, 2H), 4.19 (dd, J = 4.8, 11.2 Hz, 1H), 2.88-2.69 (m, 2H), 2.50-2.37 (m, 1H), 2.36-2.27 (m, 1H). | MS-ESI m/z: 340.0 [M + H]$^+$. |
| 56 | WX056 | $^1$H NMR (400 MHZ, DMSO_$d_6$) δ: 10.90 (s, 1H), 7.94 (s, 1H), 7.86 (d, J = 1.6 Hz, 1H), 7.67 (d, J = 1.6 Hz, 1H), 7.64 (s, 1H), 7.59 (dd, J = 1.8, 8.6 Hz, 1H), 7.52 (dd, J = 2.0, 8.4 Hz, 1H), 7.48 (d, J = 8.0 Hz, 1H), 4.21 (dd, J = 4.8, 12.0 Hz, 1H), 2.80-2.70 (m, 1H), 2.69-2.55 (m, 1H), 2.48-2.42 (m, 1H), 2.41 (s, 3H), 2.19-2.09 (m, 1H). | MS-ESI m/z: 354.0 [M + H]$^+$. |

Embodiment 57: WX057

Synthetic Route:

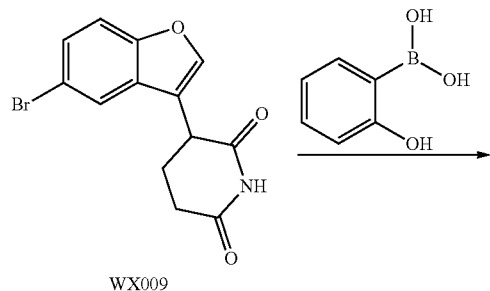

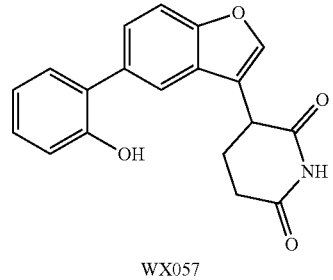

Compound WX009 (0.3 g, 1.06 mmol) was dissolved in a mixed solution of dioxane (4.00 mL) and water (1.00 mL) under the protection of nitrogen at room temperature, then 2-hydroxyphenylboronic acid (134.29 mg, 973.62 μmol), potassium carbonate (269.13 mg, 1.95 mmol) and 1,1'-bis(diphenylphosphino)ferrocene-palladium(II) dichloride dichloromethane complex (79.51 mg, 97.36 μmol) were sequentially added, and the reaction mixture heated to 80° C. and reacted with stirring at 80° C. for 15 hours. After the reaction was completed, the mixture was cooled to room temperature, and the solvent was removed under reduced pressure. The obtained residue was diluted with water (50 mL), and extracted with ethyl acetate (50 mL×3). The organic phases were combined, washed with saturated brine (100 mL×2), dried with anhydrous sodium sulfate, filtered, and the filtrate was concentrated under reduced pressure to remove the solvent, and the obtained residue was separated by preparative HPLC (eluent: acetonitrile/water; acidic system: 0.05% HCl) to obtain target compound WX057. MS-ESI m/z: 322.1 [M+H]$^+$. $^1$H NMR (400 MHz, DMSO_d$_6$) δ: 10.89 (s, 1H), 9.46 (s, 1H), 7.91 (s, 1H), 7.67 (d, J=1.2 Hz, 1H), 7.59-7.55 (m, 1H), 7.52-7.47 (m, 1H), 7.25 (dd, J=1.4, 7.4 Hz, 1H), 7.15 (td, J=1.2, 7.7 Hz, 1H), 6.94 (d, J=7.6 Hz, 1H), 6.88 (t, J=7.4 Hz, 1H), 4.17 (dd, J=4.8, 11.6 Hz, 1H), 2.80-2.66 (m, 1H), 2.62-2.53 (m, 1H), 2.38-2.28 (m, 1H), 2.18-2.08 (m, 1H).

Embodiment 58: WX058

Synthetic Route:

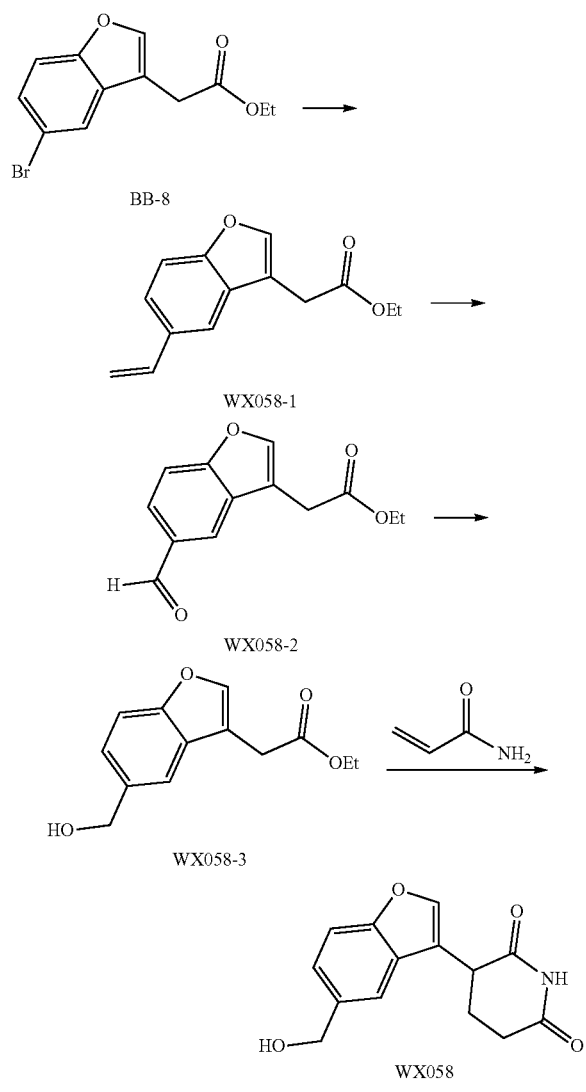

Step 1: Synthesis of Compound WX058-1

Compound BB-8 (19 g, 67.11 mmol) and pinacol vinylboronate (12.40 g, 80.53 mmol) were dissolved in a mixed solution of water (30 mL) and dioxane (90 mL) under the protection of nitrogen at room temperature, then potassium carbonate (18.55 g, 134.22 mmol) and 1,1'-bis(diphenylphosphino)ferrocene-palladium(II) dichloride dichloromethane complex (2.74 g, 3.36 mmol) were sequentially added, and the reaction mixture was heated to 80° C. and reacted with stirring at 80° C. for 12 hours. After the reaction was completed, the mixture was cooled to room temperature, and the reaction mixture was quenched by water (300 mL), and extracted with ethyl acetate (200 mL×3). The organic phases were combined, washed with brine (100 mL×2), dried with anhydrous sodium sulfate, filtered, and the filtrate was concentrated under reduced pressure to remove the solvent, and the obtained residue was separated by column chromatography (eluent: petroleum ether/ethyl acetate=100/1-v/v) to obtain compound WX058-1. MS-ESI m/z: 231.0 [M+H]$^+$. $^1$H NMR (400 MHz, CDCl$_3$) δ: 7.54 (s, 1H), 7.50 (s, 1H), 7.37-7.28 (m, 2H), 6.74 (dd, J=6.8, 17.6 Hz, 1H), 5.66 (dd, J=2.8, 14.8 Hz, 1H), 5.15 (dd, J=0.8, 10.8 Hz, 1H), 4.12 (q, J=7.2 Hz, 2H), 3.62 (s, 2H), 1.20 (t, J=7.2 Hz, 3H).

Step 2: Synthesis of Compound WX058-2

Compound WX058-1 (9.2 g, 39.96 mmol) was dissolved in tetrahydrofuran (60 mL) and water (20 mL) at 0° C. under the protection of nitrogen, then sodium periodate (17.09 g, 79.91 mmol) and potassium osmate (VI) dihydrate (2.94 g, 7.99 mmol) were sequentially added, and the reaction mixture was raised to room temperature and reacted with stirring at room temperature for 12 hours. After the reaction was completed, the reaction was quenched by water (300 mL), and the mixture was extracted with ethyl acetate (200 mL×3). The organic phases were combined, washed with saturated sodium thiosulfate solution (100 mL×2), dried with anhydrous sodium sulfate, filtered, and the filtrate was concentrated under reduced pressure to remove the solvent, and the obtained residue was separated by column chromatography (eluent: petroleum ether/ethyl acetate=10/1-4/1, v/v) to obtain compound WX058-2. MS-ESI m/z: 233.0 [M+H]$^+$. $^1$H NMR (400 MHz, DMSO_d$_6$) δ: 10.08 (s, 1H), 8.25 (d, J=1.2 Hz, 1H), 8.09 (s, 1H), 7.91 (dd, J=1.6, 8.4 Hz, 1H), 7.79 (d, J=8.4 Hz, 1H), 4.14 (q, J=7.0 Hz, 2H), 3.89 (s, 2H), 1.21 (t, J=7.0 Hz, 3H).

Step 3: Synthesis of Compound WX058-3

Compound WX058-2 (3.95 g, 17.01 mmol) was dissolved in tetrahydrofuran (40 mL) under the protection of nitrogen at 0° C., and sodium borohydride (965.17 mg, 25.51 mmol) was added, then the reaction mixture was raised to room temperature and reacted with stirring at room temperature for 12 hours. After the reaction was completed, the reaction was quenched by water (100 mL), and the mixture was extracted with ethyl acetate (60 mL×3). The organic phases were combined, dried with anhydrous sodium sulfate, filtered, and the filtrate was concentrated under reduced pressure to remove the solvent, and the obtained residue was separated by column chromatography (eluent: petroleum ether/ethyl acetate=10/1-2/1, v/v) to obtain compound WX058-3. MS-ESI m/z: 217.0 [M−OH]$^+$. $^1$H NMR (400 MHz, DMSO_d$_6$) δ: 7.89 (s, 1H), 7.54 (d, J=0.8 Hz, 1H), 7.51 (d, J=8.4 Hz, 1H), 7.27 (dd, J=1.2, 8.4 Hz, 1H), 5.21 (t, J=5.8 Hz, 1H), 4.58 (d, J=6.0 Hz, 2H), 4.12 (q, J=7.0 Hz, 2H), 3.77 (s, 2H), 1.21 (t, J=7.0 Hz, 3H).

Step 4: Synthesis of Compound WX058

Compound WX058-3 (0.15 g, 640.35 µmol) was dissolved in N,N-dimethylformamide (10 mL) at 0° C. under the protection of nitrogen, then potassium tert-butoxide (71.85 mg, 640.35 µmol) was added, and the reaction mixture was reacted with stirring at 0° C. for 1 hour, then acrylamide (91.03 mg, 1.28 mmol) was added, and the reaction mixture was raised to room temperature and reacted with stirring at room temperature for 2 hours. After the reaction was completed, water (50 mL) was added to dilute, and the mixture was extracted with ethyl acetate (30 mL×3). The organic phases were combined, washed with saturated brine (30 mL×2), dried with anhydrous sodium sulfate, filtered, and the filtrate was concentrated under reduced pressure to remove the solvent, and the obtained residue was separated by preparative HPLC (mobile phase: acetonitrile/water; acidic system: 0.05% HCl) to obtain target compound WX058. MS-ESI m/z: 242.1 [M-OH]$^+$. $^1$H NMR (400 MHz, DMSO_d$_6$) δ: 10.91 (s, 1H), 7.88 (s, 1H), 7.55-7.46 (m, 2H), 7.27 (dd, J=1.2, 8.4 Hz, 1H), 5.20 (t, J=6.2 Hz, 1H), 4.57 (d, J=5.6 Hz, 2H), 4.14 (dd, J=4.8, 12.0 Hz, 1H), 2.82-2.71 (m, 1H), 2.63-2.55 (m, 1H), 2.38-2.28 (m, 1H), 2.17-2.07 (m, 1H).

Embodiment 59: WX059

Synthetic Route:

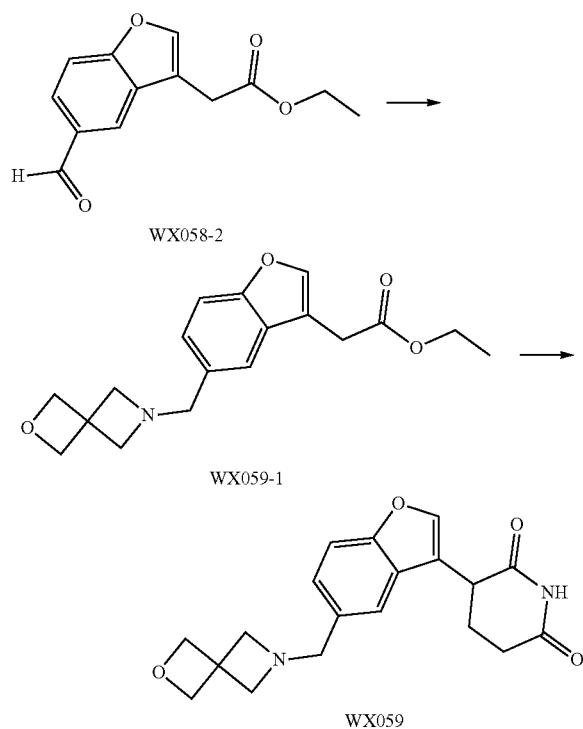

Step 1: Synthesis of Compound WX059-1

Compound WX058-2 (145 mg, 624.38 µmol) and 2-oxa-6-azaspiro[3.3]heptane (61.89 mg, 624.38 µmol) were added to dichloromethane (10 mL) at 20° C. under the protection of nitrogen, then triethylamine (268.52 mg, 2.65 mmol, 369.35 µL) was added, and the reaction mixture was stirred at 20° C. for 2 hours, and sodium borohydride acetate (201.14 mg, 949.05 µmol) was added to the above reaction solution, and the reaction mixture was reacted with stirring at 20° C. under the protection of nitrogen for 15 hours. After the reaction was completed, the reaction solution was concentrated under reduced pressure to remove the solvent. The obtained residue was separated by silica gel plate (eluent: petroleum ether/ethyl acetate=2/1, v/v), to obtain compound WX059-1. MS-ESI m/z: 315.8 [M+H]$^+$.

Step 2: Synthesis of Compound WX059

Compound WX059-1 (125 mg, 396.37 µmol) was added to N,N-dimethylformamide (10 mL) at 0° C. under the protection of nitrogen, then potassium tert-butoxide (44.48 mg, 396.37 µmol) was added, and the reaction mixture was stirred at 0° C. for 1 hour, then acrylamide (28.17 mg, 396.37 µmol) was added to the above reaction solution, and the reaction mixture was reacted with stirring for 1.5 hours at room temperature under the protection of nitrogen. After the reaction was completed, water (50 mL) was added, and the mixture was extracted with ethyl acetate (60 mL×3). The organic phases were combined, washed with saturated brine (100 mL×2), dried with anhydrous sodium sulfate, filtered, and the filtrate was concentrated under reduced pressure to remove the solvent, and the obtained residue was separated by preparative HPLC (mobile phase: acetonitrile/water; acidic system: 0.05% HCl) to obtain target compound WX059. MS-ESI m/z: 341.2 [M+H]$^+$. $^1$H NMR (400 MHz, MeOD_d$_4$) δ: 7.85 (s, 1H), 7.76 (dd, J=1.6, 4.4 Hz, 1H), 7.62 (d, J=8.4 Hz, 1H), 7.44 (td, J=1.6, 6.8 Hz, 1H), 4.49 (d, J=14.8 Hz, 2H), 4.21-4.17 (m, 1H), 4.17-4.10 (m, 2H), 4.08-4.00 (m, 2H), 3.83 (d, J=12.8 Hz, 2H), 3.75 (s, 1H), 3.65 (s, 1H), 2.89-2.72 (m, 2H), 2.51-2.40 (m, 1H), 2.34-2.27 (m, 1H).

Embodiment 60: WX060

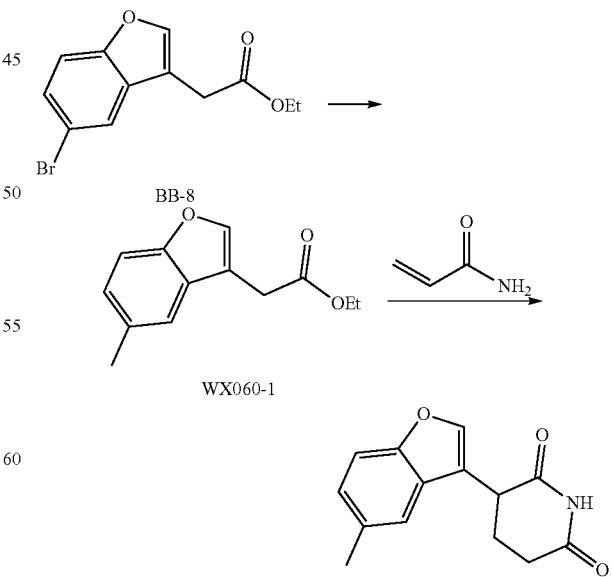

Step 1: Synthesis of Compound WX060-1

Compound BB-8 (0.40 g, 1.41 mmol), methylboronic acid (84.57 mg, 1.41 mmol) and potassium carbonate (390.54 mg, 2.83 mmol) were dissolved in a mixed solution of dioxane (4.00 mL) and water (1 mL) under the protection of nitrogen at room temperature, then 1,1'-bis(diphenylphosphino)ferrocene-palladium(II) dichloride dichloromethane complex (115.38 mg, 141.28 μmol) was added, and the reaction mixture was heated to 80° C. and reacted with stirring at 80° C. for 15 hours. After the reaction was completed, the mixture was cooled to room temperature, and the solvent was removed under reduced pressure. The obtained residue was added with water (30 mL), and extracted with ethyl acetate (30 mL×3). The organic phases were combined, washed with saturated brine (50 mL×2), dried with anhydrous sodium sulfate, filtered, and the filtrate was concentrated under reduced pressure to remove the solvent, and the obtained residue was separated by preparative chromatographic plate (eluent: petroleum ether/ethyl acetate=5/1, v/v) to obtain compound WX060-1. MS-ESI m/z: 218.9 [M+H]$^+$.

Step 2: Synthesis of Compound WX060

Compound WX060-1 (222.00 mg, 914.76 μmol, purity: 89.93%) was dissolved in N,N-dimethylformamide (3.00 mL) at 0° C. under the protection of nitrogen, then potassium tert-butoxide (102.65 mg, 914.76 μmol) was added, and the reaction mixture was reacted with stirring at 0° C. for 1 hour, then acrylamide (65.02 mg, 914.76 μmol) was added, and the reaction mixture was raised to room temperature and continued to react with stirring for 2 hours. After the reaction was completed, water (50 mL) was added to dilute, and the mixture was extracted with ethyl acetate (50 mL×3). The organic phases were combined, washed with saturated brine (100 mL×2), dried with anhydrous sodium sulfate, filtered, and the filtrate was concentrated under reduced pressure to remove the solvent, and the obtained residue was separated by preparative HPLC (eluent: acetonitrile/water; acidic system: 0.05% HCl) to obtain target compound WX060. MS-ESI m/z: 244.0 [M+H]$^+$. $^1$H NMR (400 MHz, DMSO_d$_6$) δ: 10.89 (s, 1H), 7.84 (s, 1H), 7.44 (d, J=8.4 Hz, 1H), 7.37 (s, 1H), 7.12 (d, J=8.0 Hz, 1H), 4.10 (dd, J=5.2, 12.0 Hz, 1H), 2.79-2.68 (m, 1H), 2.61-2.53 (m, 1H), 2.38 (s, 3H), 2.35-2.27 (m, 1H), 2.13-2.06 (m, 1H).

Embodiment 61: WX061

Synthetic Route:

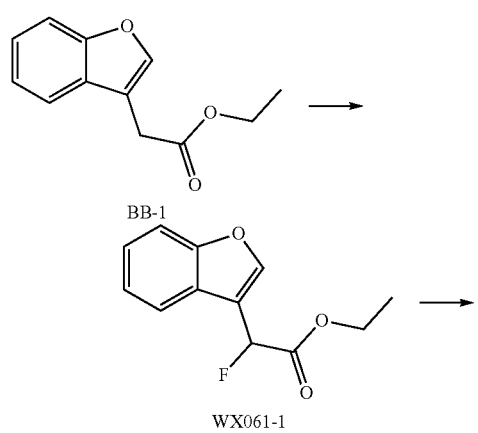

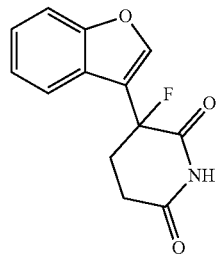

WX061

Step 1: Synthesis of Compound WX061-1

Compound BB-1 (1 g, 4.90 mmol) was dissolved in tetrahydrofuran (15 mL) at −78° C. under the protection of nitrogen, then lithium diisopropylamide (2 M, 4.90 mL) was added, and the reaction mixture was stirred at −78° C. for 1 hour. A tetrahydrofuran (5 mL) solution of N-fluorobenzenesulfonimide (1.70 g, 5.39 mmol) was added dropwise to the above reaction system, and the reaction mixture was reacted with stirring for 2 hours under the protection of nitrogen at −78° C. After the reaction was completed, saturated ammonium chloride solution (30 mL) was added, and the mixture was extracted with ethyl acetate (20 mL×3). The organic phases were combined, washed with saturated brine (20 mL×2), dried with anhydrous sodium sulfate, filtered, and the filtrate was concentrated under reduced pressure to remove the solvent, and the obtained residue was separated by column chromatography (eluent: petroleum ether/ethyl acetate=50/1-20/1, v/v) to obtain compound WX061-1. $^1$H NMR (400 MHz, DMSO_d$_6$) δ: 8.31 (d, J=4.4 Hz, 1H), 7.67 (d, J=8.4 Hz, 1H), 7.63 (d, J=7.6 Hz, 1H), 7.40 (t, J=7.8 Hz, 1H), 7.34 (t, J=7.4 Hz, 1H), 6.44 (d, J=46.8 Hz, 1H), 4.31-4.15 (m, 2H), 1.17 (t, J=7.2 Hz, 3H).

Step 2: Synthesis of Compound WX061

Compound WX061-1 (314 mg, 1.41 mmol) was added to N,N-dimethylformamide (2 mL) under the protection of nitrogen at 0° C., and potassium tert-butoxide (158.56 mg, 1.41 mmol) and acrylamide (100.44 mg, 1.41 mmol) were added, and the reaction mixture was raised to room temperature and reacted with stirring for 2 hours. After the reaction was completed, water (100 mL) was added, and the mixture was extracted with ethyl acetate (50 mL×3). The organic phases were combined, washed with saturated brine (50 mL×2), dried with anhydrous sodium sulfate, filtered, and the filtrate was concentrated under reduced pressure to remove the solvent, and the obtained residue was separated by preparative HPLC (mobile phase: acetonitrile/water; acidic system: 0.05% HCl) to obtain target compound WX061. MS-ESI m/z: 228.0 [M−F]$^+$. $^1$H NMR (400 MHz, DMSO_d$_6$) δ: 11.37 (s, 1H), 8.27 (d, J=2.8 Hz, 1H), 7.78 (d, J=8.0 Hz, 1H), 7.66 (d, J=8.0 Hz, 1H), 7.40 (t, J=7.6 Hz, 1H), 7.32 (t, J=7.4 Hz, 1H), 2.93-2.74 (m, 2H), 2.67-2.57 (m, 2H).

Embodiment 62: WX062

Synthetic Route:

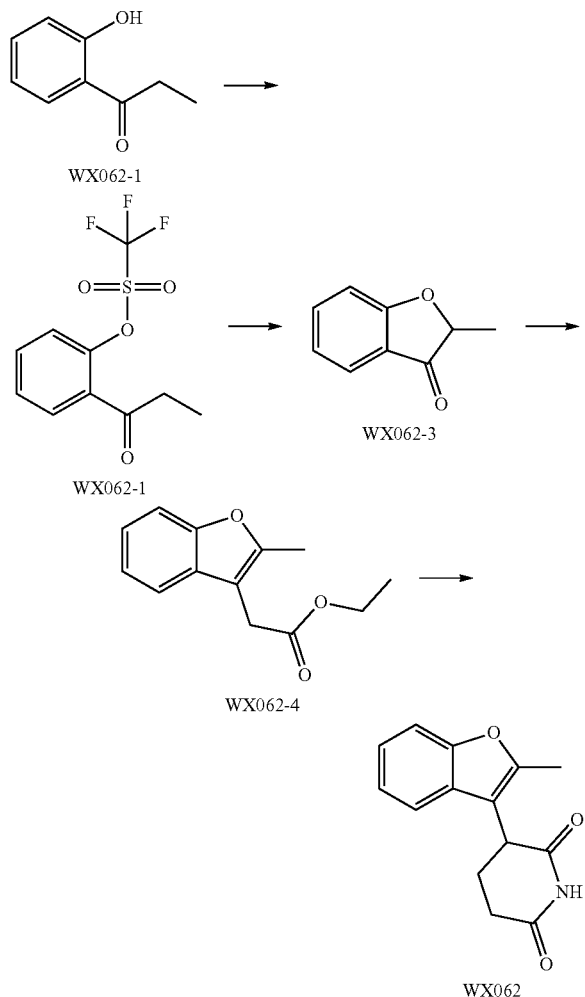

Step 1: Synthesis of Compound WX062-2

Compound WX062-1 (10 g, 66.59 mmol, 9.17 mL) was dissolved in dichloromethane (100 mL) under the protection of nitrogen at room temperature, then triethylamine (13.48 g, 133.18 mmol, 18.54 mL) was added, the mixture was cooled to −78° C., and a dichloromethane (20 mL) solution of trifluoromethanesulfonic anhydride (22.54 g, 79.91 mmol, 13.18 mL) was added dropwise, and the reaction mixture was naturally raised to room temperature and reacted with stirring for 12 hours, cooled to −40° C., then trifluoromethanesulfonic anhydride (22.54 g, 79.91 mmol, 13.18 mL) and triethylamine (13.48 g, 133.18 mmol, 18.54 mL) were supplemented, and the reaction mixture continued to react with stirring for 3 hours. After the reaction was completed, ice water (100 mL) was poured into the reaction system, and the phases were separated, then the organic phases were collected, and the aqueous phase was extracted with dichloromethane (50 mL×2). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-9/1, v/v), to obtain compound WX062-2. $^1$H NMR (400 MHz, CDCl$_3$) δ: 7.78 (dd, J=1.6, 7.6 Hz, 1H), 7.59 (td, J=1.8, 8.2 Hz, 1H), 7.48 (td, J=1.2, 7.6 Hz, 1H), 7.35 (d, J=8.4 Hz, 1H), 2.98 (q, J=7.2 Hz, 2H), 1.23 (t, J=7.2 Hz, 3H).

Step 2: Synthesis of Compound WX062-3

Compound WX062-2 (5 g, 17.72 mmol) was dissolved in N,N-dimethylformamide (50 mL) under the protection of nitrogen at room temperature, and 1,8-diazabicyclo[5.4.0]undec-7-ene (6.74 g, 44.29 mmol, 6.68 mL) was slowly added dropwise, then the reaction mixture was heated to 90° C. and reacted with stirring for 2 hours. After the reaction was completed, water (50 mL) and ethyl acetate (50 mL) were added to the reaction system to dilute, and the phases were separated, then the organic phases were collected, and the aqueous phase was extracted with ethyl acetate (30 mL×5). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-9/1, v/v), to obtain compound WX062-3. $^1$H NMR (400 MHz, CDCl$_3$) δ: 7.70-7.66 (m, 1H), 7.62 (td, J=1.6, 7.2 Hz, 1H), 7.11 (d, J=8.8 Hz, 1H), 7.07 (d, J=8.0 Hz, 1H), 4.64 (q, J=7.2 Hz, 1H), 1.54 (d, J=7.6 Hz, 3H).

Step 3: Synthesis of Compound WX062-4

Compound WX062-3 (300 mg, 2.02 mmol) was dissolved in toluene (10 mL) at room temperature under the protection of nitrogen, then ethoxyformylmethylene triphenylphosphine (1.06 g, 3.04 mmol) was added, and the reaction mixture was heated to 130° C. and reacted with stirring for 18 hours. After the reaction was completed, the reaction solution was directly concentrated under reduced pressure to remove the solvent. The obtained residue was stirred with methyl tert-butyl ether (5 mL) for 10 min at room temperature, filtered; and the filtrate was collected, and concentrated under reduced pressure to obtain a residue, and the obtained residue was separated by column chromatography (eluent: petroleum ether/ethyl acetate=1/0-9/1, v/v) to obtain compound WX062-4. $^1$H NMR (400 MHz, CDCl$_3$) δ: 7.54-7.47 (m, 1H), 7.44-7.36 (m, 1H), 7.26-7.16 (m, 2H), 4.16 (q, J=7.2 Hz, 2H), 3.61 (s, 2H), 2.45 (s, 3H), 1.26 (t, J=7.2 Hz, 3H).

Step 4: Synthesis of Compound WX062

Compound WX062-4 (230 mg, 1.05 mmol) was dissolved in N,N-dimethylformamide (5 mL) under the protection of nitrogen at 15° C., then potassium tert-butoxide (118.25 mg, 1.05 mmol) and acrylamide (74.91 mg, 1.05 mmol) were sequentially added. The reaction mixture was reacted with stirring at 15° C. for 1 hour. After the reaction was completed, ethyl acetate (10 mL) and water (10 mL) were sequentially added to the reaction system to dilute, and the phases were separated, then the organic phases were collected, and the aqueous phase was extracted with ethyl acetate (10 mL×2). The organic phases were combined, washed with semi-saturated brine (20 mL×3), dried with anhydrous sodium sulfate, filtered, and the filtrate was concentrated under reduced pressure to obtain a residue. 2 mL of methanol was added to the obtained residue, and the mixture was stirred at room temperature for 10 minutes, filtered, and the solid was collected to obtain target compound WX062. MS-ESI m/z: 244.1 [M+H]+. 1H NMR (400 MHz, DMSO_d6) δ: 10.92 (s, 1H), 7.47 (d, J=8.0 Hz, 1H), 7.37 (d, J=7.2 Hz, 1H), 7.21 (t, J=7.2 Hz, 1H), 7.15 (t, J=7.4 Hz, 1H), 4.13 (dd, J=5.2, 12.8 Hz, 1H), 2.86-2.71 (m, 1H), 2.60-2.55 (m, 1H), 2.39 (s, 3H), 2.36-2.28 (m, 1H), 2.00-1.89 (m, 1H).

Embodiment 63: WX063

Synthetic Route:

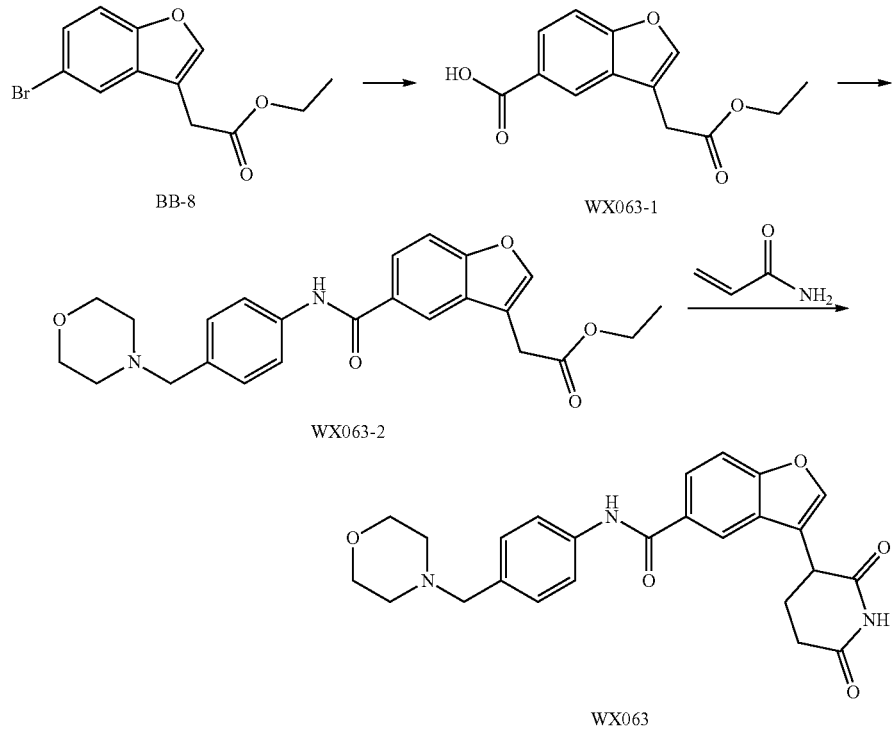

Step 1: Synthesis of Compound WX063-1

Compound BB-8 (4 g, 14.13 mmol), 4,5-bis(diphenylphosphino)-9,9-dimethylxanthene (817.50 mg, 1.41 mmol), 4-dimethylaminopyridine (863.03 mg, 7.06 mmol), molybdenum hexacarbonyl (932.48 mg, 3.53 mmol) and potassium phosphate (3.00 g, 14.13 mmol) were dissolved in dioxane (40 mL) and tert-butyl alcohol (40 mL) at room temperature under the protection of nitrogen, and tris(dibenzylideneacetone)dipalladium (158.60 mg, 706.42 μmol) was added, then the reaction mixture was heated to 120° C. and reacted with stirring for 12 hours. After the reaction was completed, the mixture was cooled to room temperature, and water (100 mL) was added, then the mixture was extracted with ethyl acetate (80 mL×3). The combined organic phases were discarded, and the aqueous phase was adjusted to pH=4 to 5 with 2M hydrochloric acid (10 mL), and extracted with ethyl acetate (80 mL×3). The organic phases were combined, washed with saturated brine (60 mL×2), dried with anhydrous sodium sulfate, filtered, and the filtrate was concentrated under reduced pressure to remove the solvent, and the obtained residue was separated by column chromatography (eluent: petroleum ether/ethyl acetate=1/0-1/1, v/v) to obtain compound WX063-1. MS-ESI m/z: 249.0 [M+H]+. 1H NMR (400 MHz, DMSO_d6) δ: 12.87 (s, 1H), 8.25 (d, J=1.2 Hz, 1H), 8.01 (s, 1H), 7.92 (dd, J=1.4, 8.6 Hz, 1H), 7.65 (d, J=8.8 Hz, 1H), 4.11 (q, J=7.0 Hz, 2H), 3.85 (s, 2H), 1.19 (t, J=7.2 Hz, 3H).

Step 2: Synthesis of Compound WX063-2

Compound WX063-1 (0.22 g, 886.27 μmol) and 4-(morpholinomethyl)aniline (340.78 mg, 1.77 mmol), O-(7-azabenzotriazol-1-yl)-N,N,N',N'-tetramethyluronium hexafluorophosphate (673.97 mg, 1.77 mmol) were add to N,N-dimethylformamide (3 mL) at room temperature under the protection of nitrogen, and triethylamine (269.05 mg, 2.66 mmol, 370.08 μL) was added, then the reaction mixture was reacted with stirring at room temperature for 12 hours. After the reaction was completed, water (60 mL) was added, and the mixture was extracted with ethyl acetate (50 mL×3). The organic phases were combined, washed with saturated brine (50 mL×2), dried with anhydrous sodium sulfate, filtered, and the filtrate was concentrated under reduced pressure to remove the solvent, and the obtained residue was separated by column chromatography (eluent: petroleum ether/ethyl acetate=1/1-0/1, v/v) to obtain compound WX063-2. MS-ESI m/z: 423.1 [M+H]+. 1H NMR (400 MHz, DMSO_d6) δ: 10.25 (s, 1H), 8.26 (d, J=1.6 Hz, 1H), 8.04 (s, 1H), 7.96 (dd, J=1.6, 8.8 Hz, 1H), 7.73 (t, J=9.2 Hz, 3H), 7.29 (d, J=8.8 Hz, 2H), 4.15 (q, J=7.0 Hz, 2H), 3.87 (s, 2H), 3.58 (t, J=4.6 Hz, 4H), 3.44 (s, 2H), 2.36 (s, 4H), 1.22 (t, J=7.2 Hz, 3H).

Step 3: Synthesis of Compound WX063

Compound WX063-2 (0.2 g, 473.40 μmol) was added to N,N-dimethylformamide (10 mL) under the protection of nitrogen at 0° C., then potassium tert-butoxide (53.12 mg, 473.40 μmol) was added, and the reaction mixture was reacted with stirring at 0° C. for 1 hour, then acrylamide (67.30 mg, 946.81 μmol) was added to the above reaction solution, and the reaction mixture was raised to room temperature and reacted with stirring for 2 hours. After the reaction was completed, water (50 mL) was added, and the mixture was extracted with ethyl acetate (30 mL×3). The organic phases were combined, washed with saturated brine (30 mL×2), dried with anhydrous sodium sulfate, filtered, and the filtrate was concentrated under reduced pressure to remove the solvent, and the obtained residue was separated by preparative HPLC (mobile phase: acetonitrile/water; acidic system: 0.05% HCl). The solvent was removed from the fraction under reduced pressure, and the obtained residue was added with water (50 mL), the pH of the mixture was adjusted to 7 with saturated sodium bicarbonate solution (0.1 mL), and the mixture was extracted with ethyl acetate (30 mL×3). The organic phases were combined, washed with saturated brine (30 mL×2), dried with anhydrous sodium sulfate, filtered, and the filtrate was concentrated under reduced pressure to remove the solvent to obtain target compound WX063. MS-ESI m/z: 448.2 [M+H]$^+$. $^1$H NMR (400 MHz, DMSO_$d_6$) δ: 10.97 (s, 1H), 10.24 (s, 1H), 8.21 (d, J=1.6 Hz, 1H), 8.04 (s, 1H), 7.96 (dd, J=2.0, 8.8 Hz, 1H), 7.72 (d, J=8.4 Hz, 3H), 7.29 (d, J=8.4 Hz, 2H), 4.23 (dd, J=4.8, 12.4 Hz, 1H), 3.58 (t, J=4.4 Hz, 4H), 3.44 (s, 2H), 2.87-2.72 (m, 1H), 2.67-2.59 (m, 1H), 2.47-2.38 (m, 1H), 2.37-2.32 (m, 4H), 2.25-2.12 (m, 1H).

Referring to the synthesis method in embodiment 63 (e.g., 4-(morpholinomethyl)aniline was replaced with fragment 2 in step 2), the embodiments in Table 11 are synthesized, and the LCMS and HNMR data are shown in Table 12.

TABLE 11

| Embodiments | Fragment 1 | Fragment 2 | Structure | Compound |
|---|---|---|---|---|
| 66 | WX063-1 | | 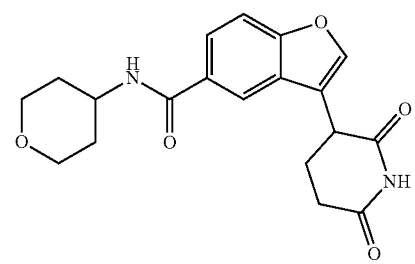 [SMILES: O=C1CCC(c2coc3ccc(C(=O)NC4CCOCC4)cc23)C(=O)N1] | WX066 |
| 67 | WX063-1 | | 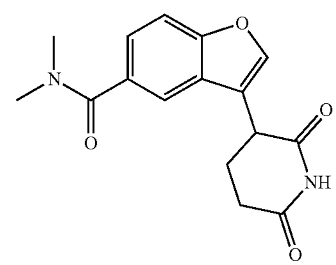 [SMILES: CN(C)C(=O)c1ccc2occ(C3CCC(=O)NC3=O)c2c1] | WX067 |
| 69 | WX063-1 | | 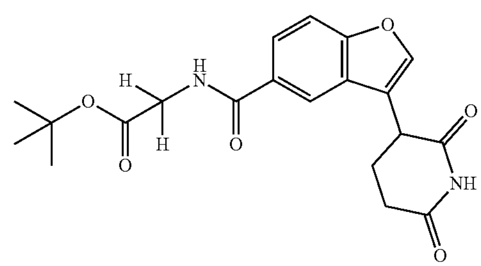 [SMILES: CC(C)(C)OC(=O)CNC(=O)c1ccc2occ(C3CCC(=O)NC3=O)c2c1] | WX069 |
| 73 | WX063-1 | | 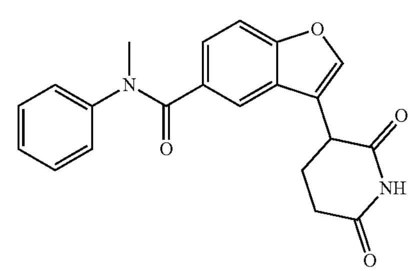 [SMILES: CN(C(=O)c1ccc2occ(C3CCC(=O)NC3=O)c2c1)c1ccccc1] | WX073 |

TABLE 11-continued

| Embodiments | Fragment 1 | Fragment 2 | Structure | Compound |
|---|---|---|---|---|
| 74 | WX063-1 | allylamine | 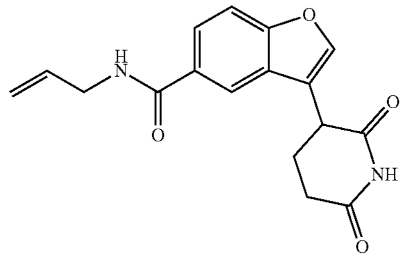 [SMILES: C=CCNC(=O)c1ccc2occ(C3CCC(=O)NC3=O)c2c1] | WX074 |
| 75 | WX063-1 | cyclopropyl(piperazin-1-yl)methanone | 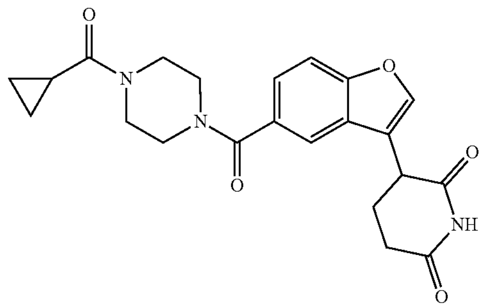 [SMILES: O=C1CCC(c2coc3ccc(C(=O)N4CCN(C(=O)C5CC5)CC4)cc23)C(=O)N1] | WX075 |
| 76 | WX063-1 | 4-aminobenzamide | 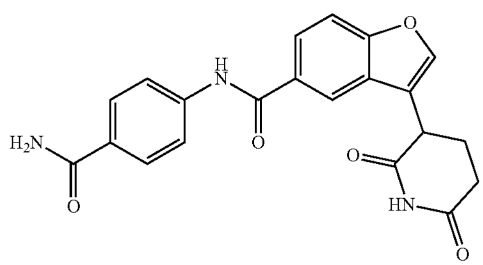 [SMILES: NC(=O)c1ccc(NC(=O)c2ccc3occ(C4CCC(=O)NC4=O)c3c2)cc1] | WX076 |

TABLE 12

| Embodiments | Compound | HNMR | LCMS |
|---|---|---|---|
| 66 | WX066 | $^1$H NMR (400 MHZ, DMSO_$d_6$) δ: 10.96 (s, 1H), 8.32 (d, J = 7.2 Hz, 1H), 8.10 (s, 1H), 7.99 (s, 1H), 7.86 (d, J = 8.8 Hz, 1H), 7.64 (d, J = 8.4 Hz, 1H), 4.20 (dd, J = 4.6, 12.2 Hz, 1H), 4.09-3.99 (m, 1H), 3.89 (d, J = 9.2 Hz, 2H), 3.39 (t, J = 11.2 Hz, 2H), 2.78-2.71 (m, 1H), 2.60-2.53 (m, 1H), 2.43-2.29 (m, 1H), 2.20-2.11 (m, 1H), 1.78 (d, J = 11.5 Hz, 2H), 1.63-1.59 (m, 2H). | MS-ESI m/z: 357.2 [M + H]$^+$. |
| 67 | WX067 | $^1$H NMR (400 MHZ, DMSO_$d_6$) δ: 10.89 (s, 1H), 7.97 (s, 1H), 7.67 (d, J = 1.2 Hz, 1H), 7.61 (d, J = 8.4 Hz, 1H), 7.35 (dd, J = 1.6, 8.4 Hz, 1H), 4.17 (dd, J = 4.8, 12.4 Hz, 1H), 2.98 (s, 3H), 2.93 (s, 3H), 2.79-2.67 (m, 1H), 2.61-2.54 (m, 1H), 2.38-2.30 (m, 1H), 2.16-2.04 (m, 1H). | MS-ESI m/z: 301.1 [M + H]$^+$. |
| 69 | WX069 | $^1$H NMR (400 MHZ, DMSO_$d_6$) δ: 10.95 (s, 1H), 8.86 (t, J = 5.6 Hz, 1H), 8.13 (s, 1H), 8.01 (s, 1H), 7.86 (dd, J = 1.2, 8.4 Hz, 1H), 7.67 (d, J = 8.8 Hz, 1H), 4.19 (dd, J = 4.6, 12.4 Hz, 1H), 3.93 (d, J = 6.0 Hz, 2H), 2.86-2.74 (m, 1H), 2.68-2.58 (m, 1H), 2.43-2.30 (m, 1H), 2.17-2.08 (m, 1H), 1.43 (s, 9H). | MS-ESI m/z: 409.0 [M + Na]$^+$. |
| 73 | WX073 | $^1$H NMR (400 MHZ, DMSO_$d_6$) δ: 10.92 (s, 1H), 7.90 (s, 1H), 7.43 (s, 1H), 7.42 (d, J = 6.0 Hz, 1H), 7.26 (dd, J = 1.2, 8.4 Hz, 1H), 7.24-7.121 (m, 2H), 7.18-7.11 (m, 3 H), 4.04 (dd, J = 6.0, 11.2 Hz, 1H), 3.39 (s, 3H), 2.77-2.54 (m, 2H), 2.00-1.88 (m, 2H). | MS-ESI m/z: 363.2 [M + H]$^+$. |
| 74 | WX074 | $^1$H NMR (400 MHZ, DMSO_$d_6$) δ: 10.96 (s, 1H), 8.69 (t, J = 5.6 Hz, 1H), 8.12 (d, J = 1.2 Hz, 1H), 7.99 (s, 1H), 7.87 (dd, J = 1.8, 8.6 Hz, 1H), 7.65 (d, J = 8.8 Hz, 1H), 5.96-5.86 (m, 1H), 5.17 (dd, J = 1.6, 17.2 Hz, 1H), 5.09 (dd, J = 1.6, 10.0 Hz, 1H), 4.18 (dd, J = 5.0, 12.6 Hz, 1H), 3.96-3.91 (m, 2H), 2.83-2.74 (m, 1H), 2.64-2.56 (m, 1H), 2.42-2.37 (m, 1H), 2.17-2.08 (m, 1H). | MS-ESI m/z: 313.0 [M + H]$^+$. |

TABLE 12-continued

| Embodiments | Compound | HNMR | LCMS |
|---|---|---|---|
| 75 | WX075 | $^1$H NMR (400 MHZ, MeOD_$d_4$) δ: 7.85 (s, 1H), 7.73 (s, 1H), 7.61 (d, J = 8.8 Hz, 1H), 7.44 (dd, J = 1.6, 8.4 Hz, 1H), 4.18 (dd, J = 5.0, 11.8 Hz, 1H), 4.00-3.46 (m, 8H), 2.88-2.68 (m, 2H), 2.49-2.35 (m, 1H), 2.34-2.25 (m, 1H), 2.06-1.90 (m, 1H), 0.94-0.79 (m, 4H). | MS-ESI m/z: 410.1 [M + H]$^+$. |
| 76 | WX076 | $^1$H NMR (400 MHZ, DMSO_$d_6$) δ: 10.96 (s, 1H), 10.45 (s, 1H), 8.22 (s, 1H), 8.04 (s, 1H), 7.96-7.90 (m, 1H), 7.88-7.84 (m, 5H), 7.75-7.73 (m, 1H), 7.27 (s, 1H), 4.23 (dd, J = 4.8, 12.0 Hz, 1H), 2.79-2.67 (m, 1H), 2.64-2.59 (m, 1H), 2.42-2.39 (m, 1H), 2.33-2.19 (m, 1H). | MS-ESI m/z: 392.1 [M + H]$^+$. |

Embodiment 77: WX077

Synthetic Route:

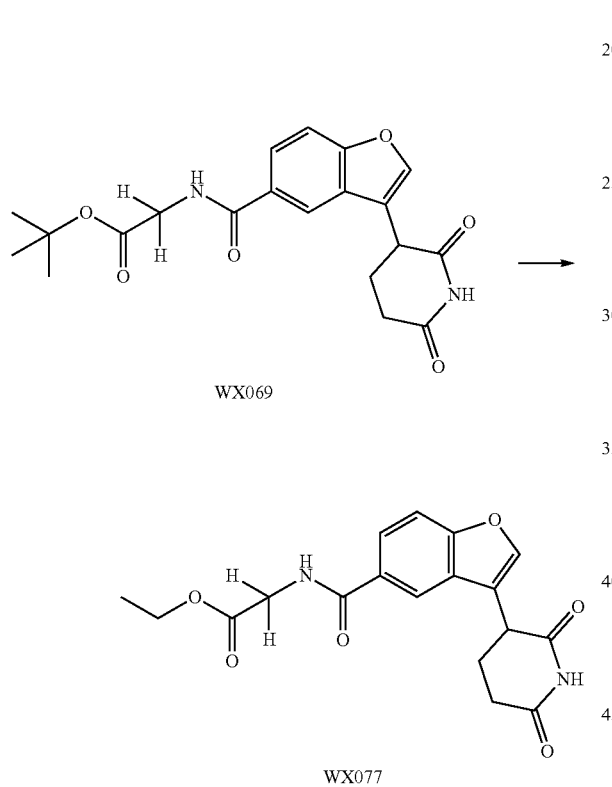

Embodiment 78: WX078

Synthetic Route:

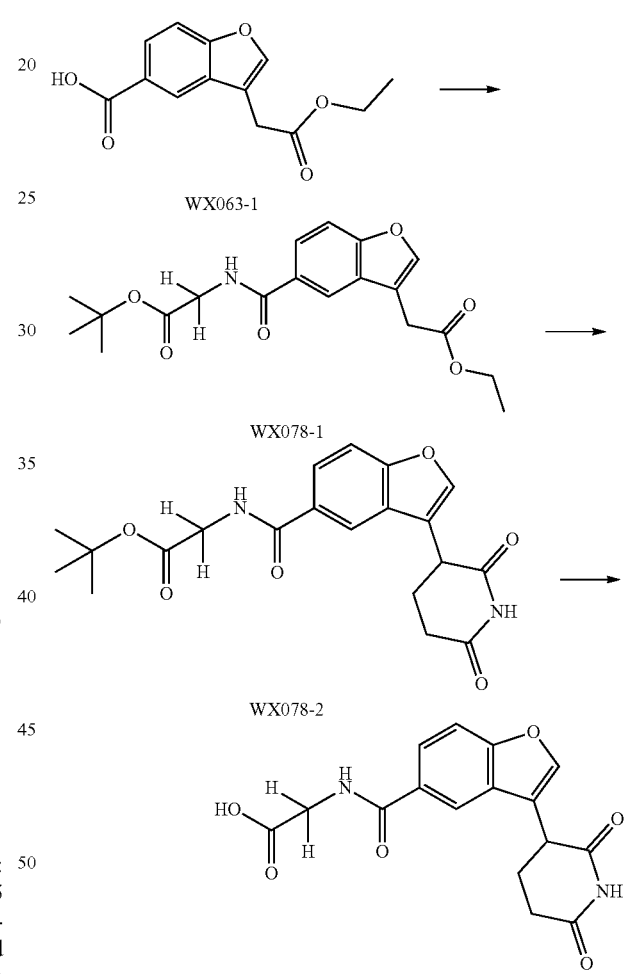

Compound WX069 (0.100 g, 256.45 μmol, purity: 99.09%) was added to ethyl acetate hydrochloride (4 M, 5 mL) at room temperature and under the protection of nitrogen, and the reaction mixture was heated to 50° C. and reacted with stirring at 50° C. for 12 hours. After the reaction was completed, the reaction mixture was cooled to room temperature, concentrated under reduced pressure to remove the solvent, and the obtained residue was separated by preparative HPLC (mobile phase: acetonitrile/water; acidic system: 0.05% HCl), to obtain target compound WX077. MS-ESI m/z: 359.0 [M+H]$^+$. $^1$H NMR (400 MHz, DMSO_$d_6$) δ: 10.96 (s, 1H), 8.96 (t, J=5.8 Hz, 1H), 8.13 (d, J=1.6 Hz, 1H), 8.01 (s, 1H), 7.87 (dd, J=1.6, 8.4 Hz, 1H), 7.67 (d, J=8.8 Hz, 1H), 4.19 (dd, J=4.8, 12.4 Hz, 1H), 4.12 (q, J=7.0 Hz, 2H), 4.02 (d, J=5.6 Hz, 2H), 2.87-2.74 (m, 1H), 2.71-2.54 (m, 1H), 2.47-2.29 (m, 1H), 2.20-2.09 (m, 1H), 1.21 (t, J=7.2 Hz, 3H).

Step 1: Synthesis of Compound WX078-1

Compound WX063-1 (0.400 g, 1.02 mmol, purity: 63.10%), glycine tert-butyl ester hydrochloride (340.90 mg, 2.03 mmol) and O-(7-azabenzotriazol-1-yl)-1N,N,N',N'-tetramethyluronium hexafluorophosphate (773.23 mg, 2.03 mmol) were dissolved in N,N-dimethylformamide (5 mL), and then triethylamine (514.45 mg, 5.08 mmol, 707.63 μL) was added, and the reaction mixture was reacted with stirring at room temperature for 2 hours. After the reaction was completed, the reaction mixture was added with water (50 mL), and extracted with ethyl acetate (30 mL×3). The organic phases were combined, washed with saturated brine (30 mL×2), dried with anhydrous sodium sulfate, filtered, and the filtrate was concentrated under reduced pressure to remove the solvent, and the obtained residue was separated by column chromatography (eluent: petroleum ether/ethyl acetate=10/1-5/1, v/v) to obtain compound WX078-1. MS-ESI m/z: 305.9 [M−55]$^+$. $^1$H NMR (400 MHz, DMSO_d$_6$) δ: 8.85 (t, J=6.0 Hz, 1H), 8.18 (d, J=1.2 Hz, 1H), 8.01 (s, 1H), 7.86 (dd, J=1.8, 8.6 Hz, 1H), 7.66 (d, J=8.4 Hz, 1H), 4.13 (q, J=7.2 Hz, 2H), 3.92 (d, J=6.0 Hz, 2H), 3.83 (s, 2H), 1.43 (s, 9H), 1.21 (t, J=7.2 Hz, 3H).

Step 2: Synthesis of Compound WX078-2

Compound WX078-1 (331 mg, 887.89 μmol, purity: 96.94%) was dissolved in N,N-dimethylformamide (20 mL), and potassium tert-butoxide (99.63 mg, 887.89 μmol) and acrylamide (63.11 mg, 887.89 μmol) were added, and the reaction mixture was stirred at 0° C. for 1 hour. After the reaction was completed, the reaction mixture was added with water (50 mL), and extracted with ethyl acetate (30 mL×3). The organic phases were combined, washed with saturated brine (30 mL×2), dried with anhydrous sodium sulfate, filtered, and the filtrate was concentrated under reduced pressure to remove the solvent, and the obtained residue was separated by column chromatography (eluent: petroleum ether/ethyl acetate=10/1-1/9, v/v) to obtain compound WX078-2. MS-ESI m/z: 331.1 [M−55]$^+$. $^1$H NMR (400 MHz, DMSO_d$_6$) δ: 10.96 (s, 1H), 8.87 (t, J=5.8 Hz, 1H), 8.13 (s, 1H), 8.01 (s, 1H), 7.86 (dd, J=1.2, 58.4 Hz, 1H), 7.67 (d, J=8.8 Hz, 1H), 4.19 (dd, J=4.8, 12.4 Hz, 1H), 3.93 (d, J=5.6 Hz, 2H), 2.86-2.71 (m, 1H), 2.69-2.55 (m, 1H), 2.43-2.31 (m, 1H), 2.20-2.06 (m, 1H), 1.44 (s, 9H).

Step 3: Synthesis of Compound WX078

Compound WX078-2 (0.100 g, 243.92 μmol, purity: 94.25%) was dissolved in ethyl acetate hydrochloride (4 M, 3.21 mL) at room temperature under the protection of nitrogen, and the reaction mixture was heated to 50° C. and reacted with stirring for 2 hours. After the reaction was completed, the reaction mixture was directly concentrated under reduced pressure to remove the solvent. The obtained residue was separated by preparative HPLC (mobile phase: acetonitrile/water; acidic system: 0.05% HCl) to obtain target compound WX078. MS-ESI m/z: 331.1 [M+H]$^+$. $^1$H NMR (400 MHz, DMSO_d$_6$) δ: 10.97 (s, 1H), 8.87 (t, J=5.8 Hz, 1H), 8.13 (d, J=1.6 Hz, 1H), 8.01 (s, 1H), 7.87 (dd, J=1.6, 8.8 Hz, 1H), 7.67 (d, J=8.8 Hz, 1H), 4.19 (dd, J=4.8, 12.4 Hz, 1H), 3.95 (d, J=6.0 Hz, 2H), 2.85-2.73 (m, 1H), 2.68-2.56 (m, 1H), 2.45-2.31 (m, 1H), 2.19-2.07 (m, 1H).

Synthetic Route:

Embodiment 79: WX079

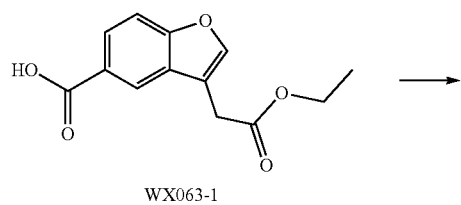

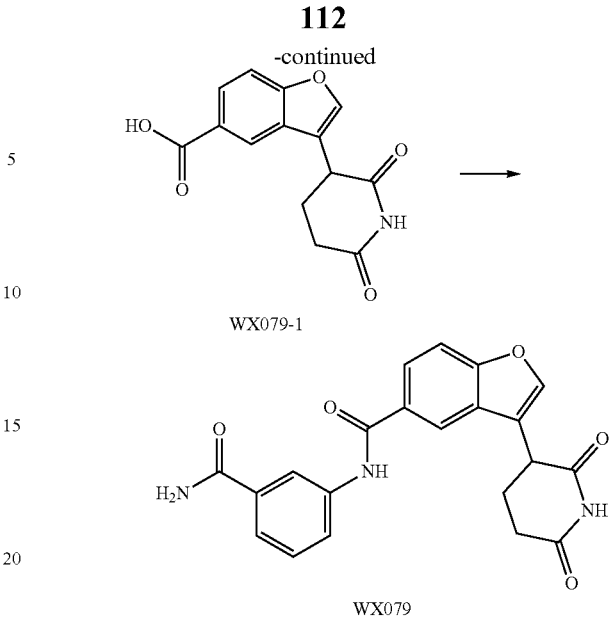

Step 1: Synthesis of Compound WX079-1

Compound WX063-1 (1.0 g, 4.03 mmol) was dissolved in tetrahydrofuran (20 mL) at 0° C., and acrylamide (286.34 mg, 4.03 mmol) and potassium tert-butoxide (904.08 mg, 8.06 mmol) were added, then the reaction mixture was stirred at 15° C. for 3 hours. After the reaction was completed, water (10 mL) was added to the reaction solution, then the pH of the mixture was adjusted to 6 with 2 M dilute hydrochloric acid, and the mixture was extracted with 2-methyltetrahydrofuran (10 mL×4), then the organic phases were combined, and sequentially washed with saturated brine (10 mL), dried with anhydrous sodium sulfate, filtered, and the filtrate was concentrated under reduced pressure to remove the solvent to obtain a crude product of compound WX079-1.

Step 2: Synthesis of Compound WX079

The crude product of compound WX079-1 (200 mg, 731.96 μmol) from the previous step was dissolved in N,N-dimethylformamide (2 mL) at room temperature and under the protection of nitrogen, and the mixture was cooled to 0° C., then hexafluorophosphate (556.62 mg, 1.46 mmol) and triethylamine (222.20 mg, 2.20 mmol) were added. The reaction mixture was reacted with stirring at 0° C. for 10 minutes, and 3-aminobenzamide (99.66 mg, 731.96 μmol) was added, and the reaction mixture was raised to 15° C. and reacted with stirring for 16 hours. After the reaction was completed, semi-saturated brine (20 mL) and 2-methyltetrahydrofuran (20 mL) were added to the reaction solution to dilute, and the phases were separated, then the organic phases were collected, and the aqueous phase was extracted with 2-methyltetrahydrofuran (20 mL×3). The organic phases were combined, washed with semi-saturated brine (10 mL×2), dried with anhydrous sodium sulfate, filtered, and the filtrate was concentrated under reduced pressure to remove the solvent, and the obtained residue was separated by preparative HPLC (mobile phase: acetonitrile/water; acidic system: 0.1% TFA) to obtain target compound WX079. MS-ESI m/z: 392.1 [M+H]$^+$. $^1$H NMR (400 MHz, DMSO_d$_6$) δ: 10.97 (s, 1H), 10.38 (s, 1H), 8.24 (d, J=1.2 Hz, 1H), 8.22 (s, 1H), 8.04 (s, 1H), 8.01-7.92 (m, 3H), 7.73 (d, J=8.4 Hz, 1H), 7.61 (d, J=8.0 Hz, 1H), 7.44 (t, J=7.8 Hz, 1H), 7.36 (s, 1H), 4.23 (dd, J=4.8, 12.4 Hz, 1H), 2.85-2.73 (m, 1H), 2.69-2.56 (m, 1H), 2.43-2.31 (m, 1H), 2.22-2.12 (m, 1H).

Referring to the synthesis method in Embodiment 79, each embodiment in Table 13 is synthesized, and the LCMS and HNMR data are shown in Table 14.

TABLE 13

| Embodiments | Fragment 1 | Fragment 2 | Structure | Compound |
|---|---|---|---|---|
| 80 | WX079-1 | | 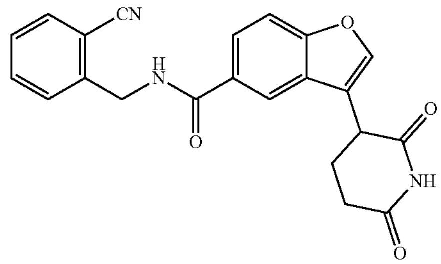 [SMILES: N#Cc1ccccc1CNC(=O)c1ccc2occ(C3CCC(=O)NC3=O)c2c1] | WX080 |

TABLE 14

| Embodiments | Compound | HNMR | LCMS |
|---|---|---|---|
| 80 | WX080 | $^1$H NMR (400 MHZ, MeOD-$d_4$) δ: 8.16 (d, J = 1.6 Hz, 1H), 7.89 (dd, J = 1.6, 8.6 Hz, 1H), 7.84 (s, 1H), 7.74 (d, J = 7.6 Hz, 1H), 7.65 (t, J = 7.6 Hz, 1H), 7.61-7.55 (m, 2H), 7.44 (t, J = 7.6 Hz, 1H), 4.79 (s, 2H), 4.18 (dd, J = 4.8, 12.0 Hz, 1H), 2.88-2.68 (m, 2H), 2.52-2.39 (m, 1H), 2.34-2.25 (m, 1H). | MS-ESI m/z: 388.1 [M + H]$^+$. |

Embodiment 81: WX081

Chemical Synthesis:

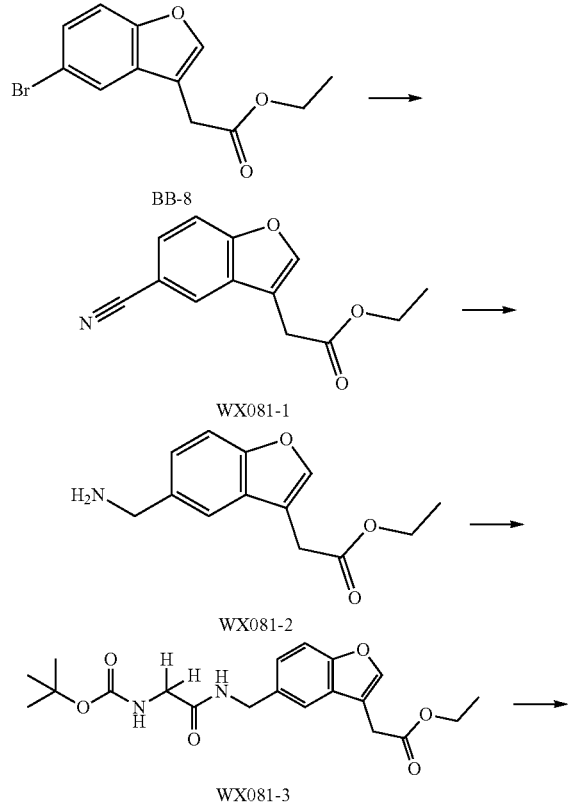

Step 1: Synthesis of Compound WX081-1

Compound BB-8 (2.00 g, 6.26 mmol, purity: 88.65%) and zinc cyanide (1.54 g, 13.10 mmol) were dissolved in N,N-dimethylformamide (30 mL), then tris(dibenzylideneacetone)dipalladium (286.73 mg, 313.12 μmol) and 2-dicyclohexylphosphino-2,4,6-triisopropylbiphenyl (298.54 mg, 626.24 μmol) were added, and the reaction mixture was heated to 80° C. and reacted with stirring at 80° C. for 12 hours. After the reaction was completed, the mixture was cooled to room temperature, and the reaction mixture was added with water (100 mL), and extracted with ethyl acetate (50 mL×3). The organic phases were combined, washed with saturated brine (50 mL×2), dried with anhydrous sodium sulfate, filtered, and the filtrate was concentrated under reduced pressure to remove the solvent, and the obtained residue was separated by column chromatography (eluent: petroleum ether/ethyl acetate=10/1-4/1, v/v) to obtain compound WX081-1. MS-ESI m/z: 230.0 [M+H]$^+$. $^1$H NMR (400 MHz, CDCl$_3$) δ: 7.95 (s, 1H), 7.76 (s, 1H), 7.60 (dd, J=1.4, 8.6 Hz, 1H), 7.56 (d, J=8.8 Hz, 1H), 4.22 (q, J=7.0 Hz, 2H), 3.71 (d, J=0.8 Hz, 2H), 1.30 (t, J=7.2 Hz, 3H).

Step 2: Synthesis of Compound WX081-2

Compound WX081-1 (2.00 g, 8.30 mmol, purity: 95.18%) was dissolved in ethanol (50 mL) at room temperature under the protection of nitrogen, then hydrochloric acid (4 M, 0.01 mL) and Raney nickel (711.47 mg, 8.30 mmol) were added, and the reaction system was evacuated under reduced pressure and replaced with hydrogen several times, then the reaction mixture was reacted with stirring at room temperature under the protection of hydrogen for 12 hours. After the reaction was completed, the reaction mixture was filtered, and the filtrate was concentrated under reduced pressure to remove the solvent, and the obtained residue was separated by column chromatography (eluent: dichloromethane/methanol=100/1-10/1, v/v) to obtain compound WX081-2. MS-ESI m/z: 234.0 [M+H]$^+$. $^1$H NMR (400 MHz, DMSO_$d_6$) δ: 8.46 (s, 2H), 7.97 (s, 1H), 7.72 (d, J=1.2 Hz, 1H), 7.63 (d, J=8.4 Hz, 1H), 7.48 (dd, J=1.6, 8.4 Hz, 1H), 4.12 (q, J=7.2 Hz, 2H), 4.09 (s, 2H), 3.77 (s, 2H), 1.21 (t, J=7.0 Hz, 3H).

Step 3: Synthesis of Compound WX081-3

Compound WX081-2 (0.350 g, 1.48 mmol, purity: 98.34%), N-tert-butoxycarbonylglycine hydrochloride (624.58 mg, 2.95 mmol) and O-(7-azabenzotriazol-1-yl)-N,N,N',N'-tetramethyluronium hexafluorophosphate (1.12 g, 2.95 mmol) were dissolved in N,N-dimethylformamide (10 mL) at room temperature under the protection of nitrogen, then triethylamine (746.55 mg, 7.38 mmol, 1.03 mL) was added, and the reaction mixture was reacted with stirring at room temperature for 2 hours. After the reaction was completed, the reaction mixture was added with water (50 mL), and extracted with ethyl acetate (30 mL×3). The organic phases were combined, washed with saturated brine (30 mL×2), dried with anhydrous sodium sulfate, filtered, and the filtrate was concentrated under reduced pressure to remove the solvent, and the obtained residue was separated by column chromatography (eluent: petroleum ether/ethyl acetate=10/1-1/2, v/v) to obtain compound WX081-3. MS-ESI m/z: 290.8 [M−99]$^+$. $^1$H NMR (400 MHz, DMSO_$d_6$) δ: 8.31 (t, J=5.8 Hz, 1H), 7.89 (s, 1H), 7.49 (d, J=8.4 Hz, 1H), 7.47 (d, J=1.2 Hz, 1H), 7.22 (d, J=8.8 Hz, 1H), 6.97 (t, J=5.8 Hz, 1H), 4.36 (d, J=6.0 Hz, 2H), 4.12 (q, J=7.0 Hz, 2H), 3.76 (s, 2H), 3.56 (d, J=6.0 Hz, 2H), 2.69 (s, 3H), 1.38 (s, 9H), 1.20 (t, J=7.2 Hz, 3H).

Step 4: Synthesis of Compound WX081

Compound WX081-3 (0.490 g, 1.26 mmol, purity: 100%) was dissolved in N,N-dimethylformamide (10 mL) at 0° C. under the protection of nitrogen, and potassium tert-butoxide (140.83 mg, 1.26 mmol) and acrylamide (89.20 mg, 1.26 mmol) were added, and the reaction mixture was stirred at 0° C. for 1 hour. After the reaction was completed, the reaction mixture was added with water (50 mL), and extracted with ethyl acetate (30 mL×3). The organic phases were combined, washed with saturated brine (30 mL×2), dried with anhydrous sodium sulfate, filtered, and the filtrate was concentrated under reduced pressure to remove the solvent, and the obtained residue was separated by preparative HPLC (mobile phase: acetonitrile/water; acidic system: 0.05% HCl) to obtain target compound WX081. MS-ESI m/z: 316.0 [M−99]$^+$. $^1$H NMR (400 MHz, DMSO_$d_6$) δ: 10.91 (s, 1H), 8.29 (t, J=5.6 Hz, 1H), 7.88 (s, 1H), 7.50 (d, J=8.4 Hz, 1H), 7.47 (s, 1H), 7.22 (d, J=8.8 Hz, 1H), 6.96 (t, J=6.0 Hz, 1H), 4.35 (d, J=6.0 Hz, 2H), 4.11 (dd, J=5.0, 11.8 Hz, 1H), 3.56 (d, J=6.0 Hz, 2H), 2.84-2.69 (m, 1H), 2.68-2.54 (m, 1H), 2.39-2.24 (m, 1H), 2.16-2.03 (m, 1H), 1.39 (s, 9H).

Embodiment 83: WX083

Synthetic Route:

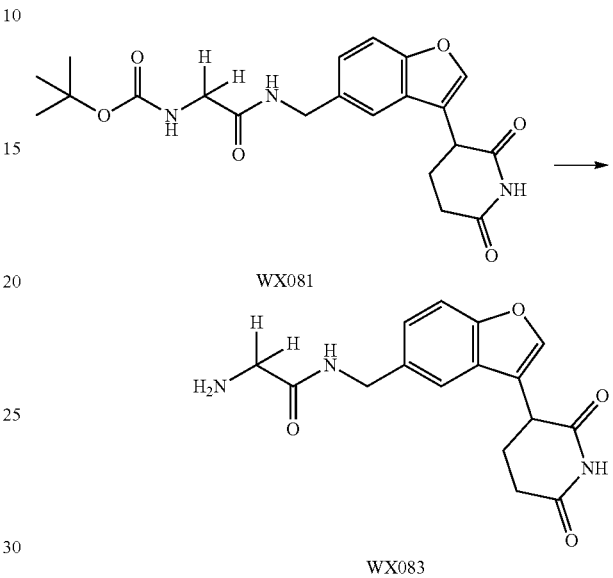

Compound WX081 (100 mg, 206.87 μmol, purity: 85.94%) was dissolved in ethyl acetate hydrochloride (4 M, 5 mL) at room temperature under the protection of nitrogen, and the reaction mixture was heated to 50° C. and reacted with stirring for 12 hours. After the reaction was completed, the reaction mixture was directly concentrated under reduced pressure to remove the solvent. The obtained residue was separated by preparative HPLC (mobile phase: acetonitrile/water; acidic system: 0.05% HCl), to obtain target compound WX083. MS-ESI m/z: 316.2 [M+H]$^+$. $^1$H NMR (400 MHz, DMSO_$d_6$) δ: 10.92 (s, 1H), 8.88 (t, J=5.8 Hz, 1H), 8.09 (s, 3H), 7.91 (s, 1H), 7.55 (d, J=8.4 Hz, 1H), 7.52 (s, 1H), 7.26 (dd, J=1.8, 8.6 Hz, 1H), 4.42 (d, J=5.6 Hz, 2H), 4.14 (dd, J=4.8, 12.0 Hz, 1H), 3.58 (d, J=5.2 Hz, 2H), 2.83-2.71 (m, 1H), 2.68-2.654 (m, 1H), 2.40-2.26 (m, 1H), 2.17-2.02 (m, 1H).

Embodiment 84: WX084

Synthetic Route:

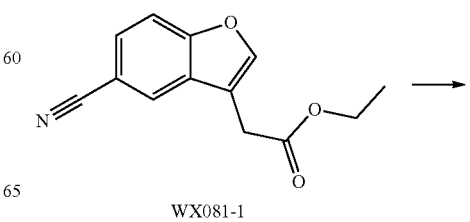

-continued

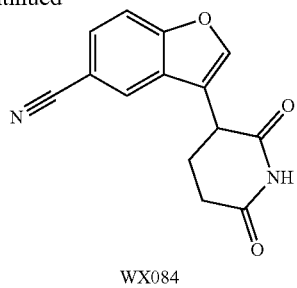

WX084

Compound WX081-1 (0.2 g, 652.62 μmol, purity: 74.8%) was dissolved in N,N-dimethylformamide (5 mL) under the protection of nitrogen at 0° C., and potassium tert-butoxide (73.23 mg, 652.62 μmol) was added, then the reaction mixture was stirred at 0° C. for 1 hour, and acrylamide (46.39 mg, 652.62 μmol) was added, and the reaction mixture was reacted with stirring at room temperature for 2 hours. After the reaction was completed, the reaction mixture was added with water (50 mL), and extracted with ethyl acetate (30 mL×3). The organic phases were combined, washed with saturated brine (30 mL×2), dried with anhydrous sodium sulfate, filtered, and the filtrate was concentrated under reduced pressure to remove the solvent. The obtained residue was separated by column chromatography (eluent: petroleum ether/ethyl acetate=10/1-0/1, v/v), then separated by preparative HPLC (mobile phase: acetonitrile/water; acidic system: 0.05% HCl) to obtain target compound WX084. MS-ESI m/z: 277.0 [M+Na]⁺. ¹H NMR (400 MHz, DMSO_d₆) δ: 10.94 (s, 1H), 8.27 (s, 1H), 8.13 (s, 1H), 7.82 (d, J=8.4 Hz, 1H), 7.76 (d, J=8.4 Hz, 1H), 4.21 (dd, J=4.6, 12.6 Hz, 1H), 2.82-2.69 (m, 1H), 2.64-2.55 (m, 1H), 2.45-2.35 (m, 1H), 2.15-2.04 (m, 1H).

Embodiment 85: WX085

Synthetic Route:

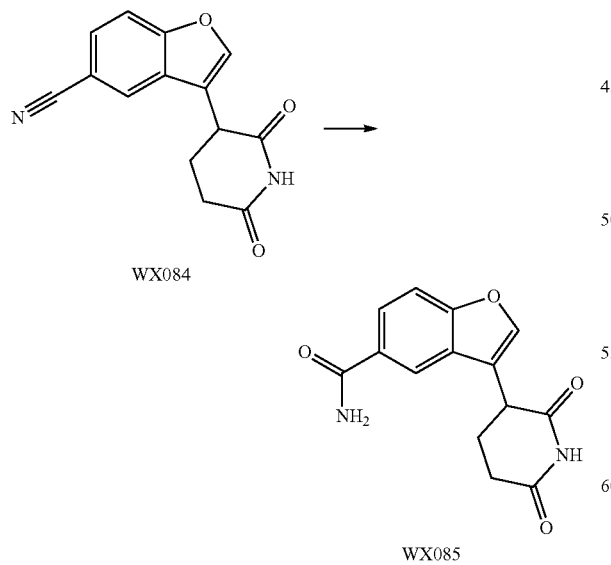

Compound WX084 (0.15 g, 589.99 μmol) was dissolved in sulfuric acid (5.52 g, 55.16 mmol, 3 mL, purity: 98%) and water (10.63 mg, 589.99 μmol, 10.63 μL) at 0° C. under the protection of nitrogen, and the reaction mixture was heated to ° C. and reacted with stirring for 12 hours. After the reaction was completed, the mixture was cooled to room temperature, and the reaction mixture was added with water (30 mL), and extracted with ethyl acetate (20 mL×3). The organic phases were combined, washed with saturated brine (20 mL×2), dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl), to obtain target compound WX085. MS-ESI m/z: 273.0 [M+H]⁺. ¹H NMR (400 MHz, DMSO_d₆) δ: 10.95 (s, 1H), 8.15 (d, J=1.2 Hz, 1H), 8.01 (s, 1H), 7.99 (s, 1H), 7.88 (dd, J=1.4, 8.6 Hz, 1H), 7.63 (d, J=8.4 Hz, 1H), 7.35 (s, 1H), 4.18 (dd, J=4.8, 12.4 Hz, 1H), 2.85-2.73 (m, 1H), 2.65-2.55 (m, 1H), 2.45-2.35 (m, 1H), 2.17-2.05 (m, 1H).

Embodiment 86: WX086

Synthetic Route:

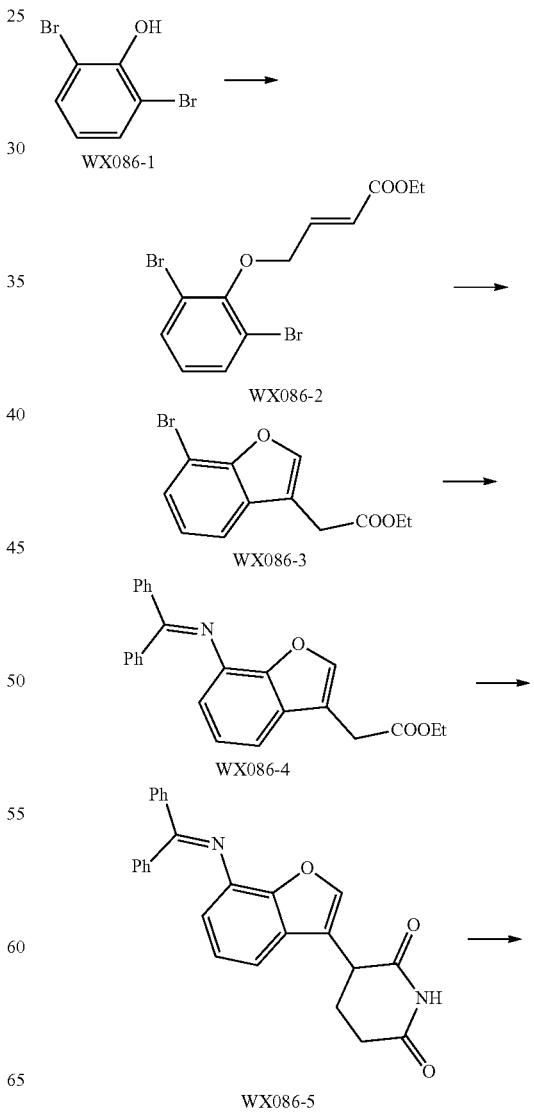

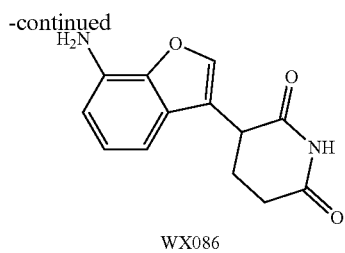

WX086

Step 1: Synthesis of Compound WX086-2

Compound WX086-1 (3 g, 11.91 mmol) was dissolved in N,N-dimethylformamide (30 mL) under the protection of nitrogen at 18° C., then potassium carbonate (3.29 g, 23.82 mmol) was sequentially added, and finally ethyl-4-bromobut-2-enoate (2.30 g, 11.91 mmol, 1.64 mL) was added, then the reaction mixture was stirred at 18° C. for 40 hours, then heated to ° C. and reacted with stirring for 12 hours. After the reaction was completed, water (40 mL) and ethyl acetate (50 mL) were added to the reaction system to dilute, and the phases were separated, then the organic phases were collected, and the aqueous phase was extracted with ethyl acetate (40 mL×2). The organic phases were combined, sequentially washed with semi-saturated brine (50 mL×2), dried with anhydrous sodium sulfate, filtered, and the filtrate was concentrated under reduced pressure to obtain a residue. The obtained residue was separated by column chromatography (eluent: petroleum ether/ethyl acetate=1/0-9/1, v/v), to obtain compound WX086-2. $^1$H NMR (400 MHz, CDCl$_3$) δ: 7.52 (d, J=8.0 Hz, 2H), 7.12 (td, J=4.4, 15.6 Hz, 1H), 6.90 (t, J=7.8 Hz, 1H), 6.35 (td, J=2.0, 15.6 Hz, 1H), 4.70 (dd, J=2.0, 4.4 Hz, 2H), 4.25 (q, J=7.2 Hz, 2H), 1.33 (t, J=7.0 Hz, 3H).

Step 2: Synthesis of Compound WX086-3

Compound WX086-2 (3 g, 8.24 mmol) was dissolved in N,N-dimethylformamide (30 mL) at room temperature under the protection of nitrogen, then sodium carbonate (1.75 g, 16.48 mmol), chloro(2-dicyclohexylphosphino-2,4,6-triisopropyl-1,1-biphenyl)[2-(2'-amino-1,1-biphenyl)]palladium(II) (648.41 mg, 824.11 µmol) were sequentially added, and the reaction mixture was heated to 80° C. and reacted with stirring for 12 hours. After the reaction was completed, water (20 mL) and ethyl acetate (50 mL) were added to the reaction system to dilute, and the phases were separated, then the organic phases were collected, and the aqueous phase was extracted with ethyl acetate (30 mL×2). The organic phases were combined, dried with anhydrous sodium sulfate, filtered, and the filtrate was concentrated under reduced pressure to obtain a residue. The obtained residue was separated by column chromatography (eluent: petroleum ether/ethyl acetate=1/0-9/1, v/v), to obtain compound WX086-3. $^1$H NMR (400 MHz, CDCl$_3$) δ: 7.72 (s, 1H), 7.53 (dd, J=0.8, 7.6 Hz, 1H), 7.48 (dd, J=1.0, 7.8 Hz, 1H), 7.15 (t, J=7.8 Hz, 1H), 4.20 (q, J=7.2 Hz, 2H), 3.70 (d, J=0.8 Hz, 2H), 1.28 (t, J=7.2 Hz, 3H).

Step 3: Synthesis of Compound WX086-4

Compound WX086-3 (200 mg, 706.42 µmol) was dissolved in 1,4-dioxane (5 mL) at room temperature under the proction of nitrogen, then benzophenone imine (192.04 mg, 1.06 mmol, 177.81 µL), tris(dibenzylideneacetone)dipalladium (51.75 mg, 56.51 µmol), 4,5-bis(diphenylphosphino)-9,9-dimethylxanthene (65.40 mg, 113.03 µmol) and cesium carbonate (690.50 mg, 2.12 mmol) were sequentially added, and the reaction mixture was heated to 80° C. and reacted with stirring for 12 hours. After the reaction was completed, the reaction mixture was filtered, and the filtrate was collected, then water (50 mL) and ethyl acetate (50 mL) were added to the filtrate to dilute, and the phases were separated, then the organic phases were collected, and the aqueous phase was extracted with ethyl acetate (50 mL×2). The organic phases were combined, dried with anhydrous sodium sulfate, filtered, and the filtrate was concentrated under reduced pressure to obtain a residue. The obtained residue was separated by column chromatography (eluent: petroleum ether/ethyl acetate=1/0-19/1, v/v), to obtain compound WX086-4. $^1$H NMR (400 MHz, CDCl$_3$) δ: 7.86-7.81 (m, 2H), 7.56 (s, 1H), 7.52-7.48 (m, 1H), 7.46-7.39 (m, 2H), 7.25-7.12 (m, 6H), 7.00 (t, J=7.8 Hz, 1H), 6.55 (dd, J=1.0, 7.4 Hz, 1H), 4.18 (q, J=7.2 Hz, 2H), 3.64 (d, J=0.8 Hz, 2H), 1.25 (t, J=7.2 Hz, 3H).

Step 4: Synthesis of Compound WX086-5

Compound WX086-4 (200 mg, 521.60 µmol) was dissolved in N,N-dimethylformamide (5 mL) at 18° C., then acrylamide (44.49 mg, 625.92 µmol) and potassium tert-butoxide (58.53 mg, 521.60 µmol) were added, and the reaction mixture was stirred at 18° C. for 2 hours. After the reaction was completed, water (10 mL) and ethyl acetate (10 mL) were added to the reaction system to dilute, and the phases were separated, then the organic phases were collected, and the aqueous phase was extracted with ethyl acetate (10 mL×2). The organic phases were combined, dried with anhydrous sodium sulfate, filtered, and the filtrate was concentrated under reduced pressure to obtain a residue. The obtained residue was separated by column chromatography (eluent: petroleum ether/ethyl acetate=1/0-1/1, v/v), to obtain compound WX086-5. $^1$H NMR (400 MHz, DMSO_d$_6$) δ: 10.87 (s, 1H), 7.80 (s, 1H), 7.71 (d, J=8.0 Hz, 2H), 7.58 (t, J=7.0 Hz, 1H), 7.50 (t, J=7.6 Hz, 2H), 7.33-7.25 (m, 3H), 7.19-7.12 (m, 3H), 6.98 (t, J=7.8 Hz, 1H), 6.53 (d, J=7.2 Hz, 1H), 4.08 (dd, J=4.8, 11.6 Hz, 1H), 2.77-2.65 (m, 1H), 2.59-2.53 (m, 1H), 2.34-2.18 (m, 1H), 2.13-2.04 (m, 1H).

Step 5: Synthesis of Compound WX086

Compound WX086-5 (75 mg, 183.62 µmol) was dissolved in hydrochloric acid/ethyl acetate (4 m, 10 mL) at 18° C., and the reaction mixture was reacted with stirring for 12 hours at 18° C. 5 drops of water were added, and the mixture was continued to stir for 12 hours, concentrated under reduced pressure to remove the solvent, and hydrochloric acid/ethyl acetate (4 M, 20 mL) and 5 drops of water were added, and the mixture was continued to stir for 12 hours, and yellow solid was formed. After the reaction was completed, the mixture was filtered, and the filter cake was washed with ethyl acetate (10 mL) to obtain target compound WX086. MS-ESI m/z: 245.1 [M+H]$^+$. $^1$H NMR (400 MHz, DMSO_d$_6$) δ: 10.91 (s, 1H), 8.01 (s, 1H), 7.35 (d, J=7.2 Hz, 1H), 7.19 (t, J=7.8 Hz, 1H), 7.14 (d, J=7.6 Hz, 1H), 4.15 (dd, J=5.0, 12.2 Hz, 1H), 2.82-2.70 (m, 1H), 2.64-2.54 (m, 1H), 2.38-2.25 (m, 1H), 2.16-2.06 (m, 1H).

Embodiment 87: WX087

Synthetic Route:

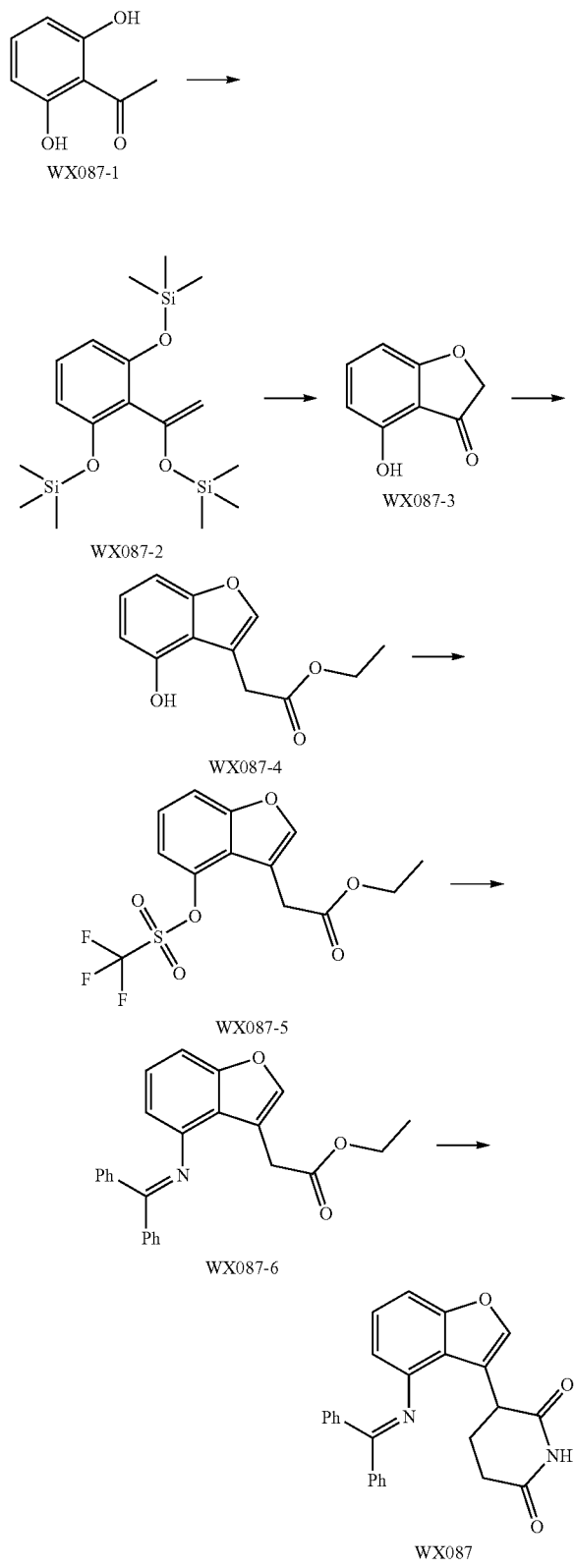

Step 1: Synthesis of Compound WX087-2

Compound WX087-1 (13 g, 85.44 mmol) was dissolved in tetrahydrofuran (300 mL) at room temperature under the protection of nitrogen, the mixture was cooled to 0° C., and lithium bis(trimethylsilyl)amide (1M, 269.15 mL) was added dropwise, then the reaction was stirred for 20 minutes, and chlorotrimethylsilane (32.49 g, 299.05 mmol, 37.96 mL) was added dropwise at 0 to 10° C., and the reaction mixture was naturally raised to room temperature and stirred for 40 minutes. After the reaction was completed, the reaction mixture was directly concentrated under reduced pressure to remove the solvent. The obtained residue was diluted with dichloromethane (100 mL), filtered, and the filtrate was collected, then the filtrate was concentrated under reduced pressure to remove the solvent to obtain a crude product of compound WX087-2, which was directly used in the next reaction.

Step 2: Synthesis of Compound WX087-3

The crude product of compound WX087-2 was dissolved in acetonitrile (300 mL) at room temperature, and N-bromosuccinimide (16.99 g, 95.47 mmol) was added in batches, and the reaction mixture was stirred at room temperature for 50 minutes, and potassium carbonate (6.00 g, 43.40 mmol) was added, then the reaction was continued to react with stirring at room temperature for 10 minutes. After the reaction was completed, water (50 mL) and ethyl acetate (200 mL) were added to the reaction solution to dilute, then the organic phases were collected, and the aqueous phase was extracted with ethyl acetate (50 mL×4). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=0/1— 4/1, v/v), to obtain compound WX087-3. $^1$H NMR (400 MHz, CDCl$_3$) δ: 7.80 (s, 1H), 7.49 (t, J=8.2 Hz, 1H), 6.62 (d, J=8.4 Hz, 1H), 6.49 (d, J=8.0 Hz, 1H), 4.66 (s, 2H).

Step 3: Synthesis of Compound WX087-4

Compound WX087-3 (8 g, 53.29 mmol) was dissolved in toluene (100 mL) at room temperature, then ethoxyformylmethylene triphenylphosphine (27.85 g, 79.93 mmol) was added, and the reaction mixture was heated to 130° C. and reacted with stirring for 48 hours. After the reaction was completed, the reaction mixture was concentrated under reduced pressure to remove the solvent, and the obtained residue was slurried at room temperature with 100 mL of methyl tert-butyl ether, filtered, and the filtrate was collected, then the filtrate was concentrated under reduced pressure to remove the solvent. The obtained residue was separated by column chromatography (eluent: petroleum ether/ethyl acetate=0/1-4/1, v/v), to obtain compound WX087-4. $^1$H NMR (400 MHz, CDCl$_3$) δ: 8.55 (s, 1H), 7.43 (s, 1H), 7.19 (t, J=8.0 Hz, 1H), 7.06 (dd, J=0.8, 8.4 Hz, 1H), 6.79 (dd, J=0.8, 8.0 Hz, 1H), 4.25 (q, J=6.8 Hz, 2H), 3.78 (d, J=0.8 Hz, 2H), 1.31 (t, J=7.0 Hz, 3H).

Step 4: Synthesis of Compound WX087-5

Compound WX087-4 (1.4 g, 6.36 mmol) was dissolved in dichloromethane (20 mL) under the protection of nitrogen at room temperature, then triethylamine (1.61 g, 15.89 mmol, 2.21 mL) was added, and the mixture was cooled to -40° C., then trifluoromethanesulfonic anhydride (2.69 g, 9.54 mmol, 1.57 mL) was added, and the reaction mixture was naturally raised to 0° C. and reacted with stirring for 2 hours. After the reaction was completed, water (20 mL) and dichloromethane (20 mL) were added to the reaction system to dilute, and the phases were separated, then the organic phases were collected, and the aqueous phase was extracted with dichloromethane (20 mL×2). The organic phases were combined, dried with anhydrous sodium sulfate, filtered, and the filtrate was concentrated under reduced pressure to obtain a residue. The obtained residue was separated by column chromatography (eluent: petroleum ether/ethyl acetate=1/0-9/1, v/v), to obtain compound WX087-5. $^1$H NMR (400 MHz, CDCl$_3$) δ: 7.71 (s, 1H), 7.53 (d, J=8.4 Hz, 1H), 7.34 (t, J=8.2 Hz, 1H), 7.22 (d, J=8.4 Hz, 1H), 4.23 (q, J=7.2 Hz, 2H), 3.86 (d, J=1.2 Hz, 2H), 1.30 (t, J=7.0 Hz, 3H).

Step 5: Synthesis of Compound WX087-6

Compound WX087-5 (2 g, 5.68 mmol) was dissolved in 1,4-dioxane (20 mL) at room temperature and under the protection of nitrogen, then benzophenone imine (1.54 g, 8.52 mmol, 1.43 mL), tris(dibenzylideneacetone)dipalladium (415.90 mg, 454.18 μmol), 4,5-bis(diphenylphosphino)-9,9-diMethylxanthene (525.59 mg, 908.36 μmol) and cesium carbonate (5.55 g, 17.03 mmol) were added, and the reaction mixture was heated to 80° C. and stirred for 12 hours. After the reaction was completed, the reaction solution was filtered, and the mother liquid was collected, then water (20 mL) and ethyl acetate (30 mL) were added to the filtrate to dilute, and the phases were separated, then the organic phases were collected, and the aqueous phase was extracted with ethyl acetate (20 mL×2). The organic phases were combined, dried with anhydrous sodium sulfate, filtered, and the filtrate was concentrated under reduced pressure to obtain a residue. The obtained residue was separated by column chromatography (eluent: petroleum ether/ethyl acetate=1/0-19/1, v/v), to obtain compound WX087-6. $^1$H NMR (400 MHz, CDCl$_3$) δ: 7.86-7.78 (m, 2H), 7.50 (s, 1H), 7.46 (dd, J=1.6, 8.0 Hz, 1H), 7.41 (td, J=1.2, 7.6 Hz, 2H), 7.32-7.21 (m, 3H), 7.20-7.13 (m, 2H), 7.04 (dd, J=1.0, 8.4 Hz, 1H), 6.85 (td, J=1.6, 8.0 Hz, 1H), 6.00 (dd, J=0.8, 7.6 Hz, 1H), 3.85 (s, 2H), 3.72 (qd, J=1.6, 7.0 Hz, 2H), 0.88 (td, J=1.8, 7.4 Hz, 3H).

Step 6: Synthesis of Compound WX087

Compound WX087-6 (350 mg, 912.79 μmol) was dissolved in N,N-dimethylformamide (5 mL) under the protection of nitrogen at 18° C., then potassium tert-butoxide (102.42 mg, 912.79 μmol) and acrylamide (64.88 mg, 912.79 μmol) were subsequently added, and the reaction mixture was reacted with stirring at 18° C. for 2 hours. After the reaction was completed, water (20 mL) and ethyl acetate (30 mL) were added to the reaction system to dilute, and the phases were separated, then the organic phases were collected, and the aqueous phase was extracted with ethyl acetate (20 mL×2). The organic phases were combined, washed with semi-saturated brine (20 mL×2), dried with anhydrous sodium sulfate, filtered, and the filtrate was concentrated under reduced pressure to obtain a residue. The obtained residue was added with 2 mL of methanol, stirred at room temperature for 10 minutes, filtered, and the solid was collected to obtain target compound WX087. MS-ESI m/z: 409.1 [M+H]$^+$. $^1$H NMR (400 MHz, DMSO_d$_6$) δ: 10.26 (s, 1H), 7.85 (s, 1H), 7.66-7.59 (m, 2H), 7.53-7.47 (m, 1H), 7.46-7.39 (m, 2H), 7.36-7.25 (m, 3H), 7.24-7.18 (m, 2H), 7.13 (d, J=8.4 Hz, 1H), 6.90 (t, J=7.8 Hz, 1H), 6.02 (dd, J=0.4, 7.6 Hz, 1H), 4.08 (dd, J=4.8, 12.4 Hz, 1H), 2.82-2.65 (m, 1H), 2.60-2.52 (m, 1H), 2.45-2.30 (m, 1H), 2.11-2.02 (m, 1H).

Embodiment 88: WX088

Synthetic Route:

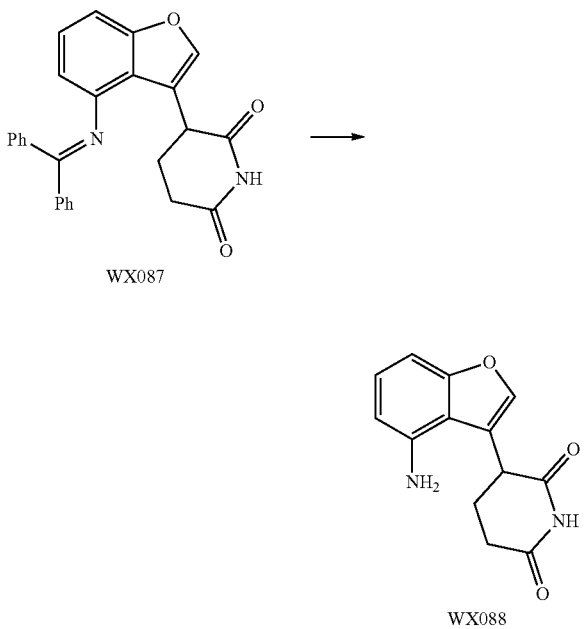

Compound WX087 (0.080 g, 195.86 μmol) was dissolved in ethyl acetate hydrochloride (4 M, 10 mL) under the protection of nitrogen at room temperature, and the reaction mixture was stirred at room temperature for 720 hours. After the reaction was completed, the reaction mixture was concentrated under reduced pressure to remove the solvent. The obtained residue was separated by preparative HPLC (mobile phase: acetonitrile/water; acidic system: 0.05% HCl), to obtain target compound WX088. MS-ESI m/z: 245.1 [M+H]$^+$. $^1$H NMR (400 MHz, DMSO_d$_6$) δ: 11.05 (s, 1H), 7.92 (s, 1H), 7.41 (d, J=8.0 Hz, 1H), 7.29 (t, J=8.0 Hz, 1H), 7.10 (d, J=7.2 Hz, 1H), 4.48 (dd, J=6.0, 10.8 Hz, 1H), 2.78-2.59 (m, 2H), 2.39-2.23 (m, 2H).

Embodiment 89: WX089

Synthetic Route:

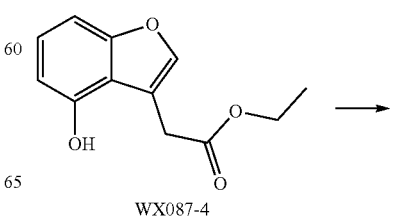

Embodiment 91: WX091

Synthetic Route:

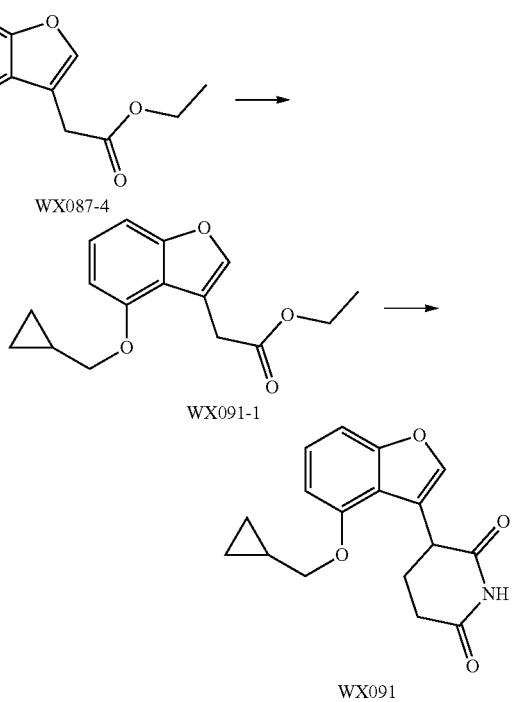

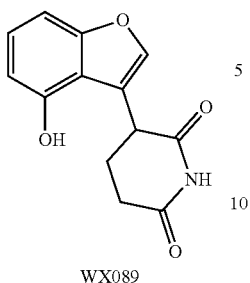

Compound WX087-4 (0.5 g, 2.27 mmol) was dissolved in tetrahydrofuran (8 mL), then potassium tert-butoxide (254.77 mg, 2.27 mmol) and acrylamide (161.38 mg, 2.27 mmol) were added, and the reaction mixture was stirred at room temperature for 12 hours, then potassium tert-butoxide (250.00 mg, 2.23 mmol) was supplemented, and the mixture was continued to stir for 1 hour. After the reaction was completed, 1 M dilute hydrochloric acid was added dropwise to the reaction system to adjust the pH to 6-7, and the mixture was diluted with ethyl acetate (20 mL), then the organic phases were collected, and the aqueous phase was extracted with ethyl acetate (20 mL×2). The organic phases were combined, dried with anhydrous sodium sulfate, filtered, and the filtrate was concentrated under reduced pressure to obtain a residue. The obtained residue was separated by column chromatography (eluent: petroleum ether/ethyl acetate=1/0-2/3, v/v), and the obtained residue was separated by preparative HPLC (mobile phase: acetonitrile/water; acidic system: 0.05% HCl) to obtain target compound WX089. MS-ESI m/z: 246.0 [M+H]⁺. ¹H NMR (400 MHz, DMSO_d₆) δ: 10.76 (s, 1H), 10.01 (s, 1H), 7.70 (s, 1H), 7.14-7.05 (m, 1H), 7.02-6.92 (m, 1H), 6.55 (d, J=7.7 Hz, 1H), 4.03 (dd, J=5.2, 12.0 Hz, 1H), 2.80-2.66 (m, 1H), 2.56-2.51 (m, 1H), 2.43-2.34 (m, 1H), 2.05-1.92 (m, 1H).

Referring to the synthesis method in embodiment 89, each embodiment in Table 15 is synthesized, and LCMS and HNMR data are shown in Table 16.

Step 1: Synthesis of Compound WX091-1

Compound WX087-4 (600 mg, 2.72 mmol) was dissolved in N,N-dimethylformamide (10 mL) under the protection of nitrogen at room temperature, then (bromomethyl)cyclopropane (367.82 mg, 2.72 mmol) and potassium carbonate (753.12 mg, 5.45 mmol) were added, and the reaction mixture was reacted with stirring at room temperature for 48 hours, then heated to 50° C. and continued to stir for 2 hours. 180 mg of (bromomethyl)cyclopropane (180 mg, 1.33 mmol) was supplemented, and the reaction mixture was

TABLE 15

| Embodiments | Fragment 1 | Fragment 2 | Structure | Compound |
|---|---|---|---|---|
| 90 | BB-9 (F-substituted benzofuran with CH₂CO₂Et) | acrylamide (CH₂=CH-C(O)-NH₂) | F-substituted benzofuran-glutarimide | WX090 |

TABLE 16

| Embodiments | Compound | HNMR | LCMS |
|---|---|---|---|
| 90 | WX090 | ¹H NMR (400 MHz, DMSO_d₆) δ: 10.94 (s, 1H), 7.99 (s, 1H), 7.50 (dd, J = 1.8, 8.9 Hz, 1H), 7.16 (dt, J = 1.9, 10.4 Hz, 1H), 4.15 (dd, J = 5.2, 12.8 Hz, 1H), 2.86-2.72 (m, 1H), 2.63-2.55 (m, 1H), 2.25-2.02 (m, 2H). | MS-ESI m/z: 266.0 [M + H]⁺. | continued to stir for 1 hour. After the reaction was completed, water (10 mL) and ethyl acetate (20 mL) were added to the reaction system to dilute, and the phases were separated, then the organic phases were collected, and the aqueous phase was extracted with ethyl acetate (10 mL×2). The organic phases were combined, washed with saturated brine (20 mL×2), dried with anhydrous sodium sulfate, filtered, and the filtrate was concentrated under reduced pressure to remove the solvent. The obtained residue was separated by column chromatography (eluent: petroleum ether/ethyl acetate=0/1— 4/1, v/v), to obtain compound WX091-1. MS-ESI m/z: 275.0 [M+H]$^+$. $^1$H NMR (400 MHz, CDCl$_3$) δ: 7.49 (s, 1H), 7.21-7.11 (m, 1H), 7.10-7.03 (m, 1H), 6.57 (d, J=7.9 Hz, 1H), 4.21 (q, J=7.1 Hz, 2H), 3.93-3.83 (m, 4H), 1.33-1.29 (m, 1H), 1.28 (t, J=7.2 Hz, 3H), 0.69-0.59 (m, 2H), 0.41-0.30 (m, 2H).

Step 2: Synthesis of Compound WX091

Compound WX091-1 (350 mg, 1.28 mmol) was dissolved in tetrahydrofuran (5 mL) under the protection of nitrogen at room temperature, then potassium tert-butoxide (143.17 mg, 1.28 mmol) and acrylamide (90.69 mg, 1.28 mmol) were added, and the reaction mixture was stirred at room temperature for 1 hour. After the reaction was completed, water (10 mL) and ethyl acetate (20 mL) were added to the reaction system to dilute, and the phases were separated, then the organic phases were collected, and the aqueous phase was extracted with ethyl acetate (10 mL×2). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=0/1— 1/1, v/v), to obtain target compound WX091. MS-ESI m/z: 300.1 [M+H]$^+$. $^1$H NMR (400 MHz, DMSO_d$_6$) δ: 10.78 (s, 1H), 7.79 (s, 1H), 7.23-7.17 (m, 1H), 7.16-7.11 (m, 1H), 6.65 (d, J=7.7 Hz, 1H), 4.09-3.92 (m, 2H), 3.64 (dd, J=8.4, 10.0 Hz, 1H), 2.82-2.64 (m, 1H), 2.61-2.52 (m, 2H), 2.00-1.86 (m, 1H), 1.22-1.09 (m, 1H), 0.59-0.44 (m, 2H), 0.36-0.16 (m, 2H).

Referring to the synthesis method in Embodiment 91, each embodiment in Table 17 is synthesized, and the LCMS and HNMR data are shown in Table 18.

TABLE 17

| Embodiments | Fragment 1 | Fragment 2 | Structure | Compound |
|---|---|---|---|---|
| 92 | 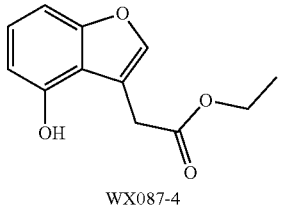<br>WX087-4 |  | 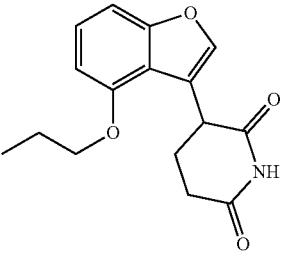 [SMILES: CCCOc1cccc2occ(C3CCC(=O)NC3=O)c12] | WX092 |
| 93 | 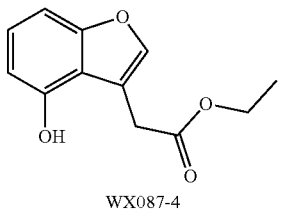<br>WX087-4 | 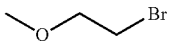 | 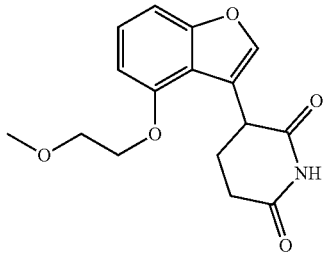 [SMILES: COCCOc1cccc2occ(C3CCC(=O)NC3=O)c12] | WX093 |
| 94 | 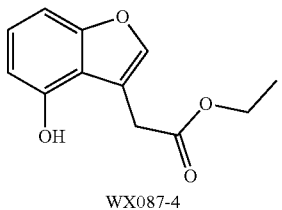<br>WX087-4 | 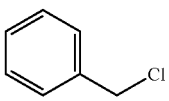 | 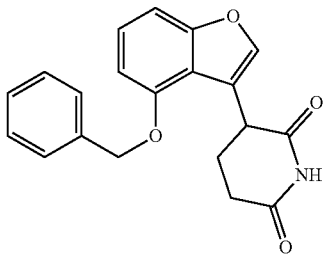 [SMILES: O=C1CCC(c2coc3cccc(OCc4ccccc4)c23)C(=O)N1] | WX094 |

TABLE 17-continued
| Embodi-ments | Fragment 1 | Fragment 2 | Structure | Compound |
|---|---|---|---|---|
| 95 | 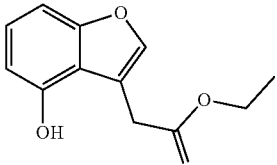 WX087-4 | 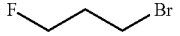 | 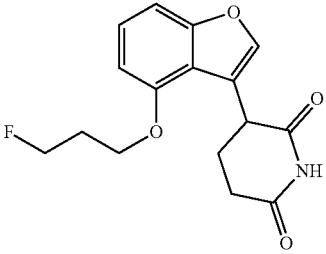 [SMILES: O=C1CCC(c2coc3cccc(OCCCF)c23)C(=O)N1] | WX095 |
| 96 | 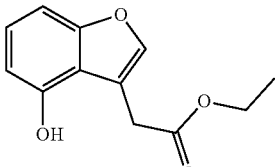 WX087-4 |  | 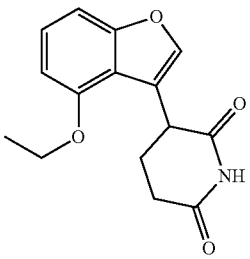 [SMILES: CCOc1cccc2occ(C3CCC(=O)NC3=O)c12] | WX096 |
| 97 | 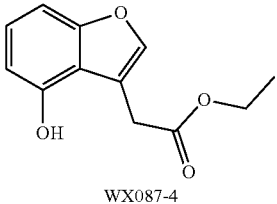 WX087-4 | 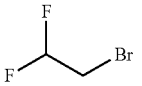 | 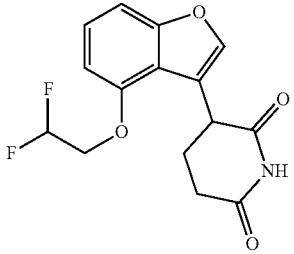 [SMILES: O=C1CCC(c2coc3cccc(OCC(F)F)c23)C(=O)N1] | WX097 |
| 98 | 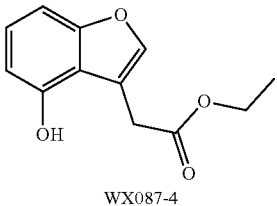 WX087-4 | 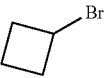 | 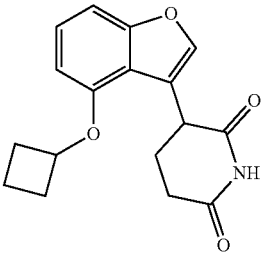 [SMILES: O=C1CCC(c2coc3cccc(OC4CCC4)c23)C(=O)N1] | WX098 |
| 99 | 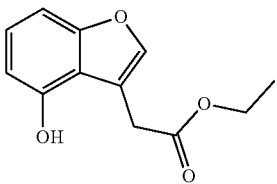 [SMILES: CCOC(=O)Cc1coc2cccc(O)c12] WX087-4 | 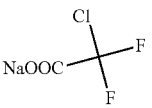 | 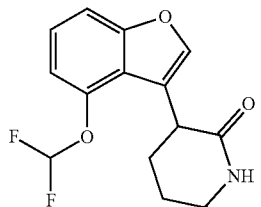 | WX099 |
| 100 | 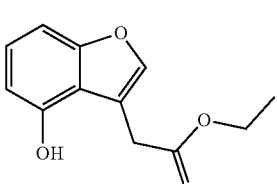 WX087-4 | 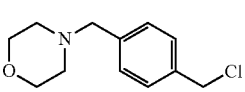 [SMILES: ClCc1ccc(CN2CCOCC2)cc1] | 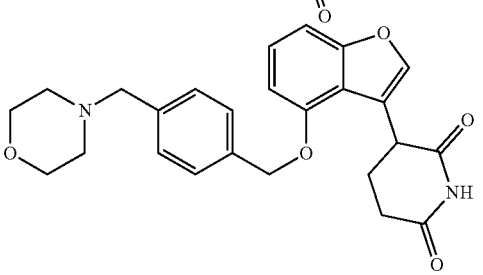 | WX100 |

TABLE 18

| Embodiments | Compound | HNMR | LCMS |
|---|---|---|---|
| 92 | WX092 | $^1$H NMR (400 MHZ, DMSO-$d_6$) δ: 10.83 (s, 1H), 7.78 (s, 1H), 7.25-7.19 (m, 1H), 7.18-7.11 (m, 1H), 6.73 (d, J = 8.0 Hz, 1H), 4.04 (dd, J = 5.2, 12.4 Hz, 1H), 4.00-3.90 (m, 2H), 2.80-2.67 (m, 1H), 2.57-2.45 (m, 1H), 2.44-2.38 (m, 1H), 2.01-1.93 (m, 1H), 1.78-1.65 (m, 2H), 0.95 (t, J = 7.5 Hz, 3H). | MS-ESI m/z: 288.1 [M + H]$^+$. |
| 93 | WX093 | $^1$H NMR (400 MHZ, DMSO-$d_6$) δ: 10.79 (s, 1H), 7.78 (s, 1H), 7.26-7.10 (m, 2H), 6.73 (d, J = 7.8 Hz, 1H), 4.19-4.08 (m, 2H), 4.00 (dd, J = 5.2, 12.4 Hz, 1H), 3.73-3.52 (m, 2H), 3.25 (s, 3H), 2.80-2.65 (m, 1H), 2.64-2.52 (m, 2H), 1.97-1.83 (m, 1H). | MS-ESI m/z: 304.0 [M + H]$^+$. |
| 94 | WX094 | $^1$H NMR (400 MHZ, DMSO-$d_6$) δ: 10.70 (s, 1H), 7.78 (s, 1H), 7.48-7.28 (m, 5H), 7.24-7.14 (m, 2H), 6.81 (d, J = 7.4 Hz, 1H), 5.16 (s, 2H), 4.10-3.99 (m, 1H), 2.69-2.52 (m, 1H), 2.43-2.19 (m, 2H), 2.02-1.91 (m, 1H). | MS-ESI m/z: 336.0 [M + H]$^+$. |
| 95 | WX095 | $^1$H NMR (400 MHZ, DMSO-$d_6$) δ: 10.85 (s, 1H), 7.79 (s, 1H), 7.27-7.20 (m, 1H), 7.19-7.14 (m, 1H), 6.78 (d, J = 7.7 Hz, 1H), 4.61 (t, J = 5.7 Hz, 1H), 4.50 (t, J = 5.7 Hz, 1H), 4.18-4.01 (m, 3H), 2.82-2.65 (m, 1H), 2.60-2.52 (m, 1H), 2.45-2.30 (m, 1H), 2.17-2.04 (m, 2H), 2.00-1.95 (m, 1H). | MS-ESI m/z: 306.2 [M + H]$^+$. |
| 96 | WX096 | $^1$H NMR (400 MHZ, DMSO-$d_6$) δ: 10.83 (s, 1H), 7.78 (s, 1H), 7.24-7.19 (m, 1H), 7.16-7.12 (m, 1H), 6.72 (d, J = 7.9 Hz, 1H), 4.11-3.96 (m, 3H), 2.80-2.65 (m, 1H), 2.58-2.50 (m, 1H), 2.47-2.31 (m, 1H), 2.00-1.91 (m, 1H), 1.30 (t, J = 6.9 Hz, 3H). | MS-ESI m/z: 274.1 [M + H]$^+$. |
| 97 | WX097 | $^1$H NMR (400 MHZ, DMSO-$d_6$) δ: 10.74 (s, 1H), 7.82 (s, 1H), 7.37-7.16 (m, 2H), 6.83 (dd, J = 1.4, 7.3 Hz, 1H), 6.52-6.14 (m, 1H), 4.39-4.30 (m, 2H), 4.06 (dd, J = 5.2, 12.4 Hz, 1H), 2.80-2.64 (m, 1H), 2.55-2.45 (m, 1H), 2.38-2.30 (m, 1H), 2.04-1.90 (m, 1H). | MS-ESI m/z: 310.0 [M + H]$^+$. |
| 98 | WX098 | $^1$H NMR (400 MHZ, DMSO-$d_6$) δ: 10.87 (s, 1H), 7.79 (s, 1H), 7.22-7.17 (m, 1H), 7.16-7.11 (m, 1H), 6.59 (d, J = 7.7 Hz, 1H), 4.80-2.70 (m, 1H), 4.03 (dd, J = 5.2, 12.6 Hz, 1H), 2.82-2.72 (m, 1H), 2.58-2.50 (m, 1H), 2.45-2.33 (m, 3H), 2.10-1.88 (m, 3H), 1.85-1.74 (m, 1H), 1.70-1.57 (m, 1H). | MS-ESI m/z: 300.1 [M + H]$^+$. |
| 99 | WX099 | $^1$H NMR (400 MHZ, DMSO-$d_6$) δ: 10.87 (s, 1H), 7.94 (s, 1H), 7.48 (d, J = 8.0 Hz, 1H), 7.35 (t, J = 8.2 Hz, 1H), 7.32-7.08 (m, 1H), 6.98 (d, J = 8.0 Hz, 1H), 4.12 (dd, J = 4.8, 12.4 Hz, 1H), 2.84-2.70 (m, 1H), 2.60-2.52 (m, 1H), 2.30-2.20 (m, 1H), 2.11-1.96 (m, 1H). | MS-ESI m/z: 296.1 [M + H]$^+$. |
| 100 | WX100 | $^1$H NMR (400 MHZ, DMSO-$d_6$) δ: 10.67 (s, 1H), 7.77 (s, 1H), 7.38 (d, J = 8.0 Hz, 2H), 7.29 (d, J = 8.0 Hz, 2H), 7.22 (t, J = 8.0 Hz, 1H), 7.16 (d, J = 7.6 Hz, 1H), 6.82 (d, J = 7.6 Hz, 1H), 5.13 (s, 2H), 4.03 (dd, J = 4.8, 12.4 Hz, 1H), 3.57 (br t, J = 4.4 Hz, 4H), 3.44 (s, 2H), 2.63-2.54 (m, 2H), 2.38-2.29 (m, 5H), 2.02-1.85 (m, 1H). | MS-ESI m/z: 435.3 [M + H]$^+$. |

Embodiment 101: WX101

Synthetic Route:

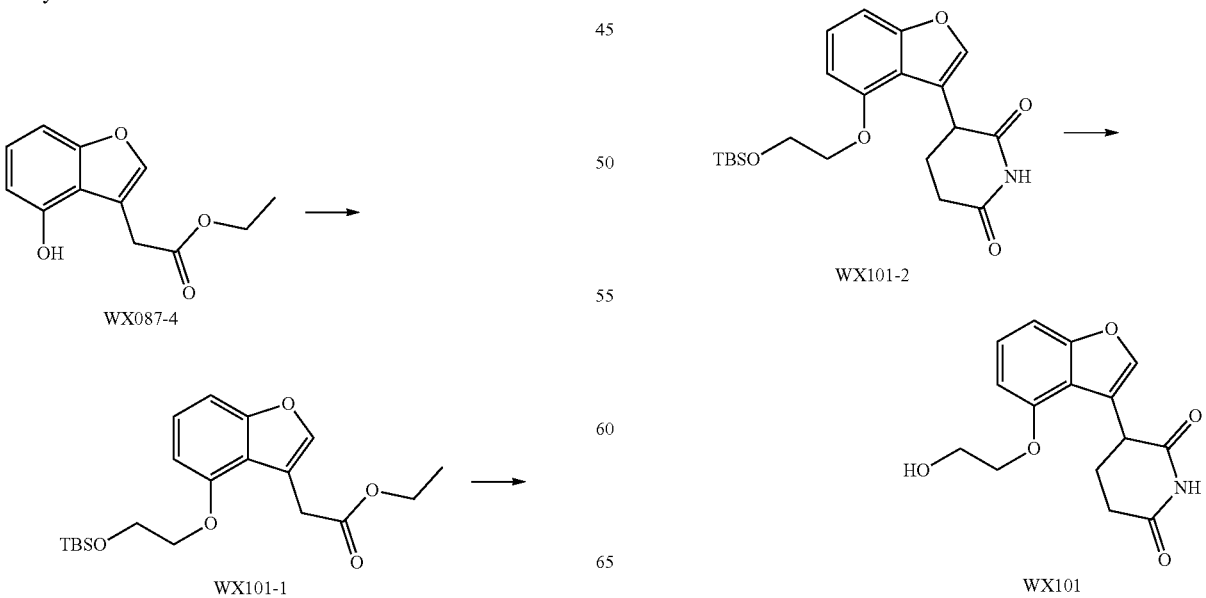

Step 1: Synthesis of Compound WX101-1

Compound WX087-4 (1 g, 4.54 mmol) was dissolved in N,N-dimethylformamide (10 mL) at room temperature, then potassium carbonate (1.26 g, 9.08 mmol) and (2-bromoethoxy)-tert-butyldimethylsilane (1.63 g, 6.81 mmol) were added, and the reaction mixture was reacted with stirring at room temperature for 12 hours. After the reaction was completed, water (20 mL) and ethyl acetate (30 mL) were added to the reaction system to dilute, and the phases were separated, then the organic phases were collected, and the aqueous phase was extracted with ethyl acetate (20 mL×2). The organic phases were combined, washed with semi-saturated brine (20 mL×2), dried with anhydrous sodium sulfate, filtered, and the filtrate was concentrated under reduced pressure to remove the solvent. The obtained residue was separated by column chromatography (eluent: petroleum ether/ethyl acetate=1/0-1/4, v/v), to obtain compound WX101-1. $^1$H NMR (400 MHz, CDCl$_3$) δ: 7.52 (s, 1H), 7.18 (t, J=8.2 Hz, 1H), 7.08 (d, J=8.4, Hz 1H), 6.64 (d, J=8.0 Hz, 1H), 4.20 (q, J=7.2 Hz, 2H), 4.14 (t, J=5.6 Hz, 2H), 3.99 (t, J=5.6 Hz, 2H), 3.89 (s, 2H), 1.28 (t, J=7.2 Hz, 3H), 0.92 (s, 9H), 0.11 (s, 6H).

Step 2: Synthesis of Compound WX101-2

Compound WX101-1 (0.9 g, 2.38 mmol) was dissolved in tetrahydrofuran (15 mL) under the protection of nitrogen at room temperature, then potassium tert-butoxide (266.79 mg, 2.38 mmol) and acrylamide (168.99 mg, 2.38 mmol) were added, and the reaction mixture was reacted with stirring at room temperature for 12 hours. After the reaction was completed, water (10 mL) and ethyl acetate (20 mL) were added to the reaction system to dilute, and the phases were separated, then the organic phases were collected, and the aqueous phase was extracted with ethyl acetate (10 mL×2). The organic phases were combined, dried with anhydrous sodium sulfate, filtered, and the filtrate was concentrated under reduced pressure to obtain a residue. The obtained residue was separated by column chromatography (eluent: petroleum ether/ethyl acetate=1/0-2/3, v/v), to obtain compound WX101-2. $^1$H NMR (400 MHz, DMSO-d$_6$) δ: 10.78 (s, 1H), 7.78 (s, 1H), 7.22 (t, J=8.0 Hz, 1H), 7.15 (d, J=8.0 Hz, 1H), 6.76 (d, J=8.0 Hz, 1H), 4.13-3.99 (m, 3H), 3.95-3.83 (m, 2H), 2.77-2.66 (m, 1H), 2.48-2.42 (m, 2H), 2.01-1.91 (m, 1H), 0.85 (s, 9H), 0.05 (s, 6H).

Step 3: Synthesis of Compound WX101

Compound WX101-2 (200 mg, 495.61 μmol) was dissolved in tetrahydrofuran (10 mL) at room temperature, then a tetrahydrofuran solution of tetrabutylammonium fluoride (1 M, 495.61 μL) was added dropwise, and the reaction mixture was reacted with stirring for 30 minutes at room temperature. After the reaction was completed, water (10 mL) and ethyl acetate (20 mL) were added to the reaction system to dilute, and the phases were separated, then the organic phases were collected, and the aqueous phase was extracted with ethyl acetate (10 mL×2). The organic phases were combined, dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl) to obtain target compound WX101. MS-ESI m/z: 290.1 [M+H]$^+$. $^1$H NMR (400 MHz, DMSO-d$_6$) δ:10.76 (s, 1H), 7.77 (s, 1H), 7.22 (t, J=4.0 Hz, 1H), 7.15 (d, J=8.0 Hz 1H), 6.74 (d, J=7.6 Hz, 1H), 4.11-3.95 (m, 3H), 3.76-3.64 (m, 2H), 2.80-2.66 (m, 1H), 2.56-2.51 (m, 2H), 1.99-1.90 (m, 1H).

Embodiment 102: WX102

Synthetic Route:

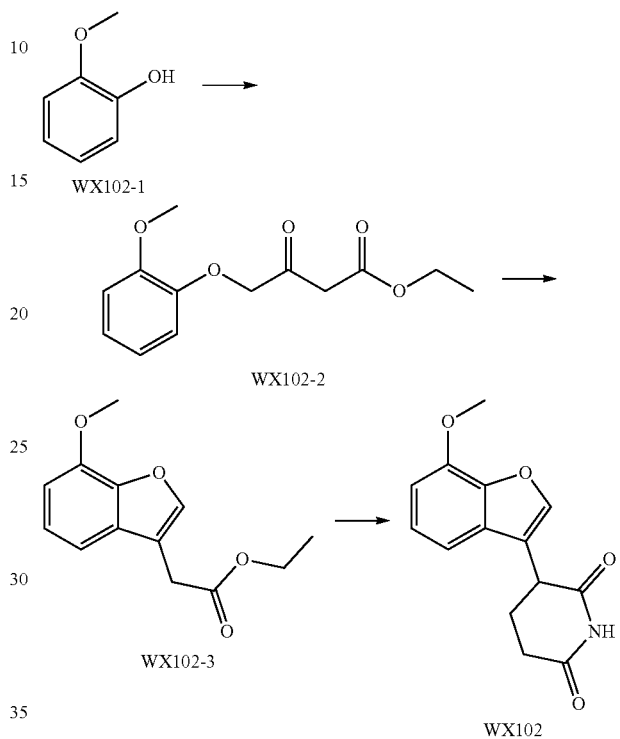

Step 1: Synthesis of Compound WX102-2

Compound WX102-1 (5 g, 40.28 mmol, 4.50 mL) was dissolved in tetrahydrofuran (50 mL) at room temperature under the protection of nitrogen. The mixture was cooled to 0° C., and sodium hydride (1.93 g, 48.33 mmol, purity: 60%) was added, then the reaction mixture was stirred at 0° C. for 1 hour. In another reaction flask, sodium hydride (2.90 g, 72.50 mmol, purity: 60%) was added to tetrahydrofuran (50 mL) at −40° C. under the protection of nitrogen, and ethyl 4-chloroacetoacetate (9.94 g, 60.42 mmol) was added dropwise, and the mixture was reacted with stirring for 1 hour. This system was then added to the previous system at 0° C., the mixture was stirred for 12 hours, then heated to 80° C. and continued to stir for 2 hours. After the reaction was completed, the reaction solution was quenched by adding to 100 mL of ice water, then 1 M dilute hydrochloric acid was added dropwise to adjust the pH to 6-7, then 100 mL of ethyl acetate was added to dilute, and the phases were separated, then the organic phases were collected, and the aqueous phase was extracted with ethyl acetate (60 mL×2). The organic phases were combined, dried with anhydrous sodium sulfate, filtered, and the filtrate was concentrated under reduced pressure to obtain a residue. The obtained residue was separated by column chromatography (eluent: petroleum ether/ethyl acetate=1/0-4/1, v/v), to obtain compound WX102-2. $^1$H NMR (400 MHz, CDCl$_3$) δ: 7.04-6.98 (m, 1H), 6.95-6.83 (m, 3H), 4.69 (s, 2H), 4.25-4.17 (m, 2H), 3.87 (s, 3H), 3.70 (s, 2H), 1.27 (t, J=7.2 Hz, 3H).

Step 2: Synthesis of Compound WX102-3

Compound WX102-2 (2.0 g, 7.93 mmol) was dissolved in toluene (30 mL) under the protection of nitrogen at room temperature, then polyphosphoric acid (1.0 g) was added, and the reaction mixture was stirred at 130° C. for 5 hours. After the reaction was completed, water (20 mL) and ethyl acetate (20 mL) were added to the reaction solution, and the phases were separated, then the organic phases were collected, and the aqueous phase was extracted with ethyl acetate (20 mL×2), then the organic phases were combined, dried with anhydrous sodium sulfate, and the filtrate was concentrated under reduced pressure to obtain a residue. The obtained residue was separated by column chromatography (eluent: petroleum ether/ethyl acetate=1/0-9/1, v/v), to obtain compound WX102-3. $^1$H NMR (400 MHz, CDCl$_3$) δ: 7.65 (s, 1H), 7.24-7.13 (m, 2H), 6.83 (dd, J=2.0, 6.9 Hz, 1H), 4.20 (q, J=7.2 Hz, 2H), 4.02 (s, 3H), 3.69 (d, J=1.0 Hz, 2H), 1.28 (t, J=7.2 Hz, 3H).

Step 3: Synthesis of Compound WX102

Compound WX102-3 (0.33 g, 1.41 mmol) was dissolved in N,N-dimethylformamide (5 mL) under the protection of nitrogen at room temperature, and the mixture was cooled to 0° C., then potassium tert-butoxide (158.08 mg, 1.41 mmol) and acrylamide (100.13 mg, 1.41 mmol) were added, and the reaction mixture was stirred at room temperature for 2 hours. After the reaction was completed, water (20 mL) and ethyl acetate (20 mL) were added to the reaction solution to dilute, and the phases were separated, then the organic phases were collected, and the aqueous phase was extracted with ethyl acetate (20 mL×2). The organic phases were combined, sequentially washed with semi-saturated brine (20 mL×2), dried with anhydrous sodium sulfate, filtered, and the obtained residue was separated by column chromatography (eluent: petroleum ether/ethyl acetate=4/1-1/1, v/v), and the crude product was slurried with 1 mL of methanol at room temperature to obtain target compound WX102. MS-ESI m/z: 260.0 [M+H]$^+$. $^1$H NMR (400 MHz, DMSO_d$_6$) δ: 10.89 (s, 1H), 7.87 (s, 1H), 7.19-7.12 (m, 2H), 6.93 (dd, J=2.1, 6.8 Hz, 1H), 4.11 (dd, J=4.8, 12.0 Hz, 1H), 3.93 (s, 3H), 2.79-2.68 (m, 1H), 2.61-2.54 (m, 1H), 2.37-2.23 (m, 1H), 2.16-2.05 (m, 1H).

Embodiment 103: WX103

Synthetic Route:

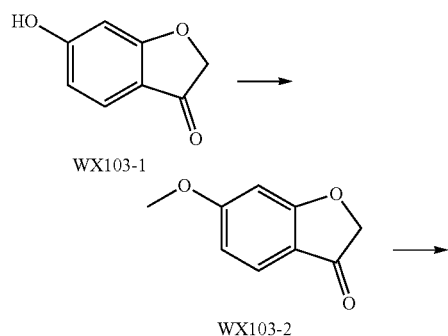

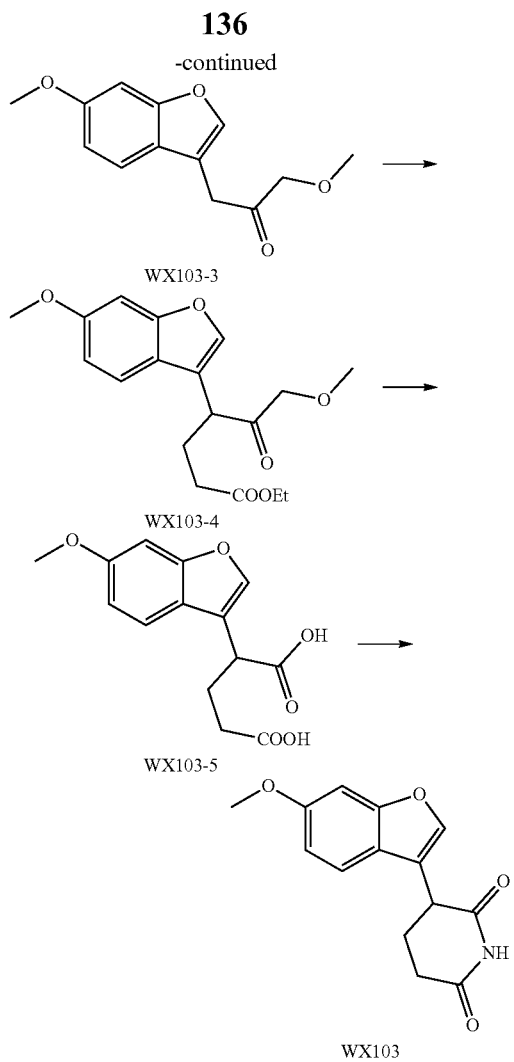

Step 1: Synthesis of Compound WX103-2

Compound WX103-1 (4 g, 26.64 mmol) and potassium carbonate (5.52 g, 39.97 mmol) were added to N,N-dimethylformamide (40 mL) under the protection of nitrogen at room temperature, then iodomethane (5.67 g, 39.97 mmol, 2.49 mL) was added, and the reaction mixture was heated to 80° C. and reacted with stirring for 12 hours. After the reaction was completed, the mixture was cooled to room temperature, and water (100 mL) was added to the reaction system, and the mixture was extracted with dichloromethane (60 mL×3). The organic phases were combined, washed with saturated brine (50 mL×2), dried with anhydrous sodium sulfate, filtered, and the filtrate was concentrated under reduced pressure to obtain a residue. The obtained residue was separated by column chromatography (eluent: petroleum ether/ethyl acetate=100/1-30/1, v/v), to obtain compound WX103-2. MS-ESI m/z: 164.8 [M+H]$^+$. $^1$H NMR (400 MHz, CDCl$_3$) δ: 7.50 (d, J=8.8 Hz, 1H), 6.58 (dd, J=2.2, 8.6 Hz, 1H), 6.48 (d, J=2.0 Hz, 1H), 4.56 (s, 2H), 3.81 (s, 3H).

Step 2: Synthesis of Compound WX103-3

Compound WX103-2 (2.02 g, 12.31 mmol) was dissolved in toluene (30 mL) at room temperature under the protection of nitrogen, then ethoxyformylmethylene triphenylphosphine (5.14 g, 14.77 mmol) was added, and the reaction mixture was heated to 130° C. and reacted with stirring for 48 hours. After the reaction was completed, the mixture was cooled to room temperature, and the reaction mixture was directly concentrated under reduced pressure to remove the solvent. The obtained residue was separated by column chromatography (eluent: petroleum ether/ethyl acetate=100/1-20/1, v/v), to obtain compound WX103-3. MS-ESI m/z: 235.0 [M+H]$^+$. $^1$H NMR (400 MHz, CDCl$_3$) δ: 7.46 (s, 1H), 7.35 (d, J=8.8 Hz, 1H), 6.93 (d, J=2.4 Hz, 1H), 6.82 (dd, J=2.4, 8.4 Hz, 1H), 4.15 (q, J=6.8 Hz, 2H), 3.76 (s, 3H), 3.58 (d, J=0.8 Hz, 2H), 1.25 (t, J=7.0 Hz, 3H).

Step 3: Synthesis of Compound WX103-4

Compound WX103-3 (0.8 g, 1.88 mmol, purity: 55.04%) was dissolved in N,N-dimethylformamide (4 mL) and tert-butanol (16 mL), then potassium tert-butoxide (42.18 mg, 375.94 μmol) was added, and the reaction mixture was stirred at 0° C. for 0.5 hours, then ethyl acrylate (207.01 mg, 2.07 mmol, 224.76 μL) was added, and the reaction mixture was reacted with stirring at room temperature for 11 hours. After the reaction was completed, the reaction mixture was added with water (80 mL), and extracted with ethyl acetate (60 mL×3). The organic phases were combined, sequentially washed with saturated brine (50 mL×2), dried with anhydrous sodium sulfate, filtered, and the filtrate was concentrated under reduced pressure to obtain a residue. The obtained residue was separated by column chromatography (eluent: petroleum ether/ethyl acetate=30/1-10/1, v/v), to obtain compound WX103-4. MS-ESI m/z: 335.0 [M+H]$^+$. $^1$H NMR (400 MHz, CDCl$_3$) δ: 7.45 (d, J=8.8 Hz, 1H), 7.41 (s, 1H), 6.93 (d, J=2.4 Hz, 1H), 6.81 (dd, J=2.4, 8.6 Hz, 1H), 4.14-4.07 (m, 2H), 4.06-4.03 (m, 2H), 3.77 (s, 3H), 3.74 (t, J=7.2 Hz, 1H), 2.38-2.30 (m, 1H), 2.27 (t, J=6.4 Hz, 2H), 2.23-2.14 (m, 1H), 1.16 (td, J=4.8, 7.2 Hz, 6H).

Step 4: Synthesis of Compound WX103-5

Compound WX103-4 (0.45 g, 1.35 mmol) was dissolved in tetrahydrofuran (8 mL) and water (2 mL) at 30° C., then lithium hydroxide monohydrate (338.86 mg, 8.08 mmol) was added, and the reaction mixture was reacted with stirring at 30° C. for 12 hours. After the reaction was completed, the reaction mixture was concentrated under reduced pressure to remove the solvent, and the obtained residue was added with water (40 mL), and extracted with ethyl acetate (10 mL×3). The organic phase was discarded, and the pH of the aqueous phase was adjusted to 3 to 4 with 3 M hydrochloric acid aqueous solution (3 mL), the mixture was extracted with ethyl acetate (20 mL×3), then the organic phases were combined, washed with saturated brine (20 mL×2), dried with anhydrous sodium sulfate, filtered, and the filtrate was concentrated under reduced pressure to obtain compound WX103-5. MS-ESI m/z: 278.9 [M+H]$^+$. $^1$H NMR (400 MHz, DMSO_d$_6$) δ: 7.77 (s, 1H), 7.51 (d, J=8.4 Hz, 1H), 7.17 (d, J=2.0 Hz, 1H), 6.89 (dd, J=2.2, 8.6 Hz, 1H), 3.80 (s, 3H), 3.75 (t, J=7.0 Hz, 1H), 2.29-2.17 (m, 3H), 2.11-2.01 (m, 1H).

Step 5: Synthesis of Compound WX103

Compound WX103-5 (0.25 g, 799.62 μmol, purity: 89.00%) and trifluoroacetamide (180.78 mg, 1.60 mmol) were dissolved in N,N-dimethylformamide (5 mL) at 30° C. under the protection of nitrogen, then 1-hydroxybenzotriazole (421.38 mg, 3.12 mmol), 1-(3-dimethylaminopropyl)-3-ethylcarbodiimide hydrochloride (582.50 mg, 3.04 mmol) and triethylamine (445.03 mg, 4.40 mmol, 612.14 μL) were added, and the reaction mixture was stirred at 30° C. for 12 hours. After the reaction was completed, the reaction mixture was added to water (50 mL), and extracted with ethyl acetate (30 mL×3). The organic phases were combined, sequentially washed with saturated brine (30 mL×2), dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl) to obtain target compound WX103. MS-ESI m/z: 260.0 [M+H]$^+$. $^1$H NMR (400 MHz, DMSO_d$_6$) δ: 10.88 (s, 1H), 7.78 (s, 1H), 7.45 (d, J=8.4 Hz, 1H), 7.18 (d, J=2.4 Hz, 1H), 6.87 (dd, J=2.2, 8.6 Hz, 1H), 4.09 (dd, J=4.8, 11.6 Hz, 1H), 3.80 (s, 3H), 2.77-2.67 (m, 1H), 2.61-2.54 (m, 1H), 2.35-2.24 (m, 1H), 2.15-2.07 (m, 1H).

Embodiment 104: WX104

Synthetic Route:

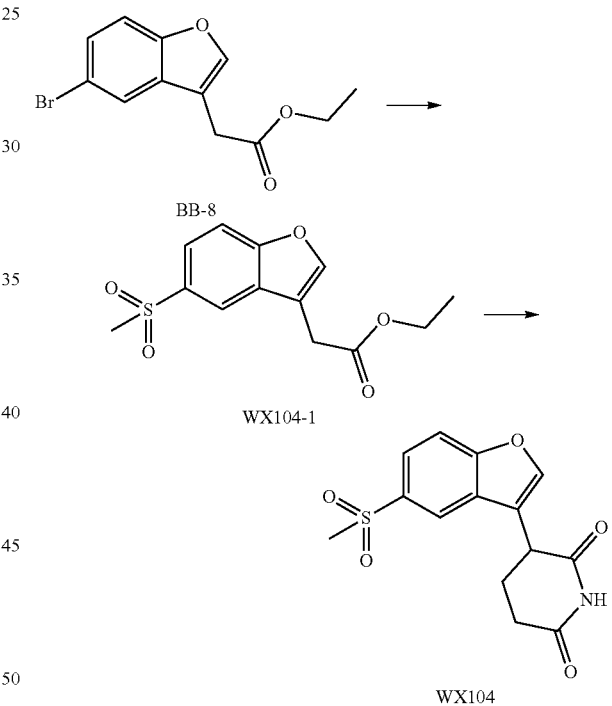

Step 1: Synthesis of Compound WX104-1

Compound BB-8 (2 g, 7.06 mmol) was dissolved in dimethyl sulfoxide (20 mL) under the protection of nitrogen at room temperature, then cuprous iodide (1.35 g, 7.06 mmol), L-proline (1.63 g, 14.13 mmol), sodium methylsulfinate (2.16 g, 21.19 mmol) and cesium carbonate (6.90 g, 21.19 mmol) were sequentially added. The reaction mixture was heated to 80° C. and reacted with stirring for 12 hours. After the reaction was completed, the reaction solution was directly filtered, and the filtrate was collected, then water (100 mL) and ethyl acetate (50 mL) were added to the filtrate to dilute, and the phases were separated, then the organic phases were collected, and the aqueous phase was extracted with ethyl acetate (50 mL×2). The organic phases were combined, dried with anhydrous sodium sulfate, filtered, and the filtrate was concentrated under reduced pressure to obtain a residue. The obtained residue was separated by column chromatography (eluent: petroleum ether/ethyl acetate=1/0-3/2, v/v), to obtain compound WX104-1. $^1$H NMR (400 MHz, CDCl$_3$) δ: 8.24 (s, 1H), 7.90 (dd, J=1.4, 8.6 Hz, 1H), 7.80 (s, 1H), 7.65 (d, J=8.8 Hz, 1H), 4.22 (q, J=7.2 Hz, 2H), 3.75 (s, 2H), 3.10 (s, 3H), 1.31 (t, J=7.2 Hz, 3H).

Step 2: Synthesis of Compound WX104

Compound WX104-1 (350 mg, 1.24 mmol) was dissolved in tetrahydrofuran (5 mL) under the protection of nitrogen 0° C., then acrylamide (88.12 mg, 1.24 mmol) and potassium tert-butoxide (139.12 mg, 1.24 mmol) were sequentially added, and the reaction mixture was slowly restored to 18° C. and reacted with stirring for 2 hours. After the reaction was completed, water (10 mL) was added to the reaction system, and white solids were precipitated. The mixture was filtered, and the filter cake was collected, and the aqueous phase was extracted with ethyl acetate (20 mL×2). The organic phases were combined, dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl) to obtain target compound WX104. MS-ESI m/z: 308.1 [M+H]$^+$. $^1$H NMR (400 MHz, DMSO_d$_6$) δ: (br s, 1H), 8.24 (s, 1H), 8.15 (s, 1H), 7.91-7.83 (m, 2H), 4.28 (dd, J=4.6, 11.8 Hz, 1H), 3.24 (s, 3H), 2.82- 2.70 (m, 1H), 2.69-2.57 (m, 1H), 2.42-2.29 (m, 1H), 2.18-2.05 (m, 1H).

Embodiment 105: WX105

Synthetic Route:

Step 1: Synthesis of Compound WX105-1

Compound BB-8 (1.8 g, 6.36 mmol) was dissolved in toluene (20 mL) under the protection of nitrogen at 18° C., then tris(dibenzylideneacetone)dipalladium (582.20 mg, 635.78 μmol), 4,5-bis(diphenylphosphino)-9,9-diMethylxanthene (735.75 mg, 1.27 mmol), N,N-diisopropylethylamine (2.47 g, 19.07 mmol, 3.32 mL) and benzyl mercaptan (1.18 g, 9.54 mmol, 1.12 mL) were sequentially added, and the reaction mixture was heated to 120° C. and reacted with stirring for 12 hours. After the reaction was completed, the reaction solution was directly filtered, and the mother liquor was collected, concentrated under reduced pressure to remove the solvent. The obtained residue was separated by column chromatography (eluent: petroleum ether/ethyl acetate=1/0-20/1, v/v), to obtain compound WX105-1.

Step 2: Synthesis of Compound WX105

Compound WX105-1 (200 mg, 612.73 μmol) was dissolved in tetrahydrofuran (5 mL) at 18° C., then acrylamide (43.55 mg, 612.73 μmol) and potassium tert-butoxide (68.76 mg, 612.73 μmol) were sequentially added, and the reaction mixture was stirred at 18° C. for 1 hour. After the reaction was completed, water (10 mL) and ethyl acetate (20 mL) were added to the reaction system to dilute, and the phases were separated, then the organic phases were collected, and the aqueous phase was extracted with ethyl acetate (20 mL×2). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-1/1, v/v), the obtained crude product was stirred with 2 mL of methanol at room temperature for 10 minutes, filtered, and the filter cake was collected, and concentrated under reduced pressure to remove the solvent to obtain target compound WX105. MS-ESI m/z: 352.0 [M+H]$^+$. $^1$H NMR (400 MHz, DMSO_d$_6$) δ: 10.90 (s, 1H), 7.90 (s, 1H), 7.54 (d, J=1.6 Hz, 1H), 7.50 (d, J=8.4 Hz, 1H), 7.33-7.16 (m, 6H), 4.20 (s, 2H), 4.11 (dd, J=4.8, 12.0 Hz, 1H), 2.80-2.65 (m, 1H), 2.62-2.53 (m, 1H), 2.34-2.17 (m, 1H), 2.10-2.00 (m, 1H).

Embodiment 106: WX106

Synthetic Route:

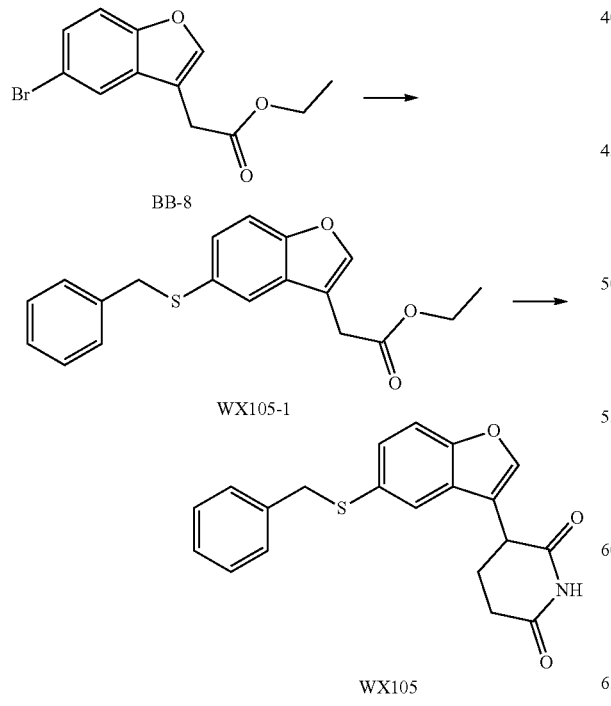

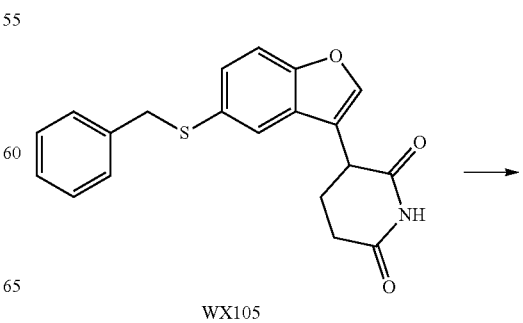

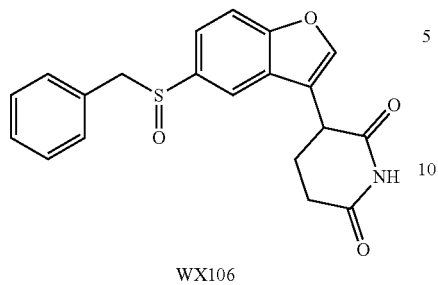

WX106

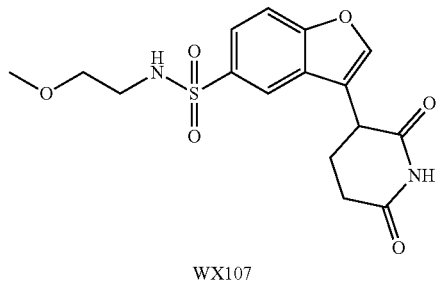

WX107

Compound WX105 (100 mg, 284.56 μmol) was dissolved in acetic acid (2 mL) at 18° C., then N-chlorosuccinimide (38.00 mg, 284.56 μmol) was added, and the reaction mixture was stirred at 18° C. for 2 hours. After the reaction was completed, water (10 mL) and ethyl acetate (10 mL) were added to the reaction system to dilute, and the phases were separated, then the organic phases were collected, and the aqueous phase was extracted with dichloromethane (10 mL×2). The organic phases were combined, dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl) to obtain target compound WX106. MS-ESI m/z: 368.1 [M+H]$^+$. $^1$H NMR (400 MHz, DMSO_d$_6$) δ: 10.93 (s, 1H), 8.04 (s, 1H), 7.76-7.71 (m, 2H), 7.50-7.45 (m, 1H), 7.29-7.22 (m, 3H), 7.11-7.04 (m, 2H), 4.25 (dd, J=4.4, 12.8 Hz, 1H), 4.21-4.14 (m, 1H), 4.09 (dd, J=3.8, 12.6 Hz, 1H), 2.82-2.70 (m, 1H), 2.69-2.55 (m, 1H), 2.35-2.16 (m, 1H), 2.13-2.02 (m, 1H).

Embodiment 107: WX107

Synthetic Route:

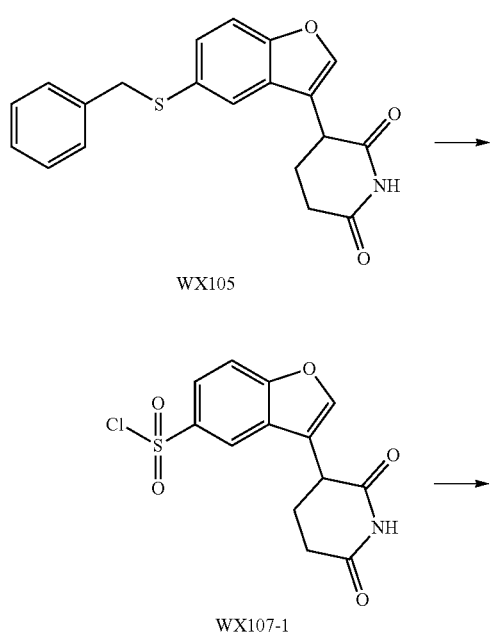

Step 1: Synthesis of Compound WX107-1

Compound WX105 (200 mg, 569.12 μmol) was dissolved in dichloromethane (1 mL) at room temperature, then hydrochloric acid (4 M, 1.42 mL) was added, and the mixture was cooled to 0° C., and sodium hypochlorite (3.18 g, 3.41 mmol, 2.63 mL, purity: 8%) was added, and the reaction mixture was stirred at 0° C. for 5 minutes. After the reaction was completed, water (10 mL) and dichloromethane (10 mL) were added to the reaction system to dilute, and the phases were separated, then the organic phases were collected, and the aqueous phase was extracted with dichloromethane (10 mL×2). The organic phases were combined, dried with anhydrous sodium sulfate, filtered, and the filtrate was concentrated under reduced pressure to remove the solvent to obtain a crude product of compound WX107-1.

Step 2: Synthesis of Compound WX107

Compound 2-methoxyethylamine (43.54 mg, 579.73 μmol) was dissolved in dichloromethane (3 mL) at 18° C., then triethylamine (117.33 mg, 1.16 mmol, 161.38 μL) and the crude product of compound WX107-1 (190 mg, 579.73 μmol) from the previous step were added, and the reaction mixture was reacted with stirring at 18° C. for 2 hours. After the reaction was completed, water (10 mL) and dichloromethane (10 mL) were added to the reaction system to dilute, and the phases were separated, then the organic phases were collected, and the aqueous phase was extracted with dichloromethane (10 mL×2). The organic phases were combined and concentrated under reduced pressure to remove the solvent. The obtained residue was stirred with 5 mL of methanol at room temperature for 10 minutes, filtered, and the filter cake was collected to obtain target compound WX107. MS-ESI m/z: 367.0 [M+H]$^+$. $^1$H NMR (400 MHz, DMSO_d$_6$) δ: 10.95 (s, 1H), 8.10 (s, 1H), 8.08 (d, J=1.2 Hz, 1H), 0.7.80 (d, J=8.8 Hz, 1H), 7.75 (dd, J=1.6, 8.4 Hz, 1H), 7.68 (t, J=5.8 Hz, 1H), 4.26 (dd, J=4.8, 12.4 Hz, 1H), 3.28 (t, J=5.8 Hz, 2H), 3.14 (s, 3H), 2.89 (q, J=5.8 Hz, 2H), 2.82-2.71 (m, 1H), 2.69-2.57 (m, 1H), 2.40-2.28 (m, 1H), 2.20-2.10 (m, 1H).

Referring to the synthesis method in Embodiment 107, each embodiment in Table 19 is synthesized, and the LCMS and HNMR data are shown in Table 20.

TABLE 19

| Embodiments | Fragment 1 | Fragment 2 | Structure | Compound |
|---|---|---|---|---|
| 108 | WX107-1 | | 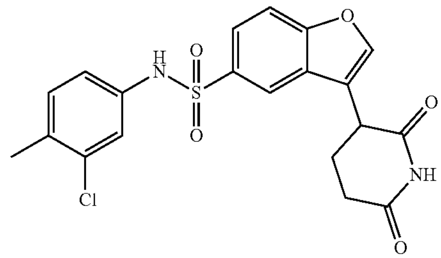 | WX108 |
| 109 | WX107-1 | | 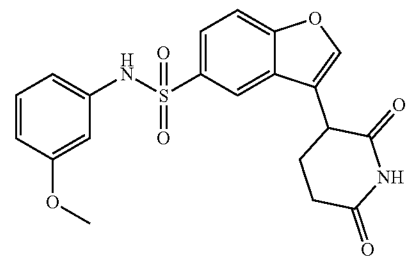 [SMILES: COc1cccc(NS(=O)(=O)c2ccc3occ(C4CCC(=O)NC4=O)c3c2)c1] | WX109 |
| 110 | WX107-1 | | 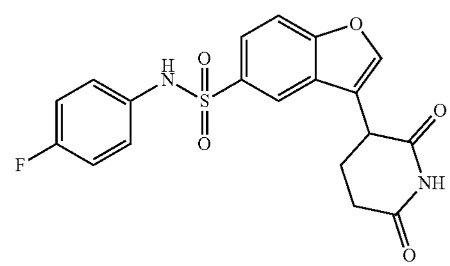 [SMILES: O=C1CCC(c2coc3ccc(S(=O)(=O)Nc4ccc(F)cc4)cc23)C(=O)N1] | WX110 |
| 111 | WX107-1 | | 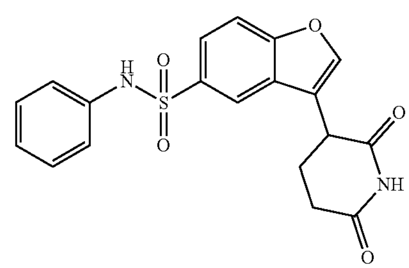 [SMILES: O=C1CCC(c2coc3ccc(S(=O)(=O)Nc4ccccc4)cc23)C(=O)N1] | WX111 |
| 112 | WX107-1 | | 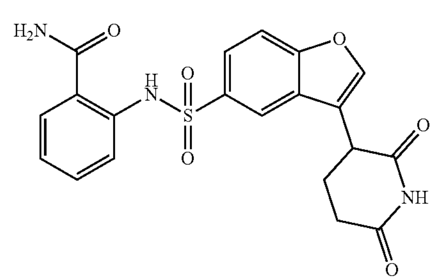 [SMILES: NC(=O)c1ccccc1NS(=O)(=O)c1ccc2occ(C3CCC(=O)NC3=O)c2c1] | WX112 |

TABLE 19-continued

| Embodiments | Fragment 1 | Fragment 2 | Structure | Compound |
|---|---|---|---|---|
| 113 | WX107-1 | 2-methylaniline | 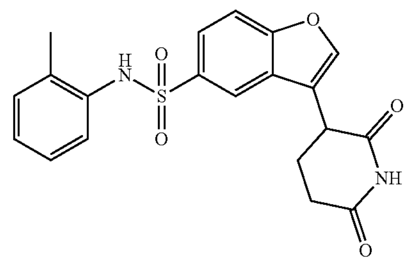 [SMILES: Cc1ccccc1NS(=O)(=O)c1ccc2occ(C3CCC(=O)NC3=O)c2c1] | WX113 |
| 114 | WX107-1 | 2-amino-3-methylpyridine | 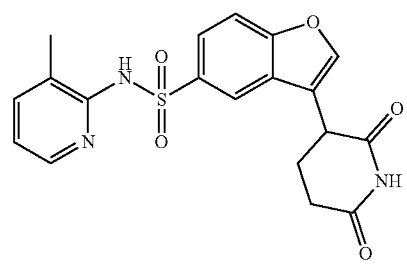 [SMILES: Cc1cccnc1NS(=O)(=O)c1ccc2occ(C3CCC(=O)NC3=O)c2c1] | WX114 |
| 115 | WX107-1 | 2-aminopyridine | 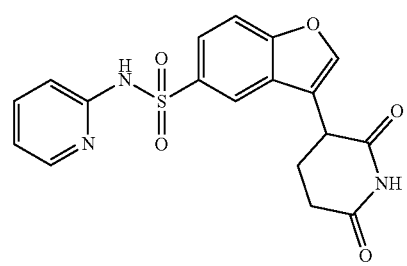 [SMILES: O=C1CCC(c2coc3ccc(S(=O)(=O)Nc4ccccn4)cc23)C(=O)N1] | WX115 |
| 116 | WX107-1 | 2-amino-5-fluoropyridine | 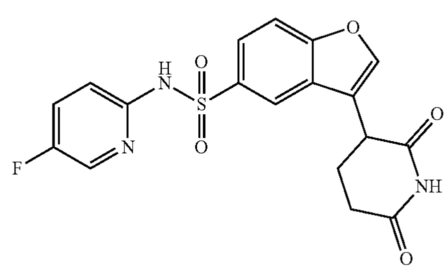 [SMILES: O=C1CCC(c2coc3ccc(S(=O)(=O)Nc4ccc(F)cn4)cc23)C(=O)N1] | WX116 |
| 117 | WX107-1 | 1-(cyclopropanecarbonyl)piperazine | 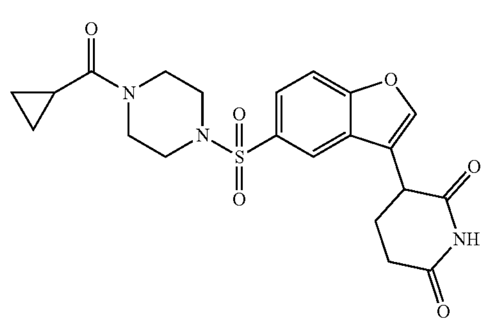 [SMILES: O=C1CCC(c2coc3ccc(S(=O)(=O)N4CCN(C(=O)C5CC5)CC4)cc23)C(=O)N1] | WX117 |

TABLE 19-continued

| Embodiments | Fragment 1 | Fragment 2 | Structure | Compound |
|---|---|---|---|---|
| 118 | WX107-1 | | 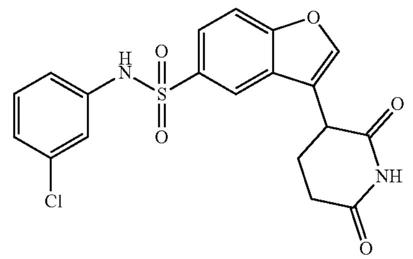 | WX118 |
| 119 | WX107-1 | | 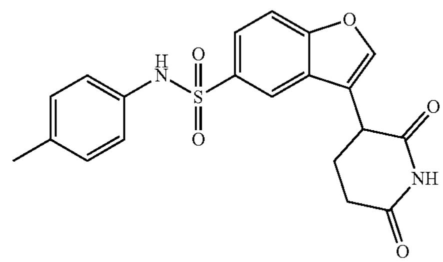 [SMILES: Cc1ccc(NS(=O)(=O)c2ccc3occ(C4CCC(=O)NC4=O)c3c2)cc1] | WX119 |
| 120 | WX107-1 | | 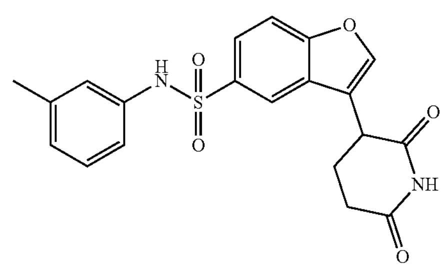 [SMILES: Cc1cccc(NS(=O)(=O)c2ccc3occ(C4CCC(=O)NC4=O)c3c2)c1] | WX120 |
| 121 | WX107-1 | | 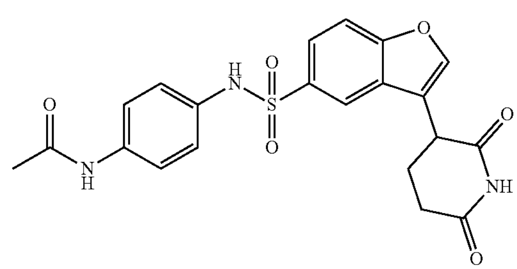 [SMILES: CC(=O)Nc1ccc(NS(=O)(=O)c2ccc3occ(C4CCC(=O)NC4=O)c3c2)cc1] | WX121 |
| 122 | WX107-1 | | 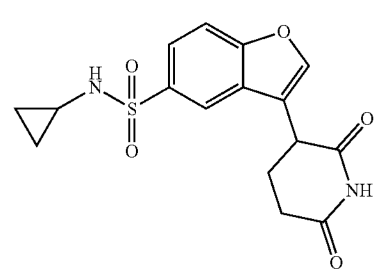 [SMILES: O=C1CCC(c2coc3ccc(S(=O)(=O)NC4CC4)cc23)C(=O)N1] | WX122 |

TABLE 19-continued

| Embodiments | Fragment 1 | Fragment 2 | Structure | Compound |
|---|---|---|---|---|
| 123 | WX107-1 | (benzamide with NH2) | 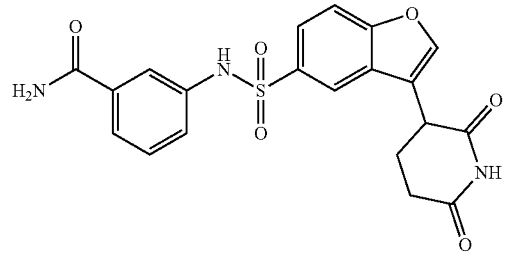 [SMILES: NC(=O)c1cccc(NS(=O)(=O)c2ccc3occ(C4CCC(=O)NC4=O)c3c2)c1] | WX123 |
| 124 | WX107-1 | (acetamido-aminopyridine) | 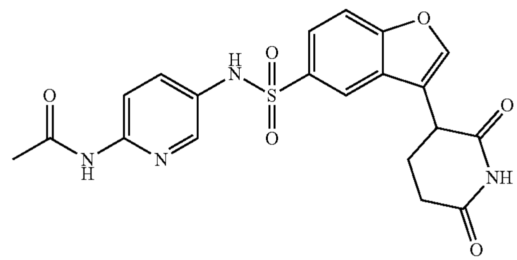 [SMILES: CC(=O)Nc1ccc(NS(=O)(=O)c2ccc3occ(C4CCC(=O)NC4=O)c3c2)cn1] | WX124 |

TABLE 20

| Embodiments | Compound | HNMR | LCMS |
|---|---|---|---|
| 108 | WX108 | ¹H NMR (400 MHZ, DMSO_d₆) δ: 10.97 (s, 1H), 10.38 (s, 1H), 8.09 (s, 1H), 8.05 (d, J = 1.6 Hz, 1H), 7.78 (d, J = 8.8 Hz, 1H), 7.69 (dd, J = 1.6, 8.8 Hz, 1H), 7.17 (d, J = 8.4 Hz, 1H), 7.12 (d, J = 2.0 Hz, 1H), 6.98 (dd, J = 2.2, 8.2 Hz, 1H), 4.24 (dd, J = 4.8, 12.4 Hz, 1H), 2.83-2.70 (m, 1H), 2.69-2.55 (m, 1H), 2.35-2.19 (m, 1H), 2.17 (s, 3H), 2.14-2.05 (m, 1H). | MS-ESI m/z: 450.1 [M + H₂O]⁺. |
| 109 | WX109 | ¹H NMR (400 MHZ, DMSO_d₆) δ: 10.99 (s, 1H), 10.29 (s, 1H), 8.09 (s, 1H), 8.05 (d, J = 1.6 Hz, 1H), 7.76 (d, J = 8.4 Hz, 1H), 7.70 (dd, J = 2.0, 8.8 Hz, 1H), 7.09 (t, J = 8.4 Hz, 1H), 6.68 (dd, J = 1.2, 5.6 Hz, 1H), 6.66 (d, J = 1.2 Hz, 1H), 6.56 (dd, J = 2.4, 8.0 Hz, 1H), 4.23 (dd, J = 4.8, 12.0 Hz, 1H), 3.63 (s, 3H), 2.83-2.70 (m, 1H), 2.65-2.56 (m, 1H), 2.27-2.16 (m, 1H), 2.14-2.02 (m, 1H). | MS-ESI m/z: 432.0 [M + H₂O]⁺. |
| 110 | WX110 | ¹H NMR (400 MHZ, DMSO_d₆) δ: 10.99 (s, 1H), 10.23 (s, 1H), 8.09 (s, 1H), 8.00 (d, J = 1.6 Hz, 1H), 7.75 (d, J = 8.8 Hz, 1H), 7.65 (dd, J = 2.0, 8.4 Hz, 1H), 7.13-6.99 (m, 4H), 4.22 (dd, J = 5.0, 12.6 Hz, 1H), 2.85-2.70 (m, 1H), 2.69-2.59 (m, 1H), 2.26-2.19 (m, 1H), 2.12-2.00 (m, 1H). | MS-ESI m/z: 420.1 [M + H₂O]⁺. |
| 111 | WX111 | ¹H NMR (400 MHZ, DMSO_d₆) δ: 10.99 (s, 1 H), 10.27 (s, 1H), 8.08 (s, 1H), 8.04 (s, 1H), 7.75 ( d, J = 8.4 Hz, 1H), 7.69 (dd, J = 1.4, 8.6 Hz, 1H), 7.19 (t, J = 7.6 Hz, 2H), 7.09 (d, J = 8.0 Hz, 2H), 6.99 (t, J = 7.2 Hz, 1H), 4.22 (dd, J = 4.8, 12.4 Hz, 1H), 2.81-2.70 (m, 1H), 2.63-2.55 (m, 1H), 2.27-2.19 (m, 1H), 2.10-2.04 (m, 1H). | MS-ESI m/z: 385.0 [M + H]⁺. |
| 112 | WX112 | ¹H NMR (400 MHZ, DMSO_d₆) δ: 12.22 (s, 1H), 10.96 (s, 1H), 8.31 (s, 1H), 8.11 (d, J = 1.6 Hz, 1H), 8.09 (s, 1H), 7.86 (s, 1H), 7.77-7.72 (m, 2H), 7.69 (dd, J = 2.0, 8.8 Hz, 1H), 7.55 (d, J = 7.6 Hz, 1H), 7.44 (td, J = 1.2, 8.0 Hz, 1H), 7.07 (t, J = 7.4 Hz, 1H), 4.24 (dd, J = 4.8, 12.4 Hz, 1H), 2.77-2.70 (m, 1H), 2.65-2.60 (m, 1H), 2.33-2.19 (m, 1H), 2.13-1.99 (m, 1H). | MS-ESI m/z: 428.1 [M + H]⁺. |
| 113 | WX113 | ¹H NMR (400 MHZ, DMSO_d₆) δ: 10.95 (s, 1H), 9.54 (s, 1H), 8.10 (s, 1H), 7.89 (d, J = 2.0 Hz, 1H), 7.77 (d, J = 8.8 Hz, 1H), 7.64 (dd, J = 1.8, 8.6 Hz, 1H), 7.14-7.02 (m, 3H), 6.99-6.91 (m, 1H), 4.21 (dd, J = 5.2, 12.0 Hz, 1H), 2.82-2.70 (m, 1H), 2.58-2.54 (m, 2H), 2.45-2.38 (m, 1H), 1.98 (s, 3H). | MS-ESI m/z: 399.1 [M + H]⁺. |
| 114 | WX114 | ¹H NMR (400 MHZ, DMSO_d₆) δ: 10.99 (s, 1H), 8.25 (d, J = 1.6 Hz, 1H), 8.07 (s, 1H), 7.87 (dd, J = 1.2, 8.4 Hz, 1H), 7.81 (d, J = 8.8 Hz, 1H), 7.73 (d, J = 8.8 Hz, 1H), 7.61 (d, J = 6.8 Hz, 1H), 6.78 (s, 1H), 4.24 (dd, J = 4.8, 12.0 Hz, 1H), 2.84-2.72 (m, 1H), 2.69-2.57 (m, 2H), 2.35-2.31 (m, 1H), 2.11 (s, 3H). | MS-ESI m/z: 400.1 [M + H]⁺. |
| 115 | WX115 | ¹H NMR (400 MHZ, DMSO_d₆) δ: 10.98 (s, 1H), 8.19 (s, 1 H), 8.07 (s, 1H), 7.99 (br s, 1H), 7.84-7.80 (m, 1H), 7.75-7.66 (m, 2H), 7.18 (br d, J = 8.8 Hz, 1H), 6.85 (br s, 1H), 4.26 (dd, J = 5.0, 12.6 Hz, 1H), 2.82-2.72 (m, 1H), 2.68-2.63 (m, 1H), 2.34-2.29 (m, 1H), 2.16-2.09 (m, 1H). | MS-ESI m/z: 386.1 [M + H]⁺. |
| 116 | WX116 | ¹H NMR (400 MHZ, DMSO_d₆) δ: 11.09 (s, 1H), 11.00 (s, 1H), 8.21 (d, J = 1.6 Hz, 1H), 8.16 (d, J = 2.8 Hz, 1H), 8.10 (s, 1H), 7.83 (dd, J = 2.0, 8.8 Hz, 1H), 7.77 (d, J = 8.8 Hz, 1H), 7.63 (td, J = 3.2, 8.8 Hz, 1H), 7.12 (dd, | MS-ESI m/z: 404.0 [M + H]⁺. |

TABLE 20-continued

| Embodiments | Compound | HNMR | LCMS |
|---|---|---|---|
| | | J = 3.6, 8.8 Hz, 1H), 4.26 (dd, J = 4.8, 12.4 Hz, 1H), 2.83-2.72 (m, 1H), 2.68-2.64 (m, 1H), 2.34-2.30 (m, 1H), 2.16-2.09 (m, 1H). | |
| 117 | WX117 | $^1$H NMR (400 MHZ, DMSO_$d_6$) δ: 10.96 (s, 1H), 8.13 (s, 1H), 8.06 (d, J = 1.6 Hz, 1H), 7.86 (d, J = 8.8 Hz, 1H), 7.69 (dd, J = 1.8, 8.6 Hz, 1H), 4.30 (dd, J = 4.6, 12.6 Hz, 1H), 3.74 (br s, 2H), 3.54 (s, 2H), 2.96-2.82 (m, 4H), 2.80-2.69 (m, 1H), 2.64-2.57 (m, 1H), 2.41-2.31 (m, 1H), 2.19-2.11 (m, 1H), 1.90-1.83 (m, 1H), 0.66-0.60 (m, 4H). | MS-ESI m/z: 446.1 [M + H]$^+$. |
| 118 | WX118 | $^1$H NMR (400 MHZ, DMSO_$d_6$) δ: 10.98 (s, 1H), 10.58 (s, 1H), 8.10 (s, 1H), 8.08 (d, J = 2.0 Hz, 1H), 7.79 (d, J = 8.8 Hz, 1H), 7.71 (dd, J = 1.6, 8.8 Hz, 1H), 7.23 (t, J = 8.2 Hz, 1H), 7.13 (t, J = 2.0 Hz, 1H), 7.07 (td, J = 2.0, 8.4 Hz, 2H), 4.24 (dd, J = 4.8, 12.4 Hz, 1H), 2.82-2.72 (m, 1H), 2.68-2.57 (m, 1H), 2.38-2.21 (m, 1H), 2.15-2.07 (m, 1H). | MS-ESI m/z: 419.1 [M + H]$^+$. |
| 119 | WX119 | $^1$H NMR (400 MHZ, DMSO_$d_6$) δ: 10.99 (s, 1H), 10.10 (s, 1H), 8.08 (s, 1H), 8.00 (d, J = 1.6 Hz, 1H), 7.74 (d, J = 8.8 Hz, 1H), 7.66 (dd, J = 1.8, 8.6 Hz, 1H), 7.05-6.91 (m, 4H), 4.22 (dd, J = 4.8, 12.4 Hz, 1H), 2.84-2.71 (m, 1H), 2.68-2.55 (m, 1H), 2.28-2.18 (m, 1H), 2.15 (s, 3H), 2.12-2.02 (m, 1H). | MS-ESI m/z: 399.1 [M + H]$^+$. |
| 120 | WX120 | $^1$H NMR (400 MHZ, DMSO_$d_6$) δ: 10.98 (s, 1H), 10.19 (s, 1H), 8.08 (s, 1H), 8.04 (d, J = 1.6 Hz, 1H), 7.76 (d, J = 8.8 Hz, 1H), 7.70 (dd, J = 2.0, 8.8 Hz, 1H), 7.06 (t, J = 7.8 Hz, 1H), 6.93 (s, 1H), 6.89 (d, J = 8.0 Hz, 1H), 6.81 (d, J = 7.6 Hz, 1H), 4.23 (dd, J = 4.8, 12.4 Hz, 1H), 2.85-2.70 (m, 1H), 2.69-2.56 (m, 1H), 2.38-2.20 (m, 1H), 2.17 (s, 3H), 2.10-2.02 (m, 1H). | MS-ESI m/z: 399.1 [M + H]$^+$. |
| 121 | WX121 | $^1$H NMR (400 MHZ, DMSO_$d_6$) δ: 10.97 (s, 1H), 10.04 (s, 1H), 9.86 (s, 1H), 8.08 (s, 1H), 7.98 (s, 1H), 7.74 (d, J = 8.8 Hz, 1H), 7.66 (d, J = 8.8 Hz, 1H), 7.39 (d, J = 8.4 Hz, 2H), 6.99 (d, J = 8.8 Hz, 2H), 4.21 (dd, J = 4.0, 12.0 Hz, 1H), 2.82-2.70 (m, 1H), 2.69-2.59 (m, 1H), 2.27-2.15 (m, 1H), 2.13-2.03 (m, 1H), 1.97 (s, 3H). | MS-ESI m/z: 442.1 [M + H]$^+$. |
| 122 | WX122 | $^1$H NMR (400 MHZ, DMSO_$d_6$) δ: 10.98 (s, 1H), 8.11 (s, 1H), 8.09 (d, J = 1.6 Hz, 1H), 7.88 (d, J = 2.4 Hz, 1H), 7.82 (d, J = 8.8 Hz, 1H), 7.76 (dd, J = 1.6, 8.8 Hz, 1H), 4.28 (dd, J = 4.8, 12.4 Hz, 1H), 2.83-2.72 (m, 1H), 2.65-2.58 (m, 1H), 2.36-2.30 (m, 1H), 2.19-2.12 (m, 1H), 2.10-2.04 (m, 1H), 0.48-0.42 (m, 2H), 0.38-0.33 (m, 2H). | MS-ESI m/z: 366.0 [M + H$_2$O]$^+$. |
| 123 | WX123 | $^1$H NMR (400 MHZ, DMSO_$d_6$) δ: 10.98 (s, 1H), 10.43 (s, 1H), 8.08 (s, 1H), 8.05 (d, J = 1.2 Hz, 1H), 7.90 (br s, 1H), 7.76 (d, J = 8.8 Hz, 1H), 7.70 (dd, J = 1.6, 8.8 Hz, 1H), 7.61 (s, 1H), 7.48 (br d, J = 6.8 Hz, 1H), 7.36 (br s, 1H), 7.27-7.22 (m, 2H), 4.21 (dd, J = 5.0, 12.6 Hz, 1H), 2.81-2.70 (m, 1H), 2.68-2.62 (m, 1H), 2.33-2.20 (m, 1H), 2.08-2.01 (m, 1H). | MS-ESI m/z: 428.0 [M + H]$^+$. |
| 124 | WX124 | $^1$H NMR (400 MHZ, DMSO_$d_6$) δ: 10.97 (s, 1H), 10.45 (s, 1H), 10.28 (s, 1H), 8.09 (s, 1H), 7.99 (d, J = 1.6 Hz, 1H), 7.94 (d, J = 2.4 Hz, 1H), 7.91 (br d, J = 8.4 Hz, 1H), 7.77 (d, J = 8.8 Hz, 1H), 7.65 (dd, J = 1.8, 8.6 Hz, 1H), 7.47 (dd, J = 2.6, 9.0 Hz, 1H), 4.22 (dd, J = 4.8, 12.2 Hz, 1H), 2.77-2.66 (m, 1H), 2.62-2.57 (m, 1H), 2.34-2.17 (m, 1H), 2.10-2.04 (m, 1 H), 2.02 (s, 3H). | MS-ESI m/z: 443.1 [M + H]$^+$. |

Embodiment 125: WX125

Synthetic Route:

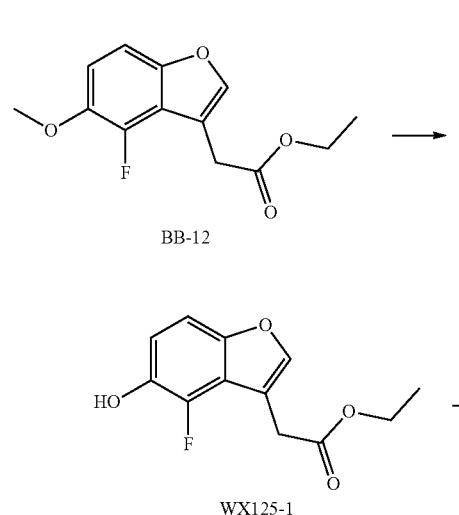

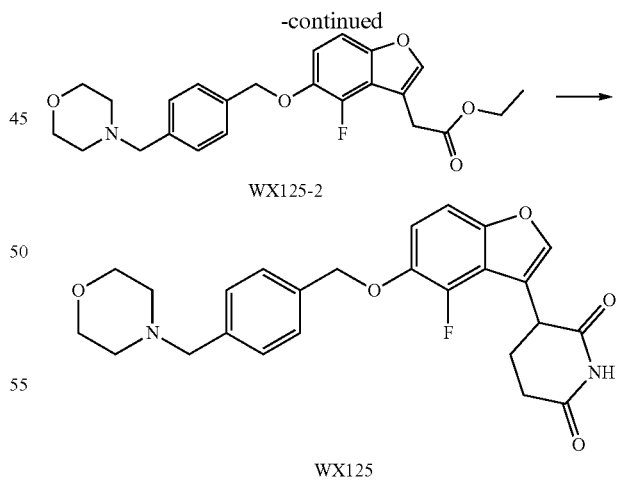

Step 1: Synthesis of Compound WX125-1

Compound BB-12 (900 mg, 3.57 mmol) was dissolved in dichloromethane (15 mL) under the protection of nitrogen at room temperature, and the mixture was cooled to −50° C., then boron tribromide (2.68 g, 10.70 mmol, 1.03 mL) was added, and the reaction mixture was naturally restored to room temperature and reacted with stirring for 2 hours. After the reaction was completed, ice water (50 mL) was slowly added dropwise to the reaction system, and dichloromethane (20 mL) were added to dilute, and the phases were separated, then the organic phases were collected, and the aqueous phase was extracted with dichloromethane (20 mL×3). The organic phases were combined and concentrated under reduced pressure to remove the solvent to obtain compound WX125-1. $^1$H NMR (400 MHz, CDCl$_3$) δ: 7.54 (s, 1H), 7.15 (d, J=8.8 Hz, 1H), 6.96 (t, J=8.8 Hz, 1H), 4.95 (d, J=3.6 Hz, 1H), 4.23 (q, J=7.2 Hz, 2H), 3.80 (d, J=0.8 Hz, 2H), 1.30 (t, J=7.2 Hz, 3H).

Step 2: Synthesis of Compound WX125-2

Compound WX125-1 (800 mg, 3.36 mmol) was dissolved in N,N-dimethylformamide (15 mL) at room temperature, then potassium carbonate (2.32 g, 16.79 mmol), 4-(4-(chloromethyl)benzyl)morpholine (1.76 g, 6.72 mmol, hydrochloride) were sequentially added, and the reaction mixture was reacted with stirring at room temperature for 144 hours. After the reaction was completed, water (30 mL) and ethyl acetate (50 mL) were added to the reaction system to dilute, and the phases were separated, then the organic phases were collected, and the aqueous phase was extracted with ethyl acetate (30 mL×2). The organic phases were combined, sequentially washed with semi-saturated brine (20 mL×2), dried with anhydrous sodium sulfate, filtered, and the filtrate was concentrated under reduced pressure to remove the solvent. The obtained residue was separated by column chromatography (eluent: petroleum ether/ethyl acetate=1/0-1/1, v/v), to obtain compound WX125-2. MS-ESI m/z: 428.2 [M+H]$^+$. $^1$H NMR (400 MHz, CDCl$_3$) δ: 7.55 (s, 1H), 7.41 (d, J=8.0 Hz, 2H), 7.34 (d, J=8.0 Hz, 2H), 7.14 (d, J=8.8 Hz, 1H), 7.01 (t, J=8.4 Hz, 1H), 5.13 (s, 2H), 4.23 (q, J=7.2 Hz, 2H), 3.82 (s, 2H), 3.75-3.67 (m, 4H), 3.51 (s, 2H), 2.50-2.37 (m, 4H), 1.30 (t, J=7.2 Hz, 3H).

Step 3: Synthesis of Compound WX125

Compound WX125-2 (300 mg, 701.81 μmol) was dissolved in N,N-dimethylformamide (1 mL) and tetrahydrofuran (5 mL) at room temperature under the protection of nitrogen, then potassium tert-butoxide (78.75 mg, 701.81 μmol) and acrylamide (49.88 mg, 701.81 μmol) were sequentially added, and the reaction mixture was reacted with stirring for 2 hours at room temperature. After the reaction was completed, water (10 mL) and ethyl acetate (20 mL) were added to the reaction system to dilute, and the phases were separated, then the organic phases were collected, and the aqueous phase was extracted with ethyl acetate (20 mL×2). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-0/1, v/v), the obtained crude product was stirred with mL of methanol at room temperature for 10 minutes, filtered, and the filter cake was collected to obtain target compound WX125. MS-ESI m/z: 453.1 [M+H]$^+$. $^1$H NMR (400 MHz, DMSO_d$_6$) δ: 10.91 (s, 1H), 7.90 (s, 1H), 7.40 (d, J=8.0 Hz, 2H), 7.36 (d, J=8.8 Hz, 1H), 7.31 (d, J=8.0 Hz, 2H), 7.25 (t, J=8.6 Hz, 1H), 5.14 (s, 2H), 4.13 (dd, J=5.0, 12.6 Hz, 1H), 3.56 (t, J=4.4 Hz, 4H), 3.45 (s, 2H), 2.90-2.71 (m, 1H), 2.69-2.53 (m, 1H), 2.38-2.28 (m, 4H), 2.25-1.97 (m, 2H).

Embodiment 126: WX126

Synthetic Route:

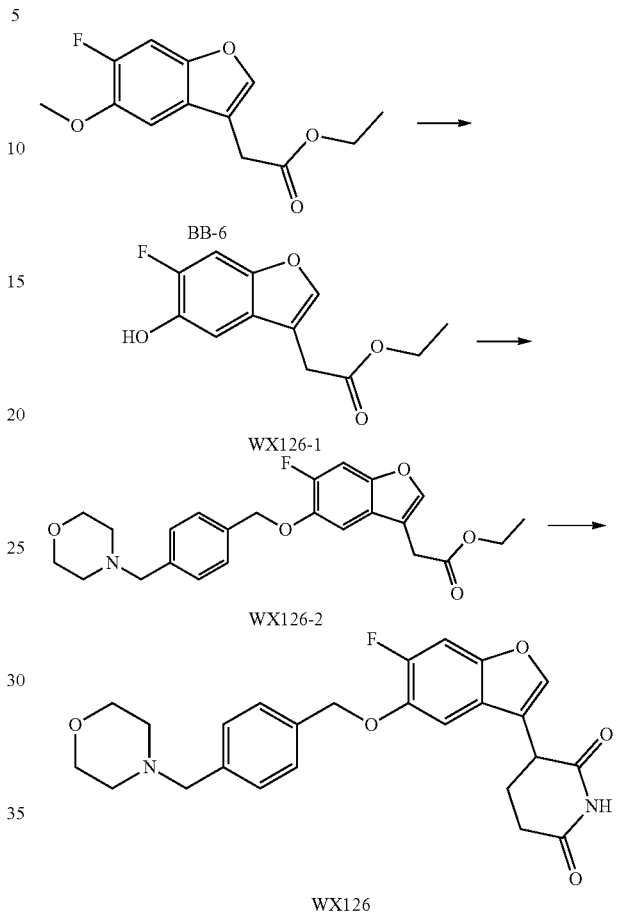

Step 1: Synthesis of Compound WX126-1

Compound BB-6 (1.0 g, 3.96 mmol) was dissolved in dichloromethane (15 mL) at room temperature, and the mixture was cooled to −78° C., then boron tribromide (2.98 g, 11.89 mmol, 1.15 mL) was added dropwise, and the reaction mixture was restored to room temperature and reacted with stirring for 12 hours. After the reaction was completed, ice water (50 mL) was slowly added dropwise to the reaction mixture, and dichloromethane (30 mL) were added to dilute, and the phases were separated, then the organic phases were collected, and the aqueous phase was extracted with dichloromethane (30 mL×2). The organic phases were combined, dried with anhydrous sodium sulfate, filtered, and the filtrate was concentrated under reduced pressure to remove the solvent to obtain a crude product of compound WX126-1.

Step 2: Synthesis of Compound WX126-2

The crude product of compound WX126-1 (700 mg, 2.94 mmol) was dissolved in N,N-dimethylformamide (10 mL) at room temperature, then potassium carbonate (2.03 g, 14.69 mmol) and 4-(4-(chloromethyl)benzyl)morpholine (1.33 g, mmol, hydrochloride) were sequentially added, and the reaction mixture was stirred at room temperature for 48 hours. After the reaction was completed, water (20 mL) and ethyl acetate (30 mL) were added to the reaction system to dilute, and the phases were separated, then the organic phases were collected, and the aqueous phase was extracted with ethyl acetate (20 mL×2). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-1/1, v/v), to obtain compound WX126-2. $^1$H NMR (400 MHz, CDCl$_3$) δ: 7.58 (s, 1H), 7.42 (d, J=8.0 Hz, 2H), 7.34 (d, J=8.0 Hz, 2H), 7.25 (d, J=2.4 Hz, 1H), 7.15 (d, J=8.4 Hz, 1H), 5.12 (s, 2H), 4.16 (d, J=7.2 Hz, 2H), 3.74-3.69 (m, 4H), 3.62 (d, J=0.8 Hz, 2H), 3.50 (s, 2H), 2.49-2.40 (m, 4H), 1.25 (t, J=7.2 Hz, 3H).

Step 3: Synthesis of Compound WX126

Compound WX126-2 (310 mg, 725.21 μmol) was dissolved in N,N-dimethylformamide (5 mL) under the protection of nitrogen at 18° C., then potassium tert-butoxide (81.38 mg, 725.21 μmol) and acrylamide (51.55 mg, 725.21 μmol) were sequentially added, and the reaction mixture was reacted with stirring at 18° C. for 1 hour. After the reaction was completed, ethyl acetate (10 mL) and water (10 mL) were added to the reaction system to dilute, and the phases were separated, then the organic phases were collected, and the aqueous phase was extracted with ethyl acetate (10 mL×2). The organic phases were combined, washed with semi-saturated brine (20 mL×3), dried with anhydrous sodium sulfate, filtered, and the filtrate was concentrated under reduced pressure to obtain a residue. The obtained residue was separated by preparative HPLC (mobile phase: acetonitrile/water; acidic system: 0.05% HCl) to obtain the hydrochloride of target compound WX126. MS-ESI m/z: 453.1 [M+H]$^+$. $^1$H NMR (400 MHz, DMSO_d$_6$) δ: 11.48 (br s, 1H), 10.87 (s, 1H), 7.88 (s, 1H), 7.67 (d, J=8.0 Hz, 2H), 7.61 (d, J=11.2 Hz, 1H), 7.56 (d, J=7.6 Hz, 2H), 7.45 (d, J=8.4 Hz, 1H), 5.25-5.14 (m, 2H), 4.33 (br s, 2H), 4.12 (dd, J=4.8, 12.0 Hz, 1H), 3.95-3.77 (m, 4H), 3.25-3.01 (m, 4H), 2.81-2.69 (m, 1H), 2.62-2.54 (m, 1H), 2.42-2.29 (m, 1H), 2.14-2.03 (m, 1H).

Embodiment 127 and Embodiment 128: WX127 and WX128

Synthetic Route:

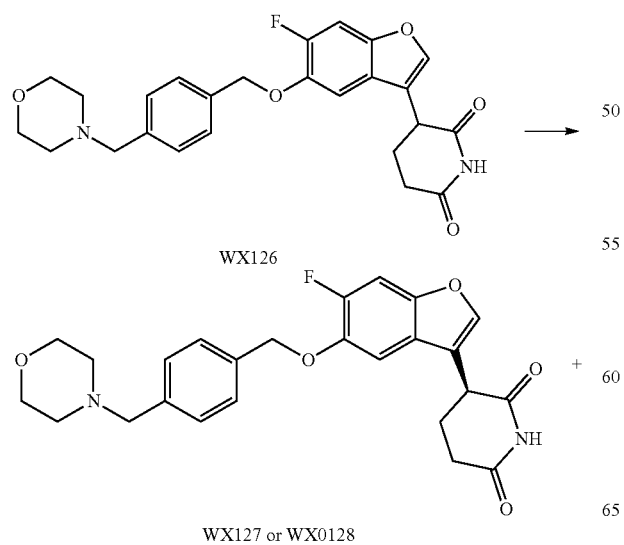

WX126

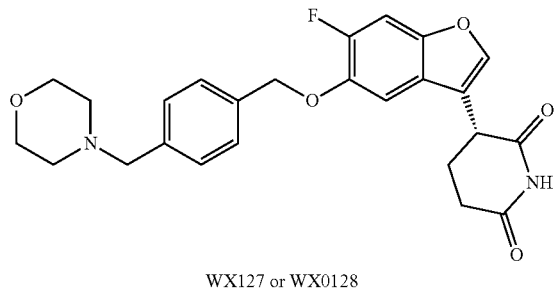

WX127 or WX0128

Compound WX126 was separated by supercritical fluid chromatography (separation conditions, chromatographic column: DAICEL CHIRALPAK AS-H (250 mm*30 mm, 5 μm); mobile phase: A: carbon dioxide; B: 0.1% NH$_3$H$_2$O-MeOH, 25%; column temperature: 40° C.; wavelength: 220 nm), the sample with a retention time of 1.57 min was collected to obtain WX127 (ee %: 99.72%) and the sample with a retention time of 1.81 min was collected to obtain WX128 (ee %: 100%).

Embodiment 129: WX129

Synthetic Route:

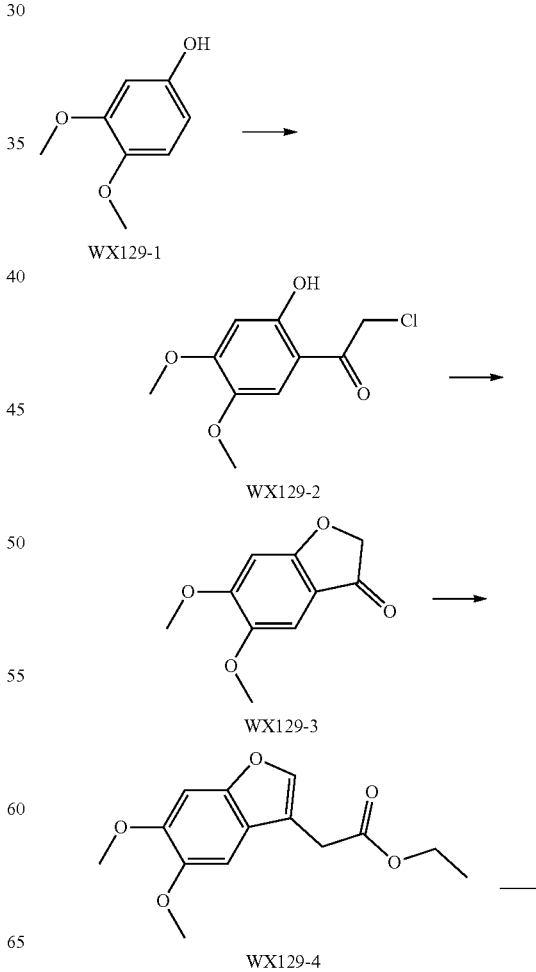

-continued

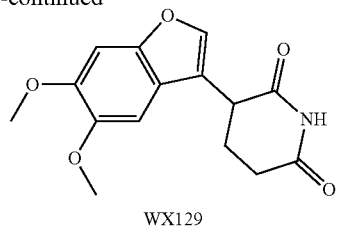

WX129

Step 1: Synthesis of Compound WX129-2

Compound WX129-1 (5.02 g, 32.56 mmol) was dissolved in dichloromethane (50 mL) at 0° C., then boron trichloride (1 M, 39.08 mL) was added dropwise, and the reaction mixture was reacted with stirring at 0° C. for 0.5 hours, then chloroacetonitrile (2.95 g, 39.08 mmol, 2.48 mL) was added to the above solution, and the reaction mixture was continued to stir at 0° C. for 0.5 hours, and aluminum trichloride (2.17 g, 16.28 mmol) was added, and the reaction mixture was continued to stir at 20° C. for 2 hours. After the reaction was completed, the reaction mixture was slowly poured into ice water (100 mL), and extracted with dichloromethane (80 mL×3). The organic phases were combined, washed with brine (150 mL×2), dried with anhydrous sodium sulfate, filtered, and the filtrate was concentrated under reduced pressure to remove the solvent. The obtained residue was separated by column chromatography (eluent: petroleum ether/ethyl acetate=10/1-4/1, v/v), to obtain compound WX129-2. $^1$H NMR (400 MHz, CDCl$_3$) δ: 12.13 (s, 1H), 7.02 (s, 1H), 6.50 (s, 1H), 4.61 (s, 2H), 3.94 (s, 3H), 3.88 (s, 3H).

Step 2: Synthesis of Compound WX129-3

Compound WX129-2 (1.08 g, 4.67 mmol) was dissolved in dichloromethane (10 mL) at 20° C., then triethylamine (472.95 mg, 4.67 mmol, 650.55 µL) was added, and the reaction mixture was reacted with stirring at 20° C. for 4 hours. After the reaction was completed, the mixture was extracted with water (30 mL) and dichloromethane (30 mL×3). The organic phases were combined, washed with brine (50 mL×2), dried with anhydrous sodium sulfate, filtered, and the filtrate was concentrated under reduced pressure to remove the solvent. The obtained residue was separated by column chromatography (eluent: petroleum ether/ethyl acetate=10/1-3/1, v/v), to obtain compound WX129-3. MS-ESI m/z: 194.9 [M+H]$^+$. $^1$H NMR (400 MHz, CDCl$_3$) δ: 7.03 (s, 1H), 6.60 (s, 1H), 4.62 (s, 2H), 3.98 (s, 3H), 3.88 (s, 3H).

Step 3: Synthesis of Compound WX129-4

Compound WX129-3 (332 mg, 1.71 mmol) was dissolved in toluene (10 mL) at 20° C., then ethyl(triphenylphosphine)acetate (595.62 mg, 1.71 mmol) was added, and the reaction mixture was heated to 130° C. and reacted with stirring for 80 hours under the protection of nitrogen. After the reaction was completed, the mixture was cooled to room temperature, and the reaction mixture was extracted with water (50 mL) and ethyl acetate (50 mL×3). The organic phases were combined, washed with brine (100 mL×2), dried with anhydrous sodium sulfate, filtered, and the filtrate was concentrated under reduced pressure to remove the solvent. The obtained residue was separated by column chromatography (eluent: petroleum ether/ethyl acetate=1/0-10/1, v/v), to obtain compound WX129-4. MS-ESI m/z: 265.1 [M+H]$^+$.

Step 4: Synthesis of Compound WX129

Compound WX129-4 (102 mg, 374.62 µmol, purity: 97.06%) was dissolved in N,N-dimethylformamide (5 mL), then potassium tert-butoxide (42.04 mg, 374.62 µmol) was added, and the reaction mixture was stirred at 0° C. for 0.5 hours, then acrylamide (26.63 mg, 374.62 µmol) was added, and the reaction mixture was stirred at 0° C. for 1 hour. After the reaction was completed, the reaction mixture was raised to room temperature, then water (50 mL) was added, and the mixture was extracted with ethyl acetate (50 mL×3). The organic phases were combined, washed with brine (80 mL×2), dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl) to obtain target compound WX129. MS-ESI m/z: 290.1 [M+H]$^+$. $^1$H NMR (400 MHz, DMSO_d$_6$) δ: 10.87 (s, 1H), 7.72 (s, 1H), 7.23 (s, 1H), 7.09 (s, 1H), 4.08 (dd, J=4.8, 11.6 Hz, 1H), 3.79 (s, 3H), 3.76 (s, 3H), 2.77-2.66 (m, 1H), 2.60-2.54 (m, 1H), 2.38-2.28 (m, 1H), 2.14-2.06 (m, 1H).

Embodiment 130: WX130

Synthetic Route:

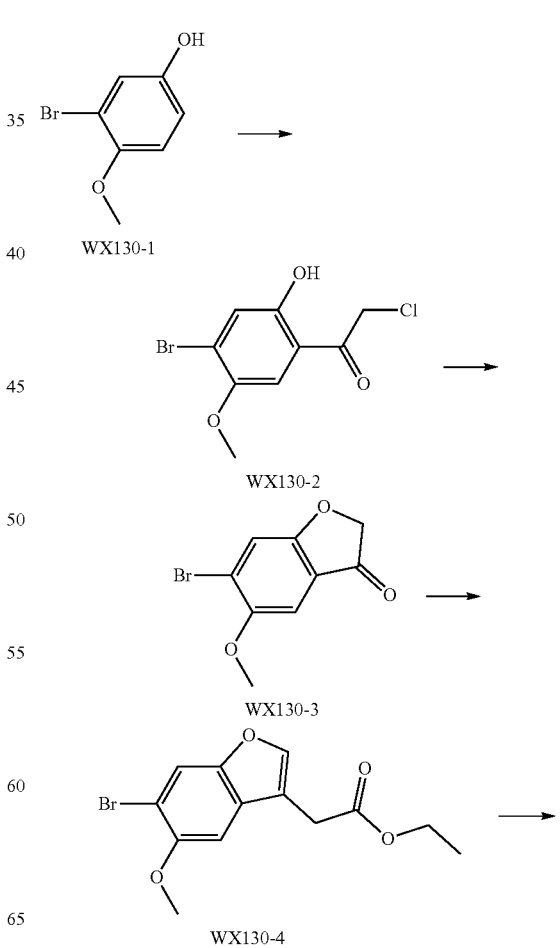

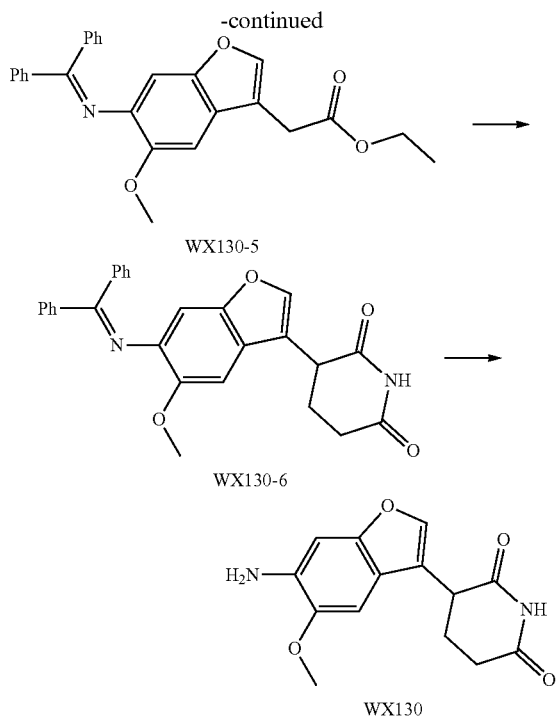

Step 1: Synthesis of Compound WX130-2

Compound WX130-1 (11.5 g, 56.64 mmol) was dissolved in dichloromethane (100 mL) at 0° C. under the protection of nitrogen, and then boron trichloride (1 M, 67.97 mL) was added dropwise, and the mixture was stirred at 0° C. for 0.5 hours, then chloroacetonitrile (5.13 g, 67.97 mmol, 4.31 mL) was added to the above solution, and the reaction mixture was continued to stir at 0° C. for 0.5 hours, and aluminum trichloride (3.78 g, 28.32 mmol) was added, then the reaction mixture was continued to stir at 20° C. for 2 hours. After the reaction was completed, the reaction mixture was slowly poured into ice water (100 mL), and extracted with dichloromethane (100 mL×3). The organic phases were combined, washed with brine (200 mL×2), dried with anhydrous sodium sulfate, filtered, and the filtrate was concentrated under reduced pressure to remove the solvent. The obtained residue was separated by column chromatography (eluent: petroleum ether/ethyl acetate=20/1-10/1, v/v), to obtain compound WX130-2.

Step 2: Synthesis of Compound WX130-3

Compound WX130-2 (11.8 g, 42.22 mmol) was dissolved in dichloromethane (150 mL) under the protection of nitrogen at room temperature, then triethylamine (7.52 g, 74.30 mmol, 10.34 mL) was added, and the reaction mixture was stirred at room temperature for 1 hour. After the reaction was completed, the mixture was extracted with water (100 mL) and dichloromethane (100 mL×3). The organic phases were combined, washed with saturated brine (200 mL×2), dried with anhydrous sodium sulfate, filtered, and the filtrate was concentrated under reduced pressure to remove the solvent. The obtained residue was separated by column chromatography (eluent: petroleum ether/ethyl acetate=20/1-10/1, v/v), to obtain compound WX130-3. MS-ESI m/z: 242.9 [M+H]$^+$, 244.9 [M+H+2]$^+$.

Step 3: Synthesis of Compound WX130-4

Compound WX130-3 (5.7 g, 10.52 mmol, purity: 44.86%) was dissolved in toluene (50 mL) at room temperature under the protection of nitrogen, then ethyl(triphenylphosphoranylidene)acetate (3.67 g, 10.52 mmol) was added, and the reaction mixture was heated to 130° C. and reacted with stirring for 34 hours. After the reaction was completed, the mixture was cooled to room temperature, and the reaction mixture was added with water (50 mL), and extracted with ethyl acetate (50 mL×3). The organic phases were combined, washed with brine (100 mL×2), dried with anhydrous sodium sulfate, filtered, and the filtrate was concentrated under reduced pressure to remove the solvent. The obtained residue was separated by column chromatography (eluent: petroleum ether/ethyl acetate=1/0-20/1, v/v), to obtain compound WX130-4. MS-ESI m/z: 313.0 [M+H]$^+$, 313.0 [M+H+2]$^+$. $^1$H NMR (400 MHz, CDCl$_3$) δ: 7.70 (s, 1H), 7.60 (s, 1H), 7.05 (s, 1H), 4.20 (q, J=7.2 Hz, 2H), 3.94 (s, 3H), 3.67 (d, J=0.8 Hz, 2H), 1.28 (t, J=6.8 Hz, 3H).

Step 4: Synthesis of Compound WX130-5

Compound WX130-4 (1.44 g, 4.26 mmol, purity: 92.59%) and benzophenone imine (848.81 mg, 4.68 mmol, 785.94 μL) were dissolved in dioxane (15 mL) at room temperature under the protection of nitrogen, then tris(dibenzylideneacetone)dipalladium (194.95 mg, 212.89 μmol), 4,5-bis(diphenylphosphino)-9,9-dimethylxanthene (246.36 mg, 425.78 μmol) and cesium carbonate (4.16 g, 12.77 mmol) were sequentially added, and the reaction mixture was heated to 80° C. and stirred for 2 hours under the protection of nitrogen. After the reaction was completed, the mixture was cooled to room temperature, and the reaction mixture was added with water (30 mL), and extracted with ethyl acetate (30×3). The organic phases were combined, washed with brine (50 mL×2), dried with anhydrous sodium sulfate, filtered, and the filtrate was concentrated under reduced pressure to remove the solvent. The obtained residue was separated by column chromatography (eluent: petroleum ether/ethyl acetate=1/0-20/1, v/v), to obtain compound WX130-5. $^1$H NMR (400 MHz, CDCl$_3$) δ: 7.80 (d, J=7.6 Hz, 2H), 7.53-7.46 (m, 2H), 7.42 (d, J=7.6 Hz, 2H), 7.27-7.20 (m, 4H), 7.19- 7.15 (m, 2H), 6.85 (s, 1H), 4.18 (q, J=7.07 Hz, 2H), 3.72 (s, 3H), 3.61 (s, 2H), 1.25 (t, J=7.2 Hz, 3H).

Step 5: Synthesis of Compound WX130-6

Compound WX130-5 (98 mg, 237.02 μmol) was dissolved in N,N-dimethylformamide (5 mL) under the protection of nitrogen at 0° C., then potassium tert-butoxide (26.60 mg, 237.02 μmol) was added, and the reaction mixture was stirred at 0° C. for 0.5 hours, then acrylamide (16.85 mg, 237.02 μmol) was added, and the reaction solution was heated to 20° C. and reacted with stirring for 1 hour. After the reaction was completed, the reaction mixture was added with water (50 mL), and extracted with ethyl acetate (50 mL×3). The organic phases were combined, washed with saturated brine (100 mL×2), dried with anhydrous sodium sulfate, filtered, and the filtrate was concentrated under reduced pressure to remove the solvent. The obtained residue was separated by silica gel plate (eluent: petroleum ether/ethyl acetate=2/1, v/v), to obtain compound WX130-6. $^1$H NMR (400 MHz, MeOD_d$_4$) δ: 7.79-7.76 (m, 2H), 7.70-7.62 (m, 2H), 7.57-7.51 (m, 3H), 7.47-7.40 (m, 2H), 7.27-7.24 (m, 1H), 7.17-7.13 (m, 1H), 6.95 (d, J=9.6

Hz, 1H), 6.88 (s, 1H), 4.05 (dd, J=5.4, 10.6 Hz, 1H), 3.88 (s, 3H), 2.79-2.67 (m, 2H), 2.40-2.23 (m, 2H).

Step 6: Synthesis of Compound WX130

Compound WX130-6 (58 mg, 132.28 μmol) was added to ethyl acetate hydrochloride (4 M, 10 mL) at room temperature under the protection of nitrogen, and the reaction mixture was reacted with stirring for 1.5 hours at room temperature. After the reaction was completed, the reaction solution was concentrated under reduced pressure to remove the solvent. The obtained residue was separated by silica gel plate (eluent: petroleum ether/ethyl acetate=1/1, v/v), to obtain target compound WX130. MS-ESI m/z: 275.1 [M+H]$^+$. $^1$H NMR (400 MHz, MeOD_d$_4$) δ: 7.45 (s, 1H), 6.95 (s, 1H), 6.89 (s, 1H), 4.05 (dd, J=5.0, 10.6 Hz, 1H), 3.89 (s, 3H), 2.81-2.64 (m, 2H), 2.41-2.23 (m, 2H).

Embodiment 132: WX132

Synthetic Route:

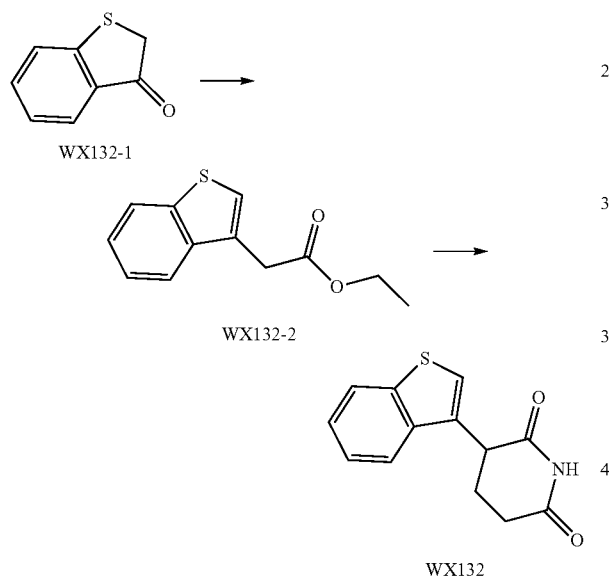

Step 1: Synthesis of Compound WX132-2

Compound WX132-1 (1 g, 6.66 mmol) was dissolved in toluene (20 mL) at room temperature under the protection of nitrogen, then ethyl(triphenylphosphoranylidene)acetate (2.32 g, 6.66 mmol) was added, and the reaction mixture was heated to 130° C. and reacted with stirring for 30 hours. After the reaction was completed, the mixture was cooled to room temperature, concentrated under reduced pressure to remove the solvent, and the obtained residue was separated by column chromatography (eluent: petroleum ether/ethyl acetate=50/1-30/1, v/v) to obtain compound WX132-2. MS-ESI m/z: 221.0 [M+H]$^+$. $^1$H NMR (400 MHz, CDCl$_3$) δ: 7.78 (d, J=7.2 Hz, 1H), 7.64 (d, J=7.2 Hz, 1H), 7.36-7.30 (m, 1H), 7.29-7.25 (m, 2H), 4.09 (q, J=7.2 Hz, 2H), 3.77 (s, 2H), 1.17 (t, J=7.2 Hz, 3H).

Step 2: Synthesis of Compound WX132

Compound WX132-1 (200 mg, 907.91 μmol) was dissolved in N,N-dimethylformamide (10 mL) at 0° C. under the protection of nitrogen, then potassium tert-butoxide (101.88 mg, 907.91 μmol) and acrylamide (64.53 mg, 907.91 μmol) were added, and the reaction mixture was raised to room temperature and reacted with stirring for 2 hours. After the reaction was completed, the reaction mixture was added with water (30 mL), and extracted with ethyl acetate (20 mL×3). The organic phases were combined, washed with saturated brine (20 mL×2), dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl) to obtain target compound WX132. MS-ESI m/z: 246.0 [M+H]$^+$. $^1$H NMR (400 MHz, DMSO_d$_6$) δ: 10.90 (s, 1H), 8.02-7.96 (m, 1H), 7.82-7.75 (m, 1H), 7.56 (s, 1H), 7.42-7.33 (m, 2H), 4.38 (dd, J=4.8, 11.6 Hz, 1H), 2.82-2.70 (m, 1H), 2.47-2.30 (m, 2H), 2.15-2.06 (m, 1H).

Embodiment 133: WX133

Synthetic Route:

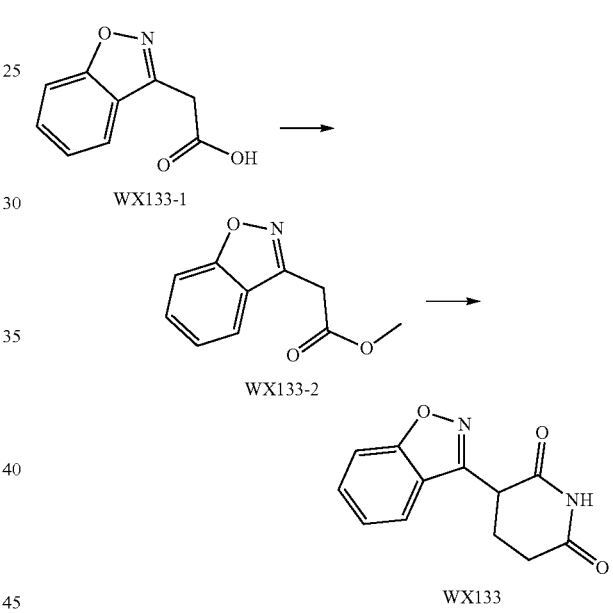

Step 1: Synthesis of Compound WX133-2

At room temperature, compound WX133-1 (2.00 g, 11.29 mmol) was dissolved in methanol (20.00 mL), and then concentrated sulfuric acid (1.13 g, 11.29 mmol, 614.05 μL, purity: 98%) was added to the above reaction solution, and the reaction mixture was reacted with stirring at room temperature for 3.5 hours under the protection of nitrogen. After the reaction was completed, the solvent was removed under reduced pressure, and the obtained residue was added with water (20 mL), then the pH was adjusted to 7 with saturated sodium bicarbonate, and the mixture was extracted with ethyl acetate (20 mL×3). The organic phases were combined, washed with saturated brine (20 mL×2), dried with anhydrous sodium sulfate, filtered, and the filtrate was concentrated under reduced pressure to remove the solvent to obtain compound WX133-2. MS-ESI m/z: 191.9 [M+H]$^+$. $^1$H NMR (400 MHz, MeOD_d$_4$) δ: 7.86-7.77 (m, 1H), 7.67-7.57 (m, 2H), 7.46-7.32 (m, 1H), 4.14 (s, 2H), 3.76 (s, 3H).

Step 2: Synthesis of Compound WX133

Compound WX133-2 (800 mg, 4.18 mmol) was dissolved in N,N-dimethylformamide (10.00 mL) at room temperature, then the mixture was cooled to 0° C., and potassium tert-butoxide (469.54 mg, 4.18 mmol) and acrylamide (297.42 mg, 4.18 mmol) were added to the above reaction solution in one portion, and the reaction mixture was raised to room temperature and reacted with stirring for 2 hours under the protection of nitrogen. After the reaction was completed, the mixture was added with water (30 mL), and extracted with ethyl acetate (20 mL×3). The organic phases were combined, washed with saturated brine (20 mL×2), dried with anhydrous sodium sulfate, filtered, and the filtrate was concentrated under reduced pressure to remove the solvent. The obtained residue was slurried with methanol (1 mL) at room temperature, filtered, and the filter cake was collected and vacuum-dried to obtain target compound WX133. MS-ESI m/z: 231.0 [M+H]$^+$. $^1$H NMR (400 MHz, DMSO_d$_6$) δ: 11.11 (s, 1H), 7.87 (d, J=8.0 Hz, 1H), 7.76 (d, J=8.4 Hz, 1H), 7.67 (t, J=6.0 Hz, 1H), 7.40 (t, J=7.6 Hz, 1H), 4.62 (dd, J=4.8, 12.0 Hz, 1H), 2.88-2.71 (m, 1H), 2.68-2.53 (m, 2H), 2.27-2.16 (m, 1H).

Embodiment 134: WX134

Synthetic Route:

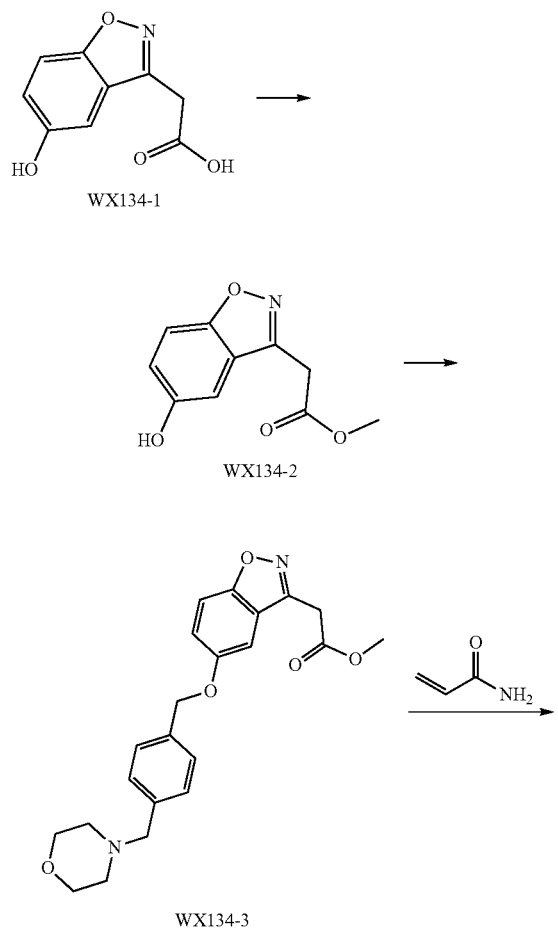

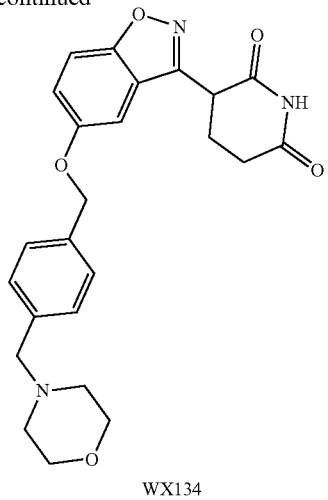

WX134

Step 1: Synthesis of Compound WX134-2

Compound WX134-1 (0.5 g, 2.59 mmol) was dissolved in hydrochloric acid methanol (4 M, 10 mL) at room temperature, and the reaction mixture was heated to 80° C. and reacted with stirring for 12 hours under the protection of nitrogen. After the reaction was completed, the mixture was cooled to room temperature, and methanol was removed under reduced pressure. The obtained residue was separated by column chromatography (eluent: petroleum ether/ethyl acetate=v/v), to obtain compound WX134-2. MS-ESI m/z: 207.9 [M+H]$^+$. $^1$H NMR (400 MHz, CDCl$_3$) δ: 7.37 (d, J=8.8 Hz, 1H), 7.04 (dd, J=2.2, 9.0 Hz, 1H), 6.98 (d, J=2.4 Hz, 1H), 5.41 (s, 1H), 3.94 (s, 2H), 3.69 (s, 3H).

Step 2: Synthesis of Compound WX134-3

Compound WX134-2 (310 mg, 1.50 mmol), 4-(morpholinomethyl)benzyl alcohol (620.26 mg, 2.99 mmol) and tributylphosphine (665.98 mg, 3.29 mmol, 812.18 μL) were added into a reaction flask at room temperature, then the reaction mixture was heated to 75° C., and a tetrahydrofuran (20 mL) solution of N,N,N',N'-tetramethylazodicarboxamide (566.80 mg, 3.29 mmol) was added to the above reaction flask in one portion, and the reaction mixture was reacted with stirring at 75° C. for 2 hours under the protection of nitrogen. After the reaction was completed, the mixture was cooled to room temperature, the reaction mixture was added with water (50 mL), and extracted with ethyl acetate (30 mL×3). The organic phases were combined, washed with water (30 mL×3), dried with anhydrous sodium sulfate, filtered, and the solvent was removed from the filtrate under reduced pressure. The obtained residue was separated by column chromatography (eluent: petroleum ether/ethyl acetate=1/1-0/1, v/v), to obtain compound WX134-3. MS-ESI m/z: 397.1 [M+H]$^+$. $^1$H NMR (400 MHz, CDCl$_3$) δ: 7.42 (d, J=8.8 Hz, 1H), 7.34 (d, J=8.4 Hz, 2H), 7.30 (d, J=8.0 Hz, 2H), 7.19 (dd, J=2.4, 9.2 Hz, 1H), 7.06 (d, J=2.0 Hz, 1H), 5.01 (s, 2H), 3.95 (s, 2H), 3.67 (s, 3H), 3.65 (t, J=4.6 Hz, 4H), 3.45 (s, 2H), 2.39 (s, 4H).

Step 3: Synthesis of Compound WX134

Compound WX134-3 (490 mg, 1.24 mmol) was dissolved in N,N-dimethylformamide (10 mL) at room temperature, then the mixture was cooled to 0° C., and potassium tert-butoxide (138.69 mg, 1.24 mmol) was added to the above reaction solution in one portion, and the reaction mixture was reacted with stirring for 1 hour at 0° C. under the protection of nitrogen. Acrylamide (87.85 mg, 1.24 mmol) was then added to the above reaction solution, and the reaction mixture was raised to room temperature and continued to react with stirring for 2 hours under the protection of nitrogen. After the reaction was completed, the mixture was added with water (50 mL), and extracted with ethyl acetate (50 mL×3). The organic phases were combined, washed with saturated brine (30 mL×2), dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl) to obtain target compound WX134. MS-ESI m/z: 436.1 [M+H]$^+$. $^1$H NMR (400 MHz, DMSO_d$_6$) δ: 11.08 (s, 1H), 11.00 (s, 1H), 7.70 (d, J=9.2 Hz, 1H), 7.63 (d, J=8.4 Hz, 2H), 7.58 (d, J=8.0 Hz, 2H), 7.45 (d, J=2.4 Hz, 1H), 7.35 (dd, J=2.4, 9.2 Hz, 1H), 5.18 (q, J=12.4 Hz, 2H), 4.57 (dd, J=4.8, 11.6 Hz, 1H), 4.35 (d, J=4.8 Hz, 2H), 3.94 (d, J=12.0 Hz, 2H), 3.76 (t, J=12.0 Hz, 2H), 3.27-3.17 (m, 2H), 3.15-3.03 (m, 2H), 2.85-2.73 (m, 1H), 2.68-2.56 (m, 2H), 2.22-2.12 (m, 1H).

Embodiment 135: WX135

Synthetic Route:

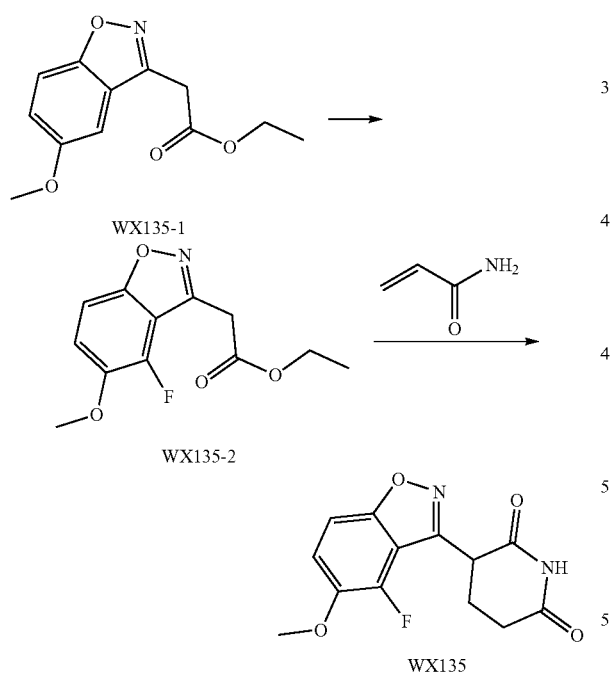

Step 1: Synthesis of Compound WX135-2

Compound WX135-1 (1.60 g, 5.05 mmol, purity: 74.2%) was dissolved in trifluoroacetic acid (10.00 mL) at room temperature, then 1-chloromethyl-4-fluoro-1,4-diazoniabicyclo[2.2.2]octane bis(tetrafluoroborate) (1.97 g, 5.55 mmol) was added, and the reaction mixture was heated to 80° C. and reacted with stirring for 16 hours at 80° C. After the reaction was completed, the reaction mixture was added with water (100 mL) to dilute, and extracted with ethyl acetate (80 mL×3). The organic phases were combined, washed with saturated brine (150 mL×2), dried with anhydrous sodium sulfate, filtered, and the filtrate was concentrated under reduced pressure to remove the solvent. The obtained residue was separated by column chromatography (eluent: petroleum ether/ethyl acetate=5/1-2/1, v/v), and then separated by preparative HPLC to obtain compound WX135-2. MS-ESI m/z: 253.9 [M+H]$^+$. $^1$H NMR (400 MHz, DMSO_d$_6$) δ: 7.65-7.54 (m, 2H), 4.21 (s, 2H), 4.15 (q, J=7.0 Hz, 2H), 3.90 (s, 3H), 1.18 (t, J=7.0 Hz, 3H).

Step 2: Synthesis of Compound WX135

Potassium tert-butoxide (225.55 mg, 2.01 mmol) was added to a N, N-dimethylformamide (5.00 mL) solution of compound WX135-2 (509.00 mg, 2.01 mmol) at 0° C. under the protection of nitrogen. The reaction mixture was reacted with stirring at 0° C. for 0.5 hours, then acrylamide (142.87 mg, 2.01 mmol) was added, and the mixture was continued to react with stirring for 1 hour at 0° C. After the reaction was completed, the mixture was raised to room temperature, and the reaction mixture was added with water (50 mL) to dilute, and extracted with ethyl acetate (50 mL×3). The organic phases were combined, washed with saturated brine (80 mL×2), dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl) to obtain target compound WX135. MS-ESI m/z: 279.1 [M+H]$^+$. $^1$H NMR (400 MHz, DMSO_d$_6$) δ: 7.67-7.56 (m, 2H), 4.60 (dd, J=5.0, 12.6 Hz, 1H), 3.91 (s, 3H), 2.89-2.80 (m, 1H), 2.69-2.58 (m, 1H), 2.35-2.25 (m, 1H), 2.24-2.15 (m, 1H).

Embodiment 136: WX136

Synthetic Route:

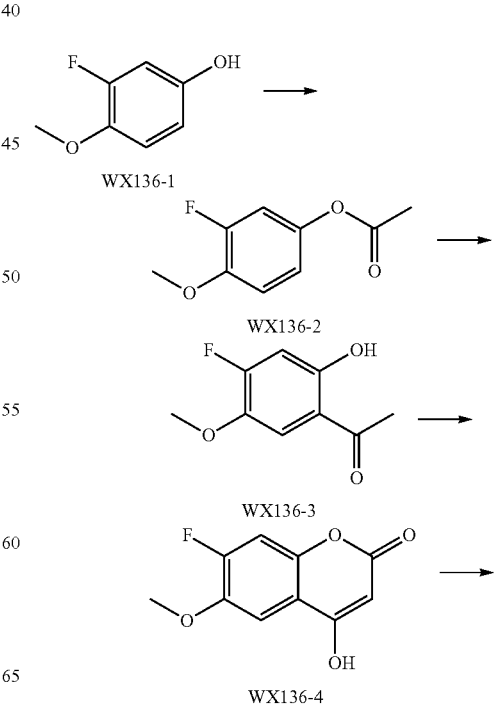

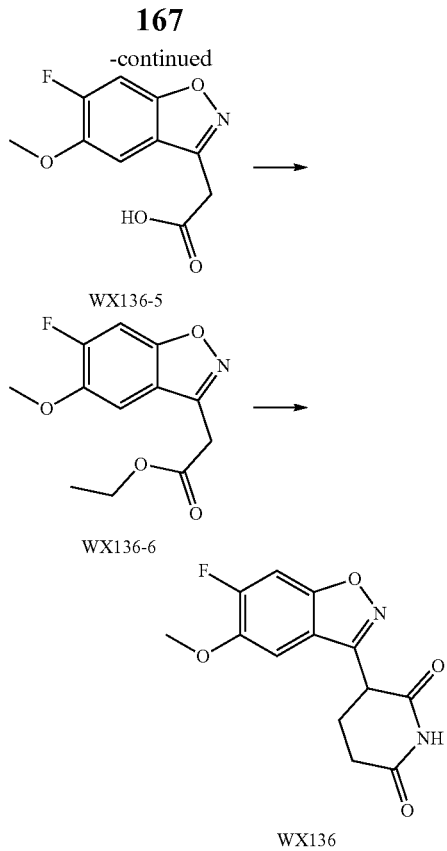

NMR (400 MHz, CDCl$_3$) δ: 12.32 (d, J=1.2 Hz, 1H), 7.24 (d, J=9.2 Hz, 1H), 6.73 (d, J=12.0 Hz, 1H), 3.89 (s, 3H), 2.61 (s, 3H).

Step 3: Synthesis of Compound WX136-4

Compound WX136-3 (1.68 g, 9.12 mmol) was dissolved in toluene (40.00 mL) at room temperature, and sodium hydride (1.46 g, 36.49 mmol, purity: 60%) was added in batches, then diethyl carbonate (4.31 g, 36.49 mmol, 4.42 mL) was added, and the reaction mixture was heated to 100° C. and reacted with stirring at 100° C. for 20 hours. After the reaction was completed, the mixture was cooled to room temperature, and water (100 mL) was added to dilute, and the mixture was extracted with ethyl acetate (100 mL×3). The organic phase was discarded, and the aqueous phase was adjusted to pH=3-4 with 2 M dilute hydrochloric acid aqueous solution, and extracted with ethyl acetate (100 mL×4). The organic phases were combined, washed with saturated brine (200 mL×2), dried with anhydrous sodium sulfate, filtered, and the filtrate was concentrated under reduced pressure to remove the solvent to obtain compound WX136-4. MS-ESI m/z: 210.9 [M+H]$^+$. $^1$H NMR (400 MHz, DMSO_d$_6$) δ: 12.70 (s, 1H), 7.47-7.37 (m, 2H), 5.57 (s, 1H), 3.90 (s, 3H).

Step 4: Synthesis of Compound WX136-5

Compound WX136-4 (1.51 g, 6.88 mmol) was dissolved in ethanol (40.00 mL) at room temperature, and hydroxylamine hydrochloride (1.43 g, 20.63 mmol) and sodium acetate (1.69 g, 20.63 mmol) were added, and the reaction mixture was heated to 80° C. and reacted with stirring at 80° C. for 16 hours. After the reaction was completed, the mixture was cooled to room temperature, and the solvent was removed under reduced pressure. The obtained residue was diluted with water (50 mL), adjusted to pH=1-2 with 2 M dilute hydrochloric acid aqueous solution, and extracted with ethyl acetate (50 mL×3). The organic phases were combined, washed with saturated brine (80 mL×2), dried with anhydrous sodium sulfate, filtered, and the filtrate was concentrated under reduced pressure to remove the solvent. The obtained residue was slurried at room temperature with petroleum ether/ethyl acetate (10:1, 50 mL, v/v) (stirred at room temperature for 0.5 hours), filtered, and the filter cake was washed with petroleum ether (20 mL), and the obtained filter cake was vacuum-dried to obtain compound WX136-5. $^1$H NMR (400 MHz, DMSO_d$_6$) δ: 12.89 (s, 1H), 7.80 (d, J=10.4 Hz, 1H), 7.57 (d, J=8.4 Hz, 1H), 4.07 (s, 2H), 3.89 (s, 3H).

Step 1: Synthesis of Compound WX136-2

Compound WX136-1 (1.77 g, 12.45 mmol) and triethylamine (1.89 g, 18.68 mmol, 2.60 mL) were dissolved in dichloromethane (20.00 mL) at room temperature, then the mixture was cooled to 0° C. and acetyl chloride (1.17 g, 14.94 mmol, 1.07 mL) was added, and the reaction mixture was raised to room temperature and reacted with stirring for 2 hours. After the reaction was completed, the reaction mixture was washed with water (50 mL×3), dried with anhydrous sodium sulfate, filtered, and the filtrate was concentrated under reduced pressure to remove the solvent, and the obtained residue was separated by column chromatography (eluent: petroleum ether/ethyl acetate=1/0-10/1, v/v) to obtain compound WX136-2. $^1$H NMR (400 MHz, CDCl$_3$) δ: 6.98-6.92 (m, 1H), 6.90 (dd, J=2.8, 11.6 Hz, 1H), 6.86-6.80 (m, 1H), 3.89 (s, 3H), 2.29 (s, 3H).

Step 2: Synthesis of Compound WX136-3

Compound WX136-2 (2.16 g, 11.73 mmol) was dissolved in trifluoromethanesulfonic acid (8.80 g, 58.64 mmol, mL) at 0° C., then the reaction mixture was heated to 60° C. and reacted with stirring at 60° C. for 1.5 hours. After the reaction was completed, the mixture was cooled to room temperature, and diluted with water (30 mL), then the pH of the mixture was adjusted to 8-9 with saturated sodium bicarbonate aqueous solution, and the mixture was extracted with dichloromethane (30 mL×3). The organic phases were combined, washed with water (50 mL×2), dried with anhydrous sodium sulfate, filtered, and the filtrate was concentrated under reduced pressure to remove the solvent to obtain compound WX136-3. MS-ESI m/z: 185.0 [M+H]$^+$. $^1$H Step 5: Synthesis of Compound WX136-6

Compound WX136-5 (1.34 g, 5.96 mmol) was dissolved in ethanol (20.00 mL) at room temperature, and concentrated sulfuric acid (1.19 g, 11.92 mmol, 648.33 µL, purity: 98%) was added, and the reaction mixture was heated to ° C. and reacted with stirring at 75° C. for 15 hours. After the reaction was completed, the mixture was cooled to room temperature, and the solvent was removed under reduced pressure. The obtained residue was diluted with dichloromethane (50 mL), washed with water (50 mL×2), and washed with saturated sodium bicarbonate aqueous solution (50 mL), dried with anhydrous sodium sulfate, filtered, and the filtrate was concentrated under reduced pressure to removed the solvent to obtain compound WX136-6. MS-ESI m/z: 253.9 [M+H]$^+$. $^1$H NMR (400 MHz, DMSO_d$_6$) δ:

7.81 (d, J=10.4 Hz, 1H), 7.57 (d, J=8.0 Hz, 1H), 4.17 (s, 2H), 4.16-4.12 (m, 2H), 3.89 (s, 3H), 1.20 (t, J=7.2 Hz, 3H).

Step 6: Synthesis of Compound WX136

Potassium tert-butoxide (219.22 mg, 1.95 mmol) was added to a N,N-dimethylformamide (5.00 mL) solution of compound WX136-6 (0.50 g, 1.95 mmol) at 0° C. under the protection of nitrogen. The reaction mixture was stirred at 0° C. for 0.5 hours, then acrylamide (138.86 mg, 1.95 mmol) was added, and the mixture was reacted with stirring at 0° C. for 1 hour. After the reaction was completed, the reaction mixture was raised to room temperature, diluted with water (50 mL), and extracted with ethyl acetate (50 mL×3). The organic phases were combined, washed with saturated brine (80 mL×2), dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl) to obtain target compound WX136. MS-ESI m/z: 279.1 [M+H]$^+$. $^1$H NMR (400 MHz, DMSO-$d_6$) δ: 11.09 (s, 1H), 7.83 (d, J=10.4 Hz, 1H), 7.55 (d, J=8.0 Hz, 1H), 4.58 (dd, J=4.8, 11.6 Hz, 1H), 3.89 (s, 3H), 2.81-2.70 (m, 1H), 2.65-2.54 (m, 2H), 2.21-2.13 (m, 1H).

Embodiment 137: WX137

Synthetic Route:

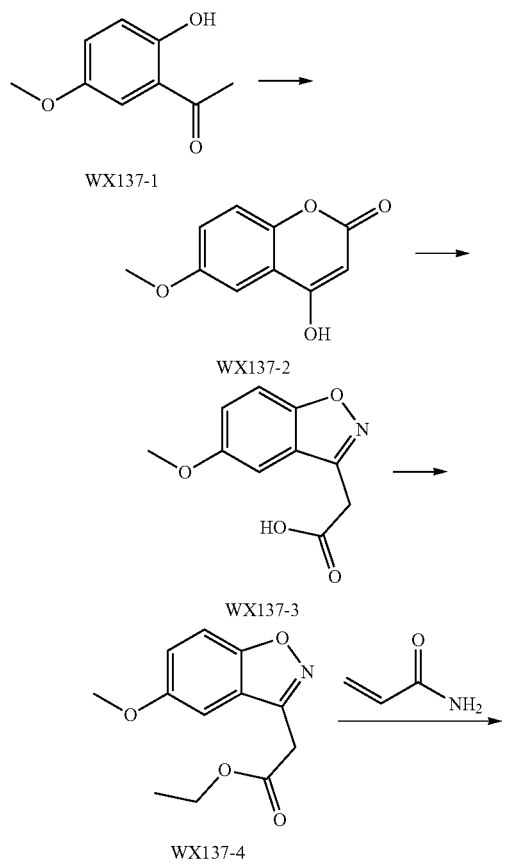

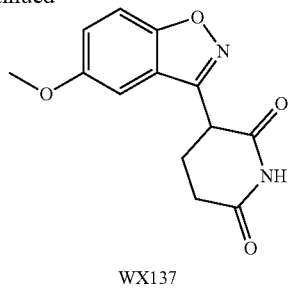

Step 1: Synthesis of Compound WX137-2

Compound WX137-1 (8 g, 48.14 mmol) was dissolved in toluene (300 mL) at room temperature, and sodium hydride (7.70 g, 192.57 mmol, purity: 60%) was added in batches then diethyl carbonate (22.75 g, 192.57 mmol, 23.33 mL) was added, and the reaction mixture was heated to 100° C. and reacted with stirring at 100° C. for 12 hours. After the reaction was completed, the mixture was cooled to room temperature, added with water (500 mL) to dilute, and extracted with ethyl acetate (200 mL×3). The organic phase was discarded, and the aqueous phase was adjusted to pH=3-4 with 37% concentrated hydrochloric acid, and extracted with ethyl acetate (200 mL×4). The organic phases were combined, washed with saturated brine (200 mL×2), dried with anhydrous sodium sulfate, filtered, and the filtrate was concentrated under reduced pressure to remove the solvent to obtain compound WX137-2. $^1$H NMR (400 MHz, DMSO-$d_6$) δ: 12.54 (s, 1H), 7.34-7.30 (m, 1H), 7.25-7.20 (m, 2H), 5.60 (s, 1H), 3.81 (s, 3H).

Step 2: Synthesis of Compound WX137-3

Compound WX137-2 (5 g, 26.02 mmol), hydroxylamine hydrochloride (5.42 g, 78.06 mmol) and sodium acetate (6.40 g, 78.06 mmol) were dissolved in ethanol (100.00 mL) at room temperature, and the reaction mixture was heated to ° C. and reacted with stirring at 80° C. for 12 hours. After the reaction was completed, the mixture was cooled to room temperature, and the solvent was removed under reduced pressure. The obtained residue was diluted with water (80 mL), adjusted to pH=1-2 with 37% concentrated hydrochloric acid, and extracted with ethyl acetate (50 mL×3). The organic phases were combined, washed with saturated brine (80 mL×2), dried with anhydrous sodium sulfate, filtered, and the filtrate was concentrated under reduced pressure to remove the solvent. The obtained residue was slurried at room temperature with petroleum ether/ethyl acetate=10:1 (50 mL, v/v), the mixture was stirred at room temperature for 0.5 hours, filtered, and the filter cake was washed with petroleum ether (20 mL), and the obtained filter cake was vacuum-dried to obtain target compound WX137-3. MS-ESI m/z: 207.9 [M+H]$^+$.

Step 3: Synthesis of Compound WX137-4

Compound WX137-3 (4 g, 18.95 mmol, purity: 98.13%) and concentrated sulfuric acid (189.61 mg, 1.89 mmol, 103.05 μL, purity: 98%) were dissolved in ethanol (50 mL) at room temperature, and the reaction mixture was heated to 80° C. and reacted with stirring at 80° C. for 4 hours. After the reaction was completed, the mixture was cooled to room temperature, quenched by adding water (50 mL), and extracted with ethyl acetate (30 mL×3). The organic phases were combined, washed with saturated brine (50 mL×2), dried with anhydrous sodium sulfate, filtered, and the filtrate was concentrated under reduced pressure to remove the solvent. The obtained residue was separated by column chromatography (eluent: petroleum ether/ethyl acetate=10/1-1/1, v/v), to obtain compound WX137-4. MS-ESI m/z 235.9 [M+H]⁺. ¹H NMR (400 MHz, CDCl₃) δ: 7.40 (d, J=9.2 Hz, 1H), 7.11 (dd, J=2.6, 9.0 Hz, 1H), 6.97 (d, J=2.4 Hz, 1H), 4.15 (q, J=7.0 Hz, 2H), 3.94 (s, 2H), 3.79 (s, 3H), 1.20 (t, J=7.0 Hz, 3H).

Step 4: Synthesis of Compound WX137

Compound WX137-4 (500 mg, 1.58 mmol, purity: 74.20%) was dissolved in N,N-dimethylformamide (10.00 mL) at −5 to 0° C. under the protection of nitrogen, then potassium tert-butoxide (353.94 mg, 3.15 mmol) was added, and the mixture was reacted with stirring at −5 to 0° C. for 0.5 hours, then acrylamide (134.52 mg, 1.89 mmol) was added, and the reaction mixture was stirred at -5 to 0° C. for 1 hour. After the reaction was completed, the mixture was added with water (50 mL) to dilute, and extracted with ethyl acetate (40 mL×3). The organic phases were combined, washed with saturated brine (30 mL×2), dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl) to obtain target compound WX137. MS-ESI m/z: 261.1. [M+H]⁺. ¹H NMR (400 MHz, DMSO_d₆) δ: 11.09 (s, 1H), 7.67 (d, J=9.2 Hz, 1H), 7.32 (d, J=2.4 Hz, 1H), 7.27 (dd, J=2.4, 9.2 Hz, 1H), 4.57 (dd, J=4.8, 11.6 Hz, 1H), 3.81 (s, 3H), 2.75 (d, J=11.8 Hz, 1H), 2.65-2.59 (m, 1H), 2.56-2.54 (m, 1H), 2.18 (q, J=13.8 Hz, 1H).

Embodiment 138: WX138

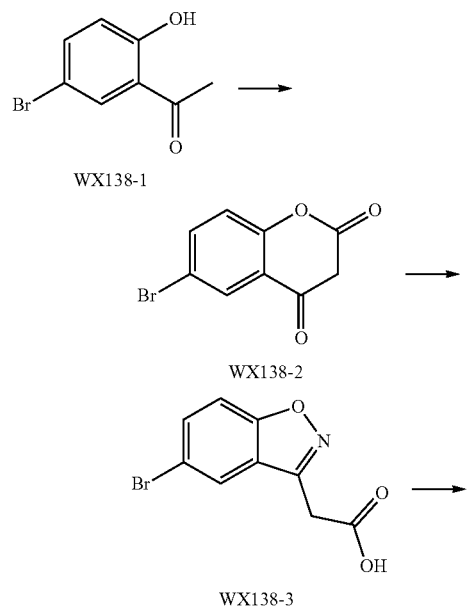

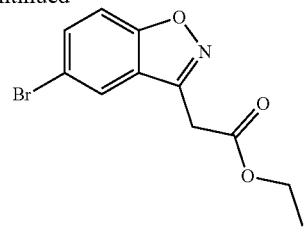

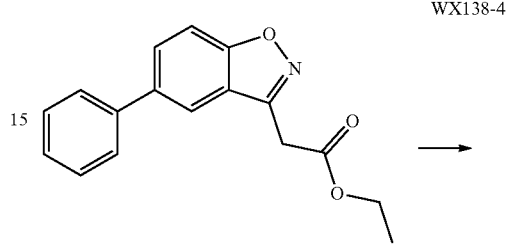

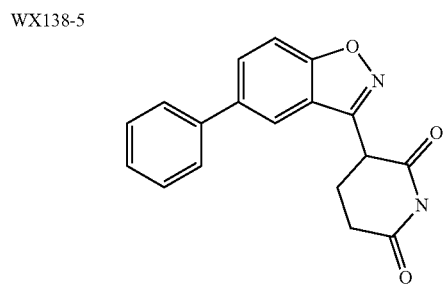

Step 1: Synthesis of Compound WX138-2

Compound WX138-1 (10 g, 46.50 mmol) was dissolved in dimethyl carbonate (53.50 g, 593.93 mmol, 50 mL) at room temperature under the protection of nitrogen, then sodium hydride (5.44 g, 136.01 mmol, purity: 60%) was added in batches, and the reaction mixture was heated to 100° C. and reacted with stirring for 10 hours. After the reaction was completed, the mixture was cooled to room temperature, and the reaction mixture was poured into water (200 mL), extracted with methyl tert-butyl ether (100 mL), and the organic phase was discarded. The aqueous phase was adjusted to pH=1 with 2 M dilute hydrochloric acid, and a large amount of white solid was precipitated, then the mixture was filtered, and the filter cake was collected. 100 mL of toluene was added to the filter cake, and the mixture was concentrated under reduced pressure to remove the solvent to obtain compound WX138-2.

Step 2: Synthesis of Compound WX138-3

Compound WX138-2 (9 g, 37.34 mmol) was dissolved in ethanol (180 mL) under the protection of nitrogen at room temperature, and sodium acetate (10.72 g, 130.68 mmol) and hydroxylamine hydrochloride (9.08 g, 130.68 mmol) were added, then the reaction mixture was heated to 80° C. and reacted with stirring for 7 hours. After the reaction was completed, the reaction mixture was concentrated under reduced pressure to remove the solvent, and the obtained residue was diluted with saturated sodium bicarbonate solution (300 mL), filtered, and the filtrate was collected, then the filtrate was adjusted to pH=3-4 with 2 M dilute hydrochloric acid, and white solid was precipitated, and the mixture was extracted with ethyl acetate (600 mL×3). The organic phases were combined, dried with anhydrous sodium sulfate, filtered, and the filtrate was concentrated under reduced pressure to remove the solvent to obtain compound WX138-3. $^1$H NMR (399 MHz, DMSO_$d_6$) δ: 12.53 (s, 1H), 8.13 (d, J=1.6 Hz, 1H), 7.78 (dd, J=2.0, 8.8 Hz, 1H), 7.73 (d, J=9.2 Hz, 1H), 4.12 (s, 2H).

Step 3: Synthesis of Compound WX138-4

Compound WX138-3 (4 g, 15.62 mmol) was dissolved in ethanol (50 mL) under the protection of nitrogen at room temperature, and sulfuric acid (469.39 mg, 4.69 mmol, 255.10 μL, purity: 98%) was added, then the reaction mixture was heated to 70° C. and reacted with stirring for 4 hours. After the reaction was completed, the reaction mixture was directly concentrated under reduced pressure to remove the solvent. The obtained residue was diluted with water (50 mL) and dichloromethane (30 mL), and the phases were separated, then the organic phases were collected, and the aqueous phase was extracted with dichloromethane (30 mL×2). The organic phases were combined, dried with anhydrous sodium sulfate, filtered, and the filtrate was concentrated under reduced pressure to remove the solvent, and the obtained residue was separated by column chromatography (eluent: petroleum ether/ethyl acetate=1/0-9/1, v/v) to obtain compound WX138-4. $^1$H NMR (399 MHz, CDCl$_3$) δ: 7.88 (d, J=2.0 Hz, 1H), 7.65 (dd, J=2.0, 8.8 Hz, 1H), 7.48 (d, J=8.8 Hz, 1H), 4.24 (q, J=7.2 Hz, 2H), 4.02 (s, 2H), 1.29 (t, J=7.2 Hz, 3H).

Step 4: Synthesis of Compound WX138-5

Compound WX138-4 (0.5 g, 1.76 mmol) was dissolved in N,N-dimethylformamide (10 mL) at room temperature under the protection of nitrogen, then potassium phosphate (373.57 mg, 1.76 mmol), [1,1-bis(triphenylphosphino)ferrocene]palladium dichloride dichloromethane (143.72 mg, 175.99 μmol) and phenylboronic acid (257.50 mg, 2.11 mmol) were added, and the reaction mixture was heated to 80° C. and reacted with stirring for 3 hours. After the reaction was completed, the mixture was cooled to room temperature, poured into water (50 mL), and extracted with dichloromethane (20 mL×3). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-9/1, v/v), to obtain compound WX138-5. $^1$H NMR (400 MHz, CDCl$_3$) δ: 7.87 (d, J=1.2 Hz, 1H), 7.81 (dd, J=1.6, 8.8 Hz, 1H), 7.65 (d, J=8.8 Hz, 1H), 7.60 (d, J=7.2 Hz, 2H), 7.48 (t, J=7.6 Hz, 2H), 7.39 (t, J=7.2 Hz, 1H), 4.24 (q, J=7.2 Hz, 2H), 4.09 (s, 2H), 1.28 (t, J=7.2 Hz, 3H).

Step 5: Synthesis of Compound WX138

Compound WX138-5 (150 mg, 533.23 μmol) was dissolved in tetrahydrofuran (15 mL) at 18° C. under the protection of nitrogen, then potassium tert-butoxide (59.83 mg, 533.23 μmol) and acrylamide (37.90 mg, 533.23 μmol) were added, and the reaction mixture was stirred at 18° C. for 2 hours. After the reaction was completed, water (30 mL) and ethyl acetate (30 mL) were added to the reaction system to dilute, and the phases were separated, then the organic phases were collected, and the aqueous phase was extracted with ethyl acetate (20 mL×3). The organic phases were combined, dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl), to obtain target compound WX138. MS-ESI m/z: 307.0 [M+H]$^+$. $^1$H NMR (399 MHz, DMSO_$d_6$) δ: 11.09 (s, 1H), 8.14 (d, J=1.6 Hz, 1H), 7.97 (dd, J=1.6, 8.8 Hz, 1H), 7.84 (d, J=8.8 Hz, 1H), 7.72 (d, J=7.2 Hz, 2H), 7.50 (t, J=7.6 Hz, 2H), 7.40 (t, J=7.4 Hz, 1H), 4.66 (dd, J=5.0, 11.4 Hz, 1H), 2.85-2.73 (m, 1H), 2.72-2.59 (m, 2H), 2.36-2.17 (m, 1H).

Referring to the synthesis method in Embodiment 138, each embodiment in Table 21 is synthesized, and the LCMS and HNMR data are shown in Table 22.

TABLE 21

| Embodiments | Fragment 1 | Fragment 2 | Structure | Compound |
|---|---|---|---|---|
| 139 | 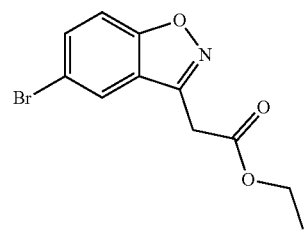 [SMILES: CCOC(=O)Cc1noc2ccc(Br)cc12]<br>WX138-4 | 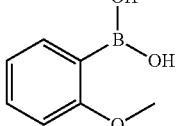 | 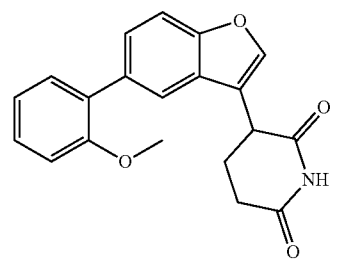 [SMILES: COc1ccccc1-c1ccc2occ(C3CCC(=O)NC3=O)c2c1] | WX139 |

TABLE 22

| Embodiments | Compound | HNMR | LCMS |
|---|---|---|---|
| 139 | WX139 | $^1$H NMR (400 MHZ, DMSO_$d_6$) δ: 11.09 (s, 1H), 7.89 (s, 1H), 7.76 (d, J = 0.8 Hz, 2H), 7.38 (td, J = 1.6, 8.4 Hz, 1H), 7.33 (dd, J = 1.6, 7.6 Hz, 1H), 7.14 (d, J = 8.0 Hz, 1H), 7.06 (t, J = 7.4 Hz, 1H), 4.63 (dd, J = 5.0, 11.8 Hz, 1H), 3.77 (s, 3H), 2.82-2.72 (m, 1H), 2.64-2.54 (m, 2H), 2.26-2.15 (m, 1H). | MS-ESI m/z: 337.1 [M + H]$^+$. |

Embodiment 140: WX140

Synthetic Route:

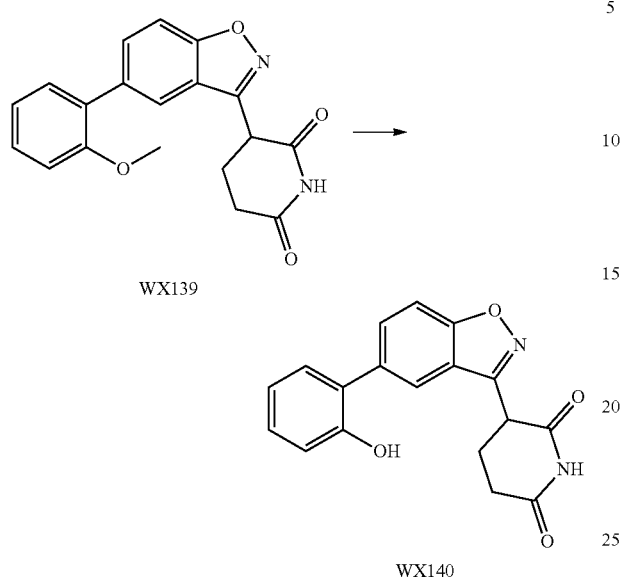

Compound WX139 (200 mg, 594.64 μmol) was dissolved in dichloromethane (20 mL) at room temperature under the protection of nitrogen, and the mixture was cooled to −30° C., and boron tribromide (2.60 g, 10.38 mmol) was added dropwise, then the reaction mixture was naturally restored to 15° C. and reacted with stirring for 2 hours. After the reaction was completed, the reaction solution was slowly poured into ice water (100 mL), diluted with N,N-dimethylformamide (3 mL) and dichloromethane (20 mL), and the phases were separated, then the organic phases were collected, and the aqueous phase was extracted with dichloromethane (20 mL×3). The organic phases were combined, dried with anhydrous sodium sulfate, filtered, and the filtrate was concentrated under reduced pressure to remove the solvent, and the obtained residue was separated by preparative HPLC (mobile phase: acetonitrile/water; acidic system: 0.05% HCl) to obtain target compound WX140. MS-ESI m/z: 323.0 [M+H]$^+$. $^1$H NMR (400 MHz, DMSO_d$_6$) δ: 11.09 (s, 1H), 9.63 (s, 1H), 7.92 (d, J=1.2 Hz, 1H), 7.85 (dd, J=1.2, 8.8 Hz, 1H), 7.75 (d, J=8.8 Hz, 1H), 7.29 (dd, J=1.2, 7.6 Hz, 1H), 7.20 (td, J=1.4, 7.8 Hz, 1H), 6.96 (d, J=7.6 Hz, 1H), 6.90 (t, J=7.4 Hz, 1H), 4.63 (dd, J=4.8, 11.6 Hz, 1H), 2.84-2.71 (m, 1H), 2.66-2.54 (m, 2H), 2.33-2.16 (m, 1H).

Embodiment 141: WX141

Synthetic Route:

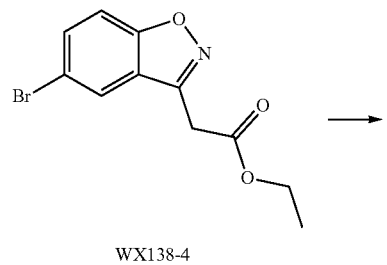

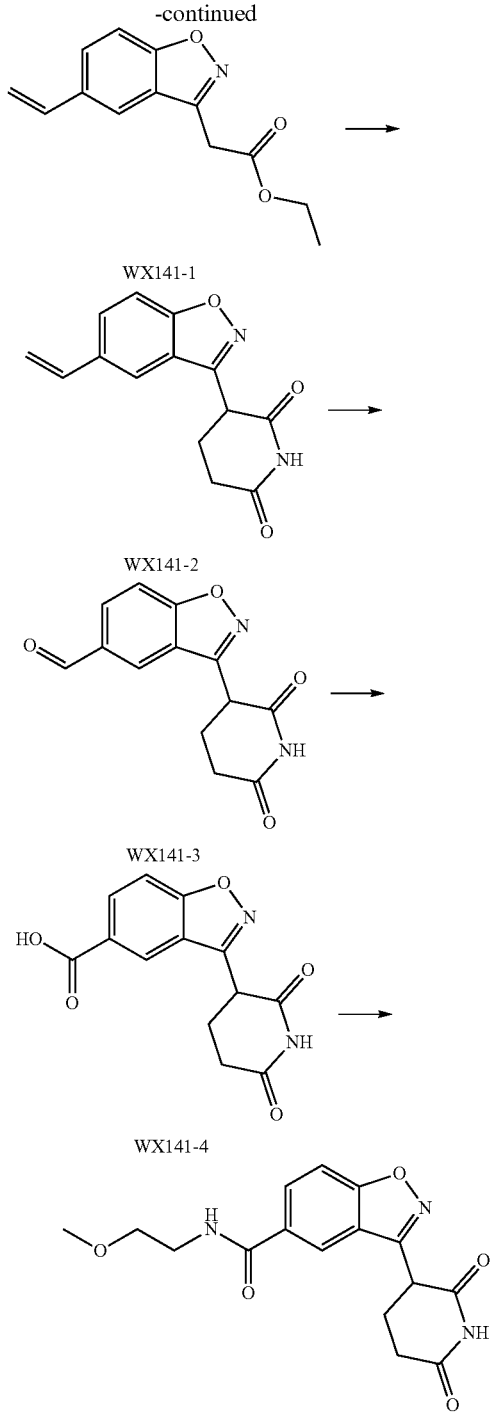

Step 1: Synthesis of Compound WX141-1

Compound WX138-4 (4.57 g, 16.09 mmol) was dissolved in N,N-dimethylformamide (60 mL) at 10° C. under the protection of nitrogen, then potassium phosphate (3.41 g, 16.09 mmol), [1,1-bis(triphenylphosphino)ferrocene]palladium dichloride dichloromethane (1.31 g, 1.61 mmol) and potassium vinyltrifluoroborate (2.80 g, 20.91 mmol) were added, and the reaction mixture was heated to 80° C. and reacted with stirring at 80° C. for 6 hours. After the reaction was completed, the mixture was cooled to room temperature, and the reaction mixture was diluted with water (100 mL), and extracted with ethyl acetate (50 mL×3). The organic phases were combined, washed with semi-saturated brine (50 mL×2), dried with anhydrous sodium sulfate, filtered, and the filtrate was concentrated under reduced pressure to remove the solvent. The obtained residue was separated by column chromatography (eluent: petroleum ether/ethyl acetate=1/0-9/1, v/v), to obtain compound WX141-1. $^1$H NMR (400 MHz, CDCl$_3$) δ: 7.73-7.65 (m, 2H), 7.56-7.51 (m, 1H), 6.82 (dd, J=10.8, 17.6 Hz, 1H), 5.77 (d, J=17.6 Hz, 1H), 5.31 (t, J=5.6 Hz, 1H), 4.23 (q, J=7.2 Hz, 2H), 4.04 (s, 2H), 1.28 (t, J=7.2 Hz, 3H).

Step 2: Synthesis of Compound WX141-2

Compound WX141-1 (2.5 g, 10.81 mmol) was dissolved in tetrahydrofuran (50 mL) under the protection of nitrogen at 10° C., then acrylamide (768.42 mg, 10.81 mmol) and potassium tert-butoxide (1.21 g, 10.81 mmol) were added, and the reaction mixture was stirred at 10° C. for 4 hours. After the reaction was completed, the reaction mixture was added with water (20 mL), and extracted with ethyl acetate (100 mL×5). The organic phases were combined, dried with anhydrous sodium sulfate, filtered, and the filtrate was concentrated under reduced pressure to remove the solvent, and the obtained residue was separated by column chromatography (eluent: petroleum ether/ethyl acetate=1/0-3/7, v/v) to obtain compound WX141-2. $^1$H NMR (400 MHz, DMSO_d$_6$) δ: 11.11 (s, 1H), 7.94 (s, 1H), 7.83 (dd, J=1.2, 8.8 Hz, 1H), 7.73 (d, J=8.4 Hz, 1H), 6.86 (dd, J=10.8, 17.6 Hz, 1H), 5.92 (d, J=17.6 Hz, 1H), 5.32 (d, J=10.8 Hz, 1H), 4.60 (dd, J=4.8, 11.6 Hz, 1H), 2.83-2.73 (m, 1H), 2.67-2.55 (m, 2H), 2.24-2.14 (m, 1H).

Step 3: Synthesis of Compound WX141-3

Compound WX141-2 (1.1 g, 4.29 mmol) was dissolved in dichloromethane (250 mL) at 10° C., and the mixture was cooled to −78° C., and ozone was introduced (time: 15 minutes; pressure: 15 psi), then the reaction system turned blue. After the reaction was completed, oxygen was continuously introduced until the reaction turned colorless, and feeding gas was stopped, and the reaction mixture was restored to 10° C., then the reaction mixture was concentrated under reduced pressure to remove the solvent, and compound WX141-3 was obtained.

Step 4: Synthesis of Compound WX141-4

Compound WX141-3 (1 g, 3.87 mmol) was dissolved in N,N-dimethylformamide (15 mL) at 10° C., then potassium peroxymonosulfate (2.38 g, 3.87 mmol) was added, and the reaction mixture was reacted with stirring at 10° C. for 12 hours. After the reaction was completed, the reaction mixture was filtered, and the filtrate was collected to obtain a N,N-dimethylformamide (15 mL) solution of compound WX141-4.

Step 5: Synthesis of Compound WX141

O-(7-azabenzotriazol-1-yl)-N,N,N',N'-tetramethyluronium hexafluorophosphate (735.75 mg, 1.94 mmol) and triethylamine (261.07 mg, 2.58 mmol, 359.11 µL) were added to a N,N-dimethylformamide solution of compound WX141-4 (0.258 M, 5 mL) under the protection of nitrogen at 0° C., then the reaction mixture was reacted with stirring at 0° C. for 10 minutes, and 2-methoxyethylamine (116.27 mg, 1.55 mmol, 134.57 µL) was added, and the reaction mixture was restored to 10° C. and reacted with stirring at 10° C. for 12 hours. After the reaction was completed, the reaction solution was added with water (50 mL), and extracted with ethyl acetate (30 mL×3). The organic phases were combined, dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl), to obtain target compound WX141. MS-ESI m/z: 332.1 [M+H]$^+$. $^1$H NMR (399 MHz, DMSO_d$_6$) δ: 11.16 (s, 1H), 8.68 (s, 1H), 8.35 (d, J=1.2 Hz, 1H), 8.16 (dd, J=2.0, 8.8 Hz, 1H), 7.83 (d, J=8.8 Hz, 1H), 4.66 (dd, J=5.0, 12.2 Hz, 1H), 3.54-3.42 (m, 4H), 3.28 (s, 3H), 2.89-2.75 (m, 1H), 2.70-2.53 (m, 2H), 2.37-2.15 (m, 1H).

Referring to the synthesis method in Embodiment 141 of step 5, each embodiment in Table 23 is synthesized, and the LCMS and HNMR data are shown in Table 23.

TABLE 23

| Embodiments | Fragment 1 | Fragment 2 | Structure | Compound |
|---|---|---|---|---|
| 142 | | | 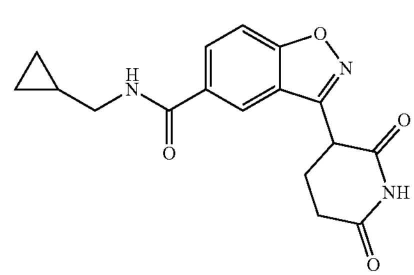 [SMILES: O=C1CCC(c2noc3ccc(C(=O)NCC4CC4)cc23)C(=O)N1] | WX142 |

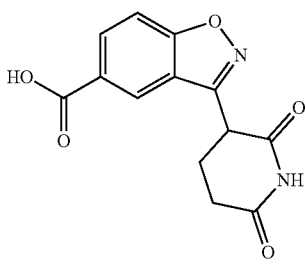 [SMILES: O=C1CCC(c2noc3ccc(C(=O)O)cc23)C(=O)N1]

TABLE 23-continued

| Embodiments | Fragment 1 | Fragment 2 | Structure | Compound |
|---|---|---|---|---|
| 143 | WX141-4 | | 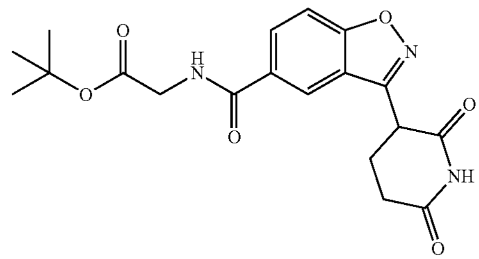 [SMILES: CC(C)(C)OC(=O)CNC(=O)c1ccc2onc(C3CCC(=O)NC3=O)c2c1] | WX143 |
| 144 | WX141-4 | | 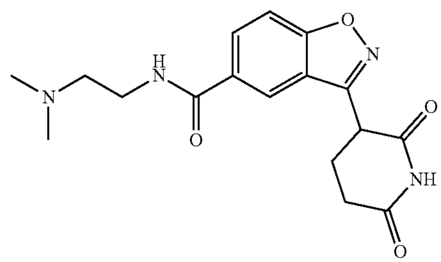 [SMILES: CN(C)CCNC(=O)c1ccc2onc(C3CCC(=O)NC3=O)c2c1] | WX144 |
| 145 | WX141-4 | | 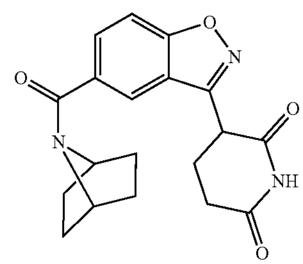 [SMILES: O=C1CCC(c2noc3ccc(C(=O)N4C5CCC4CC5)cc23)C(=O)N1] | WX145 |

TABLE 24

| Embodiments | Compound | HNMR | LCMS |
|---|---|---|---|
| 142 | WX142 | $^1$H NMR (400 MHZ, DMSO_$d_6$) δ: 11.18 (s, 1H), 8.72 (t, J = 5.6 Hz, 1H), 8.34 (d, J = 0.8 Hz, 1H), 8.17 (dd, J = 1.6, 8.8 Hz, 1H), 7.84 (d, J = 8.8 Hz, 1H), 4.67 (dd, J = 5.0, 12.2 Hz, 1H), 3.19 (t, J = 6.2 Hz, 2H), 2.89-2.75 (m, 1H), 2.71-2.58 (m, 2H), 2.29-2.16 (m, 1H), 1.15-0.99 (m, 1H), 0.54-0.39 (m, 2H), 0.31-0.18 (m, 2H). | MS-ESI m/z: 328.1 [M + H]$^+$. |
| 143 | WX143 | $^1$H NMR (399 MHz, DMSO_$d_6$) δ: 9.00 (t, J = 6.0 Hz, 1H), 8.38 (d, J = 1.2 Hz, 1H), 8.17 (dd, J = 1.4, 9.0 Hz, 1H), 7.86 (d, J = 8.8 Hz, 1H), 4.67 (dd, J = 4.8, 12.0 Hz, 1H), 3.95 (d, J = 6.0 Hz, 2H), 2.88-2.76 (m, 1H), 2.69-2.53 (m, 2H), 2.30-2.18 (m, 1H), 1.43 (s, 9H). | MS-ESI m/z: 332.0 [M + H]$^+$. |
| 144 | WX144 | $^1$H NMR (400 MHZ, DMSO_$d_6$) δ: 11.15 (s, 1H), 10.06 (br s, 1H), 9.03 (br t, J = 5.2 Hz, 1H), 8.47 (s, 1H), 8.23 (dd, J = 1.4, 9.0 Hz, 1H), 7.88 (d, J = 8.8 Hz, 1H), 4.67 (dd, J = 4.8, 12.0 Hz, 1H), 3.67 (q, J = 5.6 Hz, 2H), 3.29 (q, J = 5.6 Hz, 2H), 2.84 (s, 3H), 2.83 (s, 3H), 2.82-2.75 (m, 1H), 2.70-2.61 (m, 2H), 2.29-2.17 (m, 1H). | MS-ESI m/z: 345.1 [M + H]$^+$. |
| 145 | WX145 | $^1$H NMR (400 MHZ, MeOD_$d_4$) δ: 8.04 (s, 1H), 7.83 (d, J = 7.6 Hz, 1H), 7.73 (d, J = 8.8 Hz, 1H), 4.69 (s, 1H), 4.64-4.50 (m, 1H), 4.18 (s, 1H), 2.88-2.64 (m, 2H), 2.73-2.54 (m, 2H), 2.52-2.37 (m, 1H), 1.90 (s, 4H), 1.59 (s, 4H). | MS-ESI m/z: 354.1 [M + H]$^+$. |

Embodiment 146: WX146

Synthetic Route:

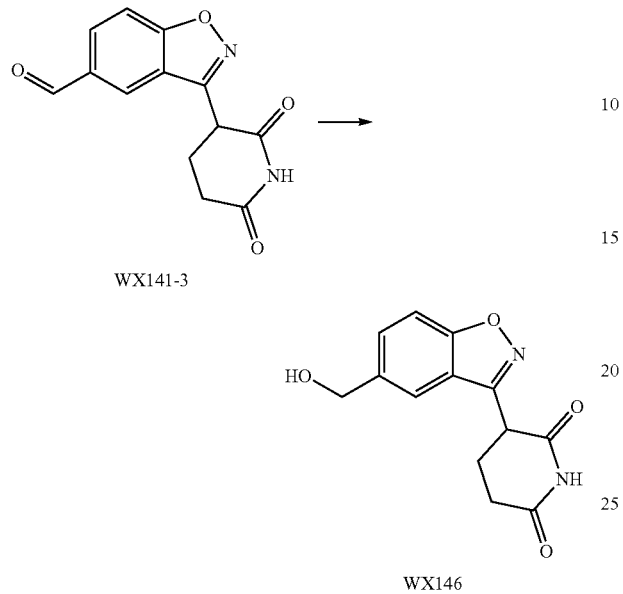

Compound WX141-3 (300 mg, 1.16 mmol) was dissolved in tetrahydrofuran (10 mL) under the protection of nitrogen at 0° C., then sodium borohydride (43.95 mg, 1.16 mmol) was added, and the reaction mixture was reacted with stirring at 0° C. for 2 hours, then restored to 15° C. and reacted with stirring for 12 hours. After the reaction was completed, the reaction solution was poured into 0.5 M dilute hydrochloric acid (50 mL), and extracted with ethyl acetate (50×3). The organic phases were combined, dried with anhydrous sodium sulfate, filtered, and the filtrate was concentrated under reduced pressure to obtain a residue. The obtained residue was separated by preparative HPLC (mobile phase: acetonitrile/water; acidic system: 0.05% HCl) to obtain target compound WX146. MS-ESI m/z: 261.0 [M+H]$^+$. $^1$H NMR (400 MHz, DMSO_$d_6$) δ: 11.12 (s, 1H), 7.76 (s, 1H), 7.71 (d, J=8.8 Hz, 1H), 7.60 (dd, J=1.2, 8.4 Hz, 1H), 4.65-4.57 (m, 3H), 2.84-2.73 (m, 1H), 2.69-2.53 (m, 2H), 2.26-2.15 (m, 1H).

Embodiment 147: WX147

Synthetic Route:

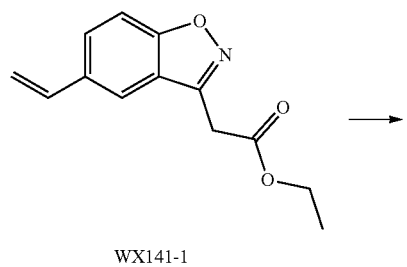

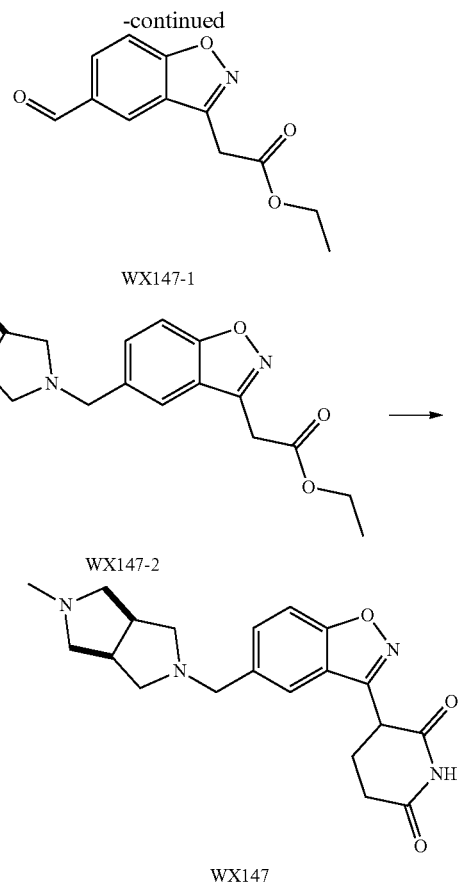

Step 1: Synthesis of Compound WX147-1

Compound WX141-1 (4 g, 17.30 mmol) was dissolved in dichloromethane (40 mL) at room temperature, and the mixture was cooled to −75° C., and ozone was introduced and the mixture was reacted for 0.5 hours, and the reaction turned blue. After the reaction was completed, air was introduced to the reaction solution for 0.5 hours until the reaction solution turned colorless, then the reaction solution was restored to room temperature, and concentrated under reduced pressure to remove the solvent. The obtained residue was separated by column chromatography (eluent: petroleum ether/ethyl acetate=1/0-7/1, v/v), to obtain a crude product of compound WX147-1.

Step 2: Synthesis of Compound WX147-2

The crude product of compound WX147-1 (400 mg, 1.72 mmol) from the previous step and cis-2-methyl-octahydro-pyrrolo[3,4-c]pyrrole (216.45 mg, 1.72 mmol) were dissolved in 1,2-dichlorethane (16 mL) at room temperature under the protection of nitrogen protection, then acetic acid (103.00 mg, 1.72 mmol) and sodium borohydride acetate (545.26 mg, 2.57 mmol) were added, and the reaction mixture was reacted with stirring at 15° C. for 16 hours. After the reaction was completed, water (20 mL) was added to the reaction solution, and the pH of the mixture was adjusted to 7 with saturated sodium bicarbonate aqueous solution, then 2-methyltetrahydrofuran (30 mL) was added, and the phases were separated, then the organic phase was collected, and the aqueous phase was extracted with 2-methyltetrahydrofuran (30 mL×6); the organic phases were combined, washed with saturated brine (30 mL×2), dried with anhydrous sodium sulfate, filtered, and the filtrate was concentrated under reduced pressure to remove the solvent. The obtained residue was separated by column chromatography (eluent: petroleum ether/ethyl acetate=1/0-9/1, v/v), to obtain compound WX147-2.

Step 3: Synthesis of Compound WX147

Compound WX147-2 (300.00 mg, 873.57 µmol) was dissolved in tetrahydrofuran (10 mL) at 20° C., then a tetrahydrofuran solution of acrylamide (58.99 mg, 829.89 µmol) and potassium tert-butoxide (1 M, 829.89 µL) was added, and the reaction mixture was stirred at 20° C. for 12 hours. After the reaction was completed, the reaction solution was concentrated under reduced pressure to remove the solvent. The obtained residue was first separated by preparative HPLC (mobile phase: acetonitrile/water; neutral system: 10 mM NH$_4$HCO$_3$), and then separated by preparative HPLC (mobile phase: acetonitrile/water; acidic system: 0.05% HCl) to obtain target compound WX147. MS-ESI m/z: 369.2 [M+H]$^+$. $^1$H NMR (400 MHz, MeOD_d$_4$) δ: 8.31-8.01 (m, 1H), 7.98-7.68 (m, 2H), 4.75-4.46 (m, 3H), 3.89-3.70 (m, 3H), 3.69-3.50 (m, 3H), 3.48-3.35 (m, 3H), 2.97 (s, 3H), 2.90-2.76 (m, 2H), 2.75-2.55 (m, 2H), 2.45-2.28 (m, 1H).

Embodiment 148: WX148

Synthetic Route:

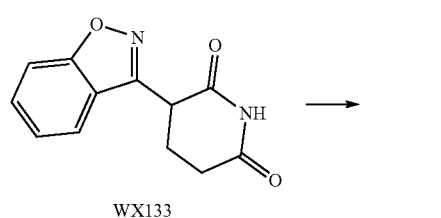

WX133

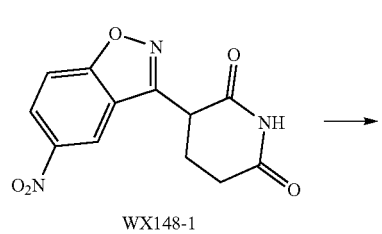

WX148-1

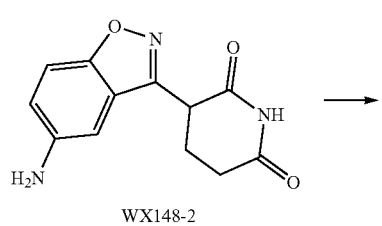

WX148-2

-continued

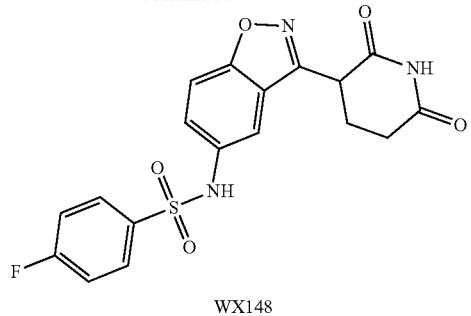

WX148

Step 1: Synthesis of Compound WX148-1

Compound WX133 (1 g, 4.34 mmol) was dissolved in sulfuric acid (5 mL, purity: 98%) at 0° C., then potassium nitrate (439.15 mg, 4.34 mmol) was added, and the reaction mixture was stirred at 0° C. for 1 hour. After the reaction was completed, the reaction mixture was poured into ice water (80 mL), and extracted with 2-methyltetrahydrofuran (60 mL×3). The organic phases were combined, successively washed with water (80 mL×3) and saturated brine (80 mL×3), dried with anhydrous sodium sulfate, filtered, and the filtrate was concentrated under reduced pressure to remove the solvent to obtain compound WX148-1. $^1$H NMR (400 MHz, DMSO_d$_6$) δ: 11.17 (s, 1H), 8.97 (s, 1H), 8.52 (dd, J=2.8, 6.4 Hz, 1H), 8.03 (d, J=9.2 Hz, 1H), 4.79 (dd, J=4.6, 12.2 Hz, 1H), 2.80-2.70 (m, 1H), 2.69-2.51 (m, 2H), 2.28-2.10 (m, 1H).

Step 2: Synthesis of Compound WX148-2

Compound WX148-1 (0.9 g, 3.27 mmol) was dissolved in ethanol (18 mL) at 20° C., then tin chloride dihydrate (5.17 g, 22.89 mmol) was added, and the reaction mixture was stirred at 20° C. for 12 hours. After reaction was completed, the reaction mixture was concentrated under reduced pressure to remove the solvent, and the obtained residue was separated by preparative HPLC (mobile phase: acetonitrile/water; acidic system: 0.05% HCl) to obtain the hydrochloride of compound WX148-2. MS-ESI m/z: 246.1 [M+H]$^+$.

Step 3: Synthesis of Compound WX148

Compound WX148-2 (0.04 g, 142.00 µmol, hydrochloride) and p-fluorobenzenesulfonyl chloride (27.63 mg, 142.00 µmol) were dissolved in tetrahydrofuran (1 mL) at 20° C., then triethylamine (35.92 mg, 354.99 µmol, 49.41 µL) was added, and the reaction mixture was reacted with stirring at 20° C. for 12 hours. After the reaction was completed, the reaction mixture was poured into water (20 mL), and extracted with 2-methyltetrahydrofuran (20 mL×3). The organic phases were combined, washed with saturated brine (20 mL×3), dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl) to obtain target compound WX148. MS-ESI m/z: 404.0 [M+H]$^+$. $^1$H NMR (400 MHz, MeOD_d$_4$) δ: 7.76 (dd, J=5.2, 8.8 Hz, 2H), 7.50-7.53 (m, 2H), 7.30-7.28 (m, 1H), 7.20 (t, J=8.6 Hz, 2H), 4.47 (dd, J=5.2, 10.8 Hz, 1H), 2.81-2.75 (m, 2H), 2.52-2.43 (m, 1H), 2.40-2.30 (m, 1H).

Embodiment 149: WX149

Synthetic Route:

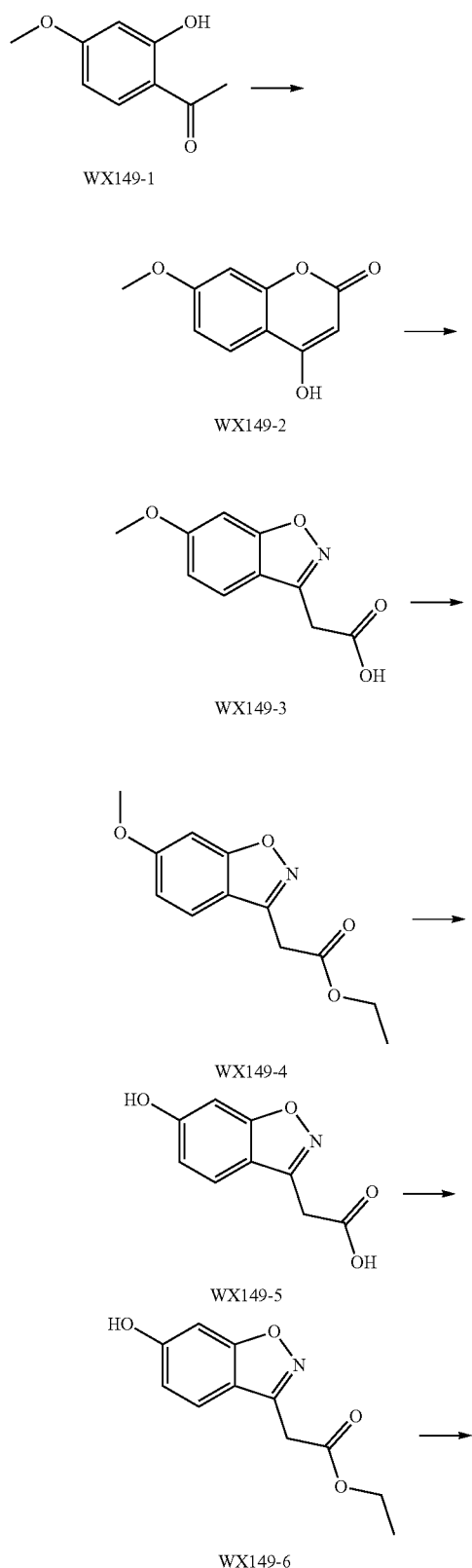

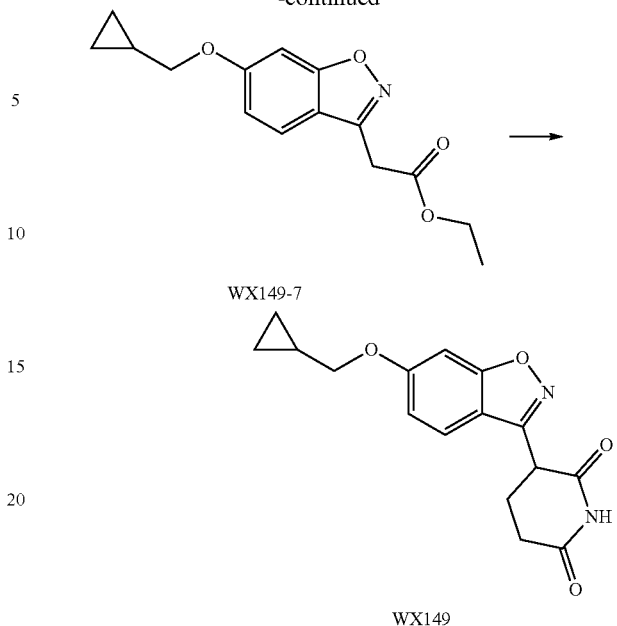

Step 1: Synthesis of Compound WX149-2

Compound WX149-1 (20 g, 120.36 mmol) was dissolved in toluene (100 mL) and diethyl carbonate (97.50 g, 825.35 mmol, 100 mL) at room temperature under the protection of nitrogen, and the mixture was cooled to 10 to 20° C., and sodium hydride (14.44 g, 361.07 mmol, purity: 60%) was added in batches, then the reaction mixture was heated to 120° C. and reacted with stirring for 1 hour. After the reaction was completed, the reaction system was added into ice water (500 mL) in batches, extracted with ethyl acetate (100 mL×3), and the organic phase was discarded, then the pH of the aqueous phase was adjusted to 3-4 with 1 M dilute hydrochloric acid, and light yellow solid was precipitated; and the mixture was filtered, and the filter cake was collected, concentrated under reduced pressure to remove the solvent to obtain compound WX149-2. MS-ESI m/z: 193.1 [M+H]$^+$.

Step 2: Synthesis of Compound WX149-3

Compound WX149-2 (5 g, 26.02 mmol) was dissolved in ethanol (100 mL) under the protection of nitrogen at room temperature, then hydroxylamine hydrochloride (6.33 g, 91.07 mmol) and sodium acetate (7.47 g, 91.07 mmol) were added, and the reaction mixture was heated to 80° C. and reacted with stirring for 6 hours. After the reaction was completed, the reaction mixture was directly concentrated under reduced pressure to remove the solvent. The obtained residue was diluted with water (300 mL), and the pH of the mixture was adjusted to 3-4 with 2 M dilute hydrochloric acid; white solid was precipitated, and the mixture was extracted with 2-methyltetrahydrofuran (100 mL×3). The organic phases were combined, dried with anhydrous sodium sulfate, filtered, and the filtrate was concentrated under reduced pressure to remove the solvent to obtain compound WX149-3. MS-ESI m/z: 208.0 [M+H]$^+$.

Step 3: Synthesis of Compound WX149-4

Compound WX149-3 (5 g, 24.13 mmol) was dissolved in ethanol (50 mL) at room temperature under the protection of nitrogen, and concentrated sulfuric acid (852.77 mg, 8.52 mmol, 463.46 μL, purity: 98%) was added, then the reaction mixture was heated to 70° C. and reacted with stirring for 3 hours. After the reaction was completed, the reaction mixture was concentrated under reduced pressure to remove most of the solvent, and water (50 mL) and dichloromethane (50 mL) were added to dilute; and the phases were separated, then the organic phases were collected, and the aqueous phase was extracted with dichloromethane (20 mL×2). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-9/1, v/v), to obtain compound WX149-4. MS-ESI m/z: 236.2 [M+H]$^+$. $^1$H NMR (399 MHz, CDCl$_3$) δ: 7.55 (d, J=8.4 Hz, 1H), 7.00 (d, J=2.0 Hz, 1H), 6.93 (dd, J=2.4, 8.8 Hz, 1H), 4.21 (q, J=7.2 Hz, 2H), 3.98 (s, 2H), 3.89 (s, 3H), 1.26 (t, J=7.2 Hz, 3H).

Step 4: Synthesis of Compound WX149-5

Compound WX149-4 (3.8 g, 16.15 mmol) was dissolved in dichloromethane (50 mL) under the protection of nitrogen at room temperature, and the mixture was cooled to −30° C.; boron tribromide (18.20 g, 72.65 mmol, 7 mL) was added, and the reaction mixture was naturally restored to 15° C. and reacted with stirring at 15° C. for 12 hours. After the reaction was completed, the reaction mixture was poured into ice water (100 mL), and extracted with dichloromethane (30 mL×3). The organic phases were combined, dried with anhydrous sodium sulfate, filtered, and the filtrate was concentrated under reduced pressure to remove the solvent to obtain compound WX149-5. MS-ESI m/z: 194.1 [M+H]$^+$.

Step 5: Synthesis of Compound WX149-6

Compound WX149-5 (3.1 g, 16.05 mmol) was dissolved in ethanol (40 mL) at room temperature under the protection of nitrogen, then sulfuric acid (920.00 mg, 9.19 mmol, 0.5 mL, purity: 98%) was added, and the reaction mixture was heated to 70° C. and reacted with stirring for 5 hours. After the reaction was completed, the mixture was cooled to room temperature, concentrated under reduced pressure to remove most of the solvent, diluted with water (50 mL), and extracted with ethyl acetate (30 mL×3). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-5/1, v/v), to obtain compound WX149-6. MS-ESI m/z: 222.2 [M+H]$^+$. $^1$H NMR (399 MHz, CDCl$_3$) δ: 7.50 (d, J=8.8 Hz, 1H), 6.98 (s, 1H), 6.94 (d, J=2.0 Hz, 1H), 6.85 (dd, J=2.0, 8.8 Hz, 1H), 4.23 (q, J=7.0 Hz, 2H), 3.99 (s, 2H), 1.28 (t, J=7.2 Hz, 3H).

Step 6: Synthesis of Compound WX149-7

Compound WX149-6 (400 mg, 1.81 mmol) was dissolved in N,N-dimethylformamide (10 mL), then potassium carbonate (999.64 mg, 7.24 mmol), potassium iodide (60.09 mg, 362.00 μmol) and bromomethylcyclopropane (300 mg, 2.22 mmol, 212.77 μL) were added, and the reaction mixture was reacted with stirring at 10° C. for 4 hours. After the reaction was completed, the reaction mixture was added with water (50 mL), and extracted with ethyl acetate (30 mL×3). The organic phases were combined, washed with semi-saturated brine (20 mL×2), dried with anhydrous sodium sulfate, filtered, and the filtrate was concentrated under reduced pressure to remove the solvent. The obtained residue was separated by column chromatography (eluent: petroleum ether/ethyl acetate=1/0-9/1, v/v), to obtain compound WX149-7. 276.0 [M+H]$^+$. $^1$H NMR (400 MHz, CDCl$_3$) δ: 7.55 (d, J=9.2 Hz, 1H), 6.97 (s, 1H), 6.95 (dd, J=2.0, 6.8 Hz, 1H), 4.21 (q, J=7.2 Hz, 2H), 3.98 (s, 2H), 3.88 (d, J=7.2 Hz, 2H), 1.38-1.30 (m, 1H), 1.26 (t, J=7.0 Hz, 3H), 0.73-0.65 (m, 2H), 0.44-0.36 (m, 2H).

Step 7: Synthesis of Compound WX149

Compound WX149-7 (250 mg, 908.10 μmol) was dissolved in tetrahydrofuran (10 mL) at 0° C., then acrylamide (64.55 mg, 908.10 μmol) and potassium tert-butoxide (101.90 mg, 908.10 μmol) were added, and the reaction mixture was stirred at 10° C. for 2 hours. After the reaction was completed, the reaction mixture was added with water (50 mL), and extracted with ethyl acetate (30 mL×3). The organic phases were combined, dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl) to obtain target compound WX149. MS-ESI m/z: 301.1 [M+H]$^+$. $^1$H NMR (400 MHz, DMSO_d$_6$) δ: 11.07 (s, 1H), 7.68 (d, J=8.8 Hz, 1H), 7.26 (d, J=2.0 Hz, 1H), 6.98 (dd, J=2.0, 8.8 Hz, 1H), 4.51 (dd, J=5.0, 11.8 Hz, 1H), 3.93 (d, J=7.2 Hz, 2H), 2.83-2.59 (m, 3H), 2.22- 2.13 (m, 1H), 1.34-1.20 (m, 1H), 0.65-0.51 (m, 2H), 0.39-0.28 (m, 2H).

Referring to the synthesis methods in Embodiment 149 of steps 6 and 7, each embodiment in Table 25 is synthesized, and the LCMS and HNMR data are shown in Table 26.

TABLE 25

| Embodiments | Fragment 1 | Fragment 2 | Structure | Compound |
|---|---|---|---|---|
| 150 | HO-[benzisoxazole]-WX149-6 | \O\~\Br | \O\~\O-[benzisoxazole]-[piperidine-2,6-dione] | WX150 |

TABLE 25-continued

| Embodiments | Fragment 1 | Fragment 2 | Structure | Compound |
|---|---|---|---|---|
| 151 | 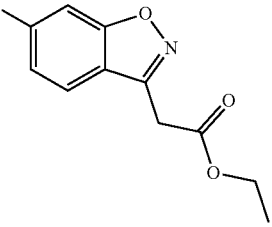 WX149-6 | 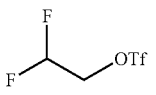 | 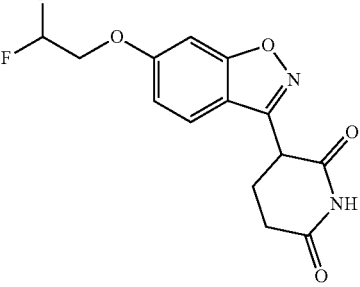 | WX151 |

TABLE 26

| Embodiments | Compound | HNMR | LCMS |
|---|---|---|---|
| 150 | WX150 | $^1$H NMR (400 MHz, DMSO_$d_6$) δ: 11.08 (s, 1H), 7.70 (d, J = 8.8 Hz, 1H), 7.32 (d, J = 2.0 Hz, 1H), 6.99 (dd, J = 2.0, 8.8 Hz, 1H), 4.52 (dd, J = 5.2, 11.6 Hz, 1H), 4.21 (t, J = 4.4 Hz, 2H), 3.70 (t, J = 4.4 Hz, 2H), 3.32 (s, 3H), 2.81-2.70 (m, 1H), 2.68-2.56 (m, 1H), 2.43-2.31 (m, 1H), 2.23-2.13 (m, 1H) | MS-ESI m/z: 305.1 [M + H]$^+$. |
| 151 | WX151 | $^1$H NMR (400 MHz, DMSO_$d_6$) δ: 11.09 (s, 1H), 7.75 (d, J = 8.8 Hz, 1H), 7.44 (d, J = 2.0 Hz, 1H), 7.06 (dd, J = 2.2, 8.6 Hz, 1H), 6.62-6.28 (m, 1H), 4.54 (dd, J = 5.0, 11.8 Hz, 1H), 4.46 (dt, J = 3.2, 14.4 Hz, 2H), 2.83-2.70 (m, 1H), 2.69-2.57 (m, 2H), 2.23-2.14 (m, 1H). | MS-ESI m/z: 311.1 [M + H]$^+$. |

Embodiment 152: WX152

Synthetic Route:

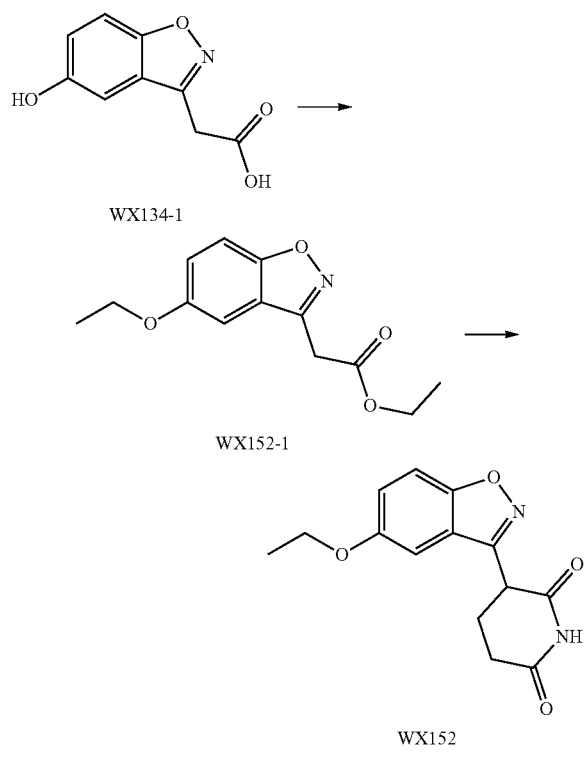

Step 1: Synthesis of Compound WX152-1

Compound WX134-1 (1.1 g, 5.69 mmol) was dissolved in N,N-dimethylformamide (15 mL) at 20° C., then potassium carbonate (1.57 g, 11.39 mmol) and iodoethane (1.78 g, 11.39 mmol, 910.98 μL) were added, and the reaction mixture was raised to 80° C. and reacted with stirring for 15 hours. After the reaction was completed, the mixture was cooled to room temperature, and the reaction mixture was added with water (60 mL), and extracted with ethyl acetate (50 mL×3). The organic phases were combined, washed with saturated brine (100 mL×2), dried with anhydrous sodium sulfate, filtered, and the filtrate was concentrated under reduced pressure to remove the solvent, and the obtained residue was separated by column chromatography (eluent: petroleum ether/ethyl acetate=20/1-10/1, v/v) to obtain compound WX152-1. $^1$H NMR (400 MHz, CDCl$_3$) δ: 7.47 (d, J=9.2 Hz, 1H), 7.18 (dd, J=2.4, 9.2 Hz, 1H), 7.04 (d, J=2.4 Hz, 1H), 4.22 (q, J=7.1 Hz, 2H), 4.07 (q, J=6.9 Hz, 2H), 4.00 (s, 2H), 1.45 (t, J=7.0 Hz, 3H), 1.27 (t, J=7.2 Hz, 3H).

Step 2: Synthesis of Compound WX152

Compound WX152-1 (435 mg, 1.75 mmol) was added to N,N-dimethylformamide (5 mL) at 0° C. under the protection of nitrogen, then potassium tert-butoxide (195.82 mg, 1.75 mmol) was added, and the reaction mixture was reacted with stirring at 0° C. for 0.5 hours; acrylamide (124.04 mg, 1.75 mmol) was added to the above reaction solution, and the reaction mixture was continued to react with stirring at 0° C. for 1 hour under the protection of nitrogen. After the reaction was completed, the reaction solution was raised to room temperature, and water (50 mL) was added, and the mixture was extracted with ethyl acetate (50 mL×3). The organic phases were combined, washed with saturated brine (80 mL×2), dried with anhydrous sodium sulfate, filtered, and the filtrate was concentrated under reduced pressure to remove the solvent. The obtained residue was diluted with ethyl acetate (15 mL), and the mixture was stirred at room temperature for 0.5 hours, filtered, then the filter cake was rinsed with ethyl acetate (5 mL), and the filter cake was collected to obtain target compound WX152. MS-ESI m/z: 274.9 [M+H]⁺. NMR (400 MHz, DMSO_d₆) δ: 11.08 (s, 1H), 7.65 (d, J=9.2 Hz, 1H), 7.31 (d, J=2.0 Hz, 1H), 7.25 (dd, J=2.6, 9.0 Hz, 1H), 4.55 (dd, J=5.2, 11.6 Hz, 1H), 4.12-4.00 (m, 2H), 2.82-2.70 (m, 1H), 2.64-2.53 (m, 2H), 2.21-2.12 (m, 1H), 1.35 (t, J=7.0 Hz, 3H).

Embodiment 153: WX153

Synthetic Route:

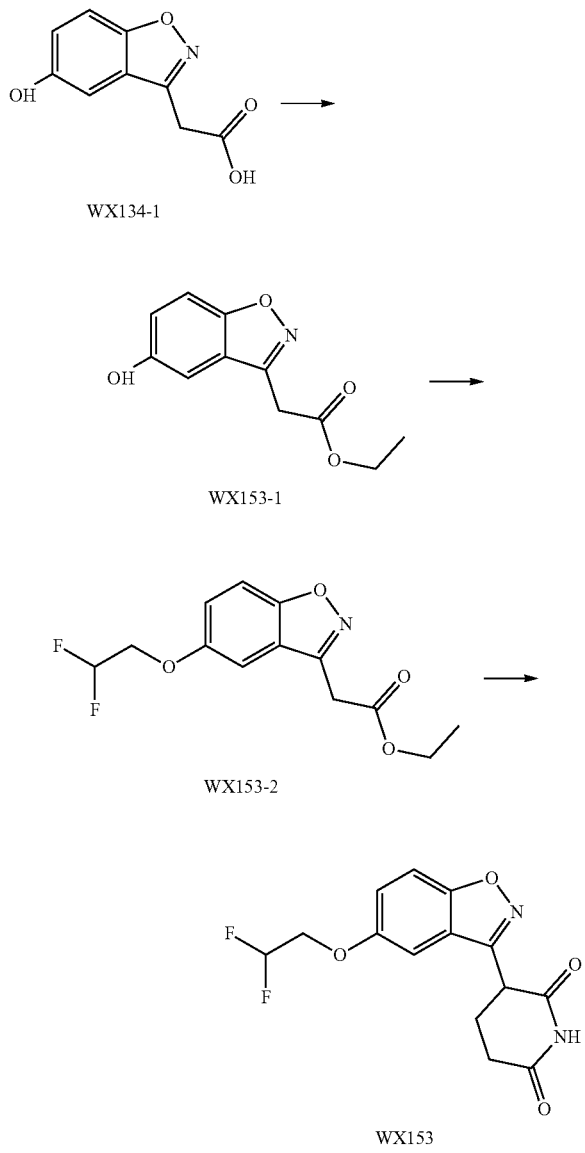

Step 1: Synthesis of Compound WX153-1

Compound WX134-1 (5.6 g, 28.99 mmol) was dissolved in ethanol (70 mL) at 20° C., and sulfuric acid (11.04 g, 110.31 mmol, 6 mL, purity:98%) was added, then the reaction solution was heated to 80° C. and reacted with stirring for 12 hours. After the reaction was completed, the reaction solution was concentrated under reduced pressure to remove the solvent, and water (50 mL) and ethyl acetate (50 mL) were added for phase separation; the organic phase was collected, dried with anhydrous sodium sulfate, filtered, and the filtrate was concentrated under reduced pressure to remove the solvent. The obtained residue was separated by column chromatography (eluent: petroleum ether/ethyl acetate=10/1-3/1, v/v) to obtain compound WX153-1. MS-ESI m/z: 222.1 [M+H]⁺.

Step 2: Synthesis of Compound WX153-2

Compound WX153-1 (0.5 g, 2.26 mmol) was dissolved in N,N-dimethylformamide (10 mL) at room temperature, then potassium carbonate (1.25 g, 9.04 mmol) and 2,2-difluoroethyl trifluoromethanesulfonate (1.45 g, 6.78 mmol) were added, and the reaction mixture was reacted with stirring at room temperature for 12 hours. After the reaction was completed, the reaction solution was poured into semi-saturated brine (25 mL) and extracted with ethyl acetate (30 mL). The organic phase was sequentially washed with semi-saturated brine (20 mL×3) and saturated brine (20 mL), dried with anhydrous sodium sulfate, filtered, and the filtrate was concentrated under reduced pressure to remove the solvent. The obtained residue was separated by column chromatography (eluent: petroleum ether/ethyl acetate=20/1-5/1, v/v), to obtain compound WX153-2. ¹H NMR (400 MHz, CDCl₃) δ: 7.52 (d, J=8.8 Hz, 1H), 7.27-7.05 (m, 2H), 6.29-5.98 (m, 1H), 4.46-4.13 (m, 4H), 4.02 (s, 2H), 1.29 (t, J=7.1 Hz, 3H).

Step 3: Synthesis of Compound WX153

Compound WX153-2 (0.24 g, 841.39 μmol) was dissolved in tetrahydrofuran (8 mL) at 20° C., then acrylamide (50.83 mg, 715.18 μmol) and a tetrahydrofuran solution of potassium tert-butoxide (1 M, 715.18 μL) were added, and the reaction mixture was stirred at 20° C. for 2 hours. After the reaction was completed, the reaction solution was quenched with water (10 mL), and extracted with ethyl acetate (20 mL×3). The organic phases were combined, dried with anhydrous sodium sulfate, filtered, and the filtrate was concentrated under reduced pressure to remove the solvent. The obtained residue was separated by preparative HPLC (mobile phase: acetonitrile/water; neutral system: 10 mM NH₄HCO₃) to obtain target compound WX153. MS-ESI m/z: 311.0 [M+H]⁺. ¹H NMR (400 MHz, DMSO_d₆) δ: 7.71 (d, J=9.2 Hz, 1H), 7.46 (d, J=2.4 Hz, 1H), 7.45-7.30 (m, 1H), 6.51-6.25 (m, 1H), 4.55 (dd, J=5.0, 7.8 Hz, 1H), 4.45-4.25 (m, 2H), 2.80-2.70 (m, 1H), 2.68-2.50 (m, 2H), 2.22-2.10 (m, 1H).

Referring to the synthesis method in Embodiment 153, each embodiment in Table 27 is synthesized, and the LCMS and HNMR data are shown in Table 28.

TABLE 27

| Embodiments | Fragment 1 | Fragment 2 | Structure | Compound |
|---|---|---|---|---|
| 154 | 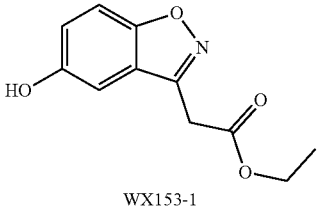 WX153-1 | 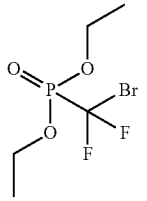 | 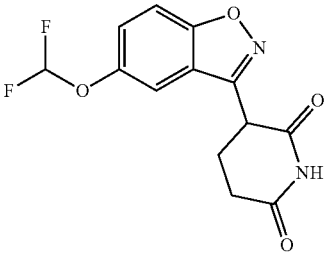 [SMILES: O=C1CCC(c2noc3ccc(OC(F)F)cc23)C(=O)N1] | WX154 |
| 155 | 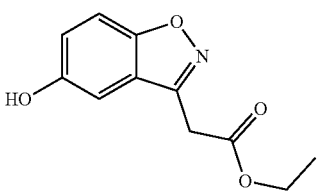 [SMILES: CCOC(=O)Cc1noc2ccc(O)cc12] WX153-1 | 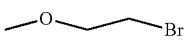 | 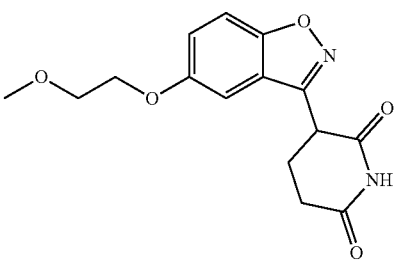 [SMILES: COCCOc1ccc2onc(C3CCC(=O)NC3=O)c2c1] | WX155 |

TABLE 28

| Embodiments | Compound | HNMR | LCMS |
|---|---|---|---|
| 154 | WX154 | $^1$H NMR (400 MHZ, CDCl$_3$) δ: 7.96 (s, 1H), 7.62 (d, J = 8.8 Hz, 1H), 7.50 (d, J = 2.0 Hz, 1H), 7.42 (dd, J = 2.2, 9.0 Hz, 1H), 6.55 (t, JF-H = 33.2 Hz, 1H), 4.31 (dd, J = 5.2, 8.8 Hz, 1H), 3.10-3.02 (m, 1H), 2.83-2.74 (m, 1H), 2.71-2.61 (m, 1H), 2.53-2.45 (m, 1H). | MS-ESI m/z: 297.0 [M + H]$^+$. |
| 155 | WX155 | $^1$H NMR (400 MHZ, DMSO_d$_6$) δ: 11.06 (s, 1H), 7.66 (d, J = 8.8 Hz, 1H), 7.34 (d, J = 2.4 Hz, 1H), 7.28 (dd, J = 2.4, 9.2 Hz, 1H), 4.55 (dd, J = 4.8, 11.6 Hz, 1H), 4.18-4.08 (m, 2H), 3.68 (t, J = 4.6 Hz, 2H), 3.32 (s, 3H), 2.80-2.70 (m, 1H), 2.69-2.63 (m, 1H), 2.40-2.26 (m, 1H), 2.19-2.13 (m, 1H). | MS-ESI m/z: 305.1 [M + H]$^+$. |

Embodiment 156: WX156

Synthetic Route:

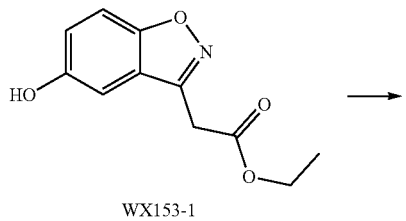

WX153-1

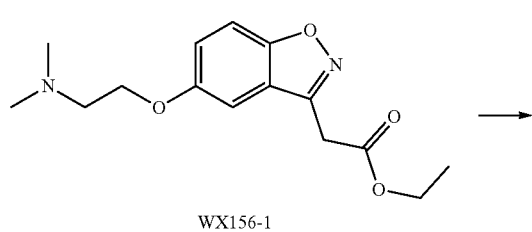

WX156-1

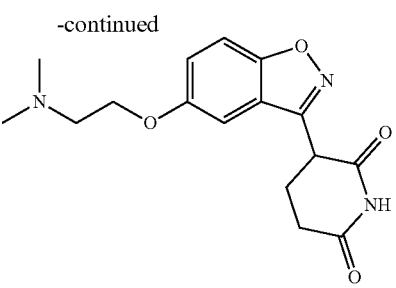

WX156

Step 1: Synthesis of Compound WX156-1

Compound WX153-1 (1.5 g, 6.78 mmol) was dissolved in tetrahydrofuran (20 mL) at 20° C., then triphenylphosphine (2.67 g, 10.17 mmol) and 2-dimethylaminoethanol (725.31 mg, 8.14 mmol, 816.79 μL) were added, and a tetrahydrofuran (5 mL) solution of diisopropyl azodicarboxylate (2.06 g, 10.17 mmol, 1.98 mL) was added dropwise, then the reaction mixture was reacted with stirring at 20° C. for 12 hours. After the reaction was completed, the reaction solution was concentrated under reduced pressure to remove the solvent. The obtained residue was separated by column chromatography (eluent: petroleum ether/ethyl acetate=7/3-0/1, v/v), to obtain compound WX156-1. MS-ESI m/z: 293.1 [M+H]+.

Step 2: Synthesis of Compound WX156

Compound WX156-1 (0.47 g, 1.61 mmol) was dissolved in tetrahydrofuran (15 mL) at 20° C., then acrylamide (114.28 mg, 1.61 mmol) and a tetrahydrofuran solution of potassium tert-butoxide (1 M, 1.61 mL) were added, and the reaction mixture was reacted with stirring at 20° C. for 6 hours. After the reaction was completed, the reaction solution was poured into water (20 mL), adjusted to pH=7 with 1 N hydrochloric acid, and extracted with 2-methyltetrahydrofuran (20×3). The organic phases were combined, dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl) to obtain the hydrochloride of target compound WX156. MS-ESI m/z: 318.1 [M+H]+. $^1$H NMR (400 MHz, MeOD_d$_4$) δ: 7.63-7.55 (m, 1H), 7.42-7.35 (m, 2H), 4.52 (dd, J=4.8, 11.6 Hz, 1H), 4.50-4.40 (m, 2H), 3.70-3.61 (m, 2H), 3.01 (s, 6H), 2.85-2.80 (m, 2H), 2.70-2.50 (m, 1H), 2.40-2.34 (m, 1H).

Embodiment 157: WX157

Synthetic Route:

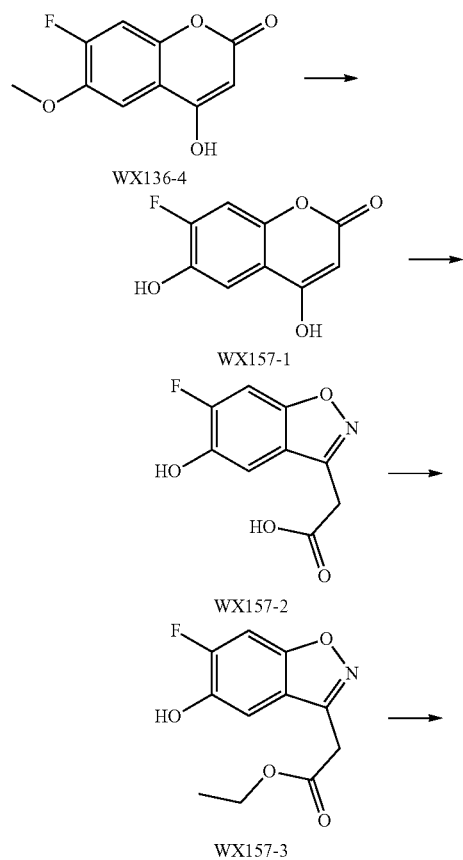

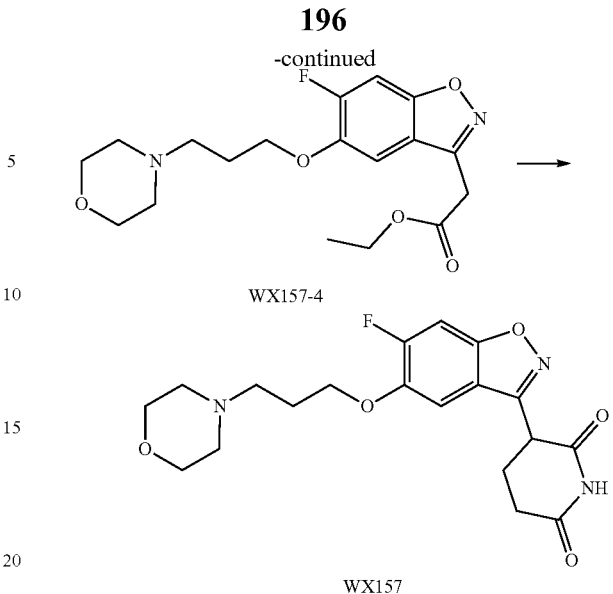

Step 1: Synthesis of Compound WX157-1

Compound WX136-4 (5.7 g, 27.12 mmol) was dissolved in dichloromethane (100 mL) under the protection of nitrogen at 15° C., then the mixture was cooled to −50° C. to −30° C., and boron tribromide (27.18 g, 108.49 mmol, 10.45 mL) was added dropwise, and the reaction mixture was reacted with stirring at 15° C. for 12 hours. After the reaction was completed, the reaction mixture was poured into ice water (500 mL), and extracted with 2-methyltetrahydrofuran (200 mL×4).

The organic phases were combined, dried with anhydrous sodium sulfate, filtered, and the filtrate was concentrated under reduced pressure to remove the solvent to obtain compound WX157-1. MS-ESI m/z: 197.0 [M+H]+. $^1$H NMR (400 MHz, DMSO_d$_6$) δ: 12.48 (s, 1H), 10.24 (br s, 1H), 7.31 (t, J=11.0 Hz, 2H), 5.52 (s, 1H).

Step 2: Synthesis of Compound WX157-2

Compound WX157-1 (2 g, 10.20 mmol) was dissolved in ethanol (30 mL) under the protection of nitrogen at room temperature, then hydroxylamine hydrochloride (2.48 g, 35.69 mmol) and sodium ethoxide (2.43 g, 35.69 mmol) were added, and the reaction mixture was heated to 80° C. and reacted with stirring for 12 hours. After the reaction was completed, 2 M dilute hydrochloric acid (30 mL) was added to the reaction solution, and the mixture was concentrated under reduced pressure to remove most of the ethanol, and extracted with ethyl acetate (50 mL×3). The organic phases were combined, dried with anhydrous sodium sulfate, filtered, and the filtrate was concentrated under reduced pressure to remove the solvent to obtain compound WX157-2. MS-ESI m/z: 212.0 [M+H]+.

Step 3: Synthesis of Compound WX157-3

Compound WX157-2 (2.1 g, 9.95 mmol) was dissolved in ethanol (30 mL) at room temperature under the protection of nitrogen, then concentrated sulfuric acid (920.00 mg, 9.19 mmol, 0.5 mL, purity:98%) was added, and the reaction mixture was heated to 70° C. and reacted with stirring for 1.5 hours at 70° C. After the reaction was completed, the mixture was cooled to room temperature, concentrated under reduced pressure to remove most of the ethanol, diluted with water (50 mL) and ethyl acetate (50 mL); the phases were separated, then the organic phase was collected, and the aqueous phase was extracted with ethyl acetate (30 mL×2). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-3/7, v/v), to obtain compound WX157-3. MS-ESI m/z: 240.1 [M+H]+. 1H NMR (400 MHz, CDCl3) δ: 7.32 (d, J=9.6 Hz, 1H), 7.25 (d, J=2.0 Hz, 1H), 5.23 (br s, 1H), 4.15 (q, J=7.2 Hz, 2H), 3.91 (s, 2H), 1.20 (t, J=7.2 Hz, 3H).

Step 4: Synthesis of Compound WX157-4

Compound WX157-3 (800 mg, 3.34 mmol) was dissolved in N,N-dimethylformamide (15 mL) at room temperature under the protection of nitrogen, then 4-(3-chloropropyl) morpholine (656.77 mg, 4.01 mmol), potassium carbonate (1.39 g, 10.03 mmol) and potassium iodide (111.04 mg, 668.90 μmol) were added, and the reaction mixture was heated to 50° C. and reacted with stirring for 20 hours at 50° C. After the reaction was completed, the mixture was cooled to room temperature, and the reaction mixture was added with water (50 mL), and extracted with ethyl acetate (50 mL×3). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-1/4, v/v), to obtain compound WX157-4. MS-ESI m/z: 367.0 [M+H]+. 1H NMR (400 MHz, CDCl3) δ: 7.32 (d, J=10.0 Hz, 1H), 7.17 (d, J=7.6 Hz, 1H), 4.22 (q, J=7.2 Hz, 2H), 4.13 (t, J=6.4 Hz, 2H), 4.00 (s, 2H), 3.80-3.66 (m, 4H), 2.57 (t, J=7.2 Hz, 2H), 2.52-2.41 (m, 4H), 2.11-1.99 (m, 2H), 1.28 (t, J=7.0 Hz, 3H).

Step 5: Synthesis of Compound WX157

Compound WX157-4 (700 mg, 1.91 mmol) was dissolved in tetrahydrofuran (30 mL) under at 10° C., then acrylamide (135.80 mg, 1.91 mmol) and potassium tert-butoxide (214.39 mg, 1.91 mmol) were added, and the reaction mixture was reacted with stirring at 10° C. for 4 hours. After the reaction was completed, the reaction mixture was added with water (30 mL), and extracted with ethyl acetate (30 mL×5). The organic phases were combined, dried with anhydrous sodium sulfate, filtered, and the filtrate was concentrated under reduced pressure to remove the solvent. The obtained residue was separated by preparative HPLC (mobile phase: acetonitrile/water; neutral system: 10 mM NH4HCO3), then separated by preparative HPLC (mobile phase: acetonitrile/water; acidic system: 0.05% HCl) to obtain the hydrochloride of target compound WX157. MS-ESI m/z: 392.1 [M+H]+. 1H NMR (400 MHz, D2O) δ: 7.51-7.34 (m, 1H), 7.27-7.15 (m, 1H), 4.55-4.42 (m, 1H), 4.21-4.12 (m, 2H), 4.07 (d, J=11.6 Hz, 2H), 3.77 (t, J=12.2 Hz, 2H), 3.57 (d, J=12.8 Hz, 2H), 3.38 (t, J=7.6 Hz, 2H), 3.16 (td, J=2.8, 12.0 Hz, 2H), 2.87-2.68 (m, 2H), 2.55-2.40 (m, 1H), 2.39-2.30 (m, 1H), 2.29-2.20 (m, 2H).

Embodiment 158: WX158

Synthetic Route:

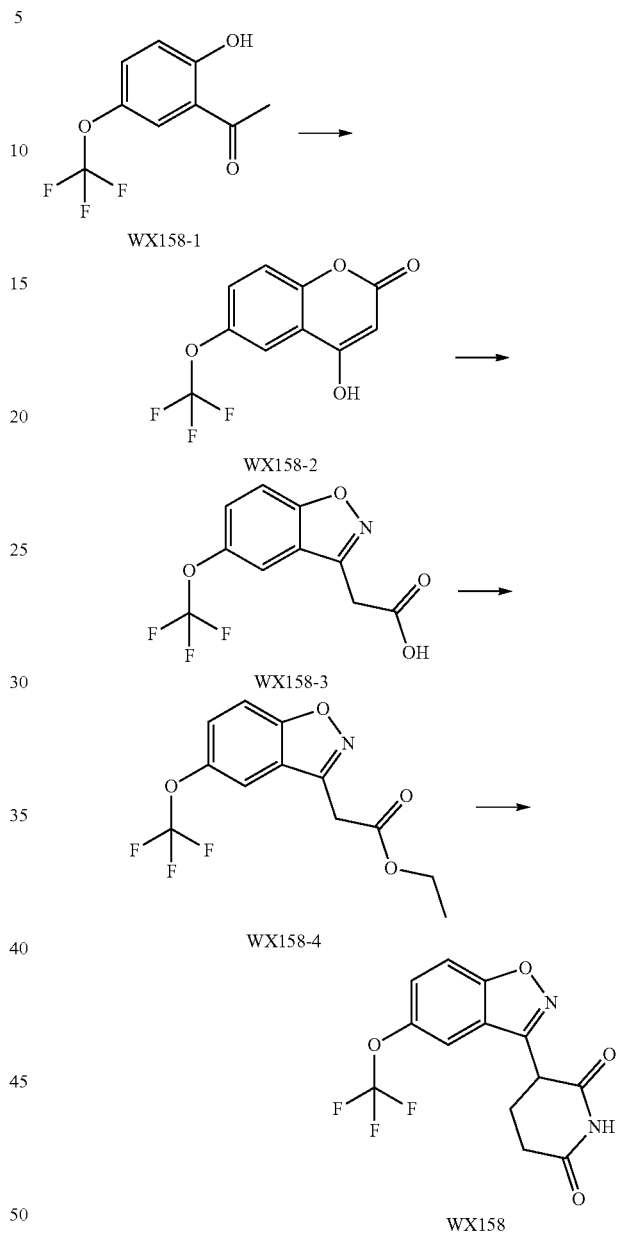

Step 1: Synthesis of Compound WX158-2

Compound WX158-1 (811 mg, 3.68 mmol) was dissolved in toluene (15 mL) under the protection of nitrogen at 20° C., then sodium hydride (589.43 mg, 14.74 mmol, purity: 60%) was added, then diethyl carbonate (1.74 g, 14.74 mmol, 1.79 mL) was added, and the reaction solution was heated to 100° C. and reacted with stirring for 16 hours at 100° C. After the reaction was completed, the mixture was cooled to room temperature, and the reaction mixture was added with water (20 mL), and extracted with ethyl acetate (30 mL×3). The organic phase was discarded, and the aqueous phase was adjusted to pH=3-4 with dilute hydrochloric acid (4 M, 8 mL), and extracted with ethyl acetate (30 mL×4). The organic phases were combined, washed with saturated brine (80 mL×2), dried with anhydrous sodium sulfate, filtered, and the filtrate was concentrated under reduced pressure to remove the solvent to obtain compound WX158-2. MS-ESI m/z: 246.9 [M+H]⁺. ¹H NMR (400 MHz, DMSO_d₆) δ: 12.89 (br s, 1H), 7.74-7.64 (m, 2H), 7.52 (d, J=9.2 Hz, 1H), 5.66 (s, 1H).

Step 2: Synthesis of Compound WX158-3

Compound WX158-2 (801 mg, 3.20 mmol, purity: 98.30%) was dissolved in ethanol (20 mL) at 20° C. under the protection of nitrogen, then hydroxylamine hydrochloride (666.89 mg, 9.60 mmol, hydrochloride) and sodium acetate (787.23 mg, 9.60 mmol) were added, and the reaction solution was heated to 80° C. and stirred for 16 hours. After the reaction was completed, the mixture was cooled to room temperature and the solvent ethanol was removed under reduced pressure. Water (50 mL) was added to the obtained residue, and the pH of the mixture was adjusted to 1-2 with dilute hydrochloric acid (4M, 10 mL), and the mixture was extracted with ethyl acetate (50 mL×3). The organic phases were combined and washed with saturated brine (80 mL×2), dried with anhydrous sodium sulfate, filtered, and the filtrate was concentrated under reduced pressure to remove the solvent. The obtained residue was separated by column chromatography (eluent: petroleum ether/ethyl acetate=10/1-3/1, v/v), to obtain compound WX158-3. ¹H NMR (400 MHz, DMSO_d₆) δ: 12.97 (br s, 1H), 7.97 (d, J=1.2 Hz, 1H), 7.89 (d, J=8.8 Hz, 1H), 7.69 (dd, J=2.0, 8.8 Hz, 1H), 4.15 (s, 2H).

Step 3: Synthesis of Compound WX158-4

Compound WX158-3 (497 mg, 1.90 mmol) was dissolved in ethanol (20 mL) at 20° C., and concentrated sulfuric acid (380.93 mg, 3.81 mmol, 207.03 μL, purity:98%) was added, then the reaction mixture was heated to 75° C. and stirred for 15 hours. After the reaction was completed, the mixture was cooled to room temperature, and the solvent ethanol was removed under reduced pressure. The obtained residue was dissolved in dichloromethane (30 mL), and sequentially washed with water (30 mL×2) and saturated sodium bicarbonate solution (20 mL). The organic phases were combined, dried with anhydrous sodium sulfate, filtered, and the filtrate was concentrated under reduced pressure to remove the solvent to obtain compound WX158-4. ¹H NMR (400 MHz, CDCl₃) δ: 7.61 (d, J=6.4 Hz, 1H), 7.60 (s, 1H), 7.45 (dd, J=1.6, 9.0 Hz, 1H), 4.24 (q, J=7.1 Hz, 2H), 4.05 (s, 2H), 1.28 (t, J=7.0 Hz, 3H).

Step 4: Synthesis of Compound WX158

Compound WX158-4 (487 mg, 1.68 mmol) was dissolved in N,N-dimethylformamide (5 mL) under the protection of nitrogen at 0° C., then potassium tert-butoxide (188.95 mg, 1.68 mmol) was added, and the reaction mixture was reacted with stirring at 0° C. for 0.5 hour; acrylamide (119.69 mg, 1.68 mmol) was added to the above reaction solution, and the reaction mixture was reacted with stirring at 0° C. for 1 hour. After the reaction was completed, the reaction mixture was slowly raised to room temperature, then water (50 mL) was added, and the mixture was extracted with ethyl acetate (50 mL×3). The organic phases were combined, washed with saturated brine (80 mL×2), dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl) to obtain target compound WX158. MS-ESI m/z: 315.1 [M+H]⁺. ¹H NMR (400 MHz, DMSO_d₆) δ: 11.11 (s, 1H), 8.05 (s, 1H), 7.92 (d, J=8.8 Hz, 1H), 7.70 (dd, J=1.4, 9.0 Hz, 1H), 4.66 (dd, J=4.8, 12.4 Hz, 1H), 2.81-2.70 (m, 1H), 2.66-2.61 (m, 1H), 2.60-2.54 (m, 1H), 2.24-2.15 (m, 1H).

Referring to the synthesis method in Embodiment 158, each embodiment in Table 29 is synthesized, and the LCMS and HNMR data are shown in Table 30.

TABLE 29

| Embodiments | Fragment 1 | Structure | Compound |
| --- | --- | --- | --- |
| 159 | 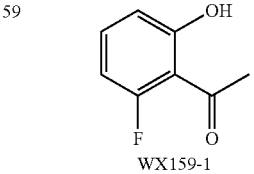<br>WX159-1 | 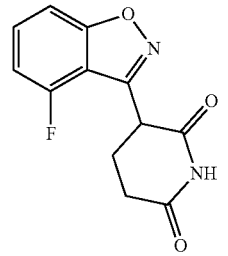 [SMILES: O=C1CCC(c2noc3cccc(F)c23)C(=O)N1] | WX159 |
| 160 | 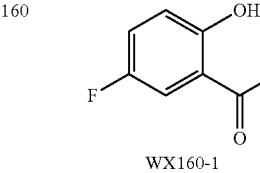<br>WX160-1 | 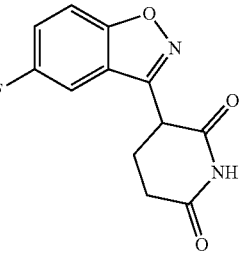 | WX160 |

TABLE 29-continued

| Embodiments | Fragment 1 | Structure | Compound |
|---|---|---|---|
| 161 | 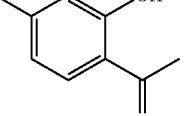<br>WX161-1 | 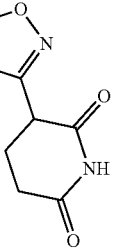 | WX161 |
| 162 | 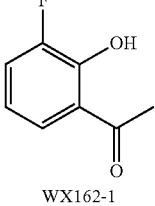<br>WX162-1 | 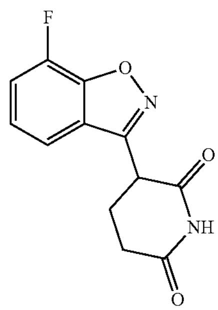 [SMILES: O=C1CCC(c2noc3c(F)cccc23)C(=O)N1] | WX162 |

TABLE 30

| Embodiments | Compound | HNMR | LCMS |
|---|---|---|---|
| 159 | WX159 | $^1$H NMR (400 MHZ, DMSO-$d_6$) δ: 11.18 (s, 1H), 7.77-7.69 (m, 1H), 7.65 (d, J = 8.4 Hz, 1H), 7.23 (dd, J = 7.8, 9.8 Hz, 1H), 4.63 (dd, J = 5.2, 12.8 Hz, 1H), 2.93-2.79 (m, 1H), 2.71-2.58 (m, 1H), 2.41-2.26 (m, 1H), 2.25-2.16 (m, 1H). | MS-ESI m/z: 249.1 [M + H]$^+$. |
| 160 | WX160 | $^1$H NMR (400 MHZ, DMSO-$d_6$) δ: 11.11 (s, 1H), 7.82 (dd, J = 3.6, 9.2 Hz, 1H), 7.78 (dd, J = 2.2, 8.2 Hz, 1H), 7.56 (td, J = 2.4, 8.8 Hz, 1H), 4.59 (dd, J = 5.0, 11.8 Hz, 1H), 2.85-2.72 (m, 1H), 2.68-2.56 (m, 2H), 2.25-2.14 (m, 1H). | MS-ESI m/z: 249.1 [M + H]$^+$. |
| 161 | WX161 | $^1$H NMR (400 MHZ, DMSO-$d_6$) δ: 11.12 (s, 1 H), 7.93 (dd, J = 5.2, 8.8 Hz, 1H), 7.75 (dd, J = 2.2, 9.0 Hz, 1H), 7.31 (td, J = 2.2, 9.0 Hz, 1H), 4.62 (dd, J = 5.0, 12.0 Hz, 1H), 2.82-2.71 (m, 1H), 2.68-2.58 (m, 1H), 2.56-2.52 (m, 1H), 2.26-2.16 (m, 1H). | MS-ESI m/z: 249.1 [M + H]$^+$. |
| 162 | WX162 | $^1$H NMR (400 MHZ, DMSO-$d_6$) δ: 11.15 (s, 1H), 7.72 (d, J = 8.4 Hz, 1H), 7.60 (dd, J = 7.8, 11.0 Hz, 1H), 7.41 (td, J = 4.2, 8.0 Hz, 1H), 4.67 (dd, J = 4.8, 12.0 Hz, 1H), 2.84-2.72 (m, 1H), 2.69-2.52 (m, 2H), 2.29-2.17 (m, 1H). | MS-ESI m/z: 249.0 [M + H]$^+$. |

Embodiment 163: WX163

Synthetic Route:

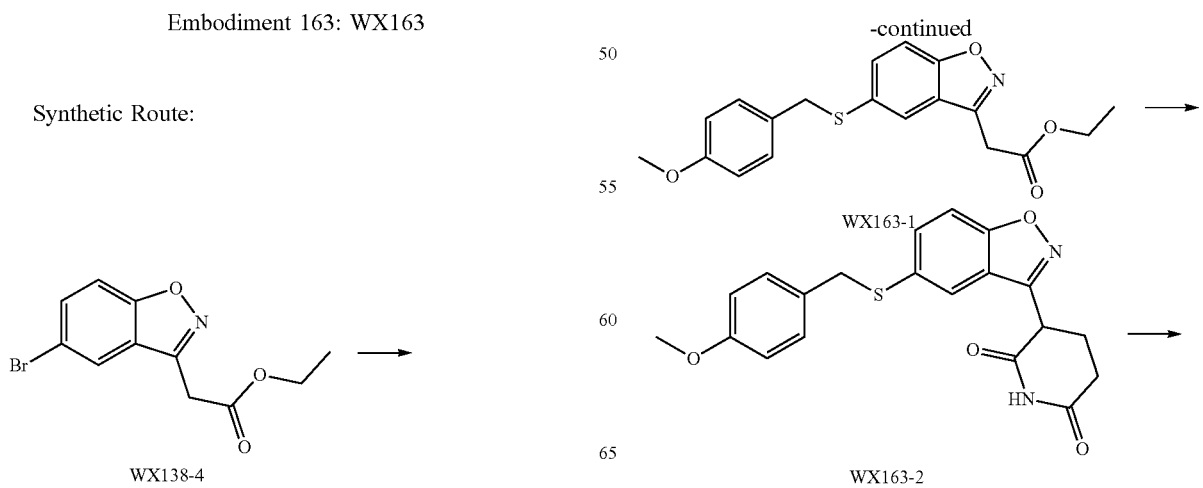

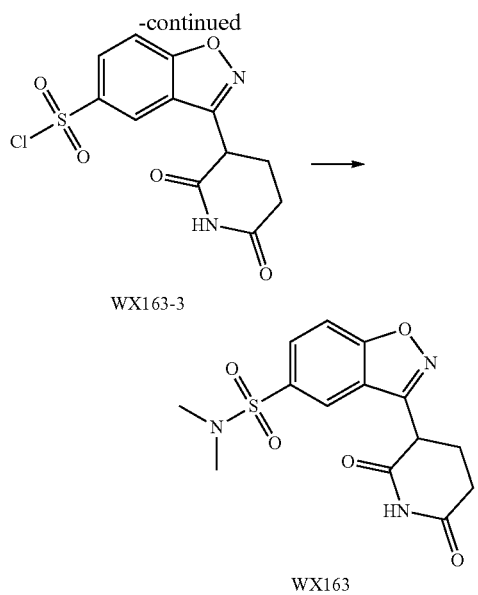

WX163-3

WX163

Step 1: Synthesis of Compound WX163-1

Compound WX138-4 (2 g, 7.04 mmol), 4-methoxythioanisole (1.09 g, 7.04 mmol) and N,N-diisopropylethylamine (1.82 g, 14.08 mmol) were dissolved in dioxane (30 mL) at room temperature under the protection of nitrogen, then 4,5-bis(diphenylphosphino)-9,9-dimethylxanthene (407.33 mg, 704.00 μmol) and tris(dibenzylideneacetone)dipalladium (322.32 mg, 352.00 μmol) were added, and the reaction mixture was raised to 120° C. and reacted with stirring for 12 hours. After the reaction was completed, the mixture was cooled to room temperature, then water (50 mL) and 2-methyltetrahydrofuran (50 mL) were added; and the phases were separated, then the organic phase was collected, and the aqueous phase was extracted with 2-methyltetrahydrofuran (30 mL×3); the organic phases were combined, washed with saturated brine (30 mL), dried with anhydrous sodium sulfate, filtered, and the filtrate was concentrated under reduced pressure to remove the solvent. The obtained residue was separated by column chromatography (eluent: petroleum ether/ethyl acetate=1/0-12/1, v/v), to obtain a crude product of compound WX163-1. MS-ESI m/z: 358.1 [M+H]$^+$. $^1$H NMR (400 MHz, MeOD-d$_4$) δ: 7.69 (s, 1H), 7.60-7.52 (m, 2H), 7.13 (d, J=8.8 Hz, 2H), 6.78 (d, J=8.8 Hz, 2H), 4.19 (q, J=7.2 Hz, 2H), 4.09 (s, 2H), 4.04 (s, 2H), 3.73 (m, 3H), 1.24 (t, J=7.2 Hz, 3H).

Step 2: Synthesis of Compound WX163-2

The crude product of compound WX163-1 (500 mg, 1.40 mmol) from the previous step was dissolved in dichloromethane (5 mL) under the protection of nitrogen at room temperature, then acrylamide (89.49 mg, 1.26 mmol) and potassium tert-butoxide (141.28 mg, 1.26 mmol) were added, and the reaction mixture was stirred at 15° C. for 4 hours. After the reaction was completed, water (20 mL) and 2-methyltetrahydrofuran (20 mL) was added to the reaction solution to dilute; the phases were separated, then the organic phase was collected, and the pH of the aqueous phase was adjusted to 6 with 2 M dilute hydrochloric acid, and the mixture was extracted with 2-methyltetrahydrofuran (15 mL×5). The organic phases were combined, washed with saturated brine (20 mL×2), dried with anhydrous sodium sulfate, filtered, and the filtrate was concentrated under reduced pressure to remove the solvent. The obtained residue was separated by column chromatography (eluent: petroleum ether/ethyl acetate=1/0-7/3, v/v), to obtain a crude product of compound WX163-2. MS-ESI m/z: 383.1 [M+H]$^+$.

Step 3: Synthesis of Compound WX163-3

The crude product of compound WX163-2 (290.00 mg, 758.30 μmol) from the previous step was dissolved in acetic acid (3 mL) under the protection of nitrogen at room temperature, then N-chlorosuccinimide (303.77 mg, 2.27 mmol) was added, and the reaction mixture was reacted with stirring at 15° C. for 12 hours. After the reaction was completed, water (20 mL) and 2-methyltetrahydrofuran (20 mL) were added; the phases were separated, then the organic phase was collected, and the aqueous phase was extracted with 2-methyltetrahydrofuran (10 mL×5); the organic phases were combined, and washed with saturated brine (10 mL×2), dried with anhydrous sodium sulfate, filtered, and concentrated under reduced pressure to remove the solvent to obtain a crude product of compound WX163-3. MS-ESI m/z: 329.0 [M+H]$^+$, 330.9 [M+H+2]$^+$.

Step 4: Synthesis of Compound WX163

Compound WX163-3 (400 mg, 1.22 mmol) was dissolved in tetrahydrofuran (4 mL) at room temperature under the protection of nitrogen, then N,N-diisopropylethylamine (314.53 mg, 2.43 mmol) and a tetrahydrofuran solution of dimethylamine (2 M, 608.41 μL) were added, and the reaction mixture was stirred at 15° C. for 12 hours. After the reaction was completed, the reaction mixture was concentrated under reduced pressure to remove the solvent, and the obtained residue was separated by preparative HPLC (mobile phase: acetonitrile/water; acidic system: 0.05% HCl), to obtain target compound WX163. MS-ESI m/z: 338.0 [M+H]$^+$. $^1$H NMR (400 MHz, DMSO-d$_6$) δ: 8.39 (s, 1H), 8.10-7.95 (m, 2H), 4.79 (dd, J=4.8, 12.0 Hz, 1H), 2.79-2.67 (m, 1H), 2.64-2.62 (m, 1H), 2.55-2.49 (m, 6H), 2.45-2.17 (m, 2H).

Embodiment 164: WX164

Synthetic Route:

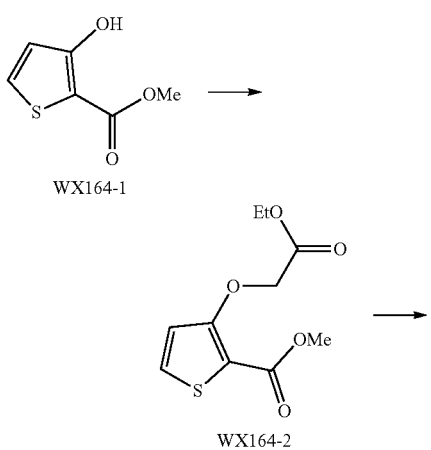

WX164-1

WX164-2

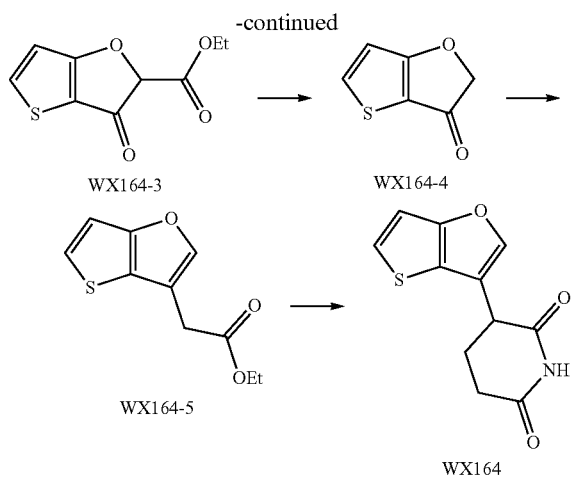

Step 1: Synthesis of Compound WX164-2

Compound WX164-1 (20 g, 126.44 mmol) was dissolved in N,N-dimethylformamide (200 mL) at room temperature, then potassium carbonate (34.95 g, 252.88 mmol) and ethyl bromoacetate (21.12 g, 126.44 mmol, 13.98 mL) were added, and the reaction mixture was stirred at room temperature for 3 hours. After the reaction was completed, the solvent was removed under reduced pressure, and the obtained residue was added with water (100 mL) and ethyl acetate (100 mL), then the phases were separated, and the aqueous phase was extracted with ethyl acetate (20 mL×3). The organic phases were combined, washed with semi-saturated brine (20 mL×3), dried with anhydrous sodium sulfate, filtered, and the filtrate was concentrated under reduced pressure to remove the solvent, to obtain compound WX164-2. MS-ESI m/z: 245.1 [M+H]⁺. $^1$H NMR (400 MHz, CDCl$_3$) δ: 7.39 (d, J=5.6 Hz, 1H), 6.74 (d, J=5.6 Hz, 1H), 4.76 (s, 2H), 4.25 (q, J=7.2 Hz, 2H), 3.85 (s, 3H), 1.28 (t, J=7.0 Hz, 3H).

Step 2: Synthesis of Compound WX164-3

Compound WX164-2 (10 g, 40.94 mmol) was dissolved in N,N-dimethylformamide (50 mL) at room temperature, then potassium tert-butoxide (9.19 g, 81.88 mmol) was added, and the reaction mixture was reacted with stirring at room temperature for 12 hours. After the reaction was completed, water (50 mL) was added, and the pH of the mixture was adjusted to 5-6 with 1 N dilute hydrochloric acid solution, and the mixture was extracted with ethyl acetate (100 mL×3). The organic phases were combined, washed with water (50 mL×3), dried with anhydrous sodium sulfate, filtered, and the filtrate was concentrated under reduced pressure to remove the solvent to obtain compound WX164-3. MS-ESI m/z: 213.1 [M+H]⁺.

Step 3: Synthesis of Compound WX164-4

Compound WX164-3 (7.5 g, 35.34 mmol) was dissolved in dioxane (50 mL) and 3 M dilute hydrochloric acid aqueous solution (3 M, 112.50 mL) at room temperature, then the reaction mixture was reacted with stirring at room temperature for 12 hours. After the reaction was completed, water (100 mL) and methyl tert-butyl ether (100 mL) were added, and the liquid was separated, and the aqueous phase was extracted with methyl tert-butyl ether (100 mL×5). The organic phases were combined, dried with anhydrous sodium sulfate, filtered, and the filtrate was concentrated under reduced pressure to remove the solvent, and the obtained residue was separated by column chromatography (eluent: petroleum ether/ethyl acetate=1/0-30/1, v/v) to obtain compound WX164-4. $^1$H NMR (400 MHz, CDCl$_3$) δ: 7.95 (d, J=5.2 Hz, 1H), 6.79 (d, J=5.6 Hz, 1H), 5.00 (s, 2H).

Step 4: Synthesis of Compound WX164-5

Compound WX164-4 (1 g, 7.13 mmol) and ethyl (triphenylphosphoranylidene)acetate (3.73 g, 10.70 mmol) were dissolved in anhydrous toluene (20 mL) at room temperature, and the reaction mixture was heated to 130° C. and reacted with stirring at 130° C. for 96 hours under the protection of nitrogen. After the reaction was completed, the solvent was removed under reduced pressure. The obtained residue was added with methyl tert-butyl ether (30 mL), filtered, and the filter cake was washed with methyl tert-butyl ether (20 mL), and the filtrate was concentrated under reduced pressure to remove the solvent, and the obtained residue was separated by column chromatography (eluent: petroleum ether/ethyl acetate=100/1-50/1, v/v) to obtain compound WX164-5. $^1$H NMR (400 MHz, CDCl$_3$) δ: 7.46 (s, 1H), 7.19 (d, J=4.0 Hz, 1H), 7.01 (d, J=5.6 Hz, 1H), 4.20 (q, J=7.2 Hz, 2H), 3.59 (s, 2H), 1.29 (t, J=7.2 Hz, 3H).

Step 5: Synthesis of Compound WX164

Compound WX164-5 (200 mg, 951.25 μmol) was dissolved in N,N-dimethylformamide (5 mL) at room temperature, then potassium tert-butoxide (106.74 mg, 951.25 μmol) and acrylamide (67.61 mg, 951.25 μmol) were added, and the reaction mixture was reacted with stirring at room temperature for 3 hours under the protection of nitrogen. After the reaction was completed, water (15 mL) and ethyl acetate (20 mL) were added to dilute, and the phases were separated, and the aqueous phase was extracted with ethyl acetate (10 mL×2). The organic phases were combined, washed with semi-saturated brine (15 mL×2), dried with anhydrous sodium sulfate, filtered, and the filtrate was concentrated under reduced pressure to remove the solvent, and the obtained residue was slurried with methanol (3 mL) at room temperature, and filtered to obtain target compound WX164. MS-ESI m/z: 236.0 [M+H]⁺. $^1$H NMR (400 MHz, DMSO-d$_6$) δ: 10.92 (s, 1H), 7.82 (s, 1H), 7.49 (d, J=5.2 Hz, 1H), 7.22 (d, J=5.2 Hz, 1H), 4.01 (dd, J=5.8, 9.9 Hz, 1H), 2.76-2.65 (m, 1H), 2.62-2.53 (m, 1H), 2.25-2.11 (m, 2H).

Embodiment 165: WX165

Synthetic Route:

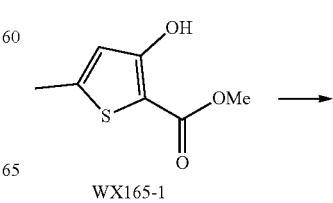

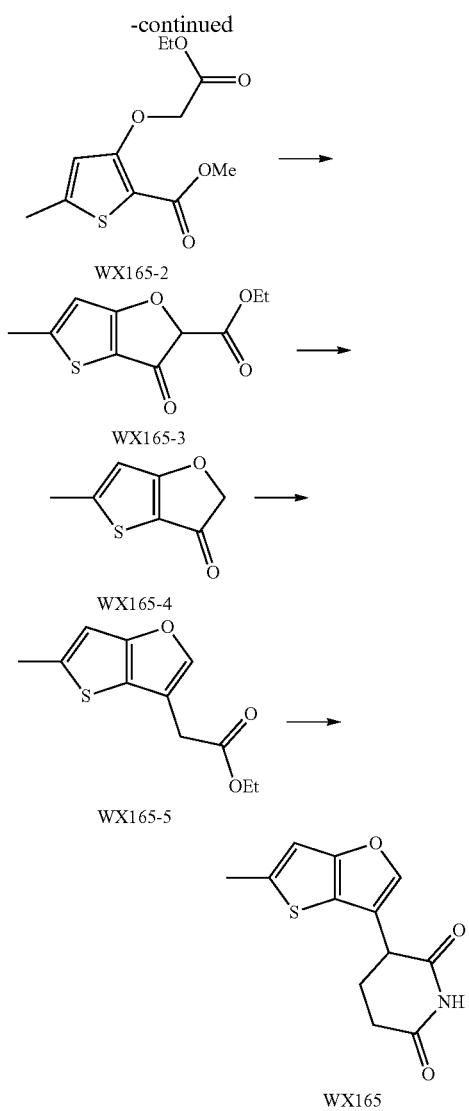

Step 1: Synthesis of Compound WX165-2

Compound WX165-1 (5 g, 29.04 mmol) was dissolved in N,N-dimethylformamide (50 mL) at room temperature, then ethyl bromoacetate (5.33 g, 31.94 mmol, 3.53 mL) and potassium carbonate (8.03 g, 58.07 mmol) were added, and the reaction mixture was stirred at room temperature for 3 hours at room temperature. After the reaction was completed, the mixture was filtered to obtain a N,N-dimethylformamide (50 mL) solution of compound WX165-2.

Step 2: Synthesis of Compound WX165-3

Potassium tert-butoxide (6.26 g, 55.75 mmol) was added to the N,N-dimethylformamide solution of compound WX165-2 (27.88 mmol, 48 mL) at room temperature, and the reaction mixture was stirred for 4 hours at room temperature. After the reaction was completed, water (50 mL) was added to dilute, and the pH of the mixture was adjusted to 5-6 with 2 M dilute hydrochloric acid aqueous solution, and the mixture was extracted with ethyl acetate (50 mL×3). The organic phases were combined, washed with semi-saturated brine (30 mL×2), dried with anhydrous sodium sulfate, filtered, and the filtrate was concentrated under reduced pressure to obtain compound WX165-3.

Step 3: Synthesis of Compound WX165-4

Compound WX165-3 (7 g, 27.88 mmol) was dissolved in dioxane (30 mL) at room temperature, then an aqueous solution (100 mL) of concentrated hydrochloric acid (12 M, 69.94 mL) was added, and the reaction mixture was reacted with stirring at room temperature for 16 hours. After the reaction was completed, water (10 mL) was added to dilute, and the mixture was extracted with ethyl acetate (20 mL×3). The organic phases were combined, dried with anhydrous sodium sulfate, filtered, and the filtrate was concentrated under reduced pressure to remove the solvent, and the obtained residue was separated by column chromatography (eluent: petroleum ether/ethyl acetate=1/0-4/1, v/v), to obtain compound WX165-4.

Step 4: Synthesis of Compound WX165-5

Compound WX165-4 (2 g, 12.97 mmol) was dissolved in toluene (30 mL) at room temperature, then ethoxyformylmethylene triphenylphosphine (5.87 g, 16.86 mmol) was added, and the reaction mixture was heated to 130° C. and reacted with stirring at 130° C. for 120 hours. After the reaction was completed, the mixture was cooled to room temperature, and the solvent from the reaction solution was removed under reduced pressure; the obtained residue was added to methyl tert-butyl ether (10 mL), filtered, and the solvent from the filtrate was removed under reduced pressure. The obtained residue was separated by column chromatography (eluent: petroleum ether/ethyl acetate=1/0-4/1, v/v), to obtain compound WX165-5. $^1$H NMR (400 MHz, CDCl$_3$) δ: 7.39 (s, 1H), 6.74 (d, J=0.8 Hz, 1H), 4.21 (q, J=7.0 Hz, 2H), 3.57 (s, 2H), 2.54 (s, 3H), 1.31 (t, J=7.0 Hz, 3H).

Step 5: Synthesis of Compound WX165

Compound WX165-5 (450 mg, 2.01 mmol) was dissolved in N,N-dimethylformamide (5 mL) at room temperature, then potassium tert-butoxide (225.15 mg, 2.01 mmol) was added, and acrylamide (142.61 mg, 2.01 mmol) was added, and the reaction mixture was reacted with stirring at room temperature for 2 hours under the protection of nitrogen. After the reaction was completed, water (15 mL) and ethyl acetate (20 mL) were added to dilute, and the phases were separated, then the organic phases were collected, and the aqueous phase was extracted with ethyl acetate (10 mL×2). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-1/1, v/v), and then slurried with methanol (2 mL) at room temperature to obtain target compound WX165. MS-ESI m/z: 250.0 [M+H]$^+$. $^1$H NMR (400 MHz, DMSO-d$_6$) δ: 10.89 (s, 1H), 7.71 (s, 1H), 6.96 (d, J=1.1 Hz, 1H), 3.95 (dd, J=5.6, 10.4 Hz, 1H), 2.75-2.64 (m, 1H), 2.61-2.52 (m, 1H), 2.49 (s, 3H), 2.24-2.06 (m, 2H).

Embodiment 166: WX166

Synthetic Route:

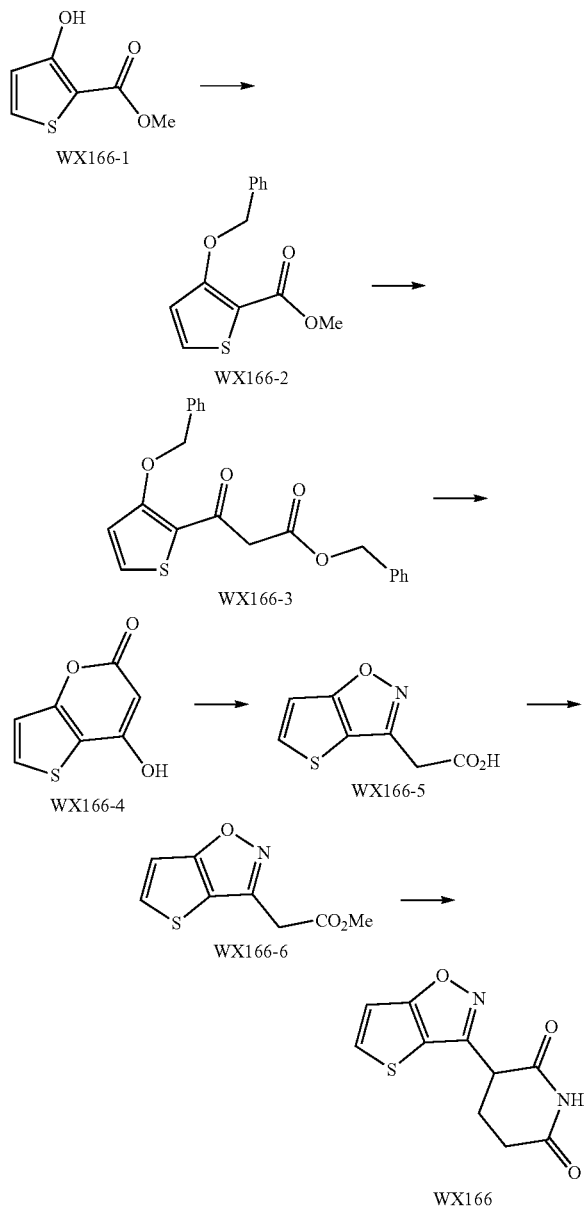

Step 1: Synthesis of Compound WX166-2

Compound WX166-1 (13.7 g, 86.61 mmol), benzyl bromide (14.81 g, 86.61 mmol, 10.29 mL) and potassium carbonate (23.94 g, 173.23 mmol) were added to acetonitrile (100 mL) at room temperature, and the reaction mixture was heated to 60° C. and reacted with stirring at 60° C. for 12 hours. After the reaction was completed, the mixture was cooled to room temperature, and the solvent from the reaction solution was removed under reduced pressure, and the obtained residue was diluted with dichloromethane (100 mL) and water (100 mL), and the phases were separated. The organic phases were washed with saturated brine (100 mL), dried with anhydrous sodium sulfate, filtered, and the filtrate was concentrated under reduced pressure to remove the solvent to obtain compound WX166-2. $^1$H NMR (400 MHz, CDCl$_3$) δ: 7.47-7.42 (m, 2H), 7.39-7.28 (m, 4H), 6.81 (d, J=5.6 Hz, 1H), 5.24 (s, 2H), 3.85 (s, 3H).

Step 2: Synthesis of Compound WX166-3

A tetrahydrofuran (20 mL) solution of benzyl acetate (9.07 g, 60.41 mmol, 8.56 mL) was slowly added dropwise to a tetrahydrofuran solution of lithium hexamethyldisilazide (1 M, 181.23 mL) at −70° C., and the reaction mixture was then reacted with stirring for 0.5 hours at −70° C. Then, a tetrahydrofuran (20 mL) solution of compound WX166-2 (15 g, 60.41 mmol) was slowly added dropwise to the reaction solution at −70° C. The reaction mixture was slowly raised to room temperature and reacted with stirring at room temperature for 12 hours. After the reaction was completed, the reaction mixture was concentrated under reduced pressure to remove the solvent, and the obtained residue was diluted with dichloromethane (100 mL) and water (100 mL), and the phases were separated. The organic phases were washed with saturated brine (100 mL), dried with anhydrous sodium sulfate, filtered, and the filtrate was concentrated under reduced pressure to obtain compound WX166-3. $^1$H NMR (400 MHz, CDCl$_3$) δ: 7.54 (d, J=5.2 Hz, 1H), 7.40-7.24 (m, 10H), 6.82 (d, J=5.6 Hz, 1H), 5.10 (s, 2H), 5.09 (s, 2H), 3.97 (s, 2H).

Step 3: Synthesis of Compound WX166-4

Compound WX166-3 (17.7 g, 48.30 mmol) was added to an acetic acid solution of hydrobromic acid (70 mL, concentration: 33%) at room temperature, and the reaction mixture was heated to 60° C. and reacted with stirring at 60° C. for 12 hours. After the reaction was completed, the mixture was cooled to room temperature, and methyl tert-butyl ether (200 mL) and petroleum ether (200 mL) were added, then a solid was precipitated; the mixture was filtered, and the obtained filter cake was washed with methyl tert-butyl ether (100 mL), and the filter cake was collected, vacuum-dried to obtain compound WX166-4. $^1$H NMR (400 MHz, DMSO-d$_6$) δ: 12.69 (s, 1H), 7.99 (d, J=5.6 Hz, 1H), 7.21 (d, J=5.2 Hz, 1H), 5.41 (s, 1H).

Step 4: Synthesis of Compound WX166-5

Compound WX166-4 (3 g, 17.84 mmol), hydroxylamine hydrochloride (4.34 g, 62.44 mmol) and sodium acetate (5.12 g, 62.44 mmol) were added to methanol (30 mL) at room temperature, and the reaction mixture was heated to 60° C. and reacted with stirring for 12 hours at 60° C. After the reaction was completed, the mixture was cooled to room temperature, and the reaction mixture was concentrated under reduced pressure to remove the solvent, and the obtained residue was added with saturated sodium bicarbonate aqueous solution (50 mL) and ethyl acetate (50 mL), and the phases were separated. The organic phase was discarded, and the pH of the aqueous phase was adjusted to 3 with concentrated hydrochloric acid, and the mixture was extracted with ethyl acetate (50 mL). The organic phase was dried with anhydrous sodium sulfate, filtered, and the filtrate was concentrated under reduced pressure to remove the solvent to obtain compound WX166-5.

Step 5: Synthesis of Compound WX166-6

Compound WX166-5 (500 mg, 2.73 mmol) was dissolved in a methanol solution of hydrochloric acid (4 M, 20 mL) at room temperature, and the reaction mixture was stirred at room temperature for 12 hours. After the reaction was completed, the reaction mixture was concentrated under reduced pressure to remove the solvent, and the obtained residue was separated by column chromatography (eluent: petroleum ether/ethyl acetate=5/1, v/v) to obtain compound WX166-6. $^1$H NMR (400 MHz, CDCl$_3$) δ: 7.66 (d, J=5.2 Hz, 1H), 7.07 (d, J=5.2 Hz, 1H), 3.95 (s, 2H), 3.81 (s, 3H).

Step 6: Synthesis of Compound WX166

Compound WX166-6 (200 mg, 1.01 mmol), acrylamide (72.08 mg, 1.01 mmol) and potassium tert-butoxide (113.80 mg, 1.01 mmol) were sequentially added to tetrahydrofuran (4 mL) at room temperature, and the reaction mixture was reacted with stirring for 1 hour at room temperature. After the reaction was completed, the reaction mixture was added with water (10 mL) and ethyl acetate (10 mL), and the phases were separated. The organic phases were washed with saturated brine (10 mL), dried with anhydrous sodium sulfate, filtered, and the filtrate was concentrated under reduced pressure to remove the solvent. The obtained residue was added with methanol (5 mL) to slurry at room temperature, filtered, and the filter cake was vacuum-dried, and separated by preparative HPLC (mobile phase: acetonitrile/water; acidic system: 0.05% HCl) to obtain target compound WX166. MS-ESI m/z: 237.0 [M+H]$^+$. $^1$H NMR (400 MHz, DMSO_d$_6$) δ: 11.06 (s, 1H), 8.03 (d, J=5.2 Hz, 1H), 7.31 (d, J=5.2 Hz, 1H), 4.45-4.34 (m, 1H), 2.79-2.65 (m, 1H), 2.62-2.51 (m, 1H), 2.34-2.23 (m, 2H).

Embodiment 167: WX167

Synthetic Route:

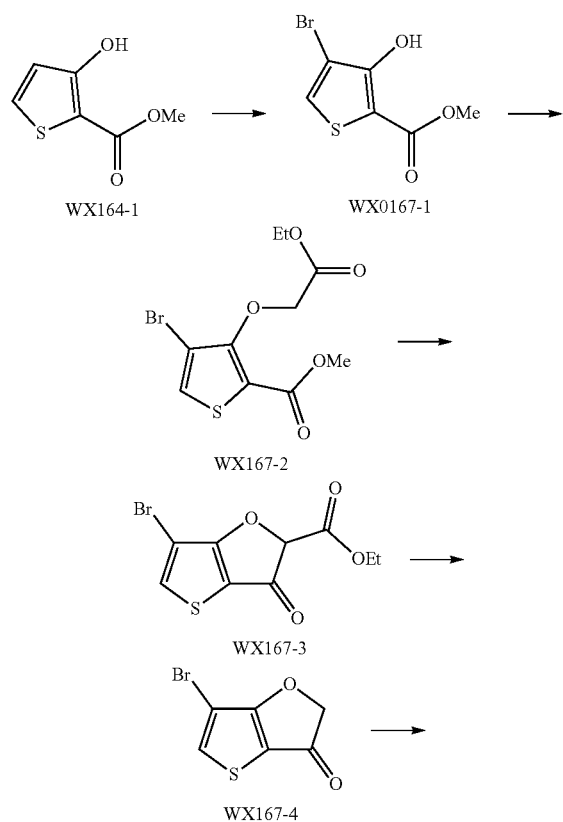

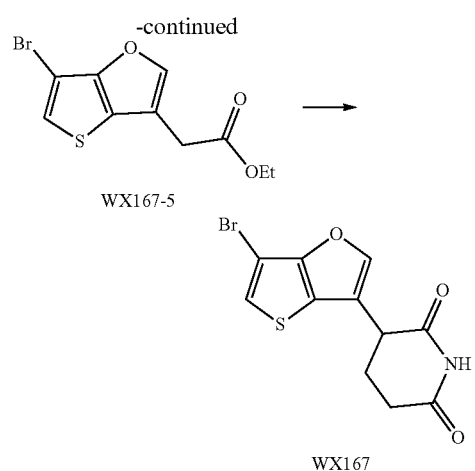

Step 1: Synthesis of Compound WX167-1

Compound WX164-1 (10 g, 63.22 mmol) was dissolved in acetic acid (30 mL) under the protection of nitrogen at 18° C., then liquid bromine (10.10 g, 63.22 mmol, 3.26 mL) was added, and the reaction mixture was reacted with stirring at 18° C. for 36 hours. After the reaction was completed, the reaction solution was directly evaporated to dryness by rotary evaporation, and the obtained residue was stirred with 10 mL of ethanol at room temperature for 10 minutes, filtered, and the filter cake was collected to obtain compound WX167-1. NMR (400 MHz, CDCl$_3$) δ: 9.73 (s, 1H), 7.38 (s, 1H), 3.92 (s, 3H). $^{13}$C NMR (100 MHz, CDCl$_3$) δ: 165.67, 160.31, 128.14, 103.76, 102.53, 52.22.

Step 2: Synthesis of Compound WX167-2

Compound WX167-1 (4.7 g, 19.83 mmol) was dissolved in N,N-dimethylformamide (40 mL) at 18° C., then potassium carbonate (5.48 g, 39.65 mmol), ethyl bromoacetate (3.31 g, 19.83 mmol, 2.19 mL) were sequentially added, and the reaction mixture was reacted with stirring at 18° C. for 3 hours; after the reaction was completed, water (60 mL) and ethyl acetate (60 mL) were added to the reaction system to dilute, and the phases were separated, then the organic phases were collected, and the aqueous phase was extracted with ethyl acetate (50 mL×2). The organic phases were combined, dried with anhydrous sodium sulfate, filtered, and the filtrate was concentrated under reduced pressure to obtain a residue. The obtained residue was separated by column chromatography (eluent: petroleum ether/ethyl acetate=1/0-5/1, v/v), to obtain a crude product of target compound WX167-2. $^1$H NMR (400 MHz, CDCl$_3$) δ: 7.41 (s, 1H), 4.89 (s, 2H), 4.28 (q, J=7.2 Hz, 2H), 3.87 (s, 3H), 1.31 (t, J=7.2 Hz, 3H).

Step 3: Synthesis of Compound WX167-3

The crude product of target compound WX167-2 (7.1 g, 21.97 mmol) from the previous step was dissolved in tetrahydrofuran (100 mL) under the protection of nitrogen at 0° C., then 4 A molecular sieve (5.0 g) and potassium tert-butoxide (2.47 g, 21.97 mmol) were sequentially added, and the reaction mixture was reacted with stirring at 0° C. for 2 hours. After the reaction was completed, water (50 mL) was added to the reaction system, then 2 M dilute hydrochloric acid was added dropwise to adjust pH=5-6, and the mixture was diluted with ethyl acetate (50 mL); and the phases were separated, then the organic phases were collected, and the aqueous phase was extracted with ethyl acetate (30 mL×2). The organic phases were combined, dried with anhydrous sodium sulfate, filtered, and the filtrate was concentrated under reduced pressure to remove the solvent to obtain compound WX167-3.

Step 4: Synthesis of Compound WX167-4

Compound WX167-3 (4.5 g, 15.46 mmol) was dissolved in dioxane (10 mL), water (0 mL) and hydrochloric acid (12 M, 15 mL) at room temperature, then the reaction mixture was heated to 50° C. and reacted with stirring for 12 hours. After the reaction was completed, water (30 mL) and ethyl acetate (50 mL) were added to the reaction system to dilute, and the phases were separated, then the organic phases were collected, and the aqueous phase was extracted with ethyl acetate (30 mL×2). The organic phases were combined, dried with anhydrous sodium sulfate, filtered, and the filtrate was concentrated under reduced pressure to remove the solvent. The obtained residue was stirred with 10 mL of methyl tert-butyl ether at room temperature for 10 minutes, filtered, and the filter cake was collected to obtain compound WX167-4. MS-ESI m/z: 218.9 [M+H]$^+$, 220.9 [M+H+2]$^+$. $^1$H NMR (400 MHz, CDCl$_3$) δ: 7.89 (s, 1H), 5.09 (s, 2H).

Step 5: Synthesis of Compound WX167-5

Compound WX167-4 (2.3 g, 10.50 mmol) was dissolved in toluene (30 mL) at room temperature under the protection of nitrogen, then ethoxyformylmethylene triphenylphosphine (5.49 g, 15.75 mmol) was added, and the reaction mixture was heated to 120° C. and reacted with stirring for 32 hours. After the reaction was completed, the reaction solution was directly concentrated under reduced pressure to remove the solvent. The obtained residue was stirred with 15 mL of methyl tert-butyl ether at room temperature for 10 minutes, filtered, and the filtrate was collected, and the filtrate was concentrated under reduced pressure to remove the solvent. The obtained residue was separated by column chromatography (eluent: petroleum ether/ethyl acetate=1/0-5/1, v/v), to obtain compound WX167-5. MS-ESI m/z: 289.0 [M+H]$^+$, 291.1 [M+H+2]$^+$. $^1$H NMR (400 MHz, CDCl$_3$) δ: 7.52 (d, J=1.2 Hz, 1H), 7.15 (d, J=1.2 Hz, 1H), 4.22 (q, J=7.2 Hz, 2H), 3.61 (d, J=0.8 Hz, 2H), 1.31 (t, J=7.2 Hz, 3H).

Step 6: Synthesis of Compound WX167

Compound WX167-5 (200 mg, 691.69 μmol) was dissolved in N,N-dimethylformamide (3 mL) at 18° C. under the protection of nitrogen, then a N,N-dimethylformamide (0.5 mL) solution of potassium tert-butoxide (77.61 mg, 691.69 μmol) and acrylamide (49.16 mg, 691.69 μmol) was added, and the reaction mixture was stirred at 18° C. for 1 hour. After the reaction was completed, water (10 mL) and ethyl acetate (20 mL) were added to the reaction system to dilute, and the phases were separated, then the organic phases were collected, and the aqueous phase was extracted with ethyl acetate (10 mL×2). The organic phases were combined and concentrated under reduced pressure to remove the solvent. The obtained residue was separated by column chromatography (eluent: petroleum ether/ethyl acetate=1/0-4/1, v/v), and then separated by preparative HPLC (mobile phase: acetonitrile/water; acidic system: 0.05% HCl) to obtain target compound WX167. MS-ESI m/z: 313.9 [M+H]$^+$, 315.9 [M+H+2]$^+$. $^1$H NMR (400 MHz, DMSO_d$_6$) δ: 10.95 (br s, 1H), 7.94 (s, 1H), 7.65 (d, J=1.2 Hz, 1H), 4.03 (dd, J=5.6, 10.4 Hz, 1H), 2.78-2.65 (m, 1H), 2.62-2.53 (m, 1H), 2.26-2.13 (m, 2H).

Embodiment 168: WX168

Synthetic Route:

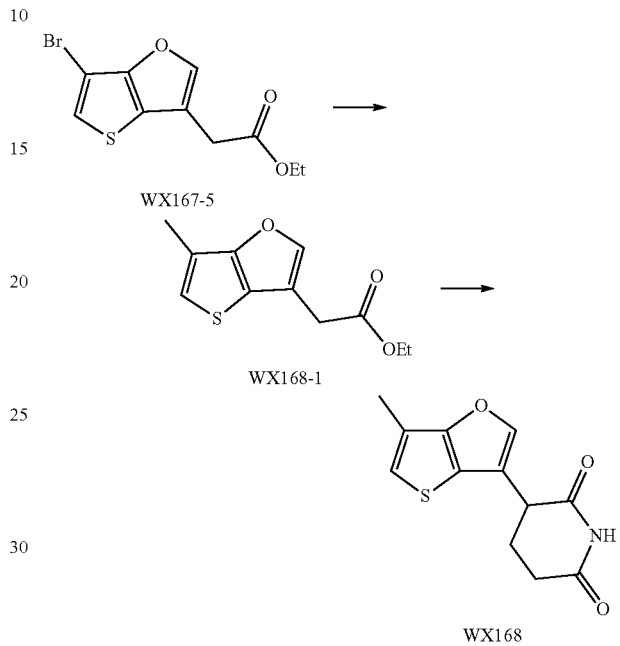

Step 1: Synthesis of Compound WX168-1

Compound WX167-5 (900 mg, 3.11 mmol) was dissolved in 1,4-dioxane (15 mL) and water (5 mL) at room temperature, then methylboronic acid (931.61 mg, 15.56 mmol), sodium carbonate (989.72 mg, 9.34 mmol) and 1,1-bis(diphenylphosphino)ferrocene palladium dichloride dichloromethane complex (507.60 mg, 693.72 μmol) were added, and the reaction mixture was heated to 80° C. and reacted with stirring for 7 hours. After the reaction was completed, water (30 mL) and ethyl acetate (30 mL) were added to the reaction system to dilute, and the phases were separated, then the organic phases were collected, and the aqueous phase was extracted with ethyl acetate (20 mL×2). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-17/3, v/v), to obtain compound WX168-1. $^1$H NMR (400 MHz, CDCl$_3$) δ: 7.47 (d, J=0.8 Hz, 1H), 6.83 (t, J=1.2 Hz, 1H), 4.21 (q, J=7.2 Hz, 2H), 3.60 (d, J=0.8 Hz, 2H), 2.32 (d, J=0.8 Hz, 3H), 1.31 (t, J=7.2 Hz, 3H).

Step 2: Synthesis of Compound WX168

Compound WX168-1 (100 mg, 445.88 μmol) was dissolved in N,N-dimethylamide (10 mL) under the protection of nitrogen at 15° C., then a N,N-dimethylamide (0.5 mL) solution of potassium tert-butoxide (50.03 mg, 445.88 μmol) and acrylamide (31.69 mg, 445.88 μmol) was added, and the reaction mixture was reacted with stirring at 15° C. for 10 minutes. After the reaction was completed, water (10 mL) and ethyl acetate (10 mL) were added to the reaction system to dilute, and the phases were separated, then the organic phases were collected, and the aqueous phase was extracted with ethyl acetate (10 mL×2). The organic phases were combined, concentrated under reduced pressure to remove the solvent, and the obtained residue was separated by column chromatography (eluent: petroleum ether/ethyl acetate=1/0-1/1, v/v), and then separated by preparative HPLC (mobile phase: acetonitrile/water; acidic system: 0.05% HCl) to obtain target compound WX168. MS-ESI m/z: 250.0 [M+H]$^+$ $^1$H NMR (400 MHz, DMSO_d$_6$) δ: 10.91 (s, 1H), 7.81 (s, 1H), 7.11 (t, J=1.2 Hz, 1H), 3.98 (dd, J=5.6, 10.0 Hz, 1H), 2.75-2.63 (m, 1H), 2.62-2.53 (m, 1H), 2.25 (d, J=0.8 Hz, 3H), 2.23-2.10 (m, 2H).

Embodiment 169: WX169

Synthetic Route:

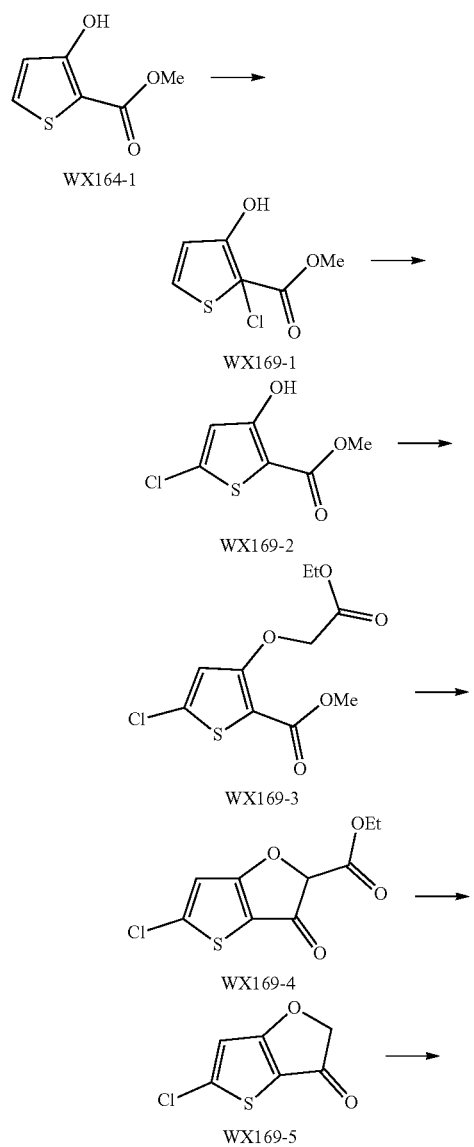

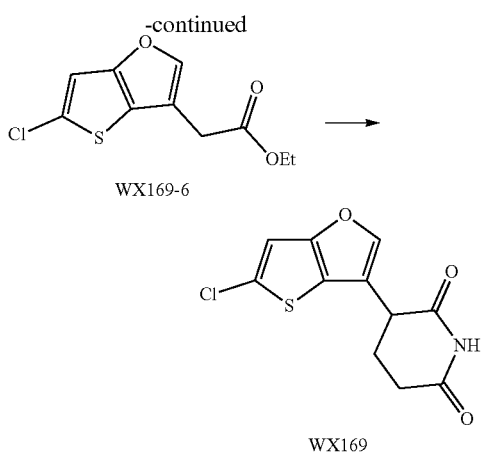

Step 1: Synthesis of Compound WX169-1

Compound WX164-1 (15 g, 94.83 mmol) was dissolved in dichloromethane (75 mL) at 15° C., then a dichloromethane (30 mL) solution of thionyl chloride (25.60 g, 189.66 mmol, 18.96 mL) was slowly added dropwise, and the reaction mixture was stirred at 15° C. for 12 hours. After the reaction was completed, the reaction solution was directly concentrated under reduced pressure to remove the solvent, and the obtained residue was added with n-hexane (50 mL) and stirred at room temperature for 10 minutes, filtered, and the filter cake was collected, and the solvent was removed under reduced pressure to obtain compound WX169-1. MS-ESI m/z: 192.9 [M+H]$^+$. $^1$H NMR (400 MHz, CDCl$_3$) δ: 8.38 (d, J=6.4 Hz, 1H), 6.22 (d, J=6.0 Hz, 1H), 3.84 (s, 3H).

Step 2: Synthesis of Compound WX169-2

Compound WX169-1 (13 g, 67.49 mmol) was dissolved in acetic acid (50 mL) at 15° C., then hydrochloric acid gas was introduced until the system was saturated, and the reaction mixture was reacted with stirring at 15° C. for 72 hours. After the reaction was completed, the reaction solution was filtered directly and the filter cake was discarded. The obtained filtrate was added with ethyl acetate (200 mL) and water (100 mL), then the phases were separated, and the organic phase was collected, dried with anhydrous sodium sulfate, filtered, and the filtrate was concentrated under reduced pressure to remove the solvent. The obtained residue was separated by column chromatography (eluent: petroleum ether/ethyl acetate=1/0-19/1, v/v), to obtain compound WX169-2. $^1$H NMR (400 MHz, CDCl$_3$) δ: 9.65 (br s, 1H), 6.64 (s, 1H), 3.87 (s, 3H).

Step 3: Synthesis of Compound WX169-3

Compound WX169-2 (3 g, 15.57 mmol), ethyl bromoacetate (2.86 g, 17.13 mmol, 1.89 mL), potassium carbonate (4.31 g, 31.15 mmol) were dissolved in N,N-dimethylformamide (30 mL) at 15° C., and the reaction mixture was reacted with stirring at 15° C. for 3 hours; the pH of the mixture was adjusted to 5-6 with 2 M dilute hydrochloric acid, and the mixture was extracted with ethyl acetate (200 mL×2). The organic phases were combined, dried with anhydrous sodium sulfate, filtered, and the filtrate was concentrated under reduced pressure to remove the solvent.

The obtained residue was separated by column chromatography (eluent: petroleum ether/ethyl acetate=20/1-5/1, v/v), to obtain compound WX169-3. MS-ESI m/z: 279.1 [M+H]⁺, 281.1 [M+H+2]⁺. ¹H NMR (400 MHz, CDCl₃) δ: 6.57 (d, J=4.0 Hz, 1H), 4.65 (s, 2H), 4.20 (q, J=7.0 Hz, 2H), 3.76 (s, 3H), 1.23 (t, J=7.2 Hz, 3H).

Step 4: Synthesis of Compound WX169-4

Compound WX169-3 (2.7 g, 9.69 mmol) was dissolved in N,N-dimethylformamide (30 mL) at 15° C., then potassium tert-butoxide (2.17 g, 19.38 mmol) was added, and the reaction mixture was stirred at 15° C. for 4 hours. After the reaction was completed, the pH of the mixture was adjusted to 5-6 with 2 M dilute hydrochloric acid, and the mixture was extracted with ethyl acetate (100 mL×2); the organic phases were combined, dried with anhydrous sodium sulfate, filtered, and the filtrate was concentrated under reduced pressure to remove the solvent to obtain a crude product of compound WX169-4. MS-ESI m/z: 247.1 [M+H]⁺.

Step 5: Synthesis of Compound WX169-5

The crude product of compound WX169-4 (2.3 g, 9.32 mmol) from the previous step was dissolved in hydrochloric acid (5 M, 57.50 mL) and 1,4-dioxane (1 mL) at room temperature, and the reaction mixture was stirred at 50° C. for 6 hours. After the reaction was completed, the mixture was cooled to room temperature, extracted with ethyl acetate (100 mL×2), and the organic phase was combined, dried with anhydrous sodium sulfate, filtered, and the filtrate was concentrated under reduced pressure to remove the solvent; and the obtained residue was separated by column chromatography (eluent: petroleum ether/ethyl acetate=1/0-9/1, v/v) to obtain compound WX169-5. MS-ESI m/z: 175.1 [M+H]⁺. ¹H NMR (400 MHz, CDCl₃) δ: 6.71 (d, J=4.4 Hz, 1H), 4.84 (s, 2H).

Step 6: Synthesis of Compound WX169-6

Compound WX169-5 (0.6 g, 3.44 mmol) was dissolved in toluene (9 mL) at room temperature, then ethoxyformylmethylene triphenylphosphine (1.49 g, 4.47 mmol) was added, and the reaction mixture was heated to 130° C. and reacted with stirring for 72 hours. After the reaction was completed, the reaction solution was concentrated under reduced pressure to remove the solvent. The obtained residue was added with methyl tert-butyl ether (30 mL) and stirred at room temperature for 10 minutes. The mixture was filtered, and the filtrate was collected, and concentrated under reduced pressure to remove the solvent. The obtained residue was separated by column chromatography (eluent: petroleum ether/ethyl acetate=1/0-9/1, v/v), to obtain compound WX169-6. ¹H NMR (400 MHz, CDCl₃) δ: 7.45 (d, J=1.2 Hz, 1H), 6.97 (s, 1H), 4.21 (q, J=7.2 Hz, 2H), 3.57 (s, 2H), 1.31 (t, J=7.2 Hz, 3H).

Step 7: Synthesis of Compound WX169

Compound WX169-6 (0.11 g, 449.54 μmol) was dissolved in tetrahydrofuran (4 mL) at 0° C., then acrylamide (31.95 mg, 449.54 μmol, 31.02 μL) and potassium tert-butoxide (50.44 mg, 449.54 μmol) were added, and the reaction mixture was reacted with stirring at 0° C. for 2 hours. After the reaction was completed, the reaction mixture was added with water (10 mL), and extracted with ethyl acetate (30 mL×2). The organic phases were combined, dried with anhydrous sodium sulfate, filtered, and the filtrate was concentrated under reduced pressure to remove the solvent. The obtained residue was separated by column chromatography (petroleum ether:ethyl acetate=1:1), and then separated by preparative HPLC (mobile phase: methanol/water; acidic system: 0.05% HCl) to obtain target compound WX169. MS-ESI m/z: 269.9 [M+H]⁺, 271.9 [M+H+2]⁺. ¹H NMR (400 MHz, DMSO_d₆) δ: 10.92 (s, 1H), 7.87 (d, J=1.2 Hz, 1H), 7.44 (s, 1H), 3.98 (dd, J=5.0, 10.6 Hz, 1H), 2.73-2.62 (m, 1H), 2.59-2.51 (m, 1H), 2.27-2.07 (m, 2H).

Embodiment 170: WX170

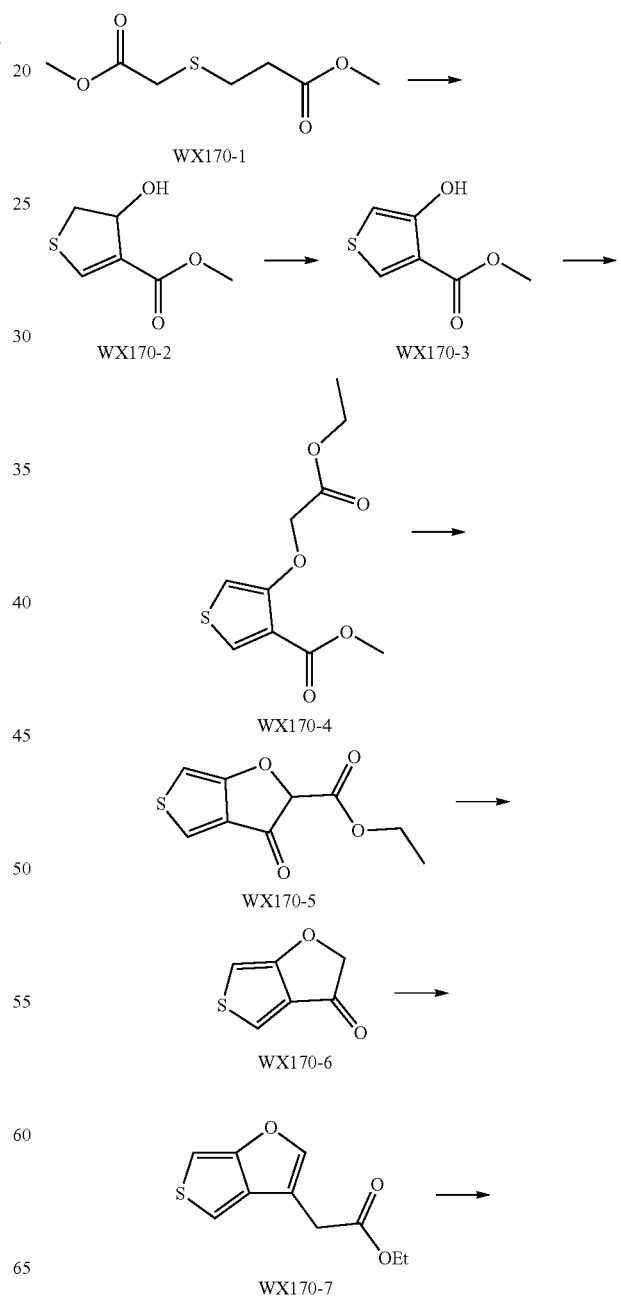

-continued

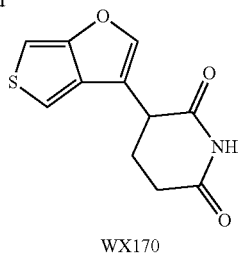

WX170

Step 1: Synthesis of Compound WX170-2

Compound WX170-1 (15 g, 78.03 mmol) was slowly added dropwise to a methanol solution of sodium methoxide (5 M, 46.82 mL) at 70° C., and the reaction mixture was stirred at 70° C. for 1 hour. After the reaction was completed, the reaction solution was concentrated under reduced pressure to remove the solvent. The obtained residue was poured into a mixed system of ice and hydrochloric acid (6 M, 600 mL) and extracted with ethyl acetate (100 mL×2). The organic phases were combined, washed with saturated brine (150 mL), dried with anhydrous sodium sulfate, filtered, and the filtrate was concentrated under reduced pressure to remove the solvent, and the obtained residue was separated by column chromatography (eluent: petroleum ether/ethyl acetate=1/0, v/v) to obtain compound WX170-2. $^1$H NMR (400 MHz, CDCl$_3$) δ: 3.82 (d, J=6.8 Hz, 2H), 3.80 (s, 3H), 3.77 (d, J=5.6 Hz, 2H).

Step 2: Synthesis of Compound WX170-3

Compound WX170-2 (6 g, 37.46 mmol) was dissolved in dichloromethane (60 mL) at 10° C., then a dichloromethane (20 mL) of thionyl chloride (5.56 g, 41.20 mmol, 4.12 mL) was slowly added dropwise, and the reaction mixture was reacted with stirring at 10° C. for 1 hour. After the reaction was completed, the reaction mixture was poured into water (100 mL), and extracted with dichloromethane (150 mL×2). The organic phases were combined, washed with saturated brine (200 mL), dried with anhydrous sodium sulfate, filtered, and the filtrate was concentrated under reduced pressure to remove the solvent. The obtained residue was separated by preparative HPLC (mobile phase: acetonitrile/water; acidic system: 0.1% TFA) to obtain compound WX170-3. MS-ESI m/z: 159.0 [M+H]$^+$. $^1$H NMR (400 MHz, CDCl$_3$) δ: 8.72 (s, 1H), 7.89 (d, J=3.6 Hz, 1H), 6.38 (d, J=3.6 Hz, 1H), 3.91 (s, 3H).

Step 3: Synthesis of Compound WX170-4

Compound WX170-3 (2.7 g, 17.07 mmol) was dissolved in N,N-dimethylformamide (40 mL) at 20° C., then potassium carbonate (3.54 g, 25.60 mmol) and ethyl bromoacetate (3.14 g, 18.78 mmol, 2.08 mL) were sequentially added, and the reaction mixture was reacted with stirring at 20° C. for 12 hours. After the reaction was completed, the reaction mixture was poured into saturated ammonium chloride aqueous solution (100 mL), and extracted with ethyl acetate (100 mL×2). The organic phases were combined, sequentially washed with saturated brine (100 mL), dried with anhydrous sodium sulfate, filtered, and the filtrate was concentrated under reduced pressure to remove the solvent. The obtained residue was separated by column chromatography (eluent: petroleum ether/ethyl acetate=1/0-4/1, v/v), to obtain compound WX170-4. $^1$H NMR (400 MHz, CDCl$_3$) δ: 8.02 (d, J=3.6 Hz, 1H), 6.32 (d, J=3.2 Hz, 1H), 4.66 (s, 2H), 4.27 (q, J=7.2 Hz, 2H), 3.88 (s, 3H), 1.30 (t, J=7.2 Hz, 3H).

Step 4: Synthesis of Compound WX170-5

Compound WX170-4 (2.4 g, 9.83 mmol) was dissolved in tetrahydrofuran (40 mL) under the protection of nitrogen at 0° C., then a tetrahydrofuran solution of potassium tert-butoxide (1 M, 19.65 mL) was added, and the reaction mixture was stirred at 10° C. for 2 hours. After the reaction was completed, water (30 mL) was added to the reaction solution, and the pH of the mixture was adjusted to about 6 with 2 M hydrochloric acid; the mixture was diluted with ethyl acetate (50 mL), and the phases were separated, then the organic phases were collected, and sequentially washed with saturated saline (50 mL), dried with anhydrous sodium sulfate, filtered, and the filtrate was concentrated under reduced pressure to remove the solvent to obtain a crude product of compound WX170-5. MS-ESI m/z: 213.0 [M+H]$^+$.

Step 5: Synthesis of Compound WX170-6

The crude product of compound WX170-5 (2 g, 9.42 mmol) was dissolved in 1,4-dioxane (10 mL) at 20° C., and an aqueous solution (35 mL) of hydrochloric acid (12 M, 21.20 mL) was added, and the mixture was reacted with stirring at 20° C. for 12 hours. After the reaction was completed, the reaction system was added with water (100 mL) and ethyl acetate (100 mL) to dilute. The phases were separated, and the organic phase was collected, and the aqueous phase was extracted with ethyl acetate (50 mL×2). The organic phases were combined, sequentially washed with saturated brine (50 mL), dried with anhydrous sodium sulfate, filtered, and the filtrate was concentrated under reduced pressure to remove the solvent. The obtained residue was separated by column chromatography (eluent: petroleum ether/ethyl acetate=1/0-9/1, v/v), to obtain compound WX170-6. $^1$H NMR (400 MHz, CDCl$_3$) δ: 7.80 (d, J=2.8 Hz, 1H), 6.40 (d, J=2.4 Hz, 1H), 4.98 (s, 2H).

Step 6: Synthesis of Compound WX170-7

Compound WX170-6 (0.4 g, 2.85 mmol) was dissolved in toluene (6 mL) at room temperature under the protection of nitrogen, then ethoxyformylmethylene triphenylphosphine (1.29 g, 3.71 mmol) was added, and the reaction mixture was heated to 130° C. and reacted with stirring for 72 hours. After the reaction was completed, the reaction solution was concentrated under reduced pressure to remove the solvent. The obtained residue was added with methyl tert-butyl ether (10 mL) and stirred at room temperature for 10 min, filtered, and the filtrate was concentrated under reduced pressure to remove the solvent, and the obtained residue was separated by column chromatography (petroleum ether/ethyl acetate=10/1) to obtain compound WX170-7. MS-ESI m/z: 211.1 [M+H]$^+$. $^1$H NMR (400 MHz, CDCl$_3$) δ: 7.55 (d, J=1.2 Hz, 1H), 6.95 (d, J=2.4 Hz, 1H), 6.76-6.70 (m, 1H), 4.20 (q, J=7.2 Hz, 2H), 3.54 (d, J=1.2 Hz, 2H), 1.32-1.23 (m, 3H).

Step 7: Synthesis of Compound WX170

Compound WX170-7 (0.2 g, 951.25 µmol) was dissolved in tetrahydrofuran (4 mL) at 0° C., then acrylamide (67.61 mg, 951.25 µmol) and potassium tert-butoxide (106.74 mg, 951.25 µmol) were added, and the reaction mixture was reacted with stirring at 0° C. for 1 hour. After the reaction was completed, the reaction mixture was added with water (10 mL), and extracted with ethyl acetate (30 mL×2). The organic phases were combined, dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl) to obtain target compound WX170. MS-ESI m/z: 236.0 [M+H]+. 1H NMR (400 MHz, DMSO_d6) δ: 10.88 (s, 1H), 7.85 (s, 1H), 7.22 (d, J=2.8 Hz, 1H), 7.12 (d, J=2.8 Hz, 1H), 3.90 (dd, J=4.8, 11.6 Hz, 1H), 2.76-2.64 (m, 1H), 2.60-2.55 (m, 1H), 2.37-2.22 (m, 1H), 2.14-2.03 (m, 1H).

Embodiment 171: WX171

Synthetic Route:

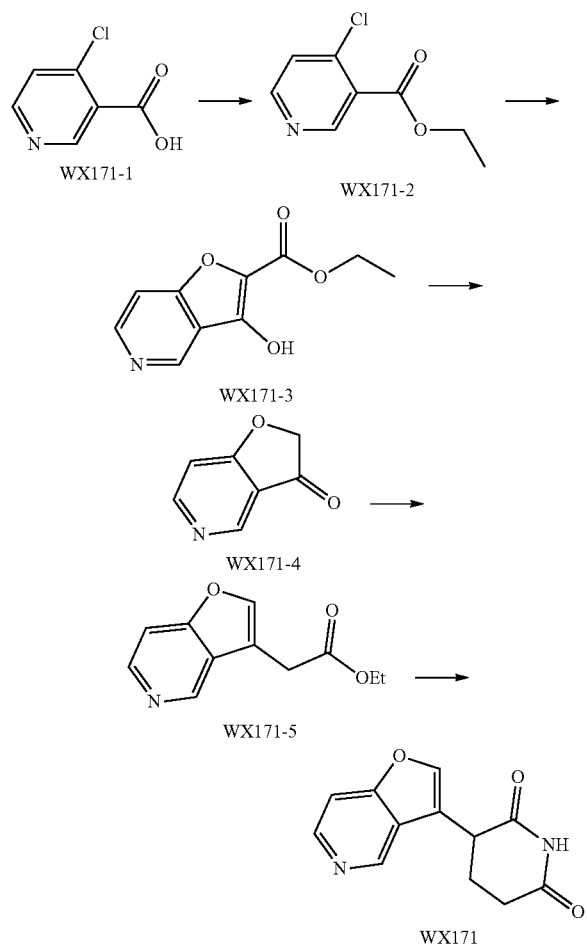

Step 1: Synthesis of Compound WX171-2

Compound WX171-1 (13.5 g, 85.68 mmol) was dissolved in N,N-dimethylamide (100 mL) at room temperature, then potassium carbonate (17.76 g, 128.53 mmol) and iodoethane (20.05 g, 128.53 mmol, 10.28 mL) were added, and the reaction mixture was stirred at 30° C. for 18 hours. After the reaction was completed, the mixture was added with water (100 mL), and extracted with ethyl acetate (100 mL×3). The organic phases were combined, washed with semi-saturated brine (50 mL×2), dried with anhydrous sodium sulfate, filtered, and the filtrate was concentrated under reduced pressure to remove the solvent to obtain a crude product of compound WX171-2. MS-ESI m/z: 186.1 [M+H]+. 1H NMR (400 MHz, CDCl3) δ: 9.00 (s, 1H), 8.55 (d, J=5.2 Hz, 1H), 7.39 (d, J=5.2 Hz, 1H), 4.41 (q, J=7.2 Hz, 2H), 1.40 (t, J=7.2 Hz, 3H).

Step 2: Synthesis of Compound WX171-3

Sodium hydride (6.90 g, 172.41 mmol, purity: 60%) was added to dimethoxyethane (300 mL) at 0° C. under the protection of nitrogen, then ethyl glycolate (22.44 g, 215.51 mmol, 20.77 mL) was slowly added, and the reaction mixture was stirred at 0° C. for 30 minutes, restored to room temperature, and a dimethoxyethane (100 mL) solution of the crude product of compound WX171-2 (16 g, 86.20 mmol) from the previous step was added; the reaction mixture was reacted with stirring at room temperature for 12 hours, then heated to 60° C. and reacted with stirring for 2 hours. After the reaction was completed, the reaction solution was directly concentrated under reduced pressure to remove the solvent. The obtained residue was added to water (200 mL), then the pH of the mixture was adjusted to 6-7 by adding acetic acid dropwise, and yellow solid was formed; the mixture was filtered, and the filter cake was collected to obtain a crude product of compound WX171-3. MS-ESI m/z: 208.1 [M+H]+. 1H NMR (400 MHz, DMSO_d6) δ: 9.14 (s, 1H), 8.57 (d, J=6.0 Hz, 1H), 7.63 (dd, J=0.8, 6.0 Hz, 1H), 4.30 (q, J=7.0 Hz, 2H), 1.29 (t, J=7.2 Hz, 3H).

Step 3: Synthesis of Compound WX171-4

The crude product of compound WX171-3 (2 g, 9.65 mmol) from the previous step was dissolved in dilute hydrochloric acid (3 M, 22.52 mL) at room temperature, and the reaction mixture was heated to 110° C. and reacted with stirring for 4 hours. After the reaction was completed, the mixture was cooled to room temperature, concentrated under reduced pressure to remove part of water. The obtained residue was poured into saturated sodium bicarbonate aqueous solution (50 mL), and chloroform (20 mL) was added, and the phases were separated, then the organic phases were collected, and the aqueous phase was extracted with chloroform (20 mL×2). The organic phases were combined, dried with anhydrous sodium sulfate, filtered, and the filtrate was concentrated under reduced pressure to remove the solvent to obtain a crude product of compound WX171-4. MS-ESI m/z: 136.1 [M+H]+.

Step 4: Synthesis of Compound WX171-5

The crude product of compound WX171-4 (400 mg, 2.96 mmol) from the previous step was dissolved in toluene (10 mL) at room temperature, then ethyl(triphenylphosphoranylidene)acetate (1.55 g, 4.44 mmol) was added, and the reaction mixture was heated to 130° C. and reacted with stirring for 17 hours. After the reaction was completed, the reaction solution was directly concentrated under reduced pressure to remove the solvent. The obtained residue was stirred at room temperature with methyl tert-butyl ether (10 mL) for 10 minutes, filtered, and the collected filtrate was concentrated under reduced pressure to remove the solvent. The obtained residue was separated by column chromatography (eluent: petroleum ether/ethyl acetate=1/0-1/1, v/v), to obtain compound WX171-5. MS-ESI m/z: 206.1 [M+H]+.

$^1$H NMR (400 MHz, CDCl$_3$) δ: 8.94 (d, J=0.8 Hz, 1H), 8.52 (d, J=6.0 Hz, 1H), 7.67 (s, 1H), 7.43 (dd, J=0.8, 5.6 Hz, 1H), 4.22 (q, J=7.2 Hz, 2H), 3.76 (d, J=1.2 Hz, 2H), 1.29 (t, J=7.2 Hz, 3H).

Step 5: Synthesis of Compound WX171

Compound WX171-5 (350 mg, 1.71 mmol) was dissolved in tetrahydrofuran (10 mL) at room temperature, then potassium tert-butoxide (191.38 mg, 1.71 mmol) and acrylamide (121.23 mg, 1.71 mmol) were sequentially added, and the reaction mixture was reacted with stirring at room temperature for 2 hours. After the reaction was completed, water (5 mL) and ethyl acetate (10 mL) were added to the reaction system to dilute, and the phases were separated, then the organic phases were collected, and the aqueous phase was extracted with ethyl acetate (10 mL×2). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-1/4, v/v), and the obtained crude product was stirred with methanol (2 mL) at room temperature for 10 minutes, filtered, and the filter cake was collected to obtain target compound WX171. MS-ESI m/z: 231.0 [M+H]$^+$. $^1$H NMR (400 MHz, DMSO_d$_6$) δ: 10.96 (s, 1H), 8.93 (d, J=0.8 Hz, 1H), 8.47 (d, J=5.6 Hz, 1H), 8.03 (s, 1H), 7.67 (dd, J=0.8, 6.0 Hz, 1H), 4.25 (dd, J=4.8, 12.4 Hz, 1H), 2.82-2.71 (m, 1H), 2.69-2.57 (m, 1H), 2.45-2.32 (m, 1H), 2.21-2.11 (m, 1H).

Embodiment 172: WX172

Synthetic Route:

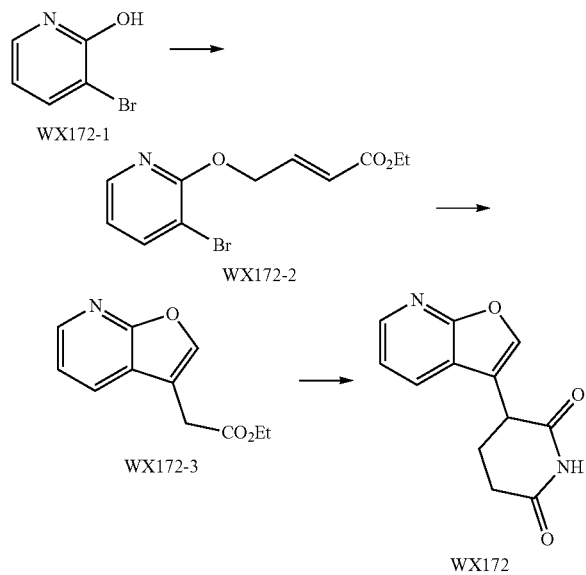

Step 1: Synthesis of Compound WX172-2

Compound WX172-1 (5.0 g, 28.74 mmol) was dissolved in toluene (50 mL) under the protection of nitrogen at room temperature, then ethyl 4-bromocrotonate (5.55 g, 28.74 mmol, 3.96 mL) and silver carbonate (15.85 g, 57.47 mmol) were added, and the reaction mixture was heated to 80° C. and reacted with stirring for 12 hours. After the reaction was completed, the mixture was cooled to room temperature, and the reaction mixture was diluted with ethyl acetate (50 mL), filtered, then the filtrate was collected, and the solvent from the filtrate was removed under reduced pressure. The obtained residue was separated by column chromatography (eluent: petroleum ether/ethyl acetate=1/0-9/1, v/v), to obtain compound WX172-2. $^1$H NMR (400 MHz, CDCl$_3$) δ: 8.07 (dd, J=1.5, 4.9 Hz, 1H), 7.84 (dd, J=1.7, 7.6 Hz, 1H), 7.12 (td, J=4.1, 15.7 Hz, 1H), 6.82 (dd, J=5.0, 7.6 Hz, 1H), 6.21 (td, J=2.1, 15.7 Hz, 1H), 5.09 (dd, J=2.1, 4.1 Hz, 2H), 4.22 (q, J=7.1 Hz, 2H), 1.31 (t, J=7.2 Hz, 3H).

Step 2: Synthesis of Compound WX172-3

Compound WX172-2 (4.8 g, 16.78 mmol) was dissolved in N,N-dimethylformamide (50 mL) under the protection of nitrogen at room temperature, then sodium carbonate (3.56 g, 33.55 mmol) was added, and chloro(2-dicyclohexylphosphino-2',4',6'-triisopropyl-1,1'-biphenyl)[2-(2'-amino-1,1'-biphenyl)]palladium (II) (1.32 g, 1.68 mmol) was added, and the reaction mixture was heated to 50° C. and reacted with stirring for 100 hours. After the reaction was completed, water (100 mL) and ethyl acetate (100 mL) were added to the reaction system to dilute, and the phases were separated, then the organic phases were collected, and the aqueous phase was extracted with ethyl acetate (50 mL×2). The organic phases were combined, sequentially washed with semi-saturated brine (30 mL×2), dried with anhydrous sodium sulfate, filtered, and the filtrate was concentrated under reduced pressure to remove the solvent. The obtained residue was separated by column chromatography (eluent: petroleum ether: /ethyl acetate=1/0-4/1, v/v), to obtain compound WX172-3. $^1$H NMR (400 MHz, CDCl$_3$) δ: 8.36 (dd, J=1.6, 4.8 Hz, 1H), 7.97 (dd, J=1.6, 7.7 Hz, 1H), 7.71 (s, 1H), 7.25 (d, J=4.9 Hz, 1H), 4.21 (q, J=7.2 Hz, 2H), 3.70 (s, 2H), 1.28 (t, J=7.2 Hz, 3H).

Step 3: Synthesis of Compound WX172

Compound WX172-3 (50 mg, 243.65 μmol) was dissolved in N,N-dimethylformamide (2 mL) at room temperature under the protection of nitrogen, then potassium tert-butoxide (27.34 mg, 243.65 μmol) and acrylamide were added (17.32 mg, 243.65 μmol), and the reaction mixture was reacted with stirring at room temperature for 2 hours. After the reaction was completed, water (10 mL) and ethyl acetate (10 mL) were added to the reaction system to dilute, and the phases were separated, then the organic phases were collected, and the aqueous phase was extracted with ethyl acetate (10 mL×2). The organic phases were combined, dried with anhydrous sodium sulfate, filtered, and the filtrate was concentrated under reduced pressure to remove the solvent. The obtained residue was separated by preparative HPLC (mobile phase: acetonitrile/water; acid system: 0.05% HCl), to obtain target compound WX172. MS-ESI m/z: 231.1 [M+H]$^+$. $^1$H NMR (400 MHz, DMSO_d$_6$) δ:10.92 (s, 1H), 8.31 (dd, J=1.6, 4.8 Hz, 1H), 8.10 (dd, J=1.6, 7.7 Hz, 1H), 8.02 (s, 1H), 7.35 (dd, J=4.8, 7.7 Hz, 1H), 4.17 (dd, J=4.8, 12.4 Hz, 1H), 2.81-2.65 (m, 1H), 2.64-2.56 (m, 1H), 2.40-2.30 (m, 1H), 2.18-2.09 (m, 1H).

Referring to the synthesis method in Embodiment 172, each embodiment in Table 31 is synthesized, and the LCMS and HNMR data are shown in Table 32.

TABLE 31

| Embodiments | Fragment 1 | Structure | Compound |
|---|---|---|---|
| 173 | 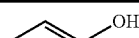 WX173-1 | 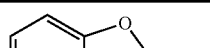 | WX173 |

TABLE 32

| Embodiments | Compound | HNMR | LCMS |
|---|---|---|---|
| 173 | WX173 | $^1$H NMR (400 MHZ, DMSO-$d_6$) δ: 10.91 (s, 1H), 8.49 (dd, J = 1.2, 4.4 Hz, 1H), 8.25 (s, 1H), 8.03 (dd, J = 1.2, 8.4 Hz, 1H), 7.35 (dd, J = 4.8, 8.4 Hz, 1H), 4.16 (dd, J = 4.8, 12.0 Hz, 1H), 2.82-2.71 (m, 1H), 2.69-2.55 (m, 1H), 2.47-2.40 (m, 1H), 2.20-2.10 (m, 1H). | MS-ESI m/z: 231.1 [M + H]$^+$. |

Embodiment 174: WX174

Synthetic Route:

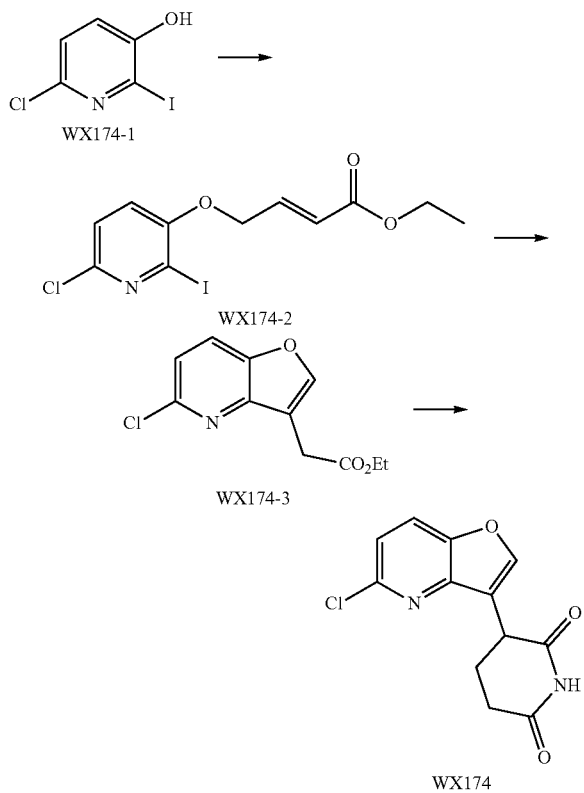

Step 1: Synthesis of Compound WX174-2

Compound WX174-1 (2.5 g, 9.79 mmol) was dissolved in toluene (30 mL) under the protection of nitrogen at room temperature, then ethyl 4-bromocrotonate (1.89 g, 9.79 mmol, 1.35 mL) and silver carbonate (5.40 g, 19.57 mmol) were sequentially added, and the reaction mixture was heated to 80° C. and reacted with stirring for 3 hours. After the reaction was completed, the reaction solution was directly filtered, and the filtrate was concentrated under reduced pressure to remove the solvent. The obtained residue was separated by column chromatography (eluent: petroleum ether/ethyl acetate=1/0-4/1, v/v), to obtain compound WX174-2. MS-ESI m/z: 368.0 [M+H]t 370.0 [M+H+2]$^+$. $^1$H NMR (400 MHz, CDCl$_3$) δ: 7.81 (s, 1H), 7.78 (s, 1H), 7.06 (td, J=4.0, 16.0 Hz, 1H), 6.31 (td, J=2.0, 16.0 Hz, 1H), 4.83 (dd, J=2.0, 4.0 Hz, 2H), 4.25 (q, J=7.0 Hz, 2H), 1.32 (t, J=7.2 Hz, 3H).

Step 2: Synthesis of Compound WX174-3

Compound WX174-2 (1.7 g, 4.63 mmol) was dissolved in N,N-dimethylformamide (20 mL) at room temperature under the protection of nitrogen, then sodium carbonate (980.40 mg, 9.25 mmol) was added, and finally chloro(2-dicyclohexylphosphino-2',4',6'-triisopropyl-1,1'-biphenyl)[2-(2'-amino-1,1'-biphenyl)]palladium (II) (363.90 mg, 462.50 µmol) was added, and the reaction mixture was heated to 80° C. and reacted with stirring for 108 hours. After the reaction was completed, water (50 mL) and ethyl acetate (50 mL) were added to the reaction system to dilute, and the phases were separated, then the organic phases were collected, and the aqueous phase was extracted with ethyl acetate (50 mL×2). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-4/1, v/v), to obtain compound WX174-3. MS-ESI m/z: 240.1 [M+H]$^+$, 242.1 [M+H+2]$^+$. $^1$H NMR (400 MHz, CDCl$_3$) δ: 8.62 (s, 1H), 7.80 (s, 1H), 7.56 (s, 1H), 4.22 (q, J=7.2 Hz, 2H), 3.68 (s, 2H), 1.30 (t, J=7.2 Hz, 3H).

Step 3: Synthesis of Compound WX174

Compound WX174-3 (100 mg, 417.27 µmol) was dissolved in N,N-dimethylformamide (2 mL) at 17° C. under the protection of nitrogen, then potassium tert-butoxide (46.82 mg, 417.27 µmol) and acrylamide (29.66 mg, 417.27 µmol) were sequentially added, and the reaction mixture was reacted with stirring at 17° C. for 1 hour. After the reaction was completed, water (10 mL) and ethyl acetate (10 mL) were added to the reaction system to dilute, and the phases were separated, then the organic phases were collected, and the aqueous phase was extracted with ethyl acetate (10 mL×2). The organic phases were combined, dried with anhydrous sodium sulfate, filtered, and the filtrate was concentrated under reduced pressure to remove the solvent. The obtained residue was separated by column chromatography (eluent: petroleum ether/ethyl acetate=1/0-1/1, v/v), and the obtained crude product was stirred with methanol (2 mL) for 10 min at room temperature, filtered and the filter cake was collected to obtain target compound WX174. MS-ESI m/z: 265.0 [M+H]+, 267.0 [M+H+2]+. 1H NMR (400 MHz, DMSO-$d_6$) δ: 10.94 (s, 1H), 8.79 (d, J=0.8 Hz, 1H), 8.24 (s, 1H), 7.84 (s, 1H), 4.19 (dd, J=5.0, 12.6 Hz, 1H), 2.80-2.65 (m, 1H), 2.64-2.54 (m, 1H), 2.45-2.31 (m, 1H), 2.15-2.04 (m, 1H).

Embodiment 175: WX175

Synthetic Route:

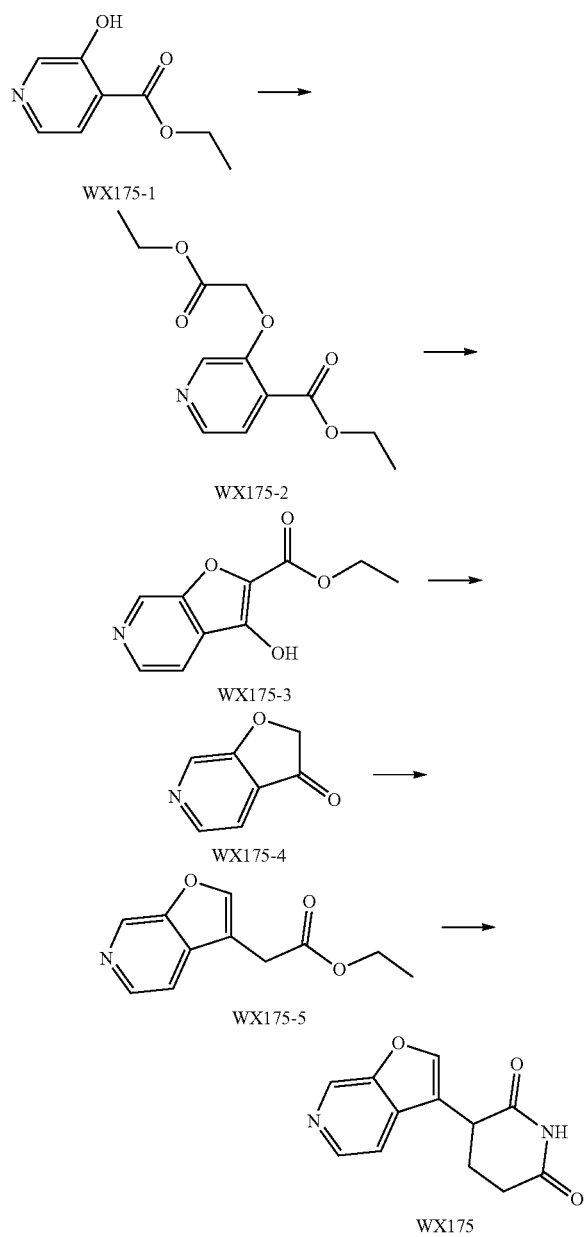

Step 1: Synthesis of Compound WX175-2

Triphenylphosphine (7.06 g, 26.92 mmol) and diisopropyl azodicarboxylate (5.49 g, 27.16 mmol, 5.28 mL) were dissolved in tetrahydrofuran (50 mL) under the protection of nitrogen at −5° C., then ethyl glycolate (3.74 g, 35.89 mmol, 3.46 mL) was added, and the reaction mixture was stirred at 0 to 5° C. for 15 min; compound WX175-1 (3 g, 17.95 mmol) was added, and the reaction mixture was reacted with stirring at 15° C. for 12 hours. After the reaction was completed, a tetrahydrofuran (50 mL) solution of compound WX175-2 was obtained. MS-ESI m/z: 254.1 [M+H]+.

Step 2: Synthesis of Compound WX175-3

Potassium tert-butoxide (2.42 g, 21.54 mmol) was slowly added to a tetrahydrofuran (50 mL) solution of compound WX175-2 (17.95 mmol) under the protection of nitrogen at 0° C. The reaction mixture was slowly restored to 15° C. and reacted with stirring for 3 hours. After the reaction was completed, the mixture was cooled to 0° C., and quenched with 10 mL of saturated ammonium chloride aqueous solution; solid was precipitated, filtered, and the filter cake was washed with ethyl acetate (10 mL×2); the filter cake was collected, and the solvent was removed by concentration under reduced pressure to obtain a crude product of compound WX175-3. MS-ESI m/z: 208.1 [M+H]+.

Step 3: Synthesis of Compound WX175-4

The crude product of compound WX175-3 (2.5 g, 12.07 mmol) from the previous step was dissolved in a mixed solution of hydrochloric acid (12 M, 5.03 mL) and water (50 mL) at room temperature, then the reaction mixture was heated to 100° C. and reacted with stirring for 13 hours. After the reaction was completed, the mixture was cooled to room temperature; the pH of the mixture was adjusted to 8-9 by adding sodium hydroxide slowly, and the mixture was extracted with ethyl acetate (50 mL×3). The organic phases were combined, dried with anhydrous sodium sulfate, filtered, and the solvent was removed by concentration under reduced pressure to obtain compound WX175-4. MS-ESI m/z: 136.1 [M+H]+.

Step 4: Synthesis of the hydrochloride of compound WX175-5

Compound WX175-4 (650 mg, 4.81 mmol) was dissolved in toluene (10 mL) at room temperature under the protection of nitrogen, then ethyl(triphenylphosphoranylidene)acetate (2.51 g, 7.22 mmol) was added, and the reaction mixture was heated to 130° C. and reacted with stirring for 50 hours. After the reaction was completed, the reaction solution was directly concentrated under reduced pressure to remove the solvent. The obtained residue was stirred at room temperature with methyl tert-butyl ether (10 mL) for 10 minutes, filtered, and the filtrate was collected and concentrated under reduced pressure to remove the solvent. The obtained residue was separated by column chromatography (eluent: petroleum ether/ethyl acetate=1/0-7/3, v/v), to obtain compound WX175-5. 1H NMR (400 MHz, CDCl3) δ: 8.90 (s, 1H), 8.47 (d, J=5.2 Hz, 1H), 7.77 (s, 1H), 7.55 (d, J=5.2 Hz, 1H), 4.21 (q, J=7.2 Hz, 2H), 3.72 (s, 2H), 1.29 (t, J=7.2 Hz, 3H).

Step 5: Synthesis of Compound WX175

Compound WX175-5 (200 mg, 974.61 μmol) was dissolved in N,N-dimethylformamide (3 mL) under the protection of nitrogen at 17° C., then potassium tert-butoxide (109.36 mg, 974.61 μmol) and acrylamide (62.35 mg, 877.15 µmol) were added, and the reaction mixture was reacted with stirring at 17° C. for 2 hours. After the reaction was completed, water (10 mL) and ethyl acetate (10 mL) were added to the reaction system to dilute, and the phases were separated, then the organic phases were collected, and the aqueous phase was extracted with ethyl acetate (10 mL×2). The organic phases were combined, dried with anhydrous sodium sulfate, filtered, and the filtrate was concentrated under reduced pressure to remove the solvent. The obtained residue was separated by preparative HPLC (mobile phase: acetonitrile/water; acidic system: 0.05% HCl) to obtain the hydrochloride of target compound WX175. MS-ESI m/z: 231.1 [M+H]$^+$ $^1$H NMR (400 MHz, DMSO-$d_6$) δ: 11.03 (s, 1H), 9.50 (s, 1H), 8.67 (s, 1H), 8.64 (d, J=6.4 Hz, 1H), 8.22 (d, J=6.0 Hz, 1H), 4.36 (dd, J=4.8, 12.8 Hz, 1H), 2.83-2.72 (m, 1H), 2.69-2.60 (m, 1H), 2.44-2.31 (m, 1H), 2.21-2.12 (m, 1H).

Experimental Embodiment 1: In Vitro Test of IKZF3 Protein Level in Multiple Myeloma Cells Experimental Purpose:

The regulation of IKZF3 protein level in multiple myeloma cell MX1.1S by compounds at different concentration conditions was studied by WB method.

Experimental Scheme:
1) MM.1S cells were thawed and passaged twice;
2) MM.1S cells were seeded in a 6-well plate at 1×10$^6$ cells per well, and then treated with a certain concentration of test compounds;
3) after 16 hours of treatment, the cultured cell samples were dissolved in RIPA buffer (Sigma-Aldrich) or NETN buffer (150 mM NaCl, 1% NP-40, 50 mm Tris-HCl, pH=8.0) with intact histone enzyme inhibitor (Roche) placed on ice, and stood for 20 minutes;
4) after centrifugation (rotational speed: 17950 rpm) for 15 minutes, the supernatant was collected and quantified for protein (Pierce BCA Protein Assay Kit, Thermo);
5) equal amounts of 20 Kg of protein were separated by SDS-PAGE, and transferred to PVDF or nylon membranes (Invitrogen);
6) 5% skimmed milk powder was added, and then incubated overnight at 4° C. in 5% BSA with primary antibodies (anti-IKZF3 (NBP2-24495, Novps Biologicals) and anti-Actin (1844-1, Epitomics));
7) finally, after 1 hour of reaction with HRP-linked second antibody (Goat-anti-rabbit IgG (sc-2004, Santa Cruz)), the bands on the membrane were detected with chemiluminescent substrate (Thermo Scientific).

The experimental results are shown in FIG. 1.

Conclusions:

After treating the multiple myeloma cells MM.'S with the compounds of the present disclosure at the concentrations of 100 nM or 50 nM and 500 nM, WB detection showes that the intracellular IKZF3 protein level is significantly decreased.

Experimental Embodiment 2: In Vivo Pharmacodynamics Study of Compounds in Human Myeloma NCI-H929 Cell Subcutaneous Xenograft Tumor NOD SCID Mouse Model Cell culture: Human myeloma NCI-H929 cells (ATCC, Manassas, Virginia, Cat. No.: CRL-9068) were cultured in vitro in monolayer, and the culture conditions were RPMI-1640 medium with 10% fetal bovine serum, plus 0.05 mM 2-mercaptoethanol, 100 U/mL penicillin and 100 Kg/mL streptomycin, 37° C., 5% $CO_2$ incubator. Trypsin-EDTA was used for routine digestion twice a week. When the cell saturation was 80%-90%, and the number reached the requirement, the cells were collected, counted and inoculated.

Animals: NOD SCID mice, female, 6-8 weeks old, weight 18-20 g.

Experimental Scheme:

0.2 mL (5×10$^6$ cells) of NCI-H929 cells (plus Matrigel, v/v=1:1) were subcutaneously inoculated into the right back of each mouse, and group administration was started when the average tumor volume reached about 150 mm 3. The experimental compound was administered orally for four cycles, with a seven-day administration cycle, twice a day (12 hours each interval) or once a day (24 hours each interval). The tested compound WX015 was administered at a dosage of 10 mg/kg (twice a day from day 0 to day 17, once a day from day 18 to day 27) and 30 mg/kg (twice a day from day 0 to day 8 and once a day from day 9 to day 27), and the tumor volume was measured twice a week with a two-dimensional caliper, and the volume was measured in cubic millimeters, calculated by the following formula: V=0.5a×b$^2$, wherein a and b were the long and short diameters of the tumor, respectively. The anti-tumor efficacy was determined by dividing the average tumor volume of the animals treated with compound by the average tumor volume of the untreated animals.

Experimental Results:

The test results are shown in Table 33.

Table 33 Test results of compounds of the present disclosure in human myeloma NCI-H929 cell subcutaneous xenograft tumor NOD SCID mouse model

| Group | Administration dose | Tumor volume (mm$^3$)$^a$ (Day 0) | Tumor volume (mm$^3$)$^a$ (Day 27) | TGI (%) (Day 27) |
|---|---|---|---|---|
| Solvent control | 0 mg/kg | 141 ± 10 | 1667 ± 375 | / |
| WX015 | 10 mg/kg | 141 ± 13 | 411 ± 153 | 82.3 |
| WX015 | 30 mg/kg | 141 ± 12 | 43 ± 17 | 106.4 |

$^a$mean + SEM, n = 6.
TGI: Tumor Growth Inhibition.
TGI(%) = [1-(average tumor volume at the end of administration of a certain treatment group-average tumor volume at the beginning of administration in this treatment group)/(average tumor volume at the end of treatment in the solvent control group-average tumor volume at the beginning of treatment in the solvent control group)] × 100%.

Conclusions:

Compound WX015 of the present disclosure exhibits significant tumor shrinking effect on the in vivo pharmacodynamic model of human myeloma NCI-H929.

The invention claimed is:

1. A compound represented by formula (III) or a pharmaceutically acceptable salt thereof,

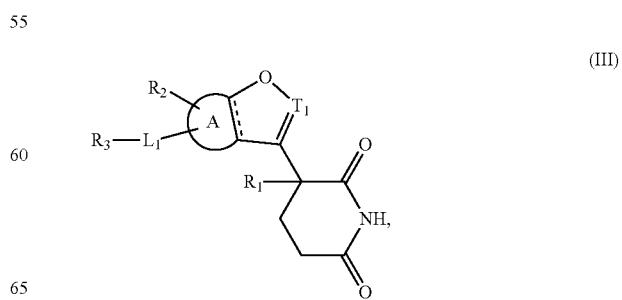

wherein,

⚡ is selected from a single bond and a double bond;

T₁ is selected from C(R₄) and N;

ring A is selected from phenyl, pyridyl and thienyl;

R₁ is selected from H, F, Cl, Br and I;

R₂ is selected from H, F, Cl, Br, I, OH, NH₂ and OCH₃;

L₁ is selected from a bond, —(CR₅)ₙ—, —O(CR₅)ₙ—, —S(CR₅)ₙ—, —NH(CR₅)ₙ—, #—NHCO—, —CONHCH₂—, —SOCH₂—, —SO₂CH₂—, —NHSO₂—, —CH═CH—, —N═C(Ph)-, —O-cyclobutyl-, —O-cyclopentyl-, —CO-piperazinyl-, and —SO₂-piperazinyl-;

R₃ is selected from H, F, Cl, Br, I, OH, NH₂, CN, COOH, NHCOOH, COOC₁₋₄ alkyl, C₁₋₃ alkyl, C₁₋₃ alkoxy, C₂₋₃ alkenyl, phenyl, pyridyl, tetrahydropyranyl,

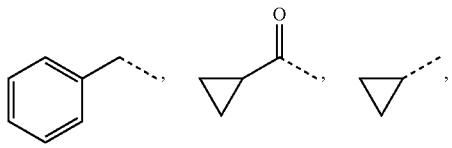

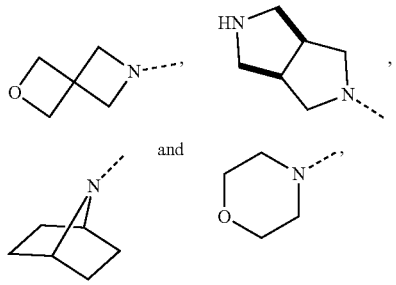

and the COOH, NHCOOH, COOC₁₋₄ alkyl, C₁₋₃ alkyl, C₁₋₃ alkoxy, C₂₋₃ alkenyl, phenyl, pyridyl, tetrahydropyranyl,

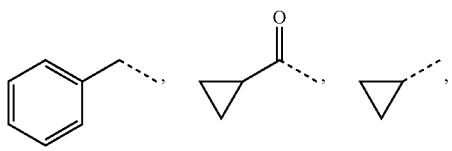

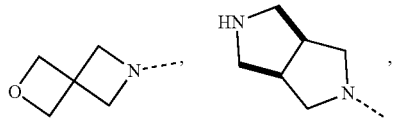

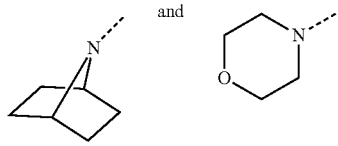

are optionally substituted by 1, 2, or 3 Rₐ;

R₄ is selected from H, F, Cl, Br, I and CH₃;

R₅ is selected from H, F, Cl, Br and I;

Rₐ is selected from H, F, Cl, Br, I, OH, NRR', CN, C₁₋₄ alkyl, C₁₋₃ alkoxy, COOCH₃, CONH₂ and

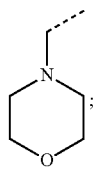

R and R' are each independently selected from H and CH₃;

n is selected from 1, 2, 3;

a site with "#" is the site connected with R₃ group.

2. The compound or the pharmaceutically acceptable salt thereof as defined in claim 1, wherein, the structural unit

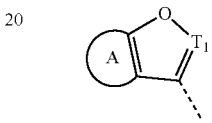

is selected from

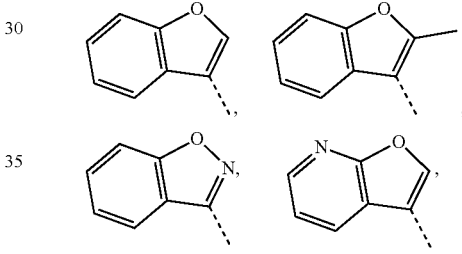

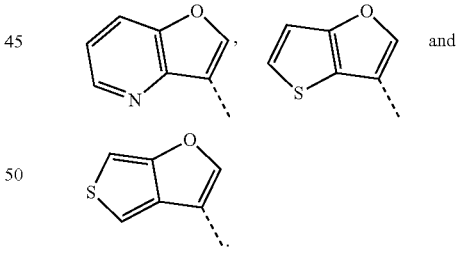

3. The compound or the pharmaceutically acceptable salt thereof as defined in claim 1, wherein, L₁ is selected from a bond, —CH₂—, —OCH₂—, —OCH₂CH₂—, —OCH₂CH₂CH₂—, —OCF₂—, —SCH₂—, —NHCH₂—, #—NHCO—, —CONHCH₂—, —SOCH₂—, —SO₂CH₂—, —NHSO₂—, —CH═CH—, —N═C(Ph)-,

233

-continued

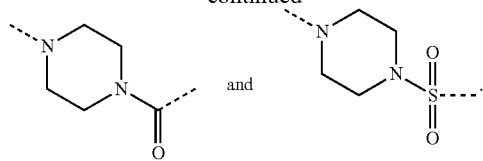
and

4. The compound or the pharmaceutically acceptable salt thereof as defined in claim 1, wherein, $R_a$ is selected from H, F, Cl, Br, I, OH, $NH_2$, $N(CH_3)_2$, CN, $CH_3$, $CH_2CH_3$, $C(CH_3)_3$, $OCH_3$, $COOCH_3$, $CONH_2$ and

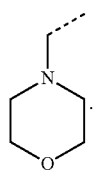

5. The compound or the pharmaceutically acceptable salt thereof as defined in claim 1, wherein, $R_3$ is selected from H, F, Cl, Br, I, OH, $NH_2$, CN, $CH_3$, $CH_2CH_3$, $CH_2CH_2CH_3$, $OCH_3$, $COOCH_2CH_3$, COOH, NHCOOH, $CH=CH_2$,

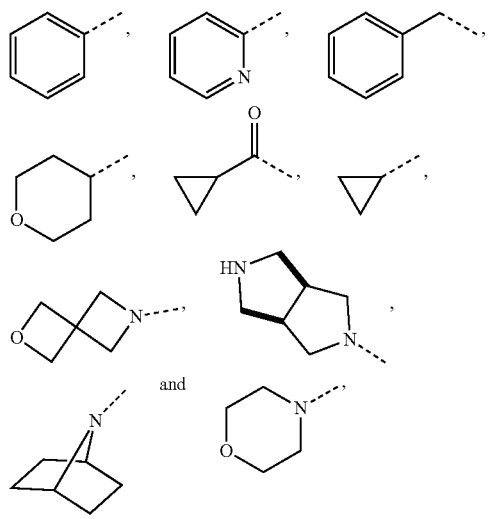

and the $CH_3$, $CH_2CH_3$, $CH_2CH_2CH_3$, $OCH_3$, $COOCH_2CH_3$, COOH, NHCOOH, $CH=CH_2$,

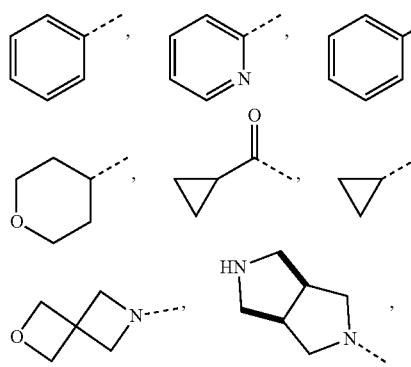

234

-continued

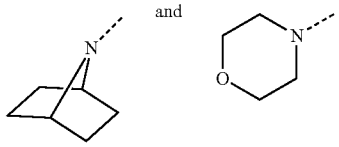
and are optionally substituted by 1, 2, or 3 $R_a$.

6. The compound or the pharmaceutically acceptable salt thereof as defined in claim 5, wherein, $R_3$ is selected from H, F, Cl, Br, I, OH, $NH_2$, CN, $CH_3$, $CH_2CH_3$, $CH_2CH_2CH_3$, $OCH_3$, $CHF_2$, $CF_3$, $CH_2NH_2$, $CH_2CH_2F$, $COOCH_2CH_3$, COOH, $CH=CH_2$,

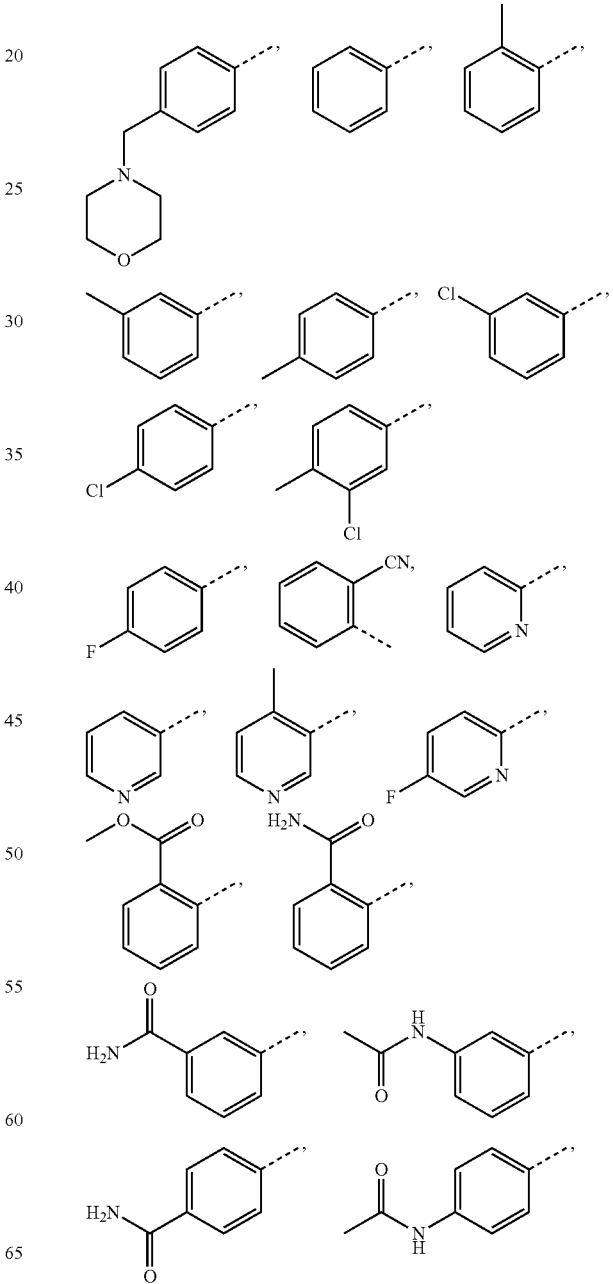

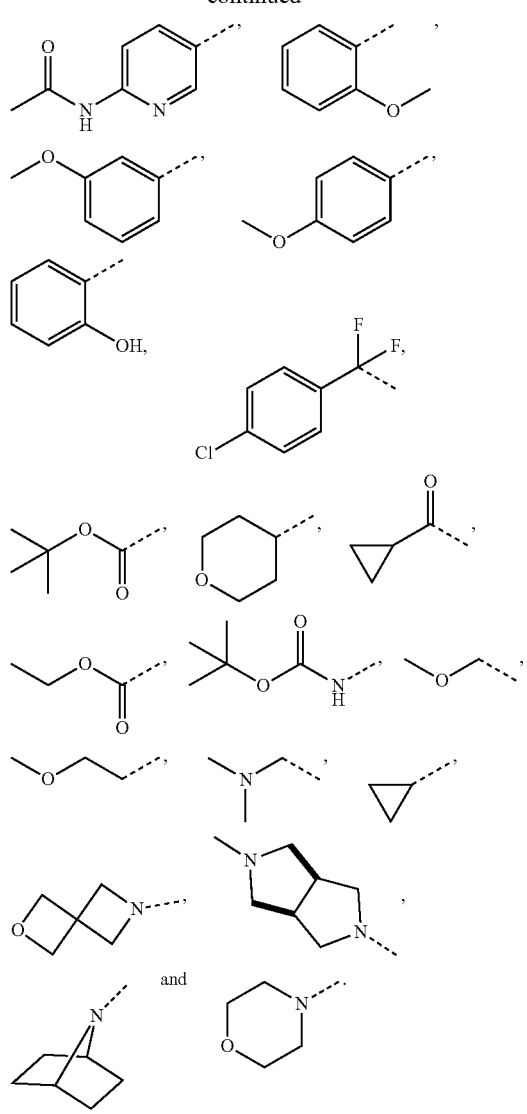
7. The compound or the pharmaceutically acceptable salt thereof as defined in claim 6, wherein, the structural unit -L$_1$-R$_3$ is selected from H, F, Cl, Br, I, OH, NH$_2$, CN, CH$_3$, OCH$_3$,
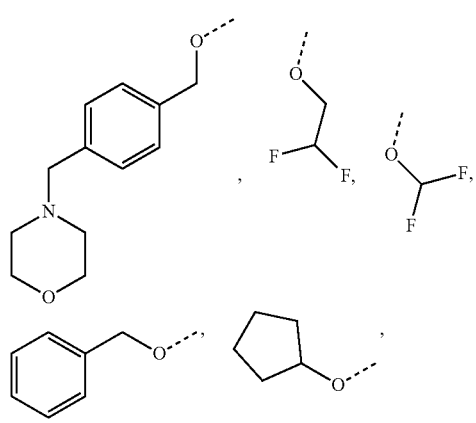
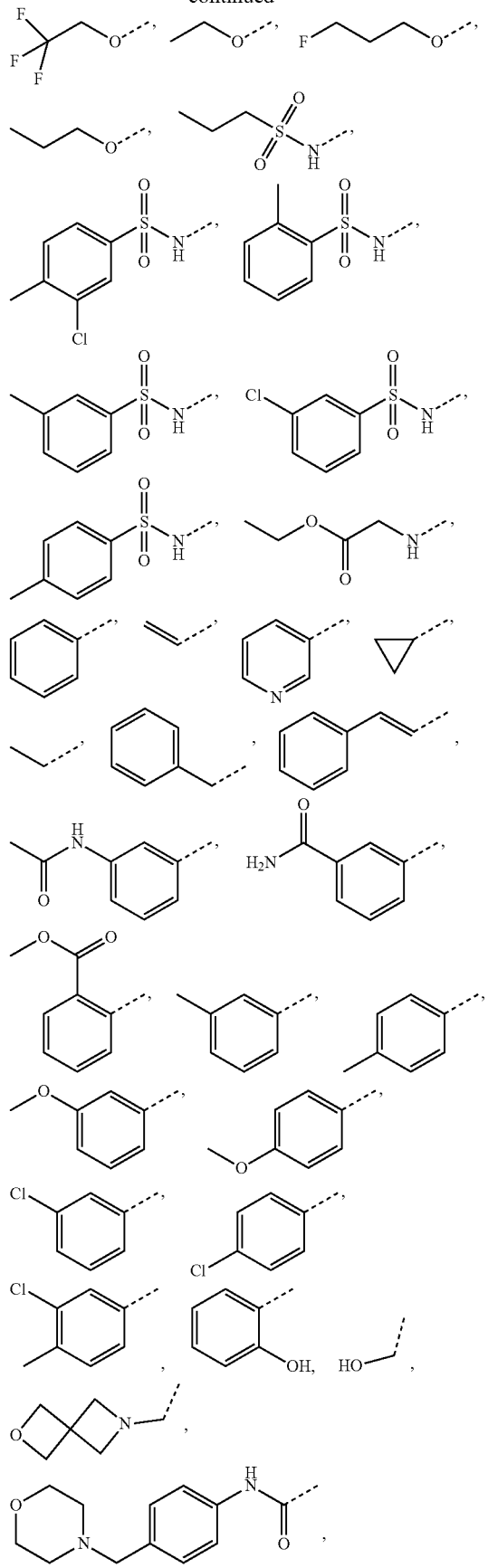

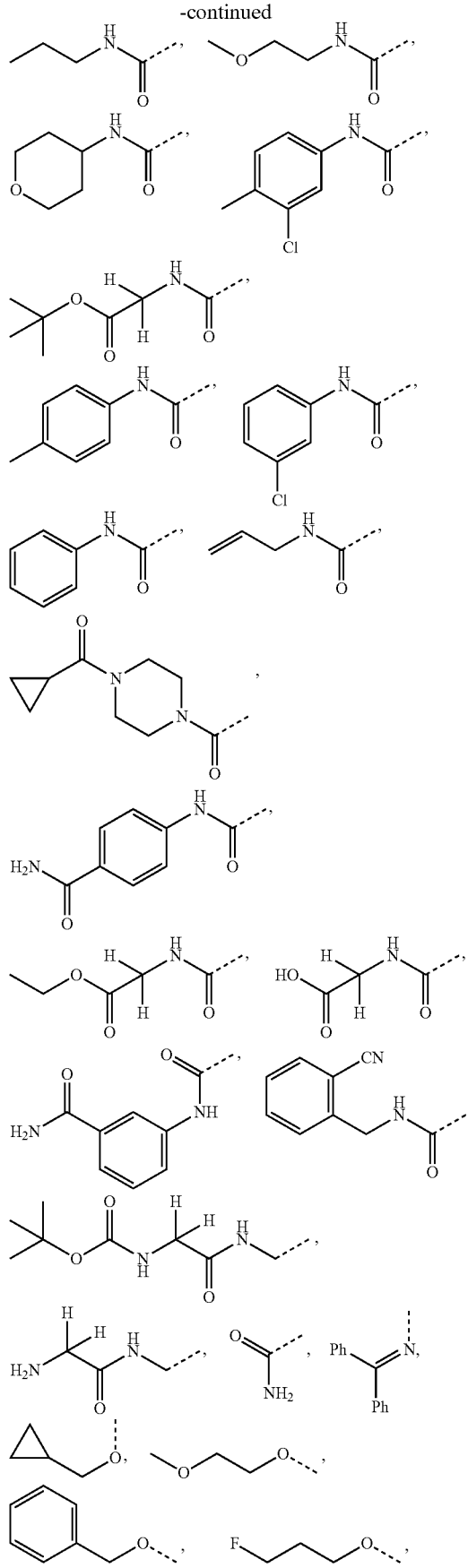
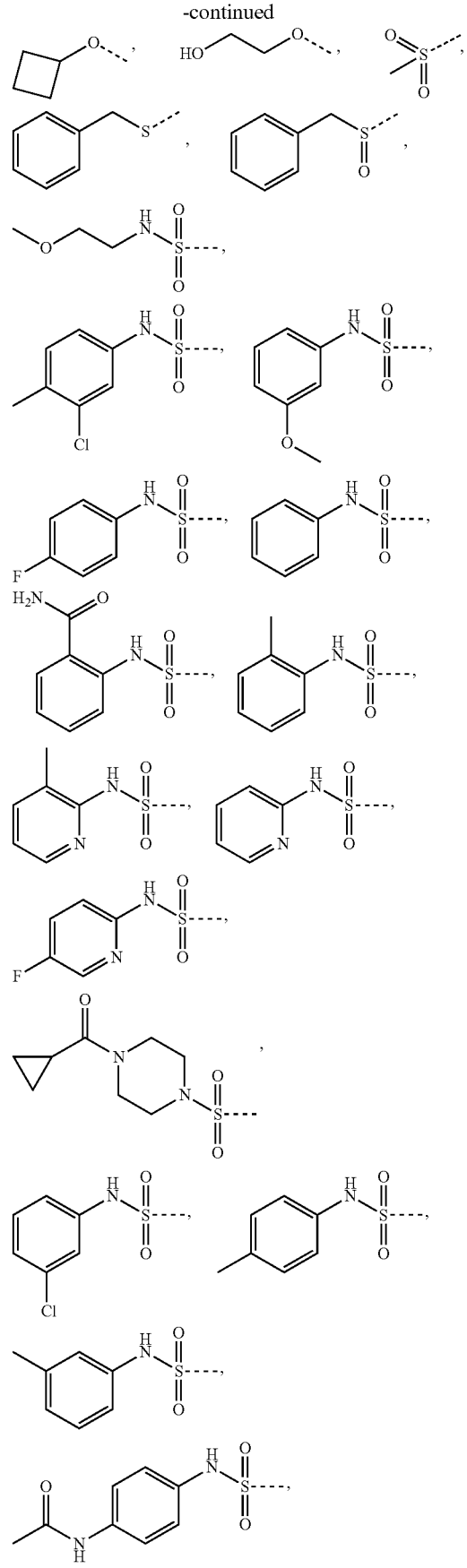

-continued

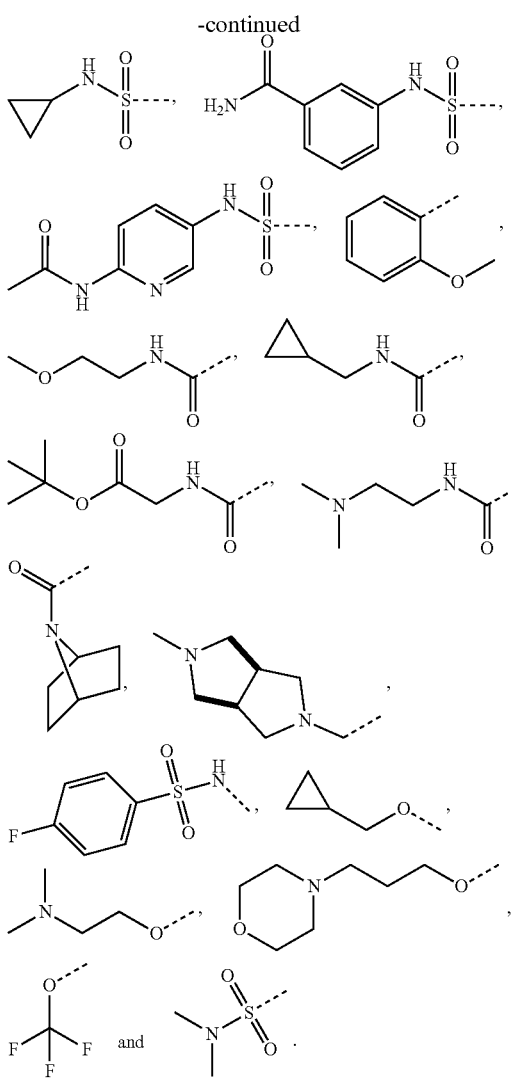

8. The compound or the pharmaceutically acceptable salt thereof as defined in claim 1 is selected from,

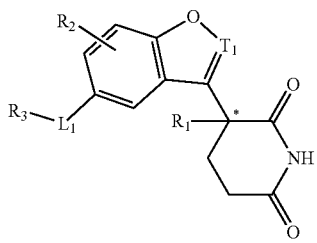
(III-1)

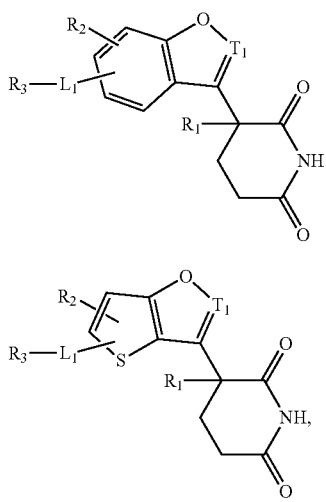
(III-2)

wherein,
T$_1$, R$_1$, R$_2$, R$_3$ and L$_1$ are defined as above.

9. The compound or the pharmaceutically acceptable salt thereof as defined in claim 8 is selected from,

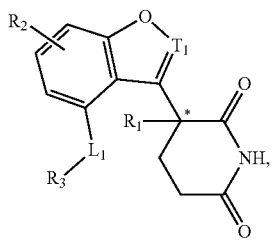
(III-1-1)

(III-1-2)

wherein,
the carbon atom with "*" is a chiral carbon atom, which exists in a (R) or (S) single enantiomer form or an enantiomer-rich form;
T$_1$, R$_1$, R$_2$, R$_3$ and L$_1$ are defined as above.

10. A compound or a pharmaceutically acceptable salt thereof as follows,

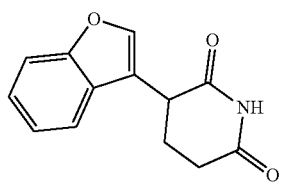

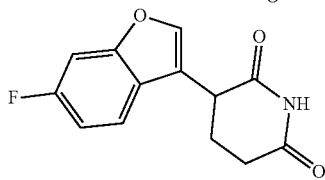

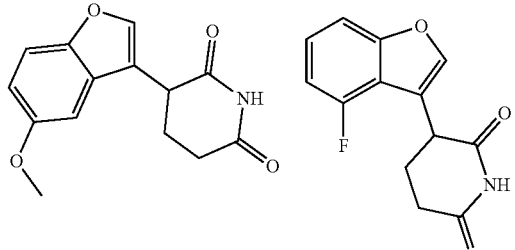

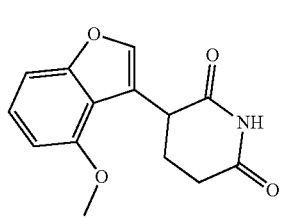

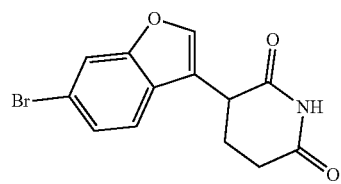
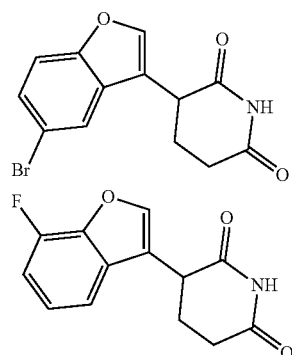
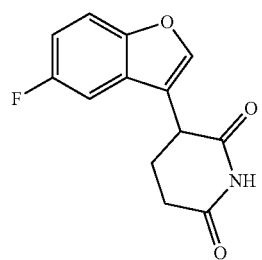
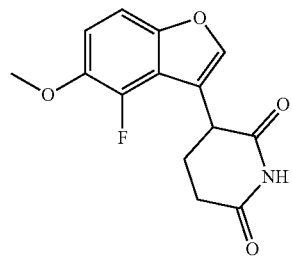
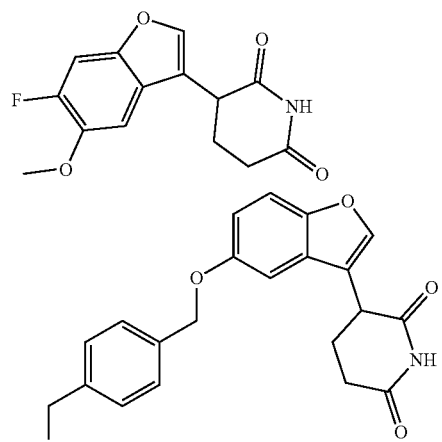
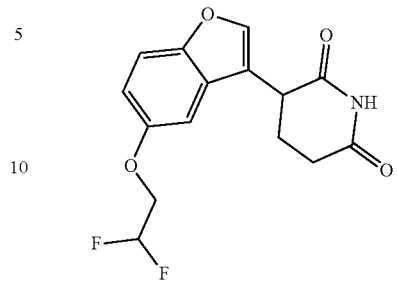
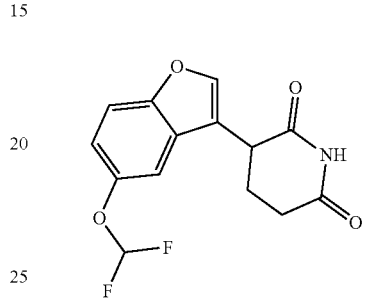
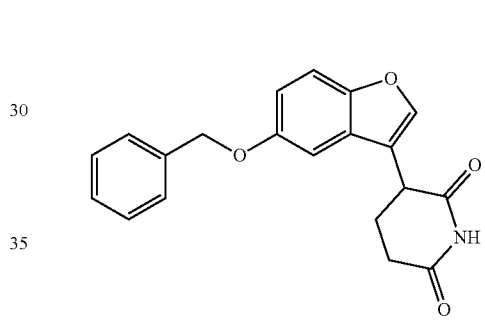
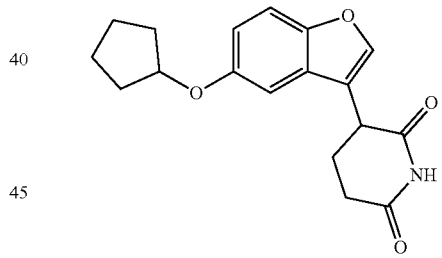
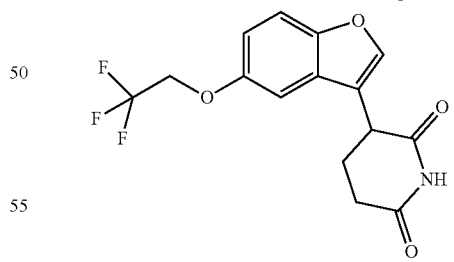
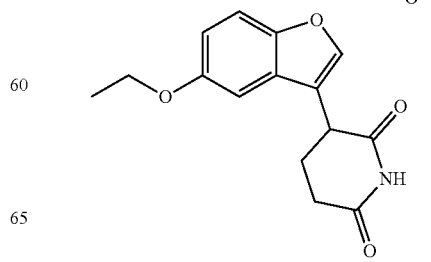

243
-continued
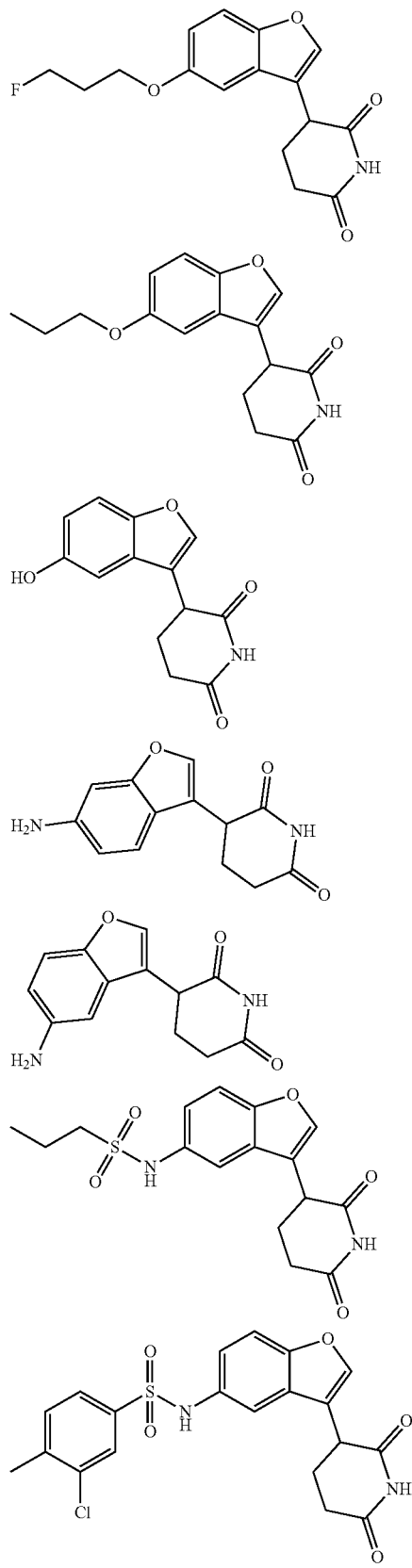
244
-continued
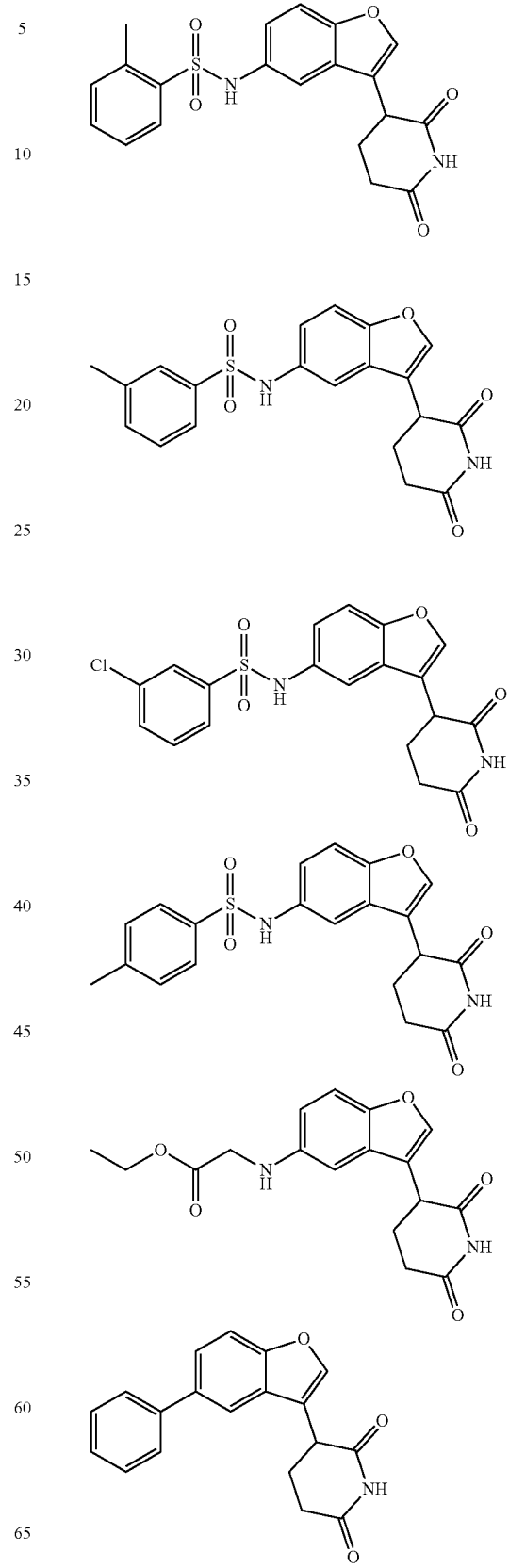

245
-continued
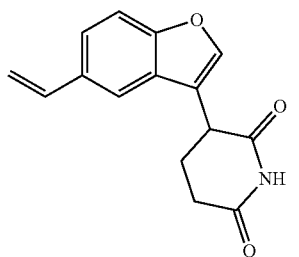
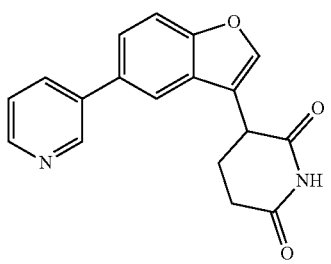
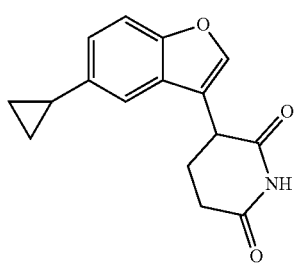
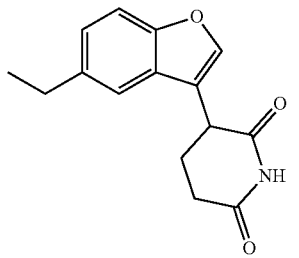
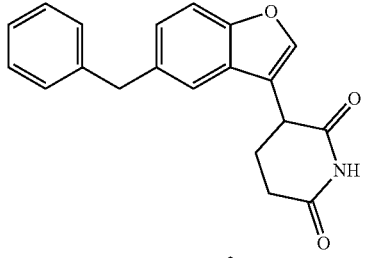
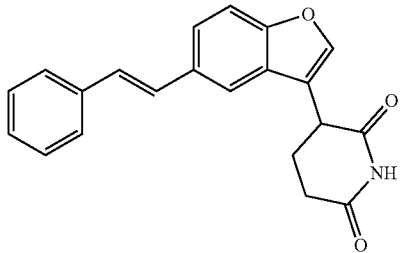
246
-continued
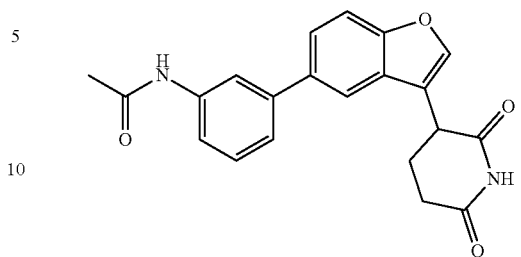
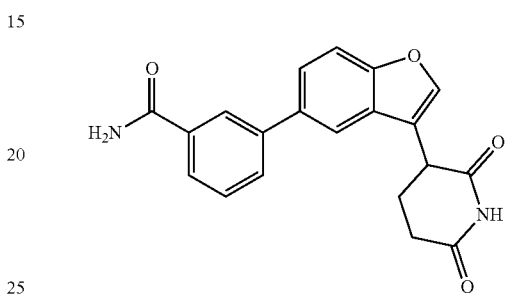
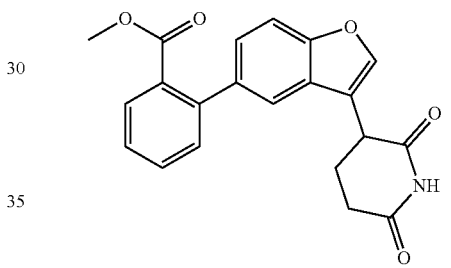
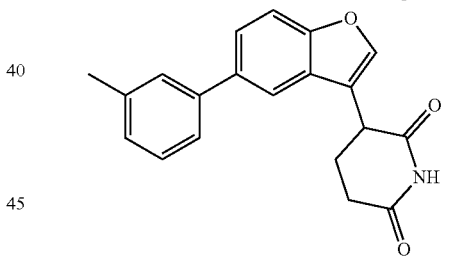
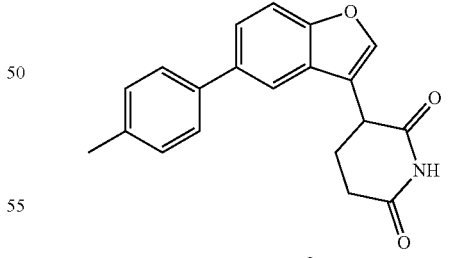
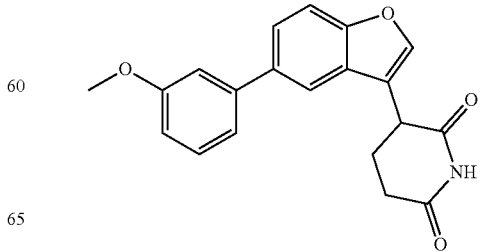

247
-continued
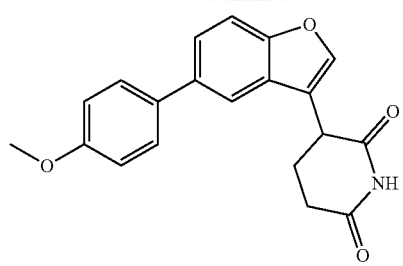
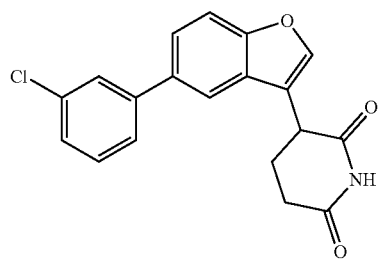
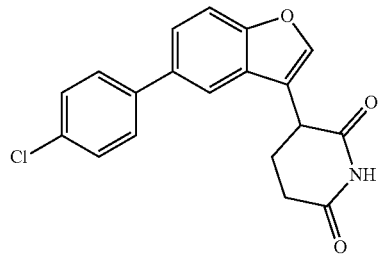
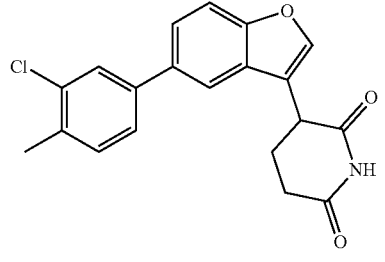
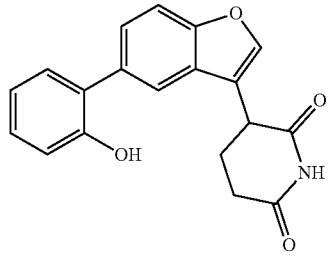
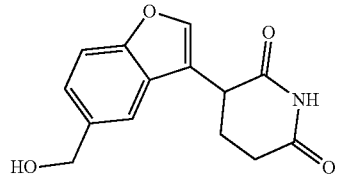
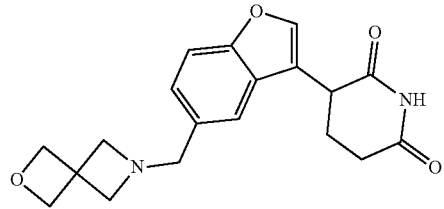
248
-continued
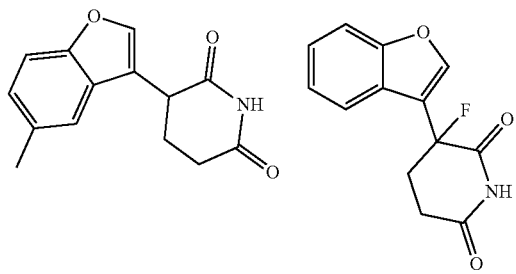
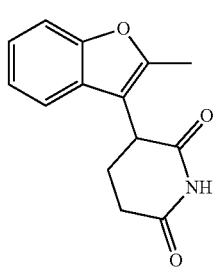 [SMILES: O=C1CCC(c2coc3cccnc23)C(=O)N1]
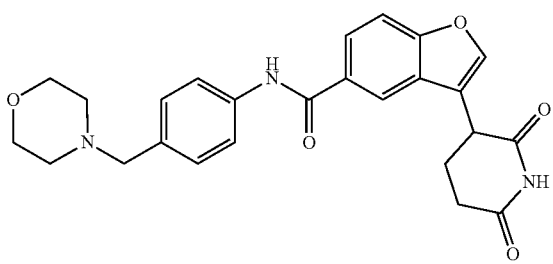
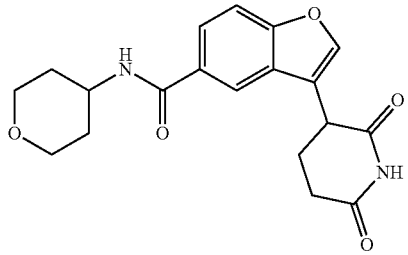
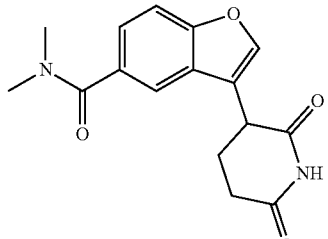
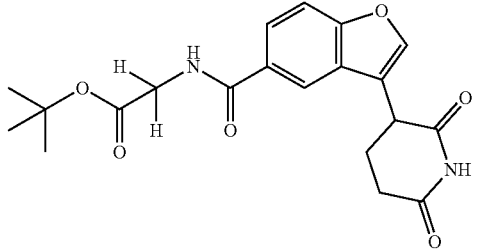

249
-continued
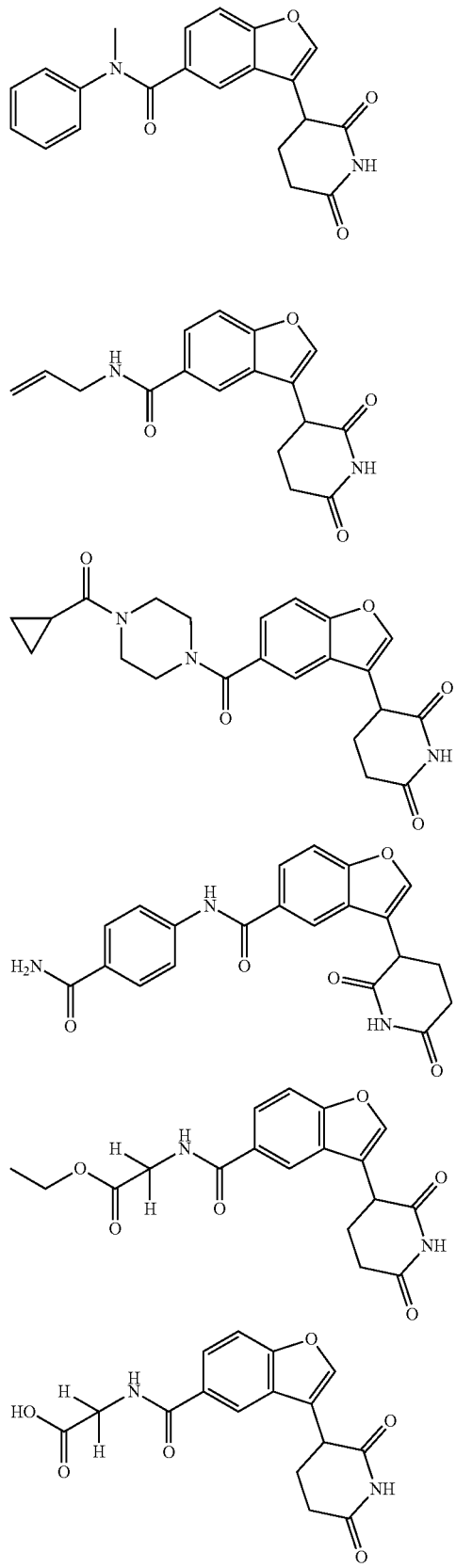
250
-continued
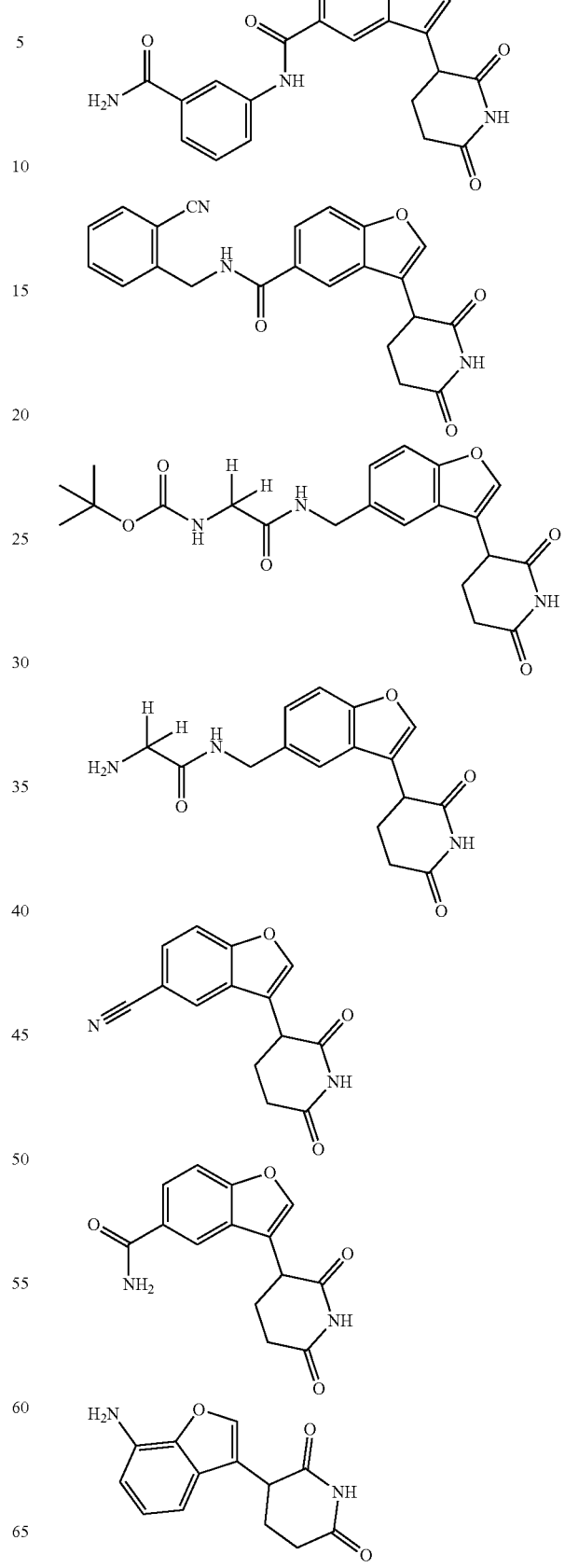

251 -continued
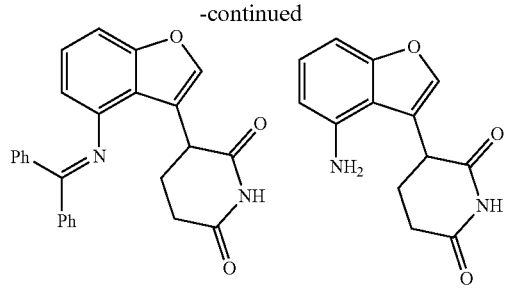
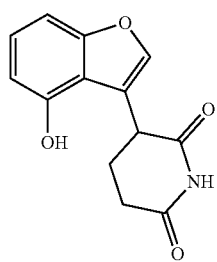
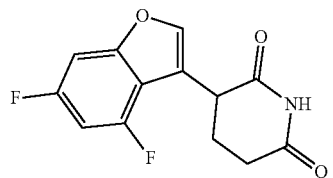
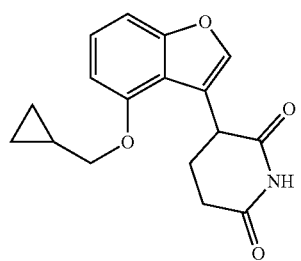
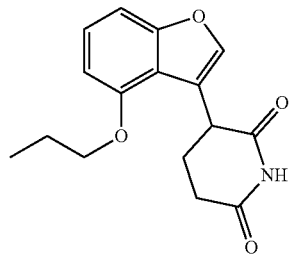
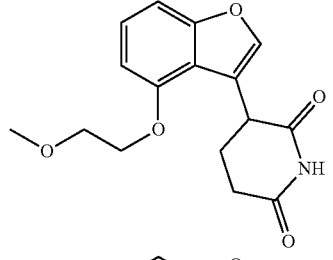
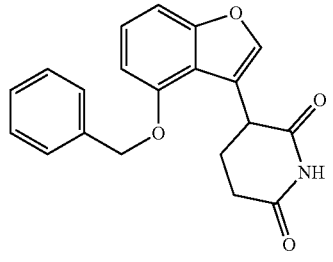
252 -continued
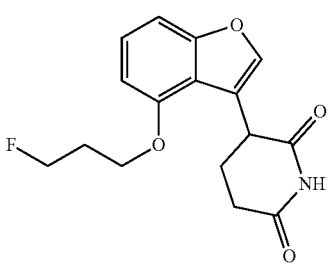
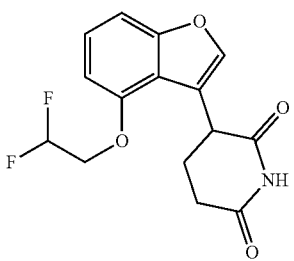
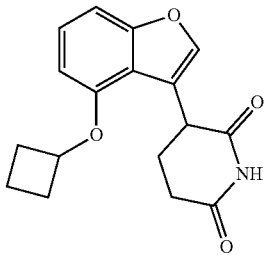
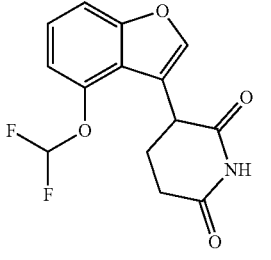
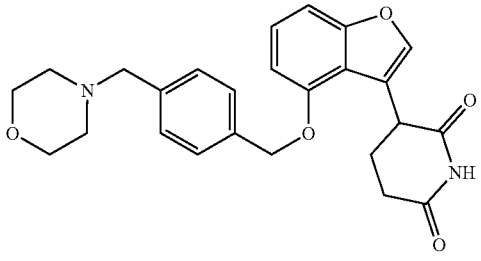

253
-continued
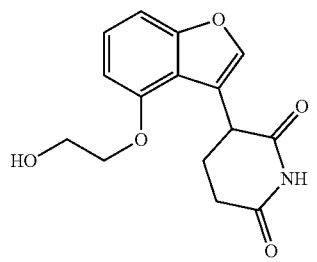
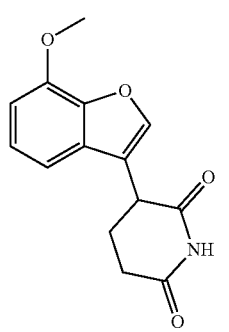
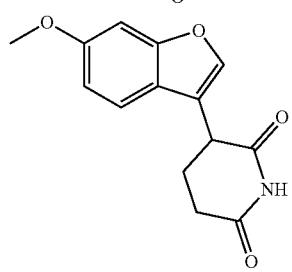
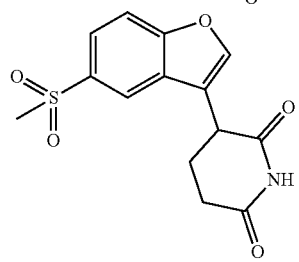
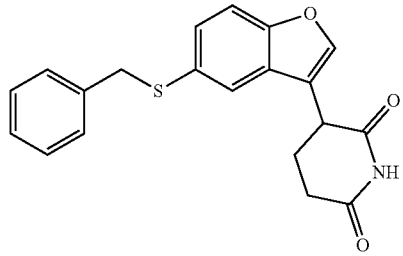
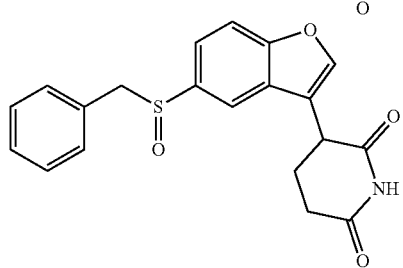
254
-continued
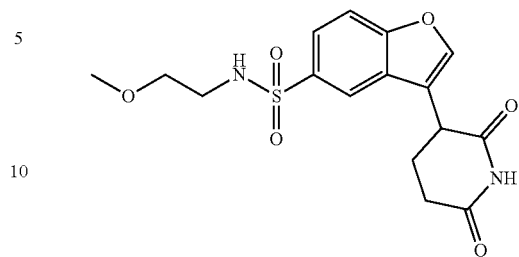
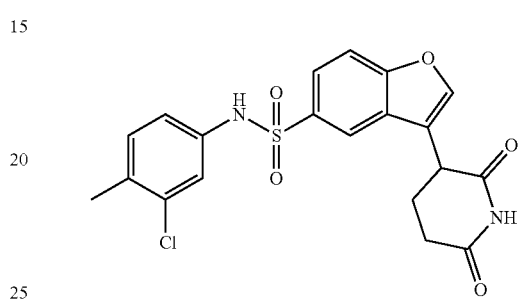
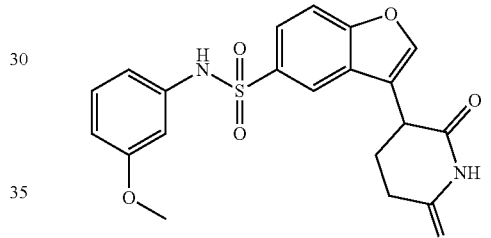
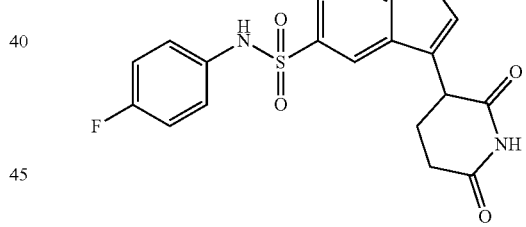
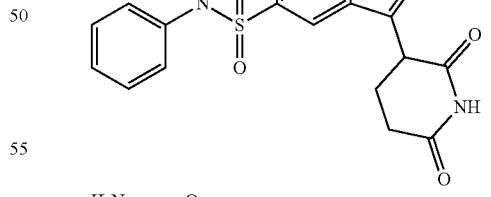
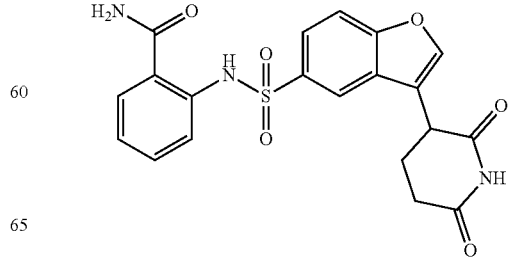

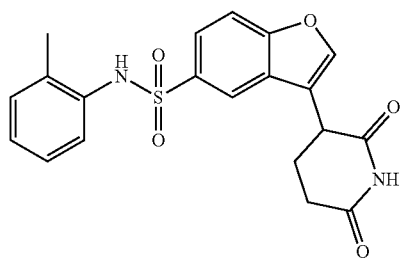
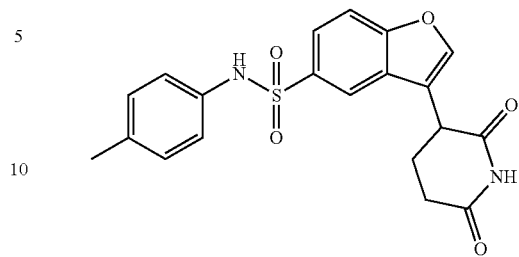
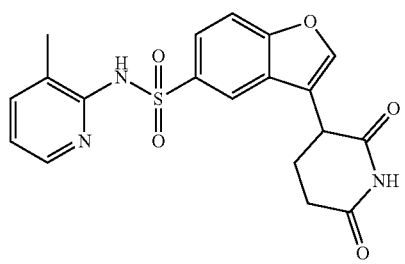
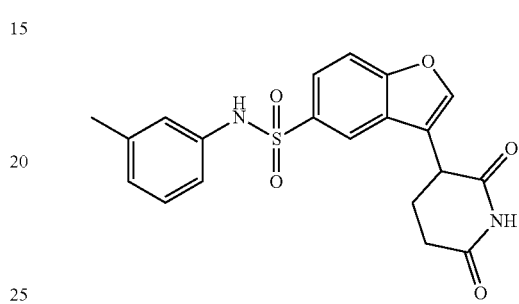
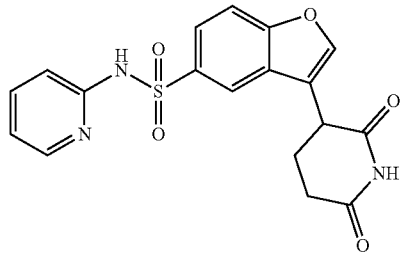
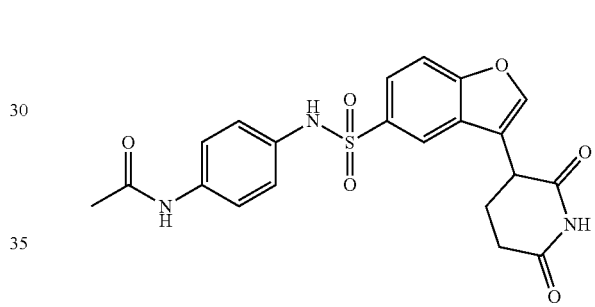
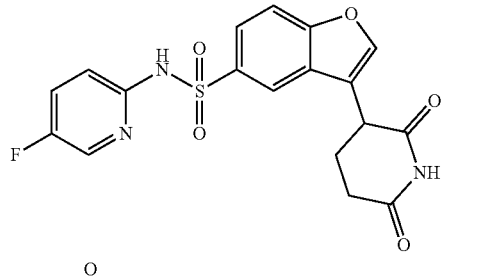
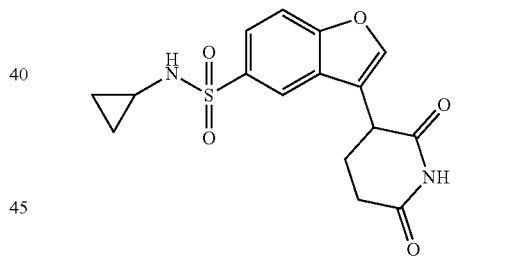
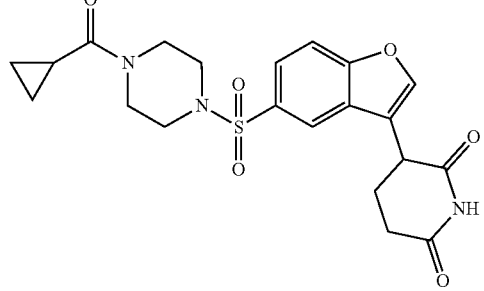
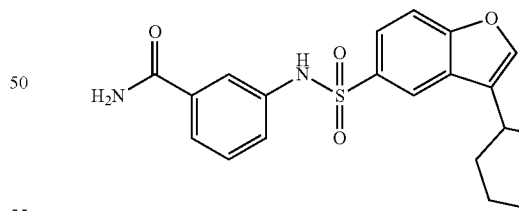
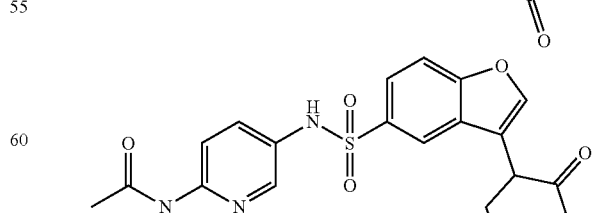

257
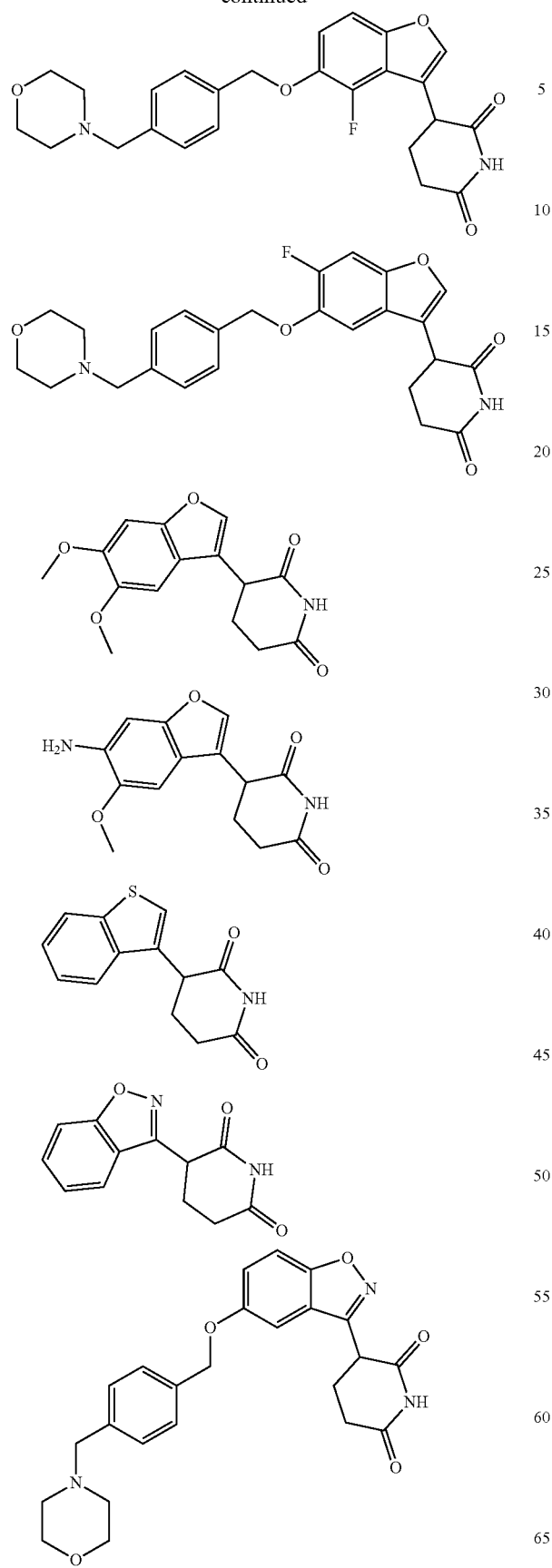
258
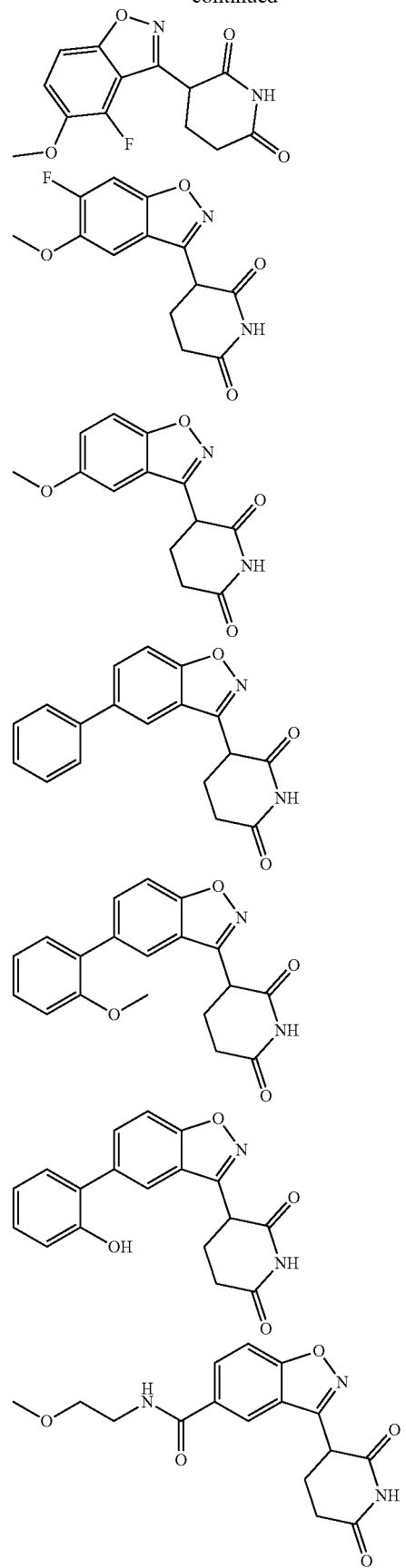

259
-continued
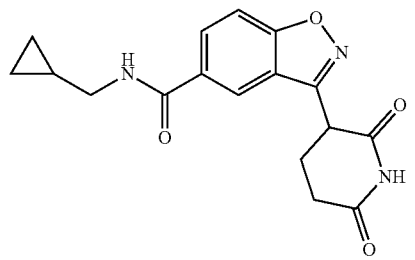
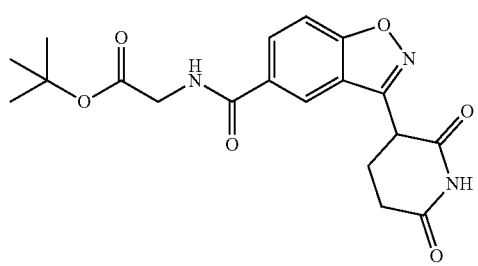
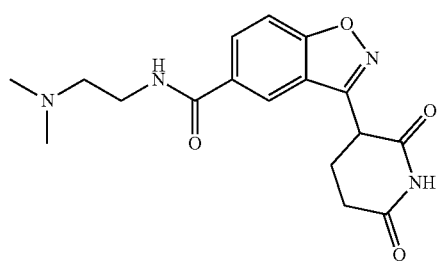
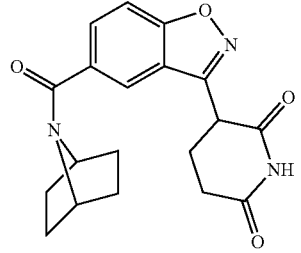
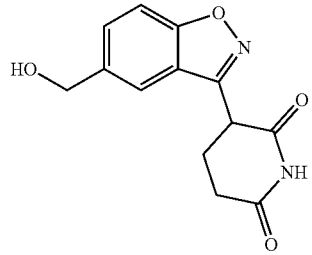
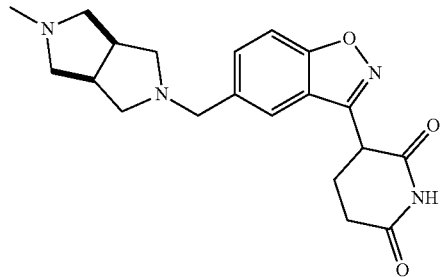
260
-continued
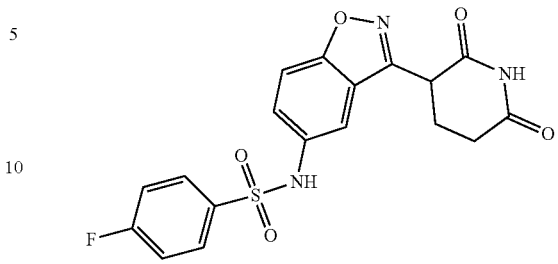
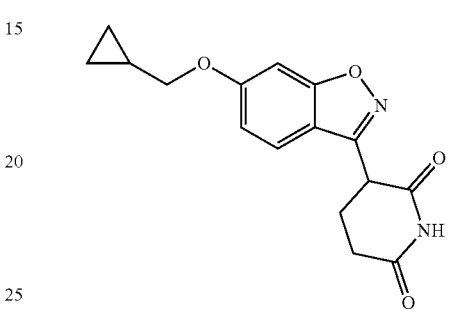
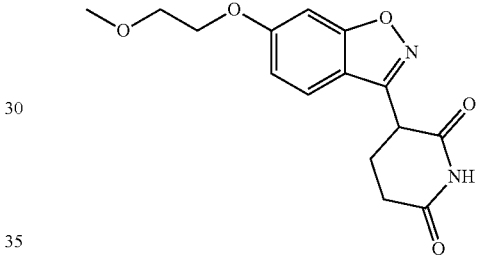
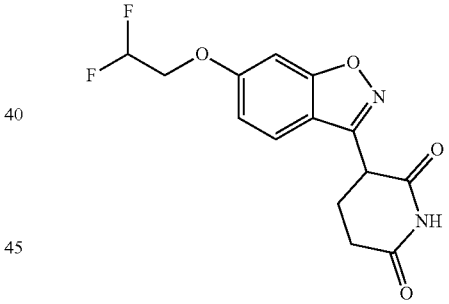
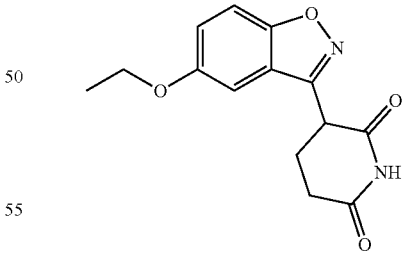
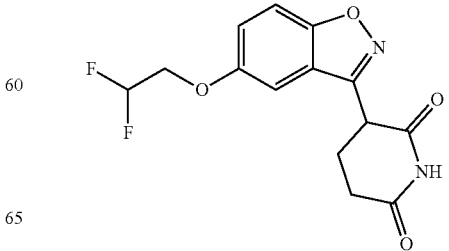

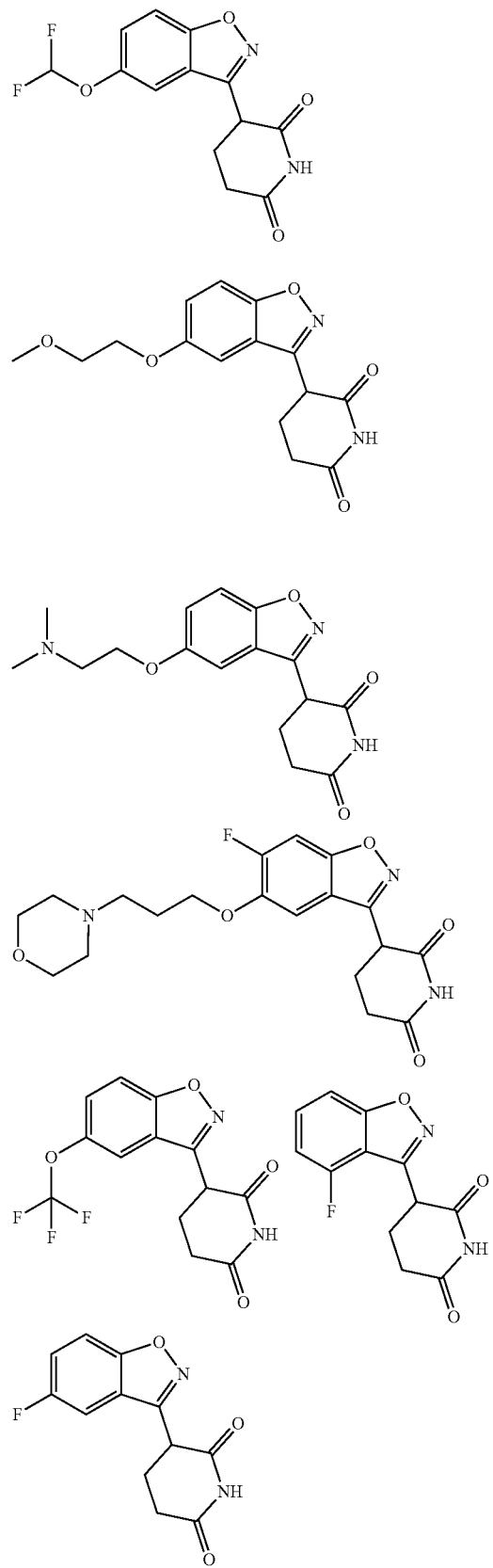
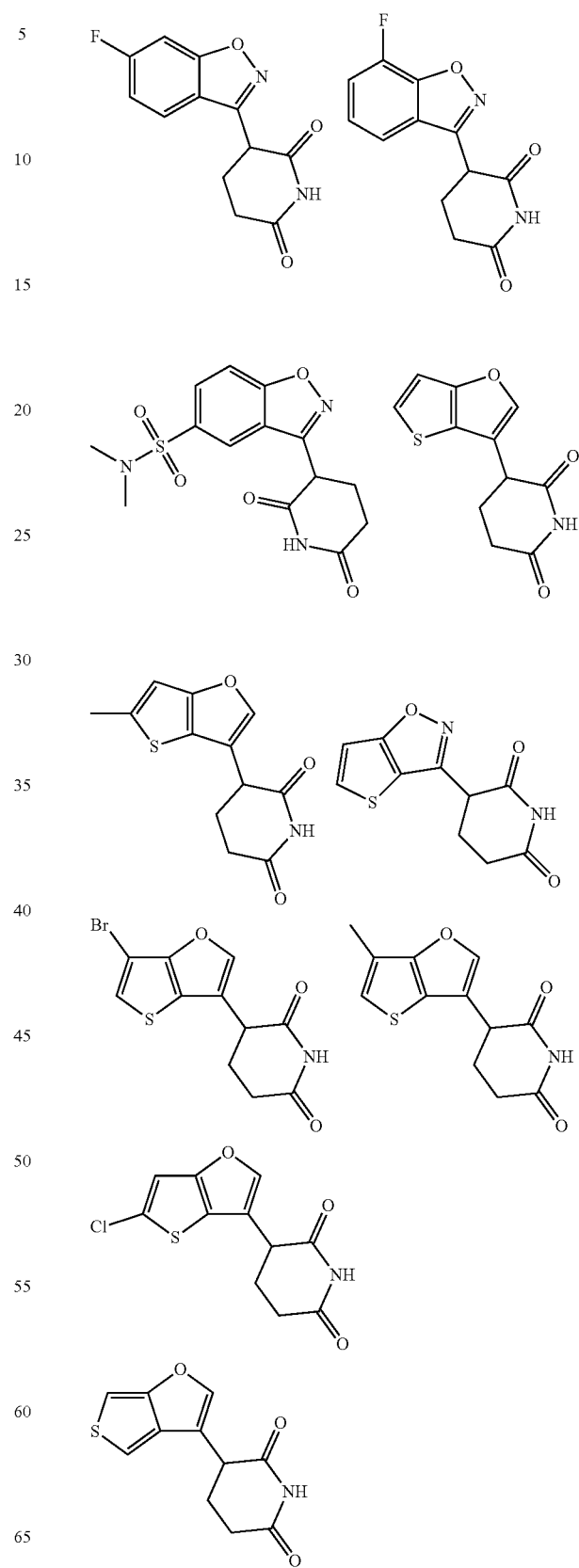

263
-continued
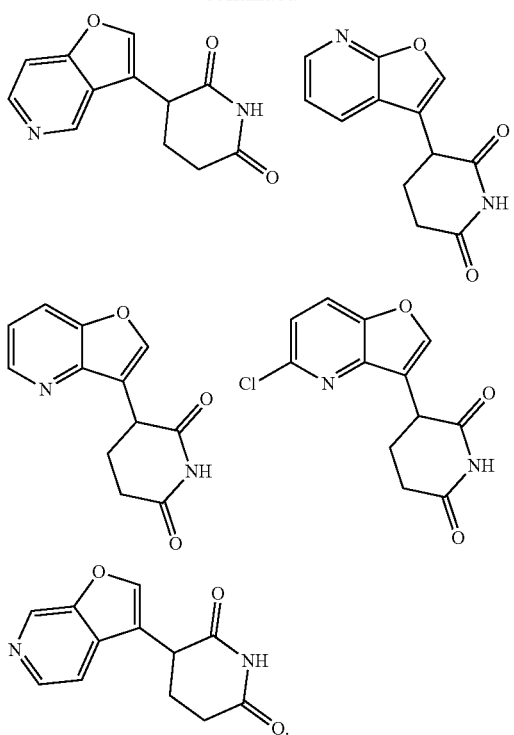
11. The compound or the pharmaceutically acceptable salt thereof as defined in claim 10 is selected from,
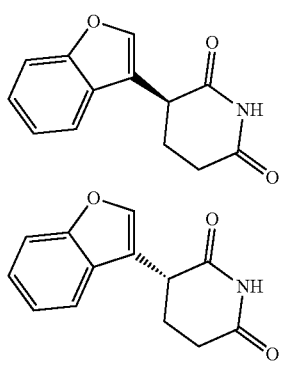
264
-continued
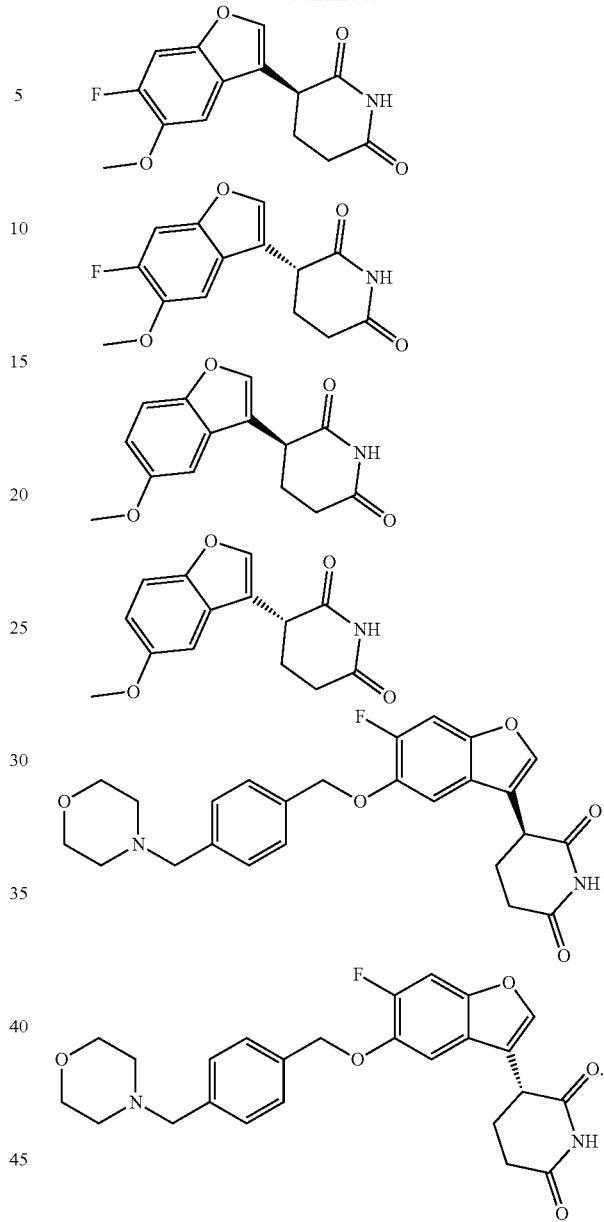
* * * * *